(12) United States Patent
Brown et al.

(10) Patent No.: US 11,773,086 B2
(45) Date of Patent: Oct. 3, 2023

(54) FUNGAL MODULATORS

(71) Applicants: TRUSTEES OF BOSTON UNIVERSITY, Boston, MA (US); THE GOVERNING COUNCIL OF THE UNIVERSITY OF TORONTO, Toronto (CA)

(72) Inventors: Lauren E. Brown, Waltham, MA (US); Kaddy Camara, Revere, MA (US); Leah E. Cowen, Toronto (CA); John A. Porco, Jr., Brookline, MA (US); Kali Rae Iyer, Toronto (CA)

(73) Assignees: TRUSTEES OF BOSTON UNIVERSITY, Boston, MA (US); THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 0 days.

(21) Appl. No.: 17/462,550

(22) Filed: Aug. 31, 2021

(65) Prior Publication Data
US 2022/0064152 A1 Mar. 3, 2022

Related U.S. Application Data

(60) Provisional application No. 63/072,721, filed on Aug. 31, 2020.

(51) Int. Cl.
C07D 405/14 (2006.01)
(52) U.S. Cl.
CPC .................................. C07D 405/14 (2013.01)
(58) Field of Classification Search
CPC .................................................. C07D 405/14
USPC ......................................................... 514/414
See application file for complete search history.

(56) References Cited

U.S. PATENT DOCUMENTS

2016/0106711 A1* 4/2016 Halperin ............ A61K 31/5377 514/35

FOREIGN PATENT DOCUMENTS

| WO | WO-2005080335 A1 * | 9/2005 | ............ C07D 209/34 |
| WO | WO-2008046083 A2 * | 4/2008 | ............ A61K 31/404 |
| WO | WO-2014047437 A1 * | 3/2014 | ............ A61K 31/404 |

OTHER PUBLICATIONS

Iyer et al. ("An oxindole efflux inhibitor potentiates azoles and impairs virulence in the fungal pathogen Candida auris," Nature Communications vol. 11, Article No. 6429 (2020), published Dec. 22, 2020.*
Andreani et al. "New isatin derivatives with antioxidant activity." European Journal of Medicinal Chemistry 45(4): 1374-1378 (2010).
Castaldi et al. "Stereoselective synthesis of spirocyclic oxindoles via Prins cyclizations." Organic Letters 11(15): 3362-3365 (2009).
Celaj et al. "Highly combinatorial genetic interaction analysis reveals a multi-drug transporter influence network." Cell Systems 10(1): 25-38 (2020).
Chowdhary et al. "A multicentre study of antifungal susceptibility patterns among 350 Candida auris isolates (2009-17) in India: role of the ERG11 and FKS1 genes in azole and echinocandin resistance." Journal of Antimicrobial Chemotherapy 73(4): 891-899 (2018).
Copping et al. "Exposure of Candida albicans to antifungal agents affects expression of SAP2 and SAP9 secreted proteinase genes." Journal of Antimicrobial Chemotherapy 55(5): 645-654 (2005).
Denoyelle et al. "Synthesis and SAR study of novel 3, 3-diphenyl-1, 3-dihydroindol-2-one derivatives as potent eIF2 GTP•Met-tRNAiMet ternary complex inhibitors." European Journal of Medicinal Chemistry 69: 537-553 (2013).
Flowers et al., "Contribution of clinically derived mutations in ERG11 to azole resistance in Candida albicans." Antimicrobial Agents and Chemotherapy 59(1): 450-460 (2015).
Healey et al. "Limited ERG11 mutations identified in isolates of Candida auris directly contribute to reduced azole susceptibility." Antimicrobial Agents and Chemotherapy 62(10): e01427-18 pp. 1-4 (2018).
Henry et al. "Upregulation of ERG genes in Candida species by azoles and other sterol biosynthesis inhibitors." Antimicrobial Agents and Chemotherapy 44(10): 2693-2700 (2000).
Hill et al. "Fitness trade-offs associated with the evolution of resistance to antifungal drug combinations." Cell Reports 10(5): 809-819 (2015).
Hoepfner et al. "An integrated approach for identification and target validation of antifungal compounds active against Erg11p." Antimicrobial Agents and Chemotherapy 56(8): 4233-4240 (2012).
Holmes et al. "Targeting efflux pumps to overcome antifungal drug resistance." Future Medicinal Chemistry 8(12): 1485-1501 (2016).
Iskar et al. "Drug-induced regulation of target expression." PLoS Ccomputational Biology 6(9): e1000925 pp. 1-8 (2010).
Ivnitski-Steele et al. "Identification of Nile red as a fluorescent substrate of the Candida albicans ATP-binding cassette transporters Cdr1p and Cdr2p and the major facilitator superfamily transporter Mdr1p." Analytical Biochemistry 394(1): 87-91 (2009).
Iyer et al. "Translation inhibition by rocaglates activates a species-specific cell death program in the emerging fungal pathogen Candida auris." MBio 11(2): e03329-19 pp. 1-17 (2020).
Kean et al. "Transcriptome assembly and profiling of Candida auris reveals novel insights into biofilm-mediated resistance." Msphere 3(4): e00334-18 pp. 1-14 (2018).

(Continued)

*Primary Examiner* — Kahsay Habte
(74) *Attorney, Agent, or Firm* — NIXON PEABODY LLP; Ronald I. Eisenstein; Ravinderjit S. Braich

(57) ABSTRACT

The present invention is directed to compounds, compositions, and methods for inhibiting drug-efflux pumps. The compounds, compositions, and methods can be used for enhancing the activity of therapeutic agents that are efflux pump substrates and for the treatment of drug-resistant diseases or disorders, such as microbial infections and cancers.

20 Claims, 40 Drawing Sheets

Specification includes a Sequence Listing.

(56) References Cited

OTHER PUBLICATIONS

Kim et al. "Genetic analysis of Candida auris implicates Hsp90 in morphogenesis and azole tolerance and Cdr1 in azole resistance." MBio 10(1): e02529-18 pp. 1-16 (2019).
Liu et al. "Mediator tall module is required for Tac1-activated CDR1 expression and azole resistance in Candida albicans." Antimicrobial Agents and Chemotherapy 61(11): e01342-17 pp. 1-20 (2017).
Mann et al. "Chemical genomics-based antifungal drug discovery: targeting glycosylphosphatidylinositol (GPI) precursor biosynthesis." ACS Infectious Diseases 1(1): 59-72 (2015).
Martel et al. "Identification and characterization of four azole-resistant erg3 mutants of Candida albicans." Antimicrobial Agents and Chemotherapy 54(11): 4527-4533 (2010).
Min et al. "Candida albicans gene deletion with a transient CRISPR-Cas9 system." MSphere 1(3): e00130-16 pp. 1-9 (2016).
Morrison et al. "Oxyphenisatin acetate (NSC 59687) triggers a cell starvation response leading to autophagy, mitochondrial dysfunction, and autocrine TNF α-mediated apoptosis." Cancer Medicine 2(5): 687-700 (2013).
Morschhauser et al. "The transcription factor Mrr1p controls expression of the MDR1 efflux pump and mediates multidrug resistance in Candida albicans." PLoS Pathogens 3(11): 1603-1616 (2007).
Morschhauser. "The genetic basis of fluconazole resistance development in Candida albicans." Biochimica et Biophysica Acta (BBA)-Molecular Basis of Disease 1587(2-3): 240-248 (2002).
Munoz et al. "Genomic insights into multidrug-resistance, mating and virulence in Candida auris and related emerging species." Nature Communications 9(1): 1-13 (2018).
Neel et al. "3, 3-Bisaryloxindoles as mineralocorticoid receptor antagonists." Bioorganic & Medicinal Chemistry Letters 15(10): 2553-2557 (2005).
Nishikawa et al. "inhibiting fungal multidrug resistance by disrupting an activator-mediator interaction." Nature 530 (7591): 485-489 (2016).
Odds. "Synergy, antagonism, and what the chequerboard puts between them." Journal of Antimicrobial Chemotherapy 52(1): 1-1 (2003).
Perea et al. "Prevalence of molecular mechanisms of resistance to azole antifungal agents in Candida albicans strains displaying high-level fluconazole resistance isolated from human immunodeficiency virus-infected patients." Antimicrobial Agents and Chemotherapy 45(10): 2676-2684 (2001).
Prasad et al. "The ABCs of Candida albicans multidrug transporter Cdr1." Eukaryotic Cell 14(12): 1154-1164 (2015).
Prasad et al. "Molecular cloning and characterization of a novel gene of Candida albicans, CDR1, conferring multiple resistance to drugs and antifungals." Current Genetics 27(4): 320-329 (1995).
Prasad et al. "Functionally relevant residues of Cdr1p: a multidrug ABC transporter of human pathogenic Candida albicans." Journal of Amino Acids 2011 pp. 1-12 (2011).
Robey et al. "Revisiting the role of ABC transporters in multidrug-resistant cancer." Nature Reviews Cancer 18(7): 452-464 (2018).
Rybak et al. "Abrogation of triazole resistance upon deletion of CDR1 in a clinical isolate of Candida auris." Antimicrobial Agents and Chemotherapy 63(4): e00057-19 pp. 1-7 (2019).
Rybak et al. "Mutations in TAC1B: a novel genetic determinant of clinical fluconazole resistance in C. auris." bioRxiv pp. 1-38 (2020).
Sharma et al. "Efflux pump inhibitors for bacterial pathogens: From bench to bedside." The Indian Journal of Medical Research 149(2): 129-145 (2019).
Shekhar-Guturja et al. "Dual action antifungal small molecule modulates muitidrug efflux and TOR signaling." Nature Chemical Biology 12(10): 867-875 (2016).
Shriram et al. "Inhibiting bacterial drug efflux pumps via phytotherapeutics to combat threatening antimicrobial resistance." Frontiers in Microbiology 9: 2990 pp. 1-18 (2018).
Spitzer et al. "Combinatorial strategies for combating invasive fungal infections." Virulence 8(2): 169-185 (2017).
Tsao et al. "Relative contributions of the Candida albicans ABC transporters Cdr1p and Cdr2p to clinical azole resistance." Antimicrobial Agents and Chemotherapy 53(4): 1344-1352 (2009).
Wasi et al. "ABC transporter genes show Upregulated expression in drug-resistant clinical isolates of Candida auris: a genome-wide characterization of ATP-binding cassette (ABC) transporter genes." Frontiers in Microbiology 10: 1445 pp. 1-16 (2019).
White, "Increased mRNA levels of ERG16, CDR, and MDR1 correlate with increases in azole resistance in Candida albicans isolates from a patient infected with human immunodeficiency virus." Antimicrobial Agents and Chemotherapy 41(7): 1482-1487 (1997).
Wright. "Antibiotic adjuvants: rescuing antibiotics from resistance." Trends in Microbiology 24(11): 862-871 (2016).
Zheng et al. "Targeting multidrug-resistant ovarian cancer through estrogen receptor α dependent ATP depletion caused by hyperactivation of the unfolded protein response." Oncotarget 9(19): 14741-14753 (2018).
Pubchem, Substance Record for SID 363506897. Available Date: Apr. 13, 2018. [retrieved on Dec. 13, 2021]. Retrieved from the Internet: <https://pubchem.ncbi.nlm.nih.gov/substance/363506897>. Entire document.
Pubchem, Substance Record for SID 375569255. Available Date: Aug. 9, 2018. [retrieved on Oct. 27, 2021]. Retrieved from the Internet: <https://pubchem.ncbi.nlm.nih.gov/substance/375569255>. Entire document.

\* cited by examiner

CMLD012336
(Azoffluxin)

Nile Red

Nile red
+ 50 μM
Azofluxin a. *C. auris cdr1Δ*

*C. auris cdr4-1Δ*

C

| Strain | Fold Change |
|---|---|
| Ci6684: I | 18.7 (± 3.7) |
| B11221: III | 14.2 (± 2.7) |
| B11222: III | 15.0 (± 4.8) |
| B12037: III | 18.6 (± 2.0) |

| Species | 10 µM Azo | 100 µM Azo |
|---|---|---|
| C. albicans | 1.5 | 7.9 |
| C. glabrata | 0.7 | 3.7 |
| C. neoformans | 2.5 | 5.3 |

R6G

| Cell line | Tariquidar (60 nM) | Azofluxin (50 µM) |
|---|---|---|
| cDNA | 1.1 | 1.2 |
| MDR1 | 42.6 | 6.0 |

FIG. 12E

Cal

| Cell line | MK571 (30 µM) | Azofluxin (50 µM) |
|---|---|---|
| cDNA | 1.2 | 1.2 |
| MRP1 | 3.4 | 2.5 |

FIG. 12F

CMLD012336

CMLD012337 enantiomer of CMLD012336

FUNGAL MODULATORS

RELATED APPLICATIONS

This application claims benefit under 35 U.S.C. § 119(e) of U.S. Provisional Application No. 63/072,721, filed Aug. 31, 2020, content of which is incorporated herein by reference in its entirety.

GOVERNMENT SUPPORT

This invention was made with Government Support under Contract No. GM111625 awarded by the National Institutes of Health. The Government has certain rights in the invention.

TECHNICAL FIELD

The present invention generally relates to fungal modulators, for example combination therapies for treatment of fungal infections.

SEQUENCE LISTING

The instant application contains a Sequence Listing which has been submitted electronically in ASCII format and is hereby incorporated by reference in its entirety. Said ASCII copy, created on Nov. 10, 2021, is named 701586-098330USPT_SL.txt and is 12,063 bytes in size.

BACKGROUND

Antimicrobial resistance is one the most pressing threats to public health. The alarming rise in resistance threatens to undermine the ability of modern medicine to keep infectious agents at bay, making standard hospital visits potentially life-threatening endeavors. Although the focus has primarily been on pan-resistant bacterial "superbugs", there is growing concern about a multidrug-resistant fungal "superbug", *Candida auris*. This emerging pathogen has galvanized researchers, health care workers, and the media due to its unprecedented rates of drug resistance and transmissibility. In its most recent report, the U.S. Centers for Disease Control and Prevention classified *C. auris* as one of only five pathogens that are the most urgent threat to public health. Thus, the emergence of *C. auris* highlights the dire need for more therapeutic options to combat drug-resistant fungal infections.

The present disclosure addresses some of these needs.

SUMMARY

In one aspect, provided herein is a compound of Formula (I) or enantiomers, prodrugs, derivatives, and pharmaceutically acceptable salts thereof. Compounds of Formula (I) have the structure:

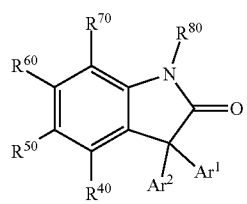

In compounds of Formula (I), each of $R^{40}$, $R^{50}$, $R^{60}$, $R^{70}$, and $R^{80}$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted.

In some embodiments, at least one of $R^{40}$, $R^{50}$, $R^6$, $R^{70}$, and $R^{80}$ is not H. For example, at least one of $R^{40}$, $R^{50}$, $R^{60}$, $R^{70}$, and $R^{80}$ is halogen or an optionally substituted $C_1$-$C_6$alkyl.

In compounds of Formula (I), $Ar^1$ and $Ar^2$ are independently optionally substituted aryl or optionally substituted heteroaryl. It is noted that $Ar^1$ and $Ar^2$ can be the same or different. Accordingly, in some embodiments of any one of the aspects described herein, $Ar^1$ and $Ar^2$ are the same. In some other embodiments of any one of the aspects described herein $Ar^1$ and $Ar^2$ are different.

In some embodiments of any one of the aspects, at least one of $Ar^1$ and $Ar^2$ is of structure:

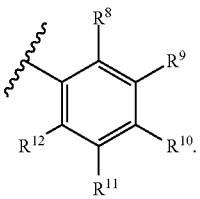

In some embodiments of any one of the aspects, each of $R^8$, $R^9$, $R^{10}$, $R^{11}$, and $R^{12}$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted.

In some embodiments of any one of the aspects, at least a vicinal pair formed from selecting two of $R^8$, $R^9$, $R^{10}$, $R^{11}$, or $R^{12}$ and the carbons to which they are attached form an optionally substituted 5- or 6-member cycloalkyl or an optionally substituted 5- or 6-member heterocycle, and the remaining $R^8$, $R^9$, $R^{10}$, $R^{11}$, or $R^{12}$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted.

In some embodiments, one of $R^8$, $R^9$, $R^{10}$, $R^{11}$, or $R^{12}$ is deuterium.

In some embodiments of any one of the aspects, at least one of $Ar^1$ and $Ar^2$ is of structure:

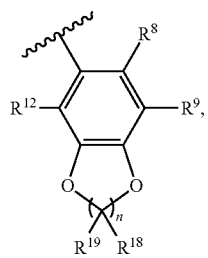

where n is 1 or 2; and $R^{18}$ and $R^{19}$ are each independently hydrogen, deuterium, or halogen.

In another aspect, provided herein is a composition comprising a compound of Formula (I). In some embodiments of any one of the aspects, the composition is a pharmaceutical composition.

In some embodiments of any one of the aspects, the composition further comprises an efflux transporter substrate. For example, the composition further comprises a substrate for a mammalian or a microbial ABC efflux transporter, e.g., Cdr1, ABCB1(MDR1/Pgp), ABCC1 (MRP1), and ABCG2 (BCRP) efflux transporter. In some embodiments of any one of the aspects, composition comprises an efflux transporter substrate that is therapeutic agent. For example, the composition comprises an antimicrobial agent or an anticancer agent, optionally the antimicrobial agent or an anticancer agent is a substrate for an efflux transporter.

In yet another aspect, provided herein is a method of inhibiting an efflux transporter in a cell. The method comprises administering a compound of Formula (I) to the cell. It is noted that administering to the cell can be in vitro, ex vivo or in vivo. Further, the cell can be a microbial cell or a mammalian cell. In some embodiments, the cell is a microbial cell. For example, the cell is a fungal cell.

In some embodiments of any one of the aspects, the cell is a microbial cell. For example, the cell is a microbial pathogen that is resistant to one or more antimicrobial agents. In some other embodiments of any one of the aspects, the cell is a cancer cell. For example, the cell is from a drug-resistant cancer.

In still another aspect, provided herein is a method for treating an infection caused by a microbial pathogen in a subject. The method comprises co-administering to the subject in need thereof an antimicrobial agent and a compound of Formula (I). In some embodiments, the co-administered antimicrobial agent can be an efflux transporter substrate.

In some embodiments of any one of the aspects, wherein the microbial pathogen is resistant to one or more antimicrobial agents. For example, the microbial pathogen is resistant to the co-administered antimicrobial agent.

Relative growth was measured after 24 hours using OD600 and normalized to no-drug control wells (see color bar). The FICI calculated for the checkerboard is shown in the top right of the plot, with values<0.5 indicating synergy.

Figure 10A:
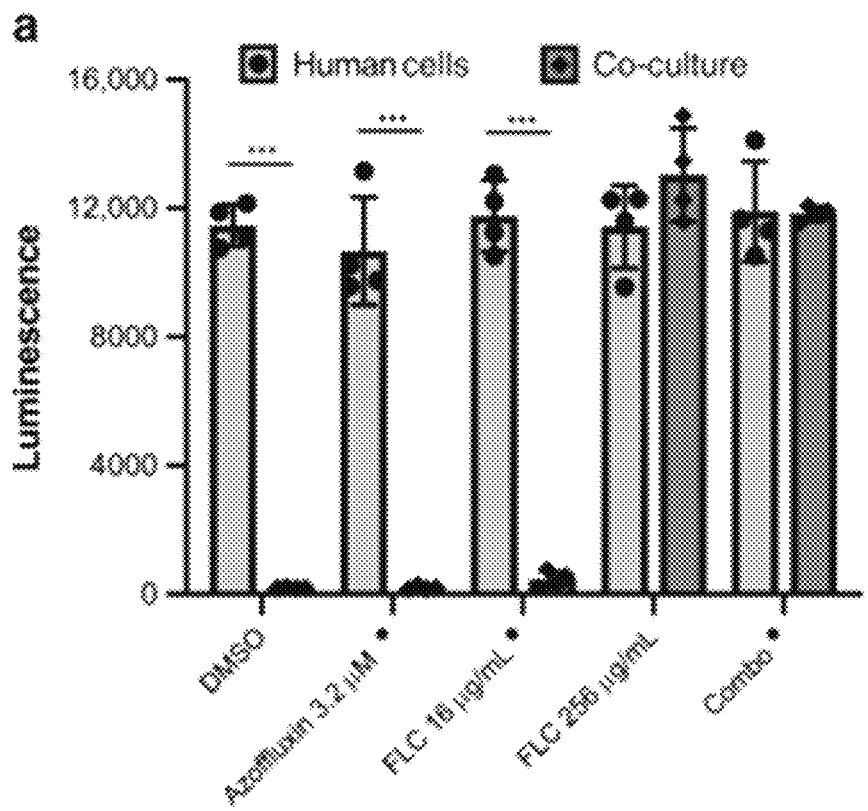
FIG. 10A depicts relative growth and survival of mammalian embryonic kidney (293T) cancer cells expressing luciferase in co-culture with fungus.
Figure 10B:
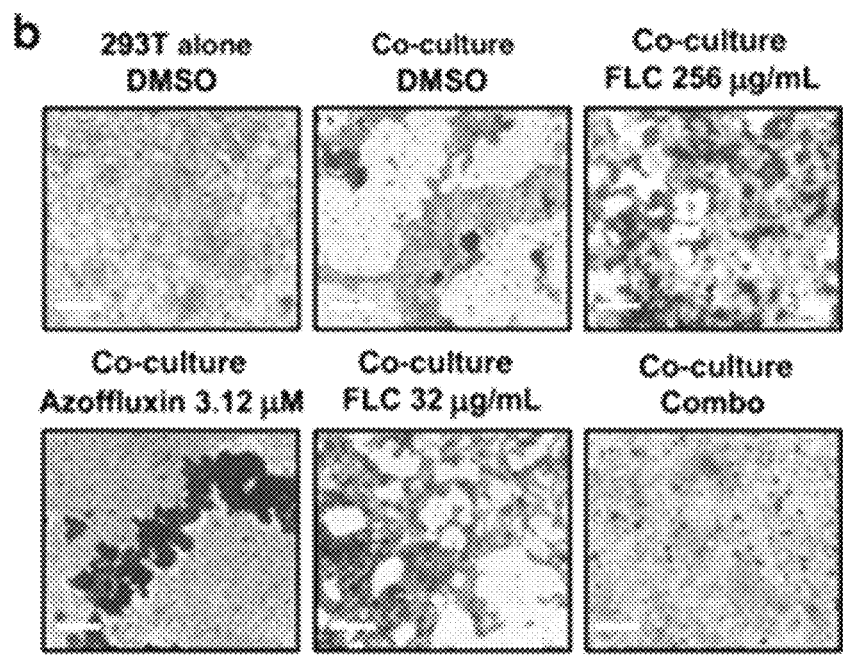
FIG. 10B depicts Periodic-Acid Schiff (PAS) staining used to visualize cells in co-culture where light purple staining shows 293T cells and the bright pink shows C. auris.
Figures 10C, 10D:
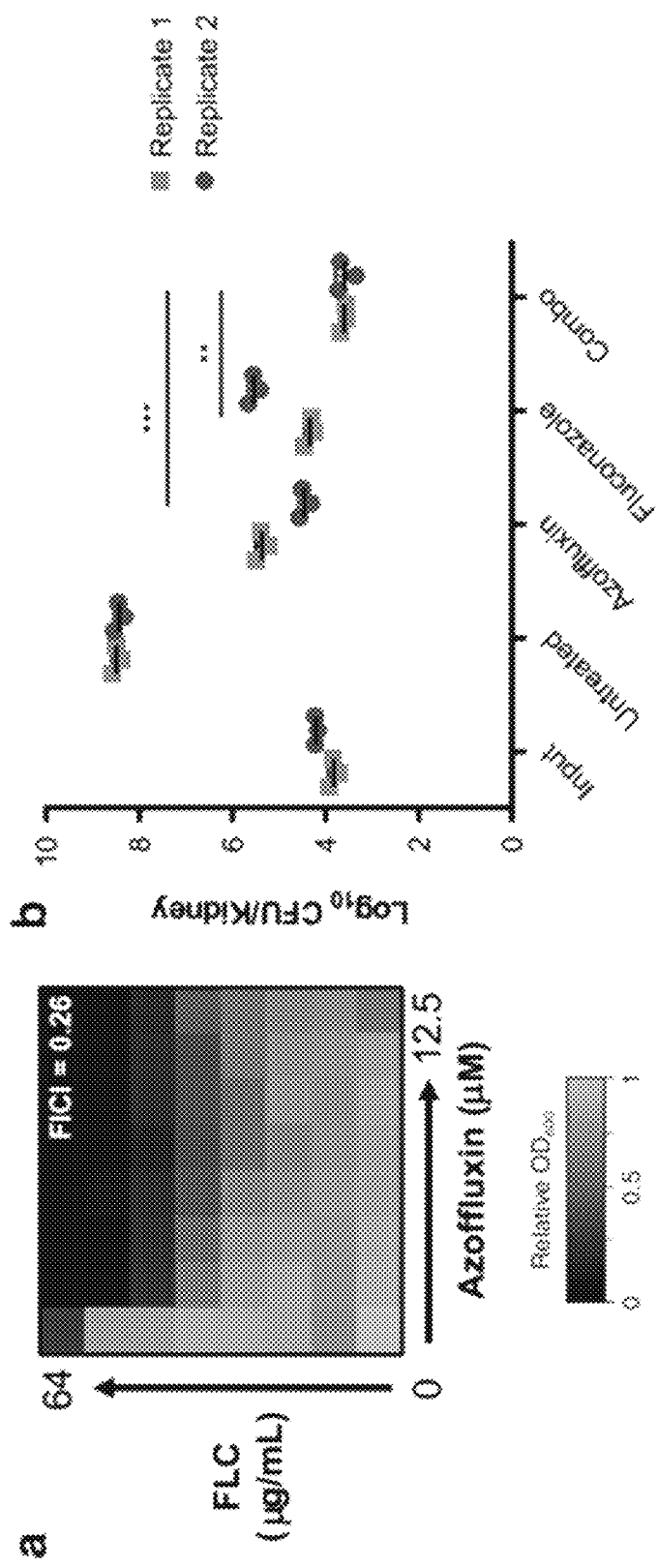
FIG. 10C depicts checkerboard assays performed as described in FIG. 2B with C. auris Clade IV isolate B11801.

FIG. 10D depicts kidney fungal burden (CFU) in mice from each treatment group (n=3) that had been infected with *C. auris* B11801 and treated with azoffluxin, fluconazole (FLC), and a combination of azoffluxin and FLC.

Figure 10E:
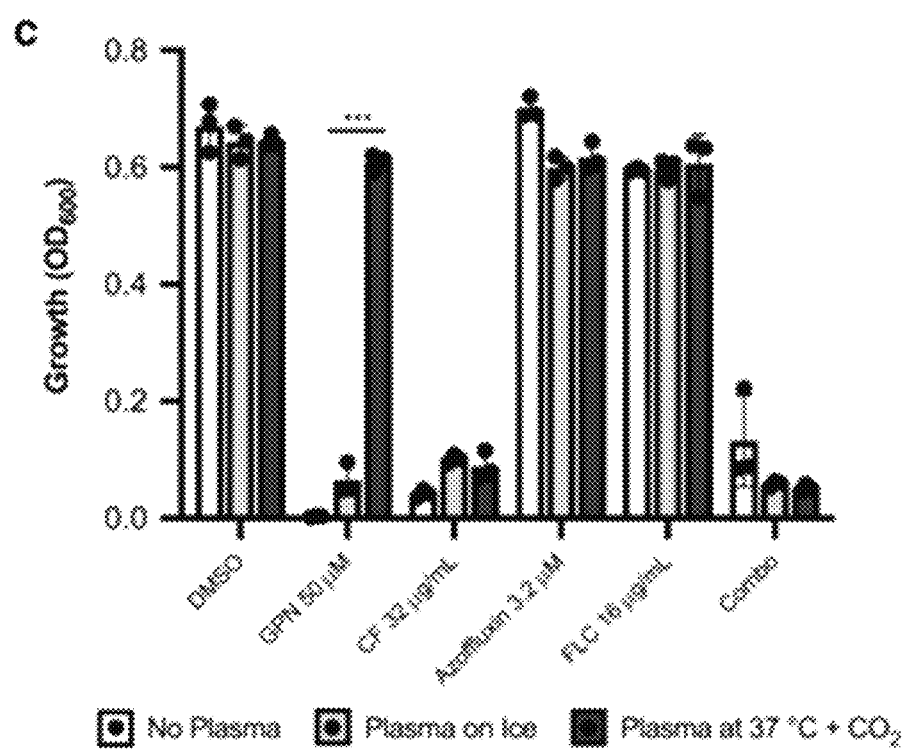

FIG. 10E depicts azoffluxin is stable and retains activity in plasma.

Figure 10F:
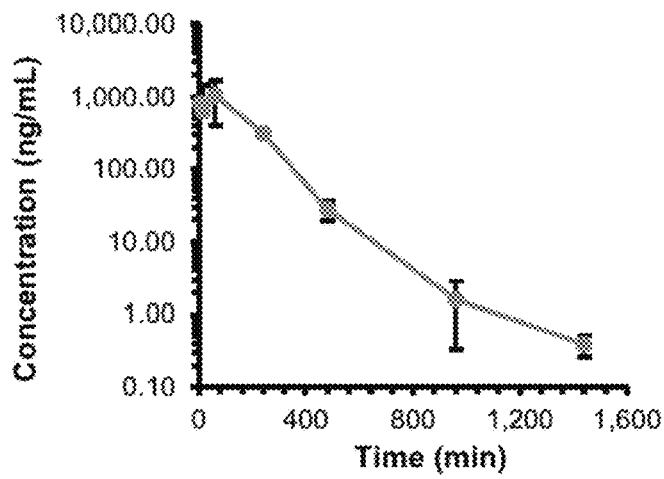

FIG. 10F shows single dose plasma pharmacokinetic profile of azoffluxin in mice.

Figure 10G:
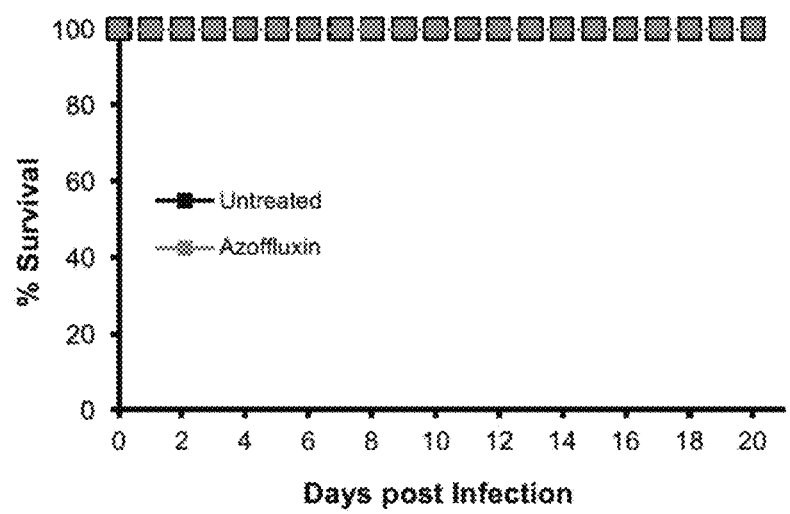

FIG. 10G is a plot showing that azoffluxin is well tolerated.

Figures 11A, 11B:
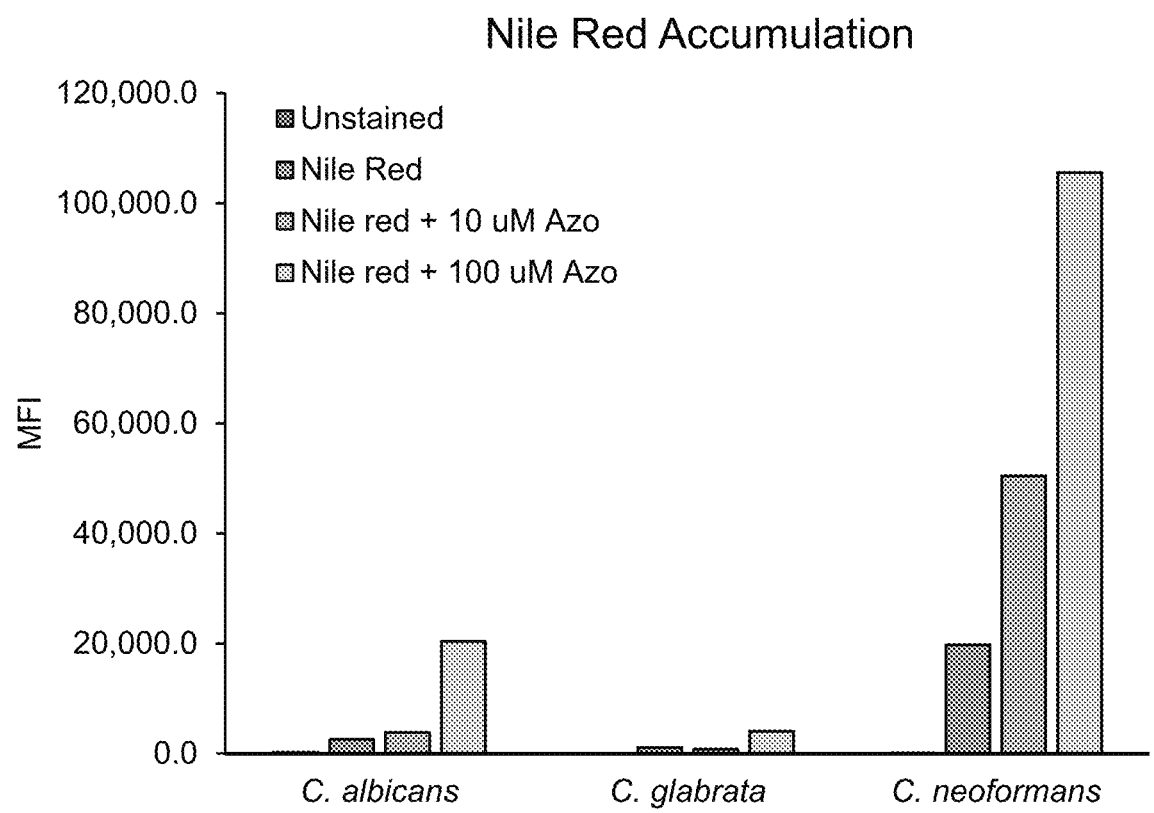

FIG. 11A is a bar graph depicting effects of azoffluxin on Nile red accumulation in diverse fungal species.

FIG. 11B shows a list of fold-change Nile red accumulation for *C. albicans, C. glabrata*, and *C. neoformans* with the addition of azoffluxin.

FIGS. 12A-12D depicts flow cytometric measurements of dye accumulation for P-gp (MDR1) and MRP1-overexpressing HEK293 cell lines monitoring whether azoffluxin treatment leads to a greater accumulation of efflux pump fluorescent substrates (MFI).

FIGS. 12E and 12F depict in tabular form results when the efflux activity of MDR1 (ABCB1) or MRP1 (ABCC1) was assessed using the fluorescent dyes rhodamine 6G (0.5 μg/mL) and Calcein AM (2.5 μg/mL). Listed data is shown by FIG. 12E (R6G) and FIG. 12F (Cal).

Figure 13A:
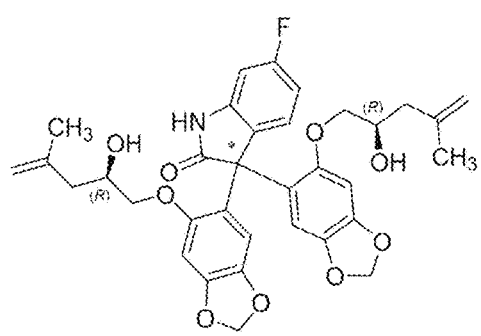
Figure 13A:
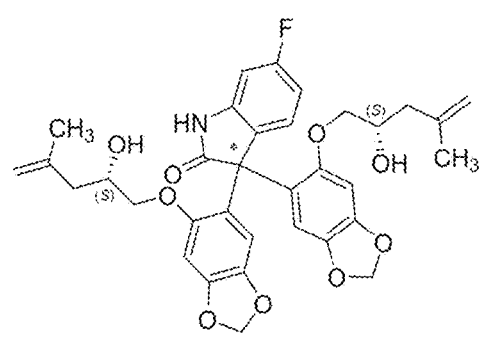
Figure 13A:
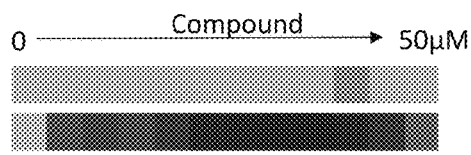

FIG. 13A shows the structure of azoffluxin (CMLD012336), and its antifungal activity alone (top green heat map) or in combination with FLC (bottom heat map).

Figure 13B:
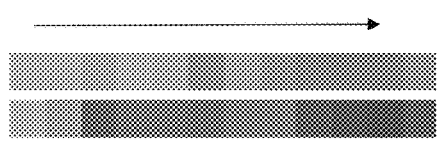

FIG. 13B shows structure of an azoffluxin enantiomer (CMLD012337) and its antifungal activity alone (top green heat-map) or in combination with FLC (bottom heat-map).

Figure 14:
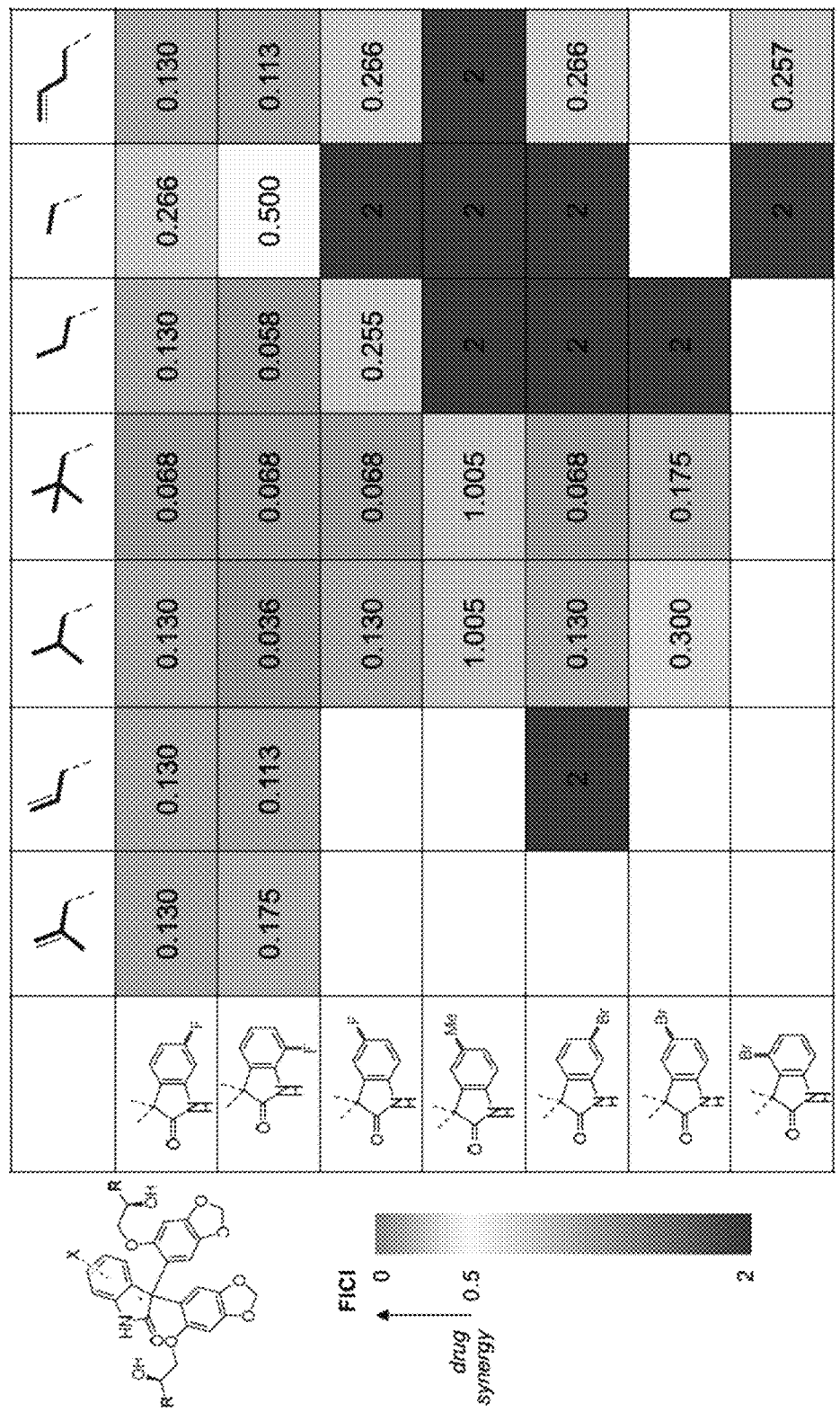

FIG. 14 shows FICI values for diarylated oxindoles.

Figure 15:
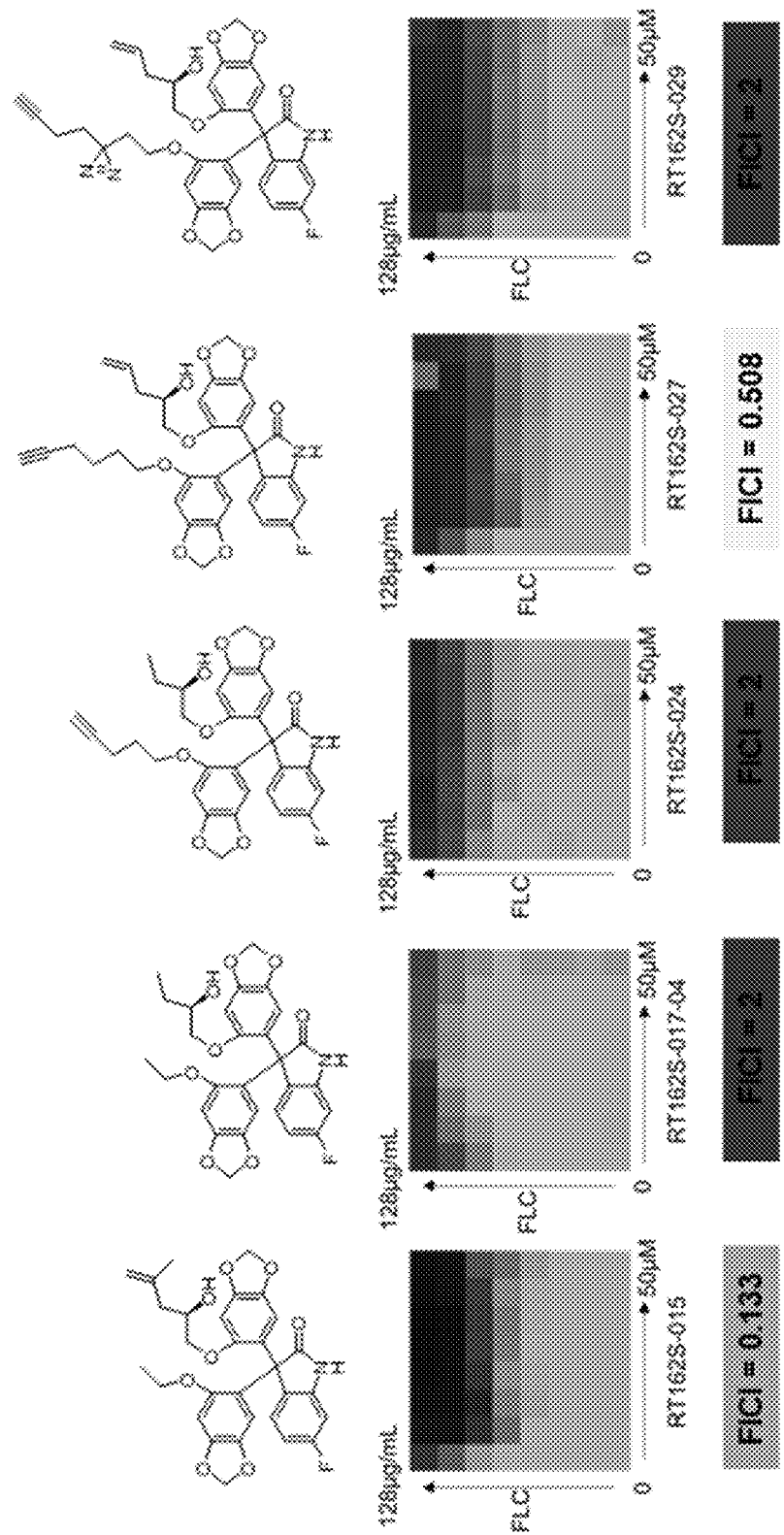

FIG. 15 shows the structures (top) and effects (bottom checkerboard assays) of mixed analogues.

Figure 16:
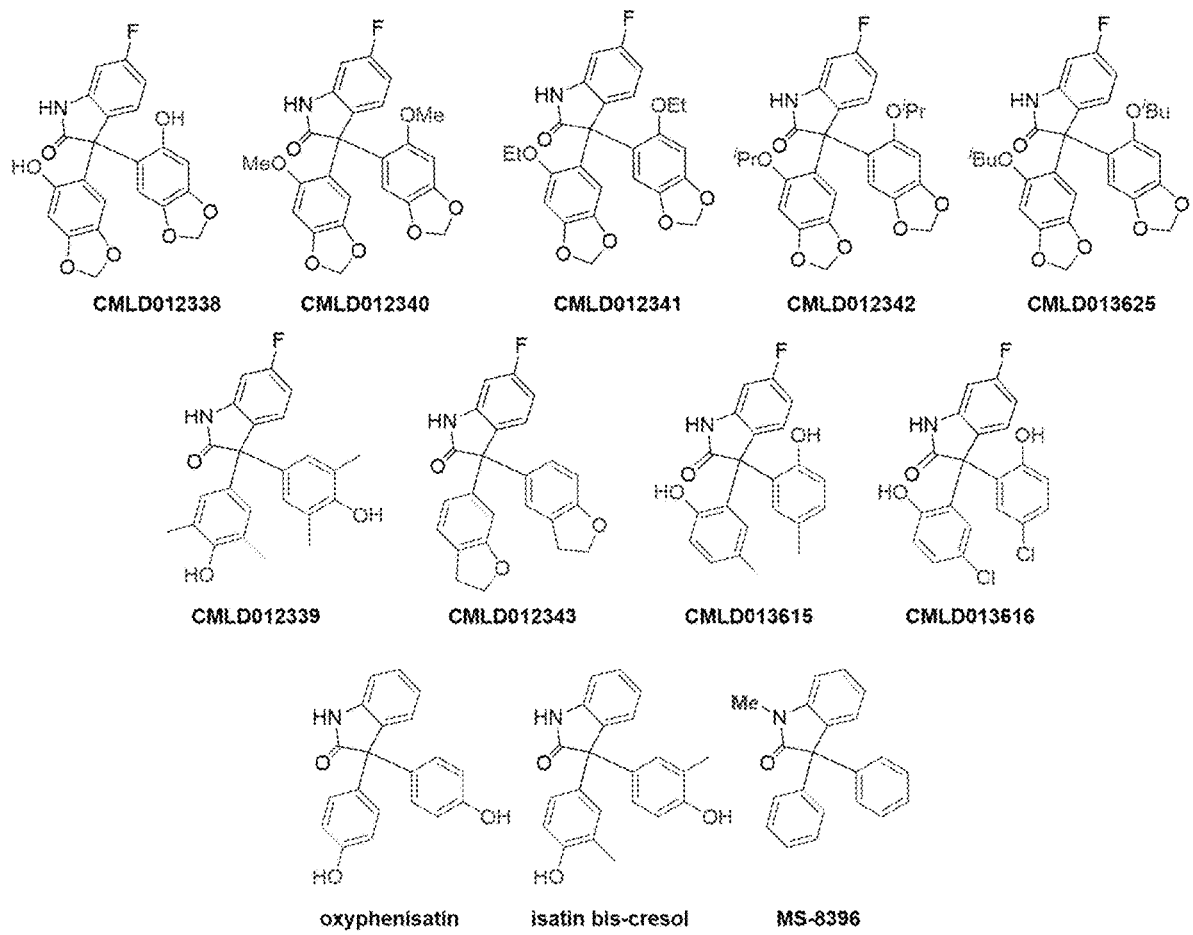

FIG. 16 shows some exemplary compounds.

Figure 17A:
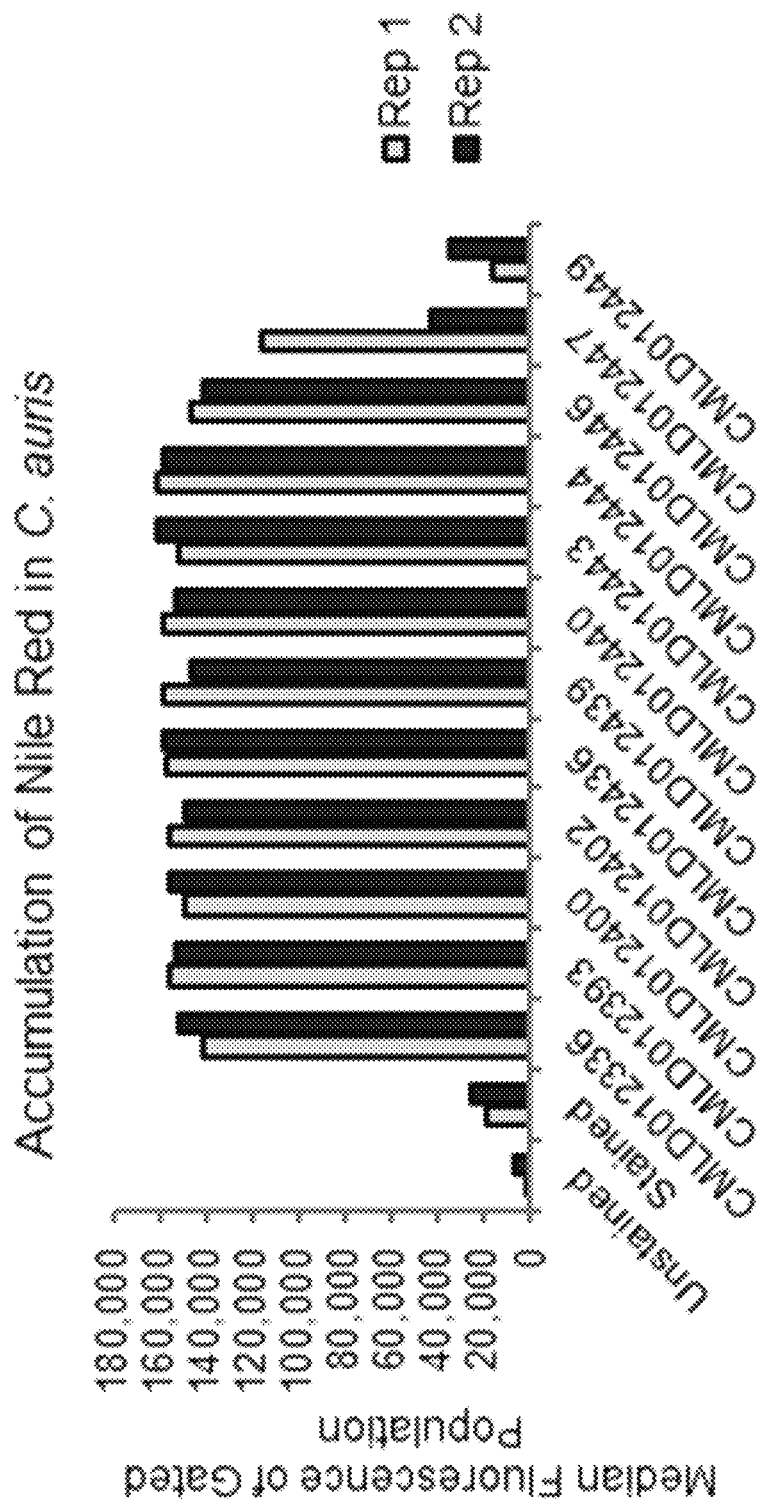
Figure 17B:

FIGS. 17A and 17B plot efflux results for Nile Red assays for compounds in Table 1 FIG. 17A Biological Replicate 1. 17B is a Biological Replicate 2.

Figure 18A:
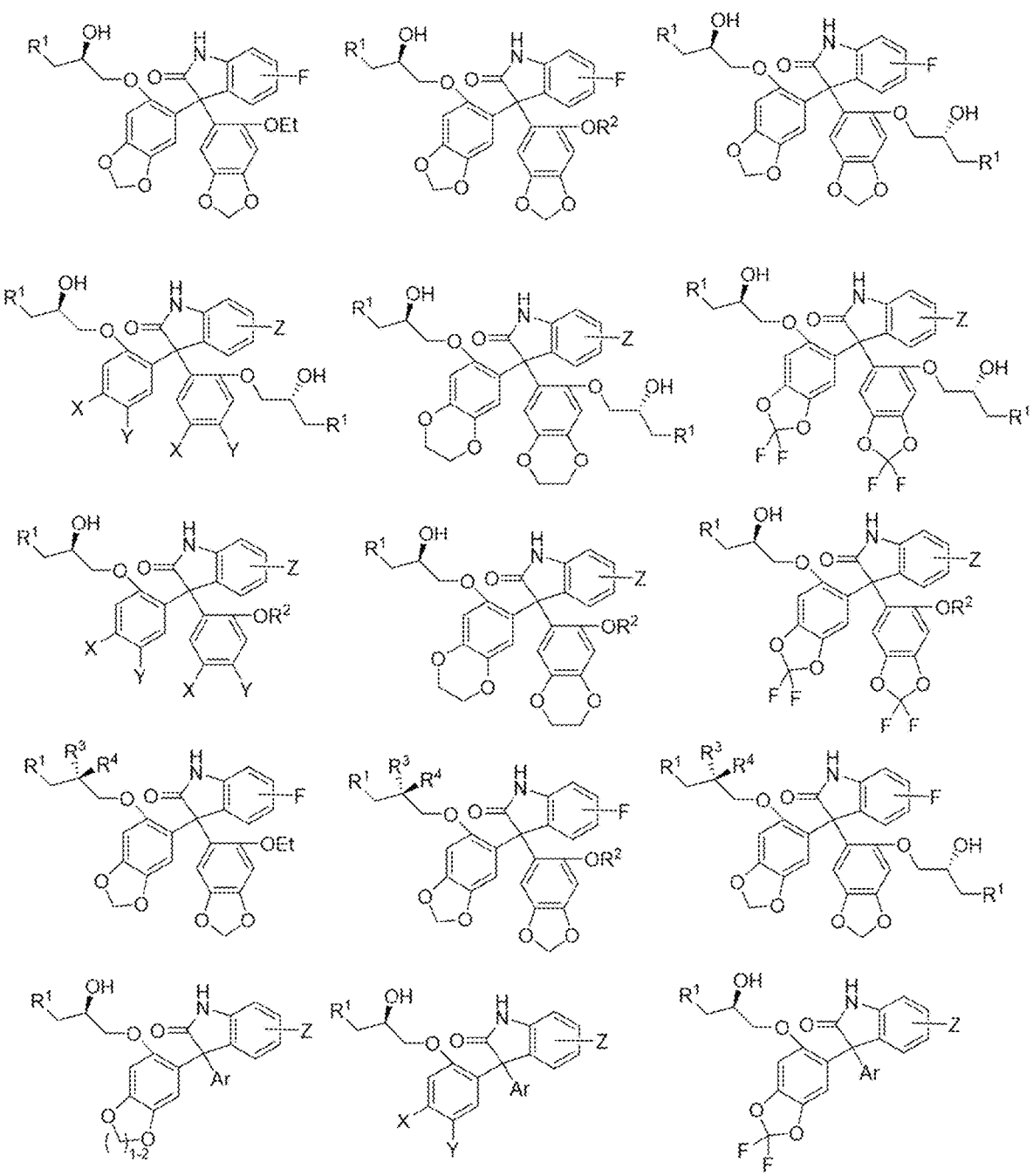
Figure 18B:
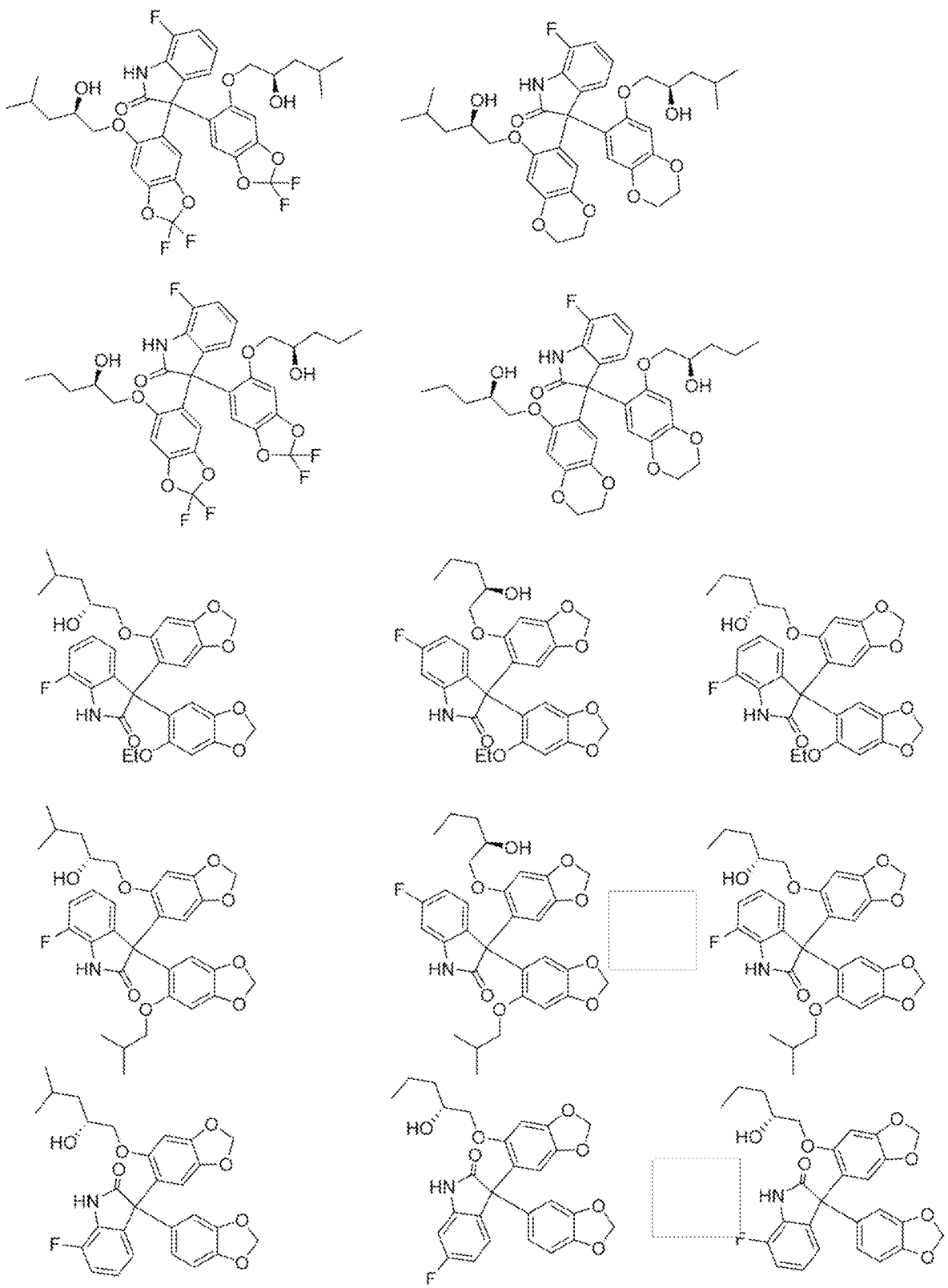
Figure 18C:
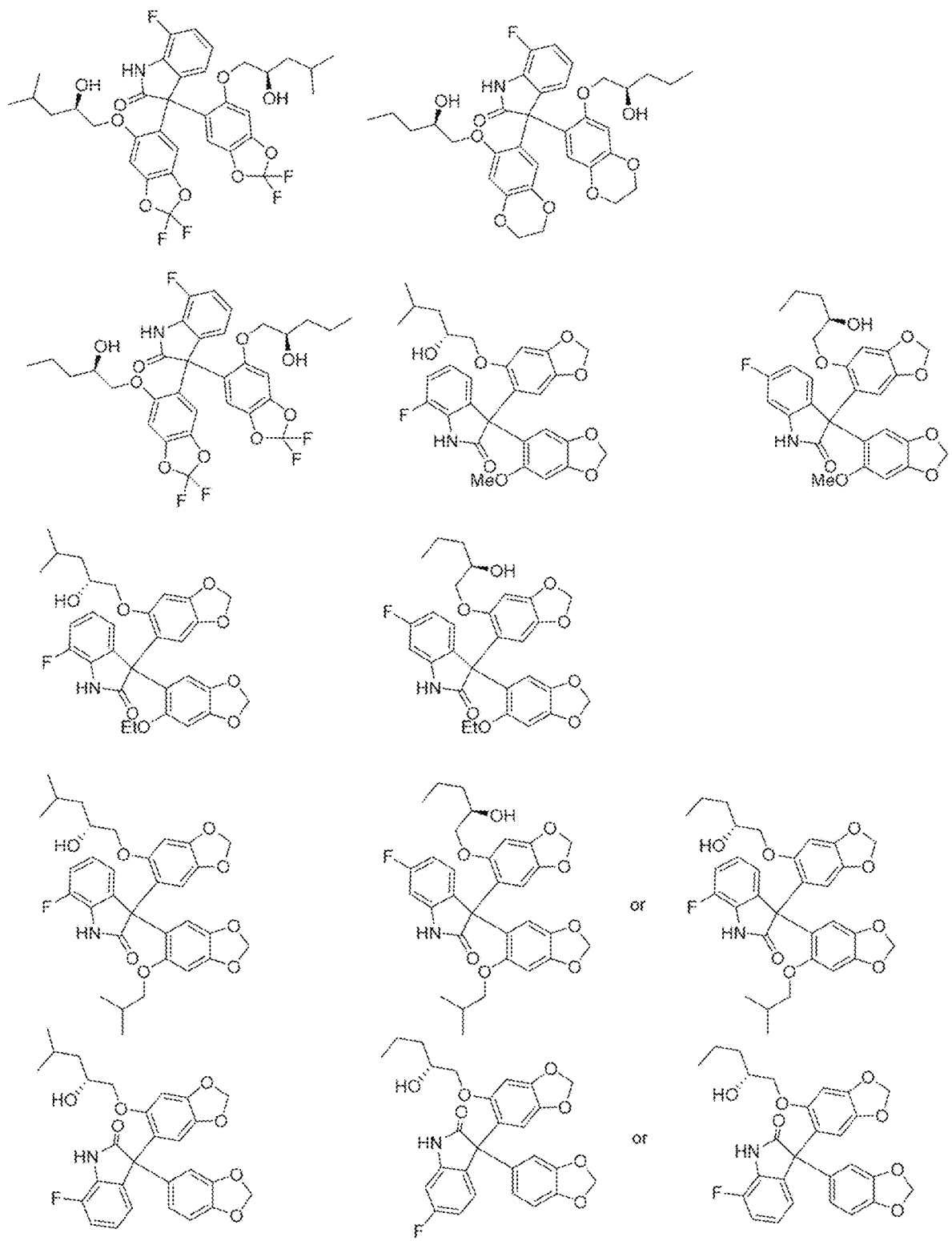

FIGS. 18A-18C show exemplary compounds of Formula (I).

Figure 19A:
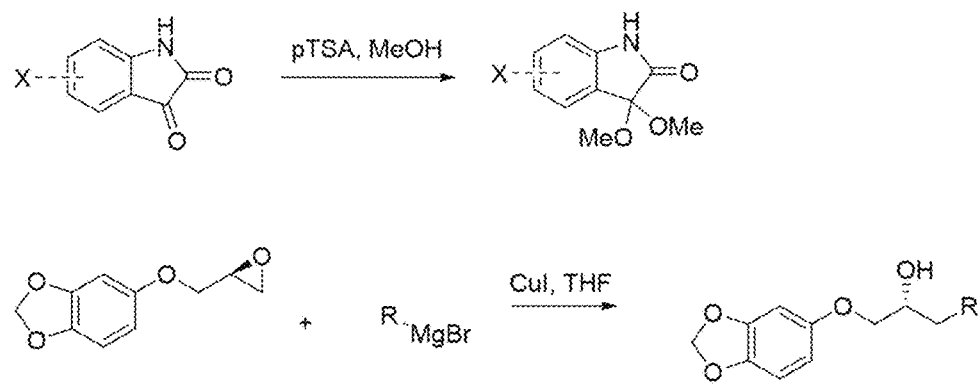

FIG. 19A illustrates general schemes for the preparation of starting input reagents.

Figure 19B:
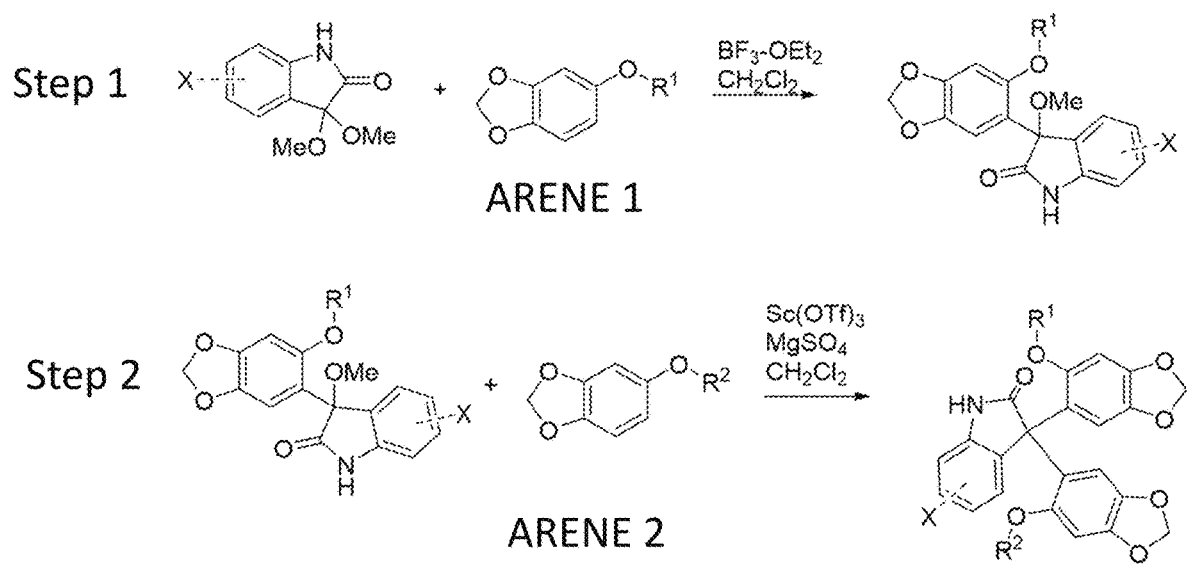

FIG. 19B depicts a scheme and general procedure for two-step production of non-symmetrical 3,3'-diarylated oxindoles.

Figure 20:
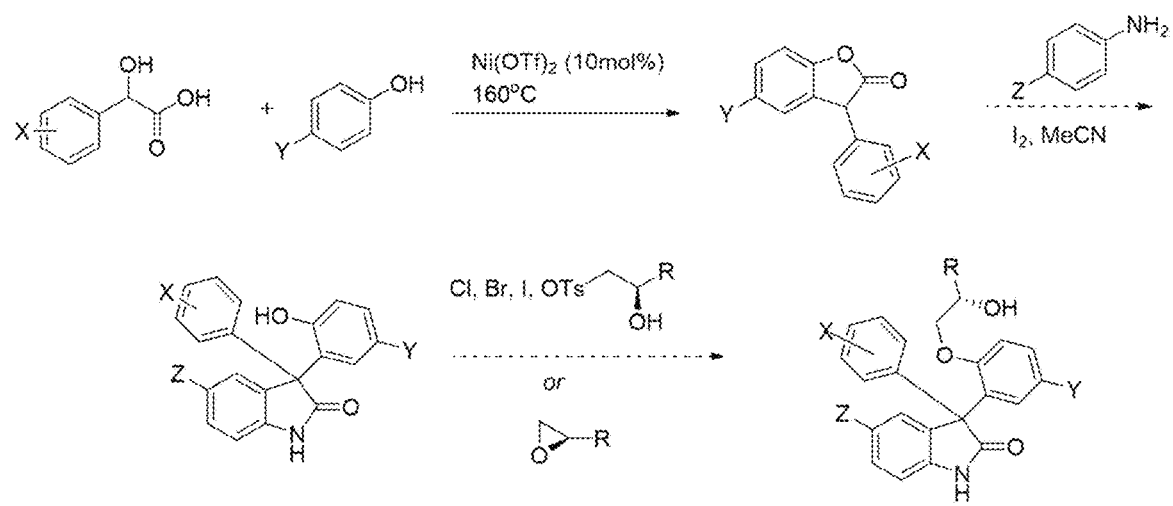

FIG. 20 depicts an alternate route to non-symmetrical 3,3'-diarylated oxindoles.

Figure 21:
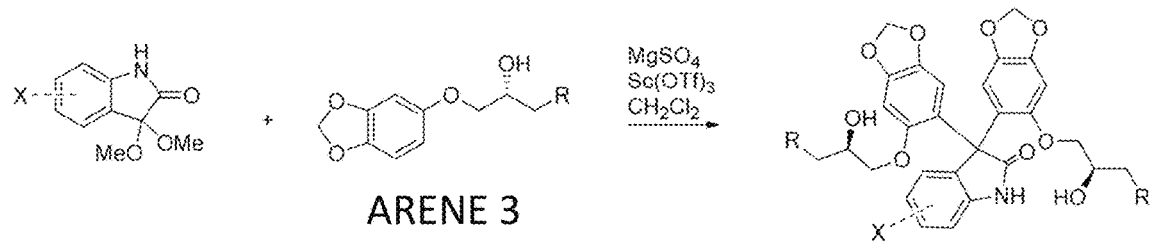

FIG. 21 depicts a scheme and general procedure for the synthesis of symmetrical 3,3'-diarylated oxindoles.

Figure 22:
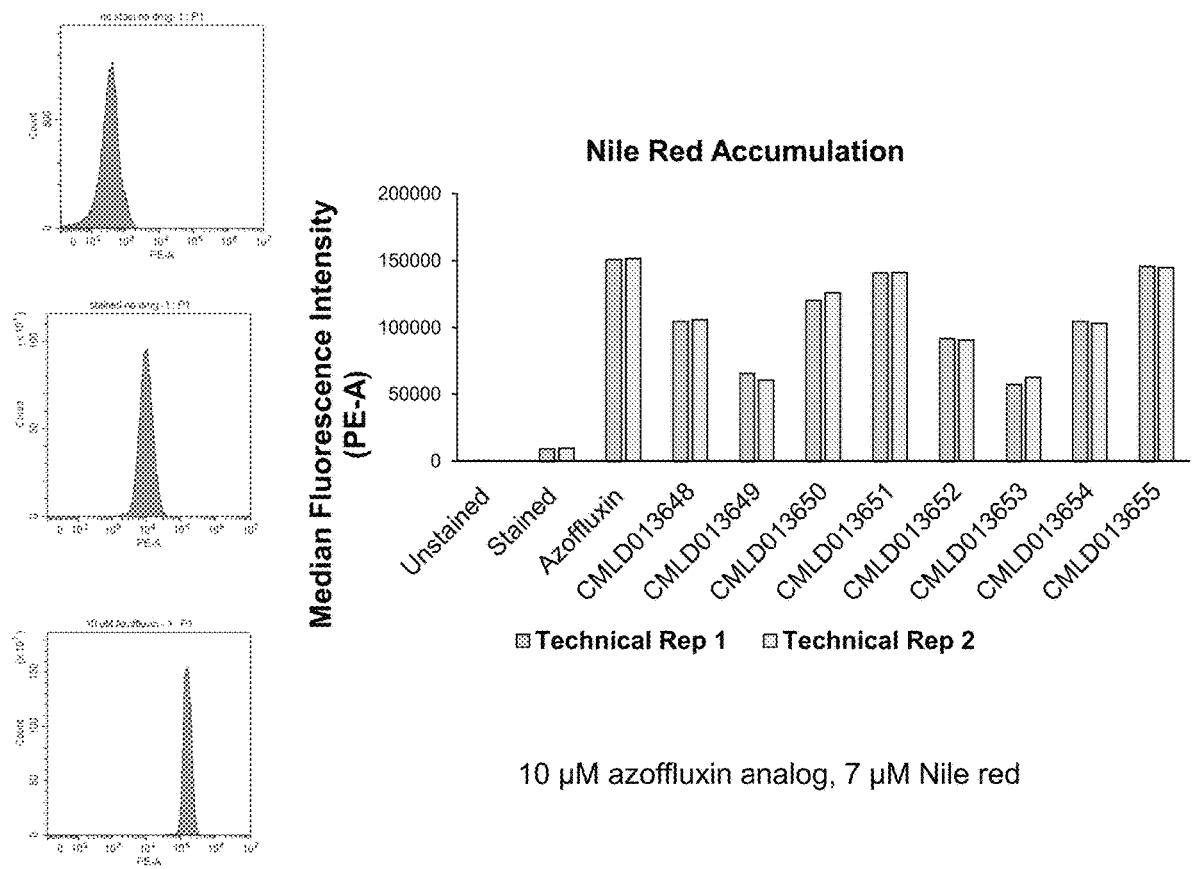

FIG. 22 depicts validation of efflux inhibition using Nile red assays. Flow cytometry was used to assess relative Nile red accumulation in *C. auris* (CauLC5083) upon treatment with azoffluxin analogs.

Figure 23A:
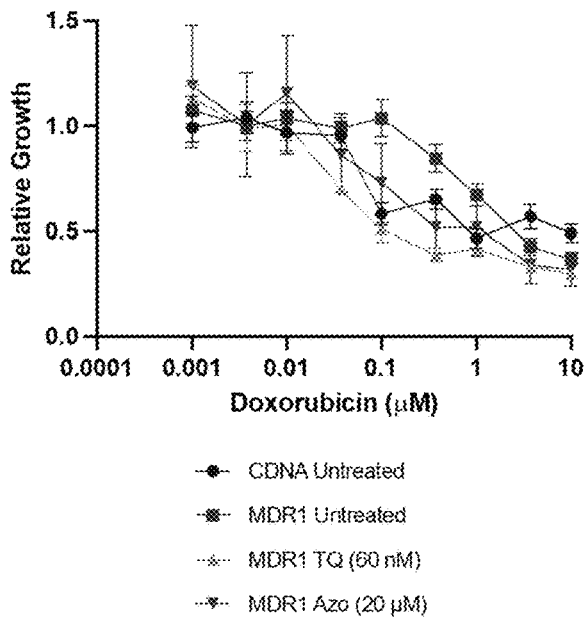
Figure 23B:
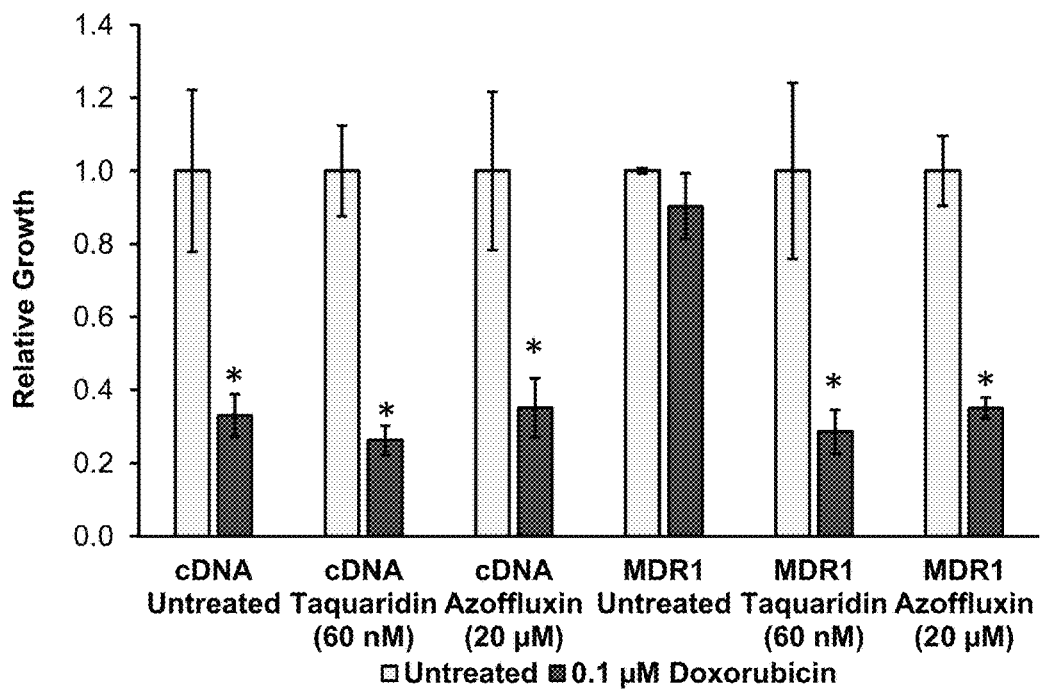

FIGS. 23A and 23B show azoffluxin enhances cytotoxicity of doxorubicin against HEK293 cancer cells that overexpress the efflux pump MDR1. Dose response (FIG. 23A) and single concentration (FIG. 23B).

DETAILED DESCRIPTION OF THE INVENTION

The inventors have discovered inter alia, compounds of Formula (I). These compounds as disclosed herein can inhibit efflux pumps. Therefore, in one aspect, the disclosure provides compounds of Formula (I):

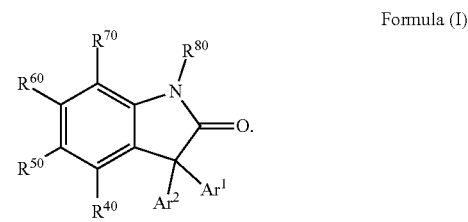

Formula (I)

In some embodiments of any one of the aspects described herein, each of $R^{40}$, $R^{50}$, $R^{60}$, $R^{70}$, and $R^{80}$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted. For example, each of $R^{40}$, $R^{50}$, $R^{60}$, $R^{70}$, and $R^{80}$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, $C_2$-$C_8$ alkynyl, sulfinyl, sulfonyl, thiocarbonyl, carbamoyl, cycloalkyl, heterocyclyl, aryl or heteroaryl, and each of which can be optionally substituted.

In some embodiments of any one of the aspects, each of $R^{40}$, $R^{50}$, $R^{60}$, $R^{70}$, and $R^{80}$ independently are hydrogen, halogen, hydroxyl, amino, alkylamino, dialkylamino, thiol, alkylthio, carboxyl, nitro, acyl, acyloxy, alkyl, haloalkyl, heteroalkyl, or alkoxy, and each of which can be optionally substituted. For example, each of $R^{40}$, $R^{50}$, $R^{60}$, $R^{70}$, and $R^{80}$ independently are hydrogen, halogen, hydroxyl, amino, alkylamino, dialkylamino, thiol, alkylthio, carboxyl, nitro, acyl, acyloxy, $C_1$-$C_6$ alkyl, $C_1$-$C_6$ haloalkyl, $C_1$-$C_6$ heteroalkyl or $C_1$-$C_6$ alkoxy, and each of which can be optionally substituted.

In some embodiments of any one of the aspects, each of $R^{40}$, $R^{50}$, $R^{60}$, $R^{70}$, and $R^{80}$ independently are hydrogen, halogen, optionally substituted $C_1$-$C_6$ alkyl, optionally substituted $C_1$-$C_6$ alkoxy. In some preferred embodiments, each of $R^{40}$, $R^{40}$, $R^{60}$, $R^{70}$, and $R^{80}$ independently are hydrogen, halogen or optionally substituted $C_1$-$C_6$ alkyl. For example, each of $R^{40}$, $R^{40}$, $R^{60}$, $R^{70}$, and $R^{80}$ independently are hydrogen, F, Cl, Br, methyl, trifluoromethyl, ethyl, propyl, i-propyl, n-butyl, t-butyl, n-pentyl or hexyl.

In some embodiments of any one of the aspects, at least one of $R^{40}$, $R^{50}$, $R^{60}$, $R^{70}$, and $R^{80}$ is not H. For example, one of $R^{40}$, $R^{50}$, $R^{60}$, $R^{70}$, and $R^{80}$ is not hydrogen and the remaining of $R^{40}$, $R^{50}$, $R^{60}$ and $R^{70}$ are H.

In some embodiments of any one of the aspects, at least one of $R^{40}$, $R^{50}$, $R^{61}$, $R^{70}$, and $R^{80}$ is halogen, hydroxyl, amino, alkylamino, dialkylamino, thiol, alkylthio, carboxyl, nitro, acyl, acyloxy, alkyl, haloalkyl, heteroalkyl, or alkoxy, each of which can be optionally substituted; and the remaining of $R^{40}$, $R^{50}$, $R^{60}$ and $R^{70}$ are H. For example, one of $R^{40}$, $R^{50}$, $R^{60}$, $R^{70}$, and $R^{80}$ is halogen or $C_1$-$C_6$alkyl and the remaining of $R^{40}$, $R^{40}$, $R^{60}$ and $R^{70}$ are H.

In some embodiments, one of $R^{40}$, $R^{50}$, $R^{60}$, $R^{70}$, and $R^{80}$ is F, Cl, Br, methyl, trifluoromethyl, ethyl, propyl, i-propyl, n-butyl, t-butyl, n-pentyl or hexyl; and the remaining of $R^{40}$, $R^{50}$, $R^{60}$ and $R^{70}$ are H. For example, one of $R^{40}$, $R^{50}$, $R^{60}$, $R^{70}$, and $R^{80}$ is F, Cl, Br or methyl, and the remaining of $R^{40}$, $R^{40}$, $R^{60}$ and $R^{70}$ are H In some embodiments, $R^{40}$ is not H and each of $R^{40}$, $R^{60}$ and $R^{70}$ are H. For example, $R^{40}$ is halogen, hydroxyl, amino, alkylamino, dialkylamino, thiol, alkylthio, carboxyl, nitro, acyl, acyloxy, alkyl, haloalkyl, heteroalkyl, or alkoxy, each of which can be optionally substituted; and each of $R^{40}$, $R^{60}$ and $R^{70}$ are H. For example, $R^{40}$ is halogen or $C_1$-$C_6$ alkyl, and each of $R^{40}$, $R^{60}$ and $R^{70}$ are H. In some embodiments, $R^{40}$ is F, Cl, Br, methyl, trifluoromethyl, ethyl, propyl, i-propyl, n-butyl, t-butyl, n-pentyl or hexyl, and each of $R^{40}$, $R^{60}$ and $R^{70}$ are H. For example, $R^{40}$ is F, Cl, Br or methyl, and each of $R^{40}$, $R^{60}$ and $R^{70}$ are H.

In some embodiments, $R^{50}$ is not H and each of $R^{40}$, $R^{60}$ and $R^{70}$ are H. For example, $R^{50}$ is halogen, hydroxyl, amino, alkylamino, dialkylamino, thiol, alkylthio, carboxyl, nitro, acyl, acyloxy, alkyl, haloalkyl, heteroalkyl, or alkoxy, each of which can be optionally substituted; and each of $R^{40}$, $R^{60}$ and $R^{70}$ are H. For example, $R^{50}$ is halogen or $C_1$-$C_6$ alkyl, and each of $R^{40}$, $R^{60}$ and $R^{70}$ are H. In some embodiments, $R^{50}$ is F, Cl, Br, methyl, trifluoromethyl, ethyl, propyl, i-propyl, n-butyl, t-butyl, n-pentyl or hexyl, and each of $R^{40}$, $R^{60}$ and $R^{70}$ are H. For example, $R^{50}$ is F, Cl, Br or methyl, and each of $R^{40}$, $R^{60}$ and $R^{70}$ are H.

In some embodiments, $R^{60}$ is not H and each of $R^{40}$, $R^{50}$ and $R^{70}$ are H. For example, $R^{60}$ is halogen, hydroxyl, amino, alkylamino, dialkylamino, thiol, alkylthio, carboxyl, nitro, acyl, acyloxy, alkyl, haloalkyl, heteroalkyl, or alkoxy, each of which can be optionally substituted; and each of $R^{40}$, $R^{50}$ and $R^{70}$ are H. For example, $R^{60}$ is halogen or $C_1$-$C_6$ alkyl, and each of $R^{40}$, $R^{50}$ and $R^{70}$ are H. In some embodiments, $R^{60}$ is F, Cl, Br, methyl, trifluoromethyl, ethyl, propyl, i-propyl, n-butyl, t-butyl, n-pentyl or hexyl, and each of $R^{40}$, $R^{50}$ and $R^{70}$ are H. For example, $R^{60}$ is F, Cl, Br or methyl, and each of $R^{40}$, $R^{50}$ and $R^{70}$ are H.

In some embodiments, $R^{70}$ is not H and each of $R^{40}$, $R^{50}$ and $R^{60}$ are H. For example, $R^{70}$ is halogen, hydroxyl, amino, alkylamino, dialkylamino, thiol, alkylthio, carboxyl, nitro, acyl, acyloxy, alkyl, haloalkyl, heteroalkyl, or alkoxy, each of which can be optionally substituted; and each of $R^{40}$, $R^{50}$ and $R^{60}$ are H. For example, $R^{70}$ is halogen or $C_1$-$C_6$ alkyl, and each of $R^{40}$, $R^{50}$ and $R^{60}$ are H. In some embodiments, $R^{70}$ is F, Cl, Br, methyl, trifluoromethyl, ethyl, propyl, i-propyl, n-butyl, t-butyl, n-pentyl or hexyl, and each of $R^{40}$, $R^{50}$ and $R^{60}$ are H. For example, $R^{70}$ is F, Cl, Br or methyl, and each of $R^{40}$, $R^{50}$ and $R^{60}$ are H.

In some embodiments, each of $R^{40}$, $R^{50}$, $R^{60}$ and $R^{70}$ are H.

In compounds of Formula (I), $R^{80}$ can be hydrogen, alkyl, alkenyl, alkynyl, cycloalkyl, heterocyclyl, aryl or heteroaryl, each of which can be optionally substituted. For example, $R^{80}$ can be hydrogen, optionally substituted $C_1$-$C_6$ alkyl, optionally substituted $C_2$-$C_8$ alkenyl, or optionally substituted $C_2$-$C_8$ alkynyl. In some embodiments, $R^{80}$ is H, methyl, trifluoromethyl, ethyl, propyl, i-propyl, n-butyl, t-butyl, n-pentyl or hexyl. For example, $R^{80}$ is H, methyl, ethyl, propyl or i-propyl. In some preferred embodiments, $R^{80}$ is H.

In compounds of Formula (I), $Ar^1$ and $Ar^2$ are each independently an optionally substituted aryl or optionally substituted heteroaryl. It is noted that $Ar^1$ and $Ar^2$ can be the same or different. Thus, in some embodiments of any one of the aspects described herein, $Ar^1$ and $Ar^2$ are the same. In some other embodiments of any one of the aspects described herein, $Ar^1$ and $Ar^2$ are different.

Exemplary aryls and heteroaryls for the $Ar^1$ and $Ar^2$ include, but are not limited to phenyl, pyridinyl, pyrimidinyl, furanyl, thienyl, imidazolyl, thiazolyl, pyrazolyl, pyridazinyl, pyrazinyl, triazinyl, tetrazolyl, indolyl, benzyl, naphthyl, anthracenyl, azulenyl, fluorenyl, indanyl, indenyl, naphthyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, each or which can be optionally substituted. For example, 1, 2, 3, or 4 hydrogen atoms of each ring can be substituted by independently selected substituents.

In some embodiments of any one of the aspects, at least one, e.g., only one or both, of $Ar^1$ and $Ar^2$ in compounds of Formula (I) can be of the structure (Ar'):

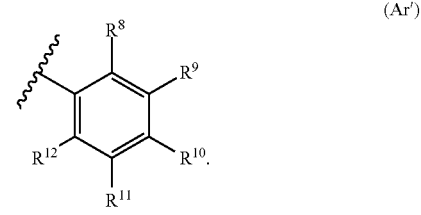

(Ar')

In structure of Ar', each of $R^8$, $R^9$, $R^{10}$, $R^{11}$, and $R^{12}$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted. For example, each of $R^8$, $R^9$, $R^{10}$, $R^{11}$, and $R^{12}$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, $C_2$-$C_8$ alkynyl, sulfinyl, sulfonyl, thiocarbonyl, carbamoyl, cycloalkyl, heterocyclyl, aryl or heteroaryl, and each of which can be optionally substituted. In some embodiments of any one of the aspects, each of $R^8$, $R^9$, $R^{10}$, $R^{11}$, and $R^{12}$ independently are hydrogen, halogen, $C_1$-$C_6$alkyl, or $C_1$-$C_6$alkoxy.

In some embodiments of any one of the aspects, $R^8$ is hydrogen, halogen, hydroxyl, amino, alkylamino, dialkylamino, acylamino, thiol, alkylthio, cyano, carbonyl, carboxyl, alkoxycarbonyl, nitro, acyl, acyloxy, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, $C_2$-$C_8$ alkynyl, sulfinyl, sulfonyl, thiocarbonyl, carbamoyl, cycloalkyl, heterocyclyl, aryl or heteroaryl, and each of which can be optionally substituted. For example, $R^8$ is hydrogen, halogen, hydroxyl, amino, alkylamino, dialkylamino, thiol, alkylthio, carboxyl, alkoxycarbonyl, acyl, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl or $C_2$-$C_8$ alkynyl, each of which can be optionally substituted. In some embodiments, $R^8$ is an optionally substituted alkoxy. For example, $R^8$ is an optionally substituted $C_1$-$C_{10}$ alkoxy. Exemplary alkoxys for the $R^8$ include, but are not limited to, methoxy, ethoxy, —O-n-propyl, —O-isopropyl, —O-sec-butyl, —O-tert-butyl, —O-n-butyl, O-isobutyl, —O-neopentyl, —O-isopropenyl, —O-n-propenyl, and —O-n-butenyl. In some embodiments, $R^8$ is ethoxy, —O-n-propyl, —O-isopropyl, —O-sec-butyl, —O-tert-butyl, —O-n-butyl, O-isobutyl, —O-neopentyl, —O-isopropenyl, —O-n-propenyl, or —O-n-butenyl.

In some embodiments of any one of the aspects, $R^8$ is

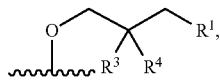

wherein each of $R^1$, $R^3$ and $R^4$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted.

In some embodiments, $R^1$ is hydrogen, halogen, hydroxyl, amino, alkylamino, dialkylamino, acylamino, thiol, alkylthio, cyano, carbonyl, carboxyl, alkoxycarbonyl, nitro, acyl, acyloxy, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, $C_2$-$C_8$ alkynyl, sulfinyl, sulfonyl, thiocarbonyl, carbamoyl, cycloalkyl, heterocyclyl, aryl or heteroaryl, and each of which can be optionally substituted. For example, $R^1$ is hydrogen, optionally substituted $C_1$-$C_6$ alkyl, optionally substituted $C_2$-$C_8$ alkenyl or optionally substituted $C_2$-$C_8$ alkynyl. In some embodiments, $R^1$ is optionally substituted $C_1$-$C_6$ alkyl, optionally substituted $C_2$-$C_8$ alkenyl or optionally substituted $C_2$-$C_8$ alkynyl. For example, $R^1$ is methyl, ethyl, n-propyl, isopropyl, sec-butyl, tert-butyl, n-butyl, isobutyl, neopentyl (—$CH_2C(CH_3)_3$), vinyl (—CH=$CH_2$), isopropenyl (—C(=$CH_2$)$CH_3$), 1-propenyl, 2-propenyl (—$CH_2C$=$CH_2$), propargyl (—$CH_2C$≡CH), or n-butenyl.

In some embodiments of any one of the aspects, $R^3$ is hydrogen, halogen, hydroxyl, amino, alkylamino, dialkylamino, acylamino, thiol, alkylthio, cyano, carbonyl, carboxyl, alkoxycarbonyl, nitro, acyl, acyloxy, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, $C_2$-$C_8$ alkynyl, sulfinyl, sulfonyl, thiocarbonyl, carbamoyl, cycloalkyl, heterocyclyl, aryl or heteroaryl, and each of which can be optionally substituted. For example, $R^3$ is hydrogen, halogen, hydroxyl, amino, or $C_1$-$C_6$ alkoxy. In some embodiments, $R^3$ is hydrogen or halogen. For example, $R^3$ is H, F, Cl or Br. For example, $R^3$ is H or F.

In some embodiments of any one of the aspects, $R^4$ is hydrogen, halogen, hydroxyl, amino, alkylamino, dialkylamino, acylamino, thiol, alkylthio, cyano, carbonyl, carboxyl, alkoxycarbonyl, nitro, acyl, acyloxy, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, $C_2$-$C_8$ alkynyl, sulfinyl, sulfonyl, thiocarbonyl, carbamoyl, cycloalkyl, heterocyclyl, aryl or heteroaryl, and each of which can be optionally substituted. For example, $R^4$ is hydrogen, halogen, hydroxyl, amino, or $C_1$-$C_6$ alkoxy. In some embodiments, $R^4$ is hydrogen, amino or $C_1$-$C_6$ alkoxy halogen. For example, $R^4$ is H, F, Cl, Br, amino, methoxy, ethoxy, —O-n-propyl, —O-isopropyl, —O-sec-butyl, —O-tert-butyl, —O-n-butyl, O-isobutyl, —O-neopentyl, —O-n-propenyl, or —O-n-butenyl. For example, $R^4$ is H, F, amino or methoxy.

In some embodiments of any one of the aspects, each of $R^3$ and $R^4$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, $C_2$-$C_8$ alkynyl, sulfinyl, sulfonyl, thiocarbonyl, carbamoyl, cycloalkyl, heterocyclyl, aryl or heteroaryl, and each of which can be optionally substituted. For example, $R^3$ is hydrogen, halogen, hydroxyl, amino, or $C_1$-$C_6$ alkoxy; and $R^4$ is hydrogen, halogen, hydroxyl, amino, or $C_1$-$C_6$ alkoxy. In some embodiments, $R^3$ is hydrogen or halogen, and $R^4$ is hydrogen, amino or $C_1$-$C_6$ alkoxy halogen. For example, $R^3$ is H, F, Cl or Br, and $R^4$ is H, F, Cl, Br, amino, methoxy, ethoxy, —O-n-propyl, —O-isopropyl, —O-sec-butyl, —O-tert-butyl, —O-n-butyl, O-isobutyl, —O-neopentyl, —O-n-propenyl, or —O-n-butenyl. For example, $R^4$ is H, F, amino or methoxy. In some embodiments, $R^3$ is H or F and $R^4$ is H, F, amino or methoxy.

In some embodiments of any one of the aspects, $R^3$ and $R^4$ are H.

It is noted that when the $R^3$ and $R^4$ groups are different, the carbon to which they are attached can be R or S configuration. Accordingly, in some embodiments of any one of the aspects, the carbon to which $R^3$ and $R^4$ are attached has the R configuration. In some other embodiments of any one of the aspects, the carbon to which $R^3$ and $R^4$ are attached has the S configuration.

In some embodiments of any one of the aspects, $R^8$ is

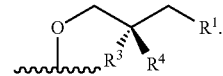

In some embodiments of any one of the aspects, one of $R^3$ and $R^4$ is H and the other is a hydroxyl. In other words, $R^8$ is

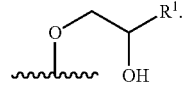

The carbon to which the hydroxyl group is attached can be R or S configuration. Accordingly, in some embodiments, $R^8$ is

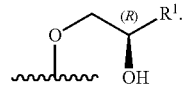

In some other embodiments, $R^8$ is

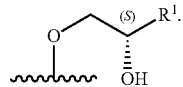

In some embodiments of any one of the aspects, each $R^8$ is independently

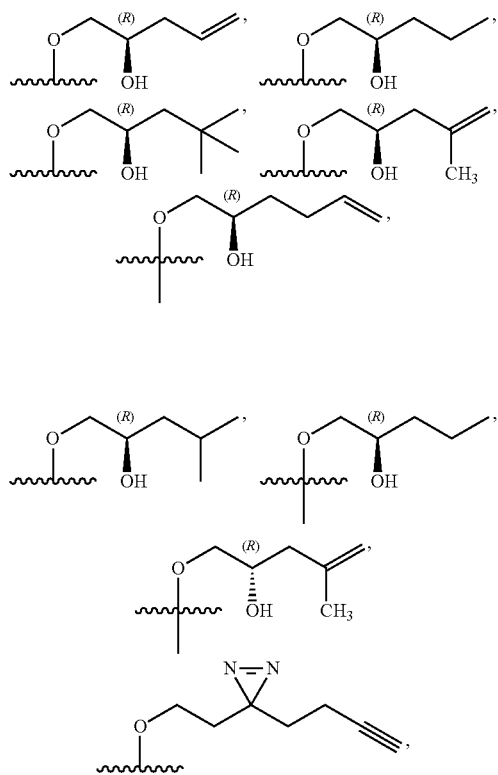

methoxy, ethoxy, —O-n-propyl, —O-isopropyl, —O-sec-butyl, —O-tert-butyl, —O-n-butyl, O-isobutyl, —O-neopentyl, —O-isopropenyl, —O-n-propenyl, and —O-n-butenyl. In some embodiments, $R^8$ is ethoxy, —O-n-propyl, —O-isopropyl, —O-sec-butyl, —O-tert-butyl, —O-n-butyl, O-isobutyl, —O-neopentyl, —O-isopropenyl, —O-n-propenyl, or —O-n-butenyl.

In compounds of Formula (I), each $R^9$ can be hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted. For example, each $R^9$ independently is hydrogen, halogen, hydroxyl, amino, alkylamino, dialkylamino, acylamino, thiol, alkylthio, cyano, carbonyl, carboxyl, alkoxycarbonyl, nitro, acyl, acyloxy, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, $C_2$-$C_8$ alkynyl, sulfinyl, sulfonyl, thiocarbonyl, carbamoyl, cycloalkyl, heterocyclyl, aryl or heteroaryl, and each of which can be optionally substituted. In some embodiments of any one of the aspects, each $R^9$ independently is hydrogen, halogen, $C_1$-$C_6$ alkyl, or $C_1$-$C_6$alkoxy. For example, each $R^9$ is H.

In compounds of Formula (I), each $R^{10}$ can be hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted. For example, each $R^{10}$ independently is hydrogen, halogen, hydroxyl, amino, alkylamino, dialkylamino, acylamino, thiol, alkylthio, cyano, carbonyl, carboxyl, alkoxycarbonyl, nitro, acyl, acyloxy, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, $C_2$-$C_8$ alkynyl, sulfinyl, sulfonyl, thiocarbonyl, carbamoyl, cycloalkyl, heterocyclyl, aryl or heteroaryl, and each of which can be optionally substituted. In some embodiments of any one of the aspects, each $R^{10}$ independently is hydrogen, halogen, $C_1$-$C_6$ alkyl, or $C_1$-$C_6$alkoxy. For example, each $R^{10}$ independently is H, F, Cl, Br, methyl, trifluoromethyl, ethyl, propyl, i-propyl, n-butyl, t-butyl, n-pentyl, hexyl, methoxy, ethoxy, —O-n-propyl, —O-isopropyl, —O-sec-butyl, —O-tert-butyl, —O-n-butyl, O-isobutyl, —O-neopentyl, —O-n-propenyl, or —O-n-butenyl. For example, each $R^{10}$ independently is H, F, Cl, Br, methyl or methoxy.

In compounds of Formula (I), each $R^{11}$ can be hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted. For example, each $R^{11}$ independently is hydrogen, halogen, hydroxyl, amino, alkylamino, dialkylamino, acylamino, thiol, alkylthio, cyano, carbonyl, carboxyl, alkoxycarbonyl, nitro, acyl, acyloxy, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, $C_2$-$C_8$ alkynyl, sulfinyl, sulfonyl, thiocarbonyl, carbamoyl, cycloalkyl, heterocyclyl, aryl or heteroaryl, and each of which can be optionally substituted. In some embodiments of any one of the aspects, each $R^{11}$ independently is hydrogen, halogen, $C_1$-$C_6$ alkyl, or $C_1$-$C_6$alkoxy. For example, each $R^{11}$ independently is H, F, Cl, Br, methyl, trifluoromethyl, ethyl, propyl, i-propyl, n-butyl, t-butyl, n-pentyl, hexyl, methoxy, ethoxy, —O-n-propyl, —O-isopropyl, —O-sec-butyl, —O-tert-butyl, —O-n-butyl, O-isobutyl, —O-neopentyl, —O-n-propenyl, or —O-n-butenyl. For example, each $R^{11}$ independently is H, F, Cl, Br, methyl or methoxy.

In some embodiments, each of $R^{10}$ and $R^{11}$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted. For example, each of $R^{10}$ and $R^{11}$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, $C_2$-$C_8$ alkynyl, sulfinyl, sulfonyl, thiocarbonyl, carbamoyl, cycloalkyl, heterocyclyl, aryl or heteroaryl, and each of which can be optionally substituted. In some embodiments of any one of the aspects, each of $R^{10}$ and $R^{11}$ independently are hydrogen, halogen, $C_1$-$C_6$ alkyl, or $C_1$-$C_6$alkoxy. For example, each of $R^{10}$ and $R^{11}$ independently are H, F, Cl, Br, methyl, trifluoromethyl, ethyl, propyl, i-propyl, n-butyl, t-butyl, n-pentyl, hexyl, methoxy, ethoxy, —O-n-propyl, —O-isopropyl, —O-sec-butyl, —O-tert-butyl, —O-n-butyl, O-isobutyl, —O- neopentyl, —O-n-propenyl, or —O-n-butenyl. For example, each of $R^{10}$ and $R^{11}$ independently are H, F, Cl, Br, methyl or methoxy.

In compounds of Formula (I), each $R^{12}$ can be hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted. For example, each $R^{12}$ independently is hydrogen, halogen, hydroxyl, amino, alkylamino, dialkylamino, acylamino, thiol, alkylthio, cyano, carbonyl, carboxyl, alkoxycarbonyl, nitro, acyl, acyloxy, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, $C_2$-$C_8$ alkynyl, sulfinyl, sulfonyl, thiocarbonyl, carbamoyl, cycloalkyl, heterocyclyl, aryl or heteroaryl, and each of which can be optionally substituted. In some embodiments of any one of the aspects, each $R^{12}$ independently is hydrogen, halogen, $C_1$-$C_6$ alkyl, or $C_1$-$C_6$ alkoxy. For example, each $R^{12}$ is H.

In some embodiments, $R^9$ and $R^{12}$ are H.

In some embodiments of any one of the aspects, at least a vicinal pair formed from selecting two of $R^8$, $R^9$, $R^{10}$, $R^{11}$, or $R^{12}$ and the carbons to which they are attached form an optionally substituted 5- or 6-member cycloalkyl or an optionally substituted 5- or 6-member heterocycle, and the remaining $R^8$, $R^9$, $R^{10}$, $R^{11}$, or $R^{12}$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted.

In some embodiments, $R^8$ and $R^9$ and the carbons to which they are attached form an optionally substituted 5- or 6-member cycloalkyl or an optionally substituted 5- or 6-member heterocycle.

In some embodiments, $R^9$ and $R^{10}$ and the carbons to which they are attached form an optionally substituted 5- or 6-member cycloalkyl or an optionally substituted 5- or 6-member heterocycle.

In some embodiments, $R^{11}$ and $R^{12}$ and the carbons to which they are attached form an optionally substituted 5- or 6-member cycloalkyl or an optionally substituted 5- or 6-member heterocycle.

In some embodiments, $R^{10}$ and $R^{11}$ and the carbons to which they are attached form an optionally substituted 5- or 6-member cycloalkyl or an optionally substituted 5- or 6-member heterocycle.

In some embodiments of any one of the aspects, at least one, e.g., only one or both, of $Ar^1$ and $Ar^2$ in compounds of Formula (I) can be of the structure (Ar"):

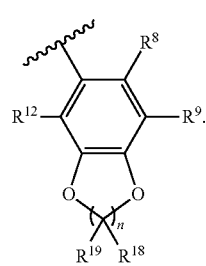

(Ar")

In structures of Ar", n can be 1 or 2. In some embodiments, n is 1. In some other embodiments, n is 2.

In structures of Ar", each of $R^{18}$ and $R^{19}$ independently are hydrogen or halogen. In some embodiments, each of $R^{18}$ and $R^{19}$ are H. In some other embodiments, each of $R^{18}$ and $R^{19}$ halogen. For example, each of $R^{18}$ and $R^{19}$ are F, Cl or Br. In some embodiments, each of $R^{18}$ and $R^{19}$ are F.

In structures of Ar", each of $R^8$, $R^9$ and $R^{12}$ are as defined for Ar' herein.

In some embodiments, at least one, e.g., only one or both, of $Ar^1$ and $Ar^2$ are selected independently from the group consisting of:

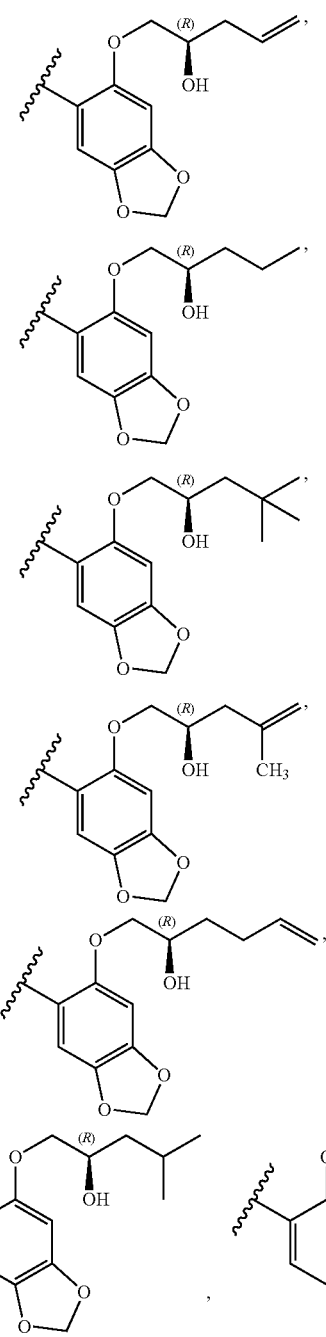

-continued

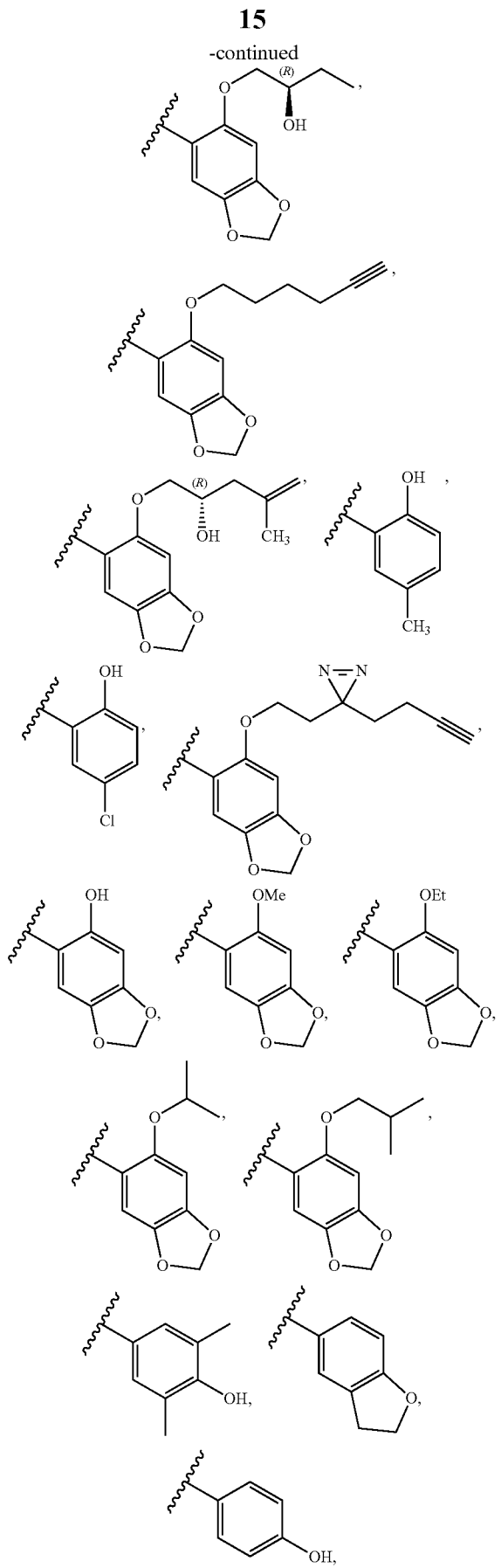

-continued

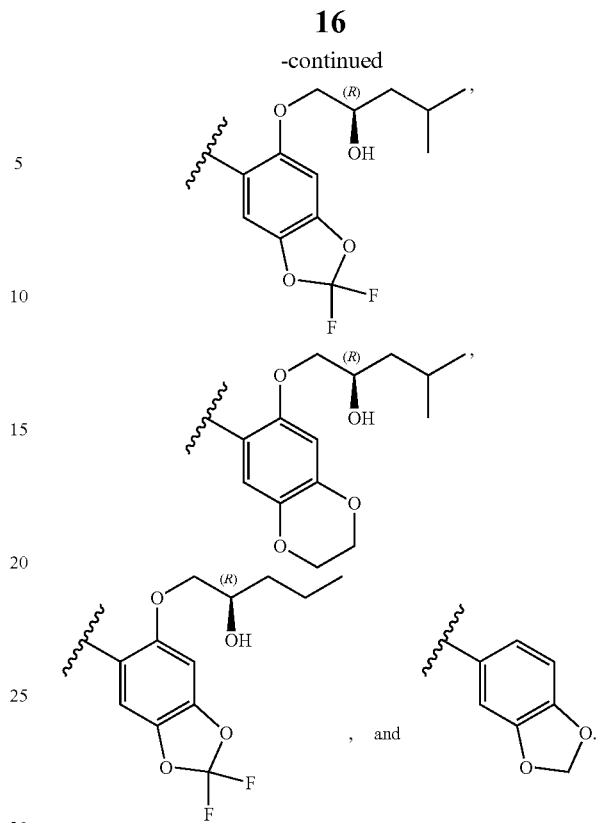

Exemplary compounds of Formula (I) are shown in FIG. 18A.

Additional exemplary compounds of Formula (I) are shown in Table 1 and FIGS. 18B and 18C.

In some embodiments of any one of the aspects, the compound is not oxyphenisatin, isatin bis-cresol or MS-8396.

In some embodiments of any one of the aspects described herein, the compound is not a compound shown in FIG. 16.

In various embodiments, compounds of Formula (I) include enantiomers, derivatives, prodrugs, solvates and pharmaceutically acceptable salts thereof.

The term "derivative" as used herein refers to a chemical substance related structurally to another, i.e., an "original" substance, which can be referred to as a "parent" compound. A "derivative" can be made from the structurally-related parent compound in one or more steps. The general physical and chemical properties of a derivative are also similar to the parent compound.

In some embodiments, prodrugs of compounds selected from any of formula (I) to (V) also fall within the scope of the invention. As used herein, a "prodrug" refers to a compound that can be converted via some chemical or physiological process (e.g., enzymatic processes and metabolic hydrolysis) to a compound selected from the group consisting of compounds of formula (I) to (V).

Thus, the term "prodrug" also refers to a precursor of a biologically active compound that is pharmaceutically acceptable. A prodrug may be inactive when administered to a subject, i.e. an ester, but is converted in vivo to an active compound, for example, by hydrolysis to the free carboxylic acid or free hydroxyl. The prodrug compound often offers advantages of solubility, tissue compatibility or delayed release in an organism. The term "prodrug" is also meant to include any covalently bonded carriers, which release the active compound in vivo when such prodrug is administered to a subject. Prodrugs of an active compound may be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. See Harper, "Drug Latentiation" in Jucker, ed. *Progress in Drug Research* 4:221-294 (1962); Morozowich et al, "Application of Physical Organic Principles to Prodrug Design" in E. B. Roche ed. *Design of Biopharmaceutical Properties through Prodrugs and Analogs*, APHA Acad. Pharm. Sci. 40 (1977); *Bioreversible Carriers in Drug in Drug Design, Theory and Application*, E. B. Roche, ed., APHA Acad. Pharm. Sci. (1987); *Design of Prodrugs*, H. Bundgaard, Elsevier (1985); Wang et al. "Prodrug approaches to the improved delivery of peptide drug" in *Curr. Pharm. Design.* 5(4):265-287 (1999); Pauletti et al. (1997) Improvement in peptide bioavailability: Peptidomimetics and Prodrug Strategies, *Adv. Drug. Delivery Rev.* 27:235-256; Mizen et al. (1998) "The Use of Esters as Prodrugs for Oral Delivery of (3-Lactam antibiotics," *Pharm. Biotech.* 11:345-365; Gaignault et al. (1996) "Designing Prodrugs and Bioprecursors I. Carrier Prodrugs," *Pract. Med. Chem.* 671-696; Asgharnejad, "Improving Oral Drug Transport", in *Transport Processes in Pharmaceutical Systems*, G. L. Amidon, P. I. Lee and E. M. Topp, Eds., Marcell Dekker, p. 185-218 (2000); Balant et al., "Prodrugs for the improvement of drug absorption via different routes of administration", *Eur. J Drug Metab. Pharmacokinet.*, 15(2): 143-53 (1990); Balimane and Sinko, "Involvement of multiple transporters in the oral absorption of nucleoside analogues", *Adv. Drug Delivery Rev.*, 39(1-3): 183-209 (1999); Browne, "Fosphenytoin (Cerebyx)", *Clin. Neuropharmacol.* 20(1): 1-12 (1997); Bundgaard, "Bioreversible derivatization of drugs—principle and applicability to improve the therapeutic effects of drugs", *Arch. Pharm. Chemi* 86(1): 1-39 (1979); Bundgaard H. "Improved drug delivery by the prodrug approach", *Controlled Drug Delivery* 17: 179-96 (1987); Bundgaard H. "Prodrugs as a means to improve the delivery of peptide drugs", Arfv. *Drug Delivery Rev.* 8(1): 1-38 (1992); Fleisher et al. "Improved oral drug delivery: solubility limitations overcome by the use of prodrugs", Arfv. *Drug Delivery Rev.* 19(2): 115-130 (1996); Fleisher et al. "Design of prodrugs for improved gastrointestinal absorption by intestinal enzyme targeting", *Methods Enzymol.* 112 (Drug Enzyme Targeting, Pt. A): 360-81, (1985); Farquhar D, et al., "Biologically Reversible Phosphate-Protective Groups", *Pharm. Sci.*, 72(3): 324-325 (1983); Freeman S, et al., "Bioreversible Protection for the Phospho Group: Chemical Stability and Bioactivation of Di(4-acetoxy-benzyl) Methylphosphonate with Carboxyesterase," *Chem. Soc., Chem. Commun.*, 875-877 (1991); Friis and Bundgaard, "Prodrugs of phosphates and phosphonates: Novel lipophilic alphaacyloxyalkyl ester derivatives of phosphate- or phosphonate containing drugs masking the negative charges of these groups", *Eur. J Pharm. Sci.* 4: 49-59 (1996); Gangwar et al., "Pro-drug, molecular structure and percutaneous delivery", *Des. Biopharm. Prop. Prodrugs Analogs*, [Symp.] Meeting Date 1976, 409-21. (1977); Nathwani and Wood, "Penicillins: a current review of their clinical pharmacology and therapeutic use", *Drugs* 45(6): 866-94 (1993); Sinhababu and Thakker, "Prodrugs of anticancer agents", *Adv. Drug Delivery Rev.* 19(2): 241-273 (1996); Stella et al., "Prodrugs. Do they have advantages in clinical practice?", *Drugs* 29(5): 455-73 (1985); Tan et al. "Development and optimization of anti-HIV nucleoside analogs and prodrugs: A review of their cellular pharmacology, structure-activity relationships and pharmacokinetics", *Adv. Drug Delivery Rev.* 39(1-3): 117-151 (1999); Taylor, "Improved passive oral drug delivery via prodrugs", *Adv. Drug Delivery Rev.*, 19(2): 131-148 (1996); Valentino and Borchardt, "Prodrug strategies to enhance the intestinal absorption of peptides", *Drug Discovery Today* 2(4): 148-155 (1997); Wiebe and Knaus, "Concepts for the design of anti-HIV nucleoside prodrugs for treating cephalic HIV infection", *Adv. Drug Delivery Rev.:* 39(1-3):63-80 (1999); Waller et al., "Prodrugs", *Br. J Clin. Pharmac.* 28: 497-507 (1989), content of all of which is herein incorporated by reference in its entirety.

Compounds of Formula (I) also include pharmaceutically acceptable salts thereof. As used herein, the term "pharmaceutically-acceptable salts" refers to the conventional non-toxic salts or quaternary ammonium salts of compound of Formula (I) described herein, e.g., from non-toxic organic or inorganic acids. These salts can be prepared in situ in the administration vehicle or the dosage form manufacturing process, or by separately reacting a compound of Formula (I) in its free base or acid form with a suitable organic or inorganic acid or base, and isolating the salt thus formed during subsequent purification. Conventional nontoxic salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), content of which is herein incorporated by reference in its entirety.

In some embodiments of any one of the aspects described herein, representative pharmaceutically acceptable salts include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

In another aspect, provided herein are composition comprising a compound of Formula (I).

Compositions

The inventors have discovered inter alia compounds of Formula (I) can inhibit efflux pumps. In other words, the compounds of Formula (I) can be used as efflux pump inhibitors. As used herein, an efflux pump inhibitor is a compound that interferes with the ability of an efflux pump to export a substrate.

The term "efflux pump" as used herein refers to a protein assembly, which transports or exports substrate molecules from the cytoplasm or periplasm of a cell, in an energy-dependent or independent fashion. It is noted that the efflux pump can be a microbial efflux pump or a mammalian efflux pump.

Microbial efflux pumps are classified into five major superfamilies: (i) the major facilitator superfamily (MFS); (ii) the ATP-binding cassette superfamily (ABC); (iii) the small multidrug resistance family (SMR); (iv) the resistance-nodulation-cell division superfamily (RND); and (v) the multi antimicrobial extrusion protein family (MATE).

In some embodiments of any one of the aspects described herein, the efflux pump is from the ABC transporter superfamily. More than 48 members of the ABC transporter superfamily have been identified in humans and three major subfamilies (ABCB, ABCC, and ABCG) are related to human multidrug resistance (MDR) and influence oral absorption and disposition of a wide variety of drugs, and as a result their expression levels have important consequences for susceptibility to drug-induced side effects, interactions, and treatment efficacy. The specific subclass members ABCB1(MDR1/Pgp), ABCC1 (MRP1), and ABCG2 (BCRP) are known to significantly influence the efficacy of drugs and have unambiguously been shown to contribute to cancer multidrug resistance.

In some embodiments, the efflux pump is a microbial efflux pump from the ABC transporter superfamily. In some other embodiments, the efflux pump is a mammalian, e.g., human efflux pump from the ABC transporter superfamily.

In some embodiments of any one of the aspects, the efflux pump is selected from the group consisting of Cdr1, ABCB1 (MDR1/Pgp), ABCC1 (MRP1), and ABCG2 (BCRP). For example, the efflux pump is fungal Cdr1 efflux pump.

In some embodiments, the efflux pump is a multidrug resistance pump. The term "multidrug resistance pump" refers to an efflux pump that is not highly specific to a particular drug. The term thus includes broad substrate pumps (efflux a number of compounds with varying structural characteristics).

The compounds of Formula (I) can be useful for inhibiting transport of an efflux pump substrate from a cell. Accordingly, in some embodiments of any one of the aspects, the composition can further comprise an efflux pump substrate. As used herein an efflux pump substrate is compound or molecule that an efflux pump can transport out from the cell. Many therapeutic agents are efflux pump substrates.

Drug resistance is the name given to the circumstance when a pathogen or disease does not respond to a treatment drug or drugs. Drug resistance can be either intrinsic, which means the pathogen or disease has never been responsive to the drug or drugs, or it can be acquired, which means the pathogen or disease ceases responding to a drug or drugs that the pathogen or disease had previously been responsive to. Different drug resistance mechanisms have been reported. One form of drug resistance is mediated by efflux pumps by increasing the efflux of the drug from the cell to the outside medium. This can lower the concentration of drug at the target site, Many drug resistance pathogens and drug resistant diseases utilize this mechanism.

The compounds of Formula (I) described herein can inhibit efflux pumps and many therapeutic agents are efflux pump substrates. Thus, without wishing to be bound by a theory, compounds of Formula (T) can be: useful for enhancing the efficacy of therapeutic agent against a pathogen or disease when co-administered with said therapeutic agent. Stated in another way, compounds of Formula (I) can be useful for enhancing the susceptibility of a pathogen or disease to a therapeutic agent when co-administered with said therapeutic agent. Accordingly, in some embodiments, the composition comprises a therapeutic agent, i.e., the composition comprises a compound of Formula (I) and a therapeutic agent.

For example, the compounds of Formula (I) can be useful for treating microbial infections when administered with an antimicrobial agent. Accordingly, in some embodiments of any one of the aspects, the therapeutic agent is an antimicrobial agent. In other words, the composition comprises a compound of Formula (I) and an antimicrobial agent. For example, the composition comprises a compound of Formula (I) and an antimicrobial agent, wherein the antimicrobial agent is an efflux pump substrate.

The term "antimicrobial agent" as used herein refers to any entity with antimicrobial activity, i.e. the ability to inhibit or reduce the growth and/or kill a microbe, e.g., by at least about 30%, at least about 40%, at least about 50%, at least about 75%, at least about 90% or more, as compared to in the absence of an antimicrobial agent. As used herein, antimicrobial agents include antibiotics. The term "antibiotic" is art recognized and includes antimicrobial agents naturally produced by microorganisms such as bacteria (including *Bacillus* species), actinomycetes (including *Streptomyces*) or fungi that inhibit growth of or destroy other microbes, or genetically-engineered thereof and isolated from such natural source. Exemplary classes of antibiotics include, but are not limited to, (1) β-lactams, including the penicillins, cephalosporins monobactams, methicillin, and carbapenems; (2) aminoglycosides, e.g., gentamicin, kanamycin, neomycin, tobramycin, netilmycin, paromomycin, and amikacin; (3) tetracyclines, e.g., doxycycline, minocycline, oxytetracycline, tetracycline, and demeclocycline; (4) sulfonamides (e.g., mafenide, sulfacetamide, sulfadiazine and sulfasalazine) and trimethoprim; (5) quinolones, e.g., ciprofloxacin, norfloxacin, and ofloxacin; (6) glycopeptides (e.g., vancomycin, telavancin, teicoplanin); (7) macrolides, which include for example, erythromycin, azithromycin, and clarithromycin; (8) carbapenems (e.g., ertapenem, doripenem, meropenem, and imipenem); (9) cephalosporins (e.g., cefadroxil, cefepime, and ceftobiprole); (10) lincosamides (e.g., clindamycin, and lincomycin); (11) monobactams (e.g., aztreonam); (12) nitrofurans (e.g., furazolidone, and nitrofurantoin); (13) Penicillins (e.g., amoxicillin, and Penicillin G); (14) polypeptides (e.g., bacitracin, colistin, and polymyxin B); and (15) other antibiotics, e.g., ansamycins, polymycins, carbacephem, chloramphenicol, lipopeptide, and drugs against mycobacteria (e.g., the ones causing diseases in mammals, including tuberculosis (*Mycobacterium tuberculosis*) and leprosy (*Mycobacterium leprae*), and any combinations thereof.

Exemplary antimicrobial agents include, but are not limited to, antifungal agents, antibacterial agents, antiprotozoal agents, and antiviral agents.

In some embodiments of any one of the aspects, the antimicrobial agent is an antifungal agent. For example, the composition comprises a compound of Formula (I) and an antifungal agent, wherein the antifungal agent is an efflux pump substrate. Examples of antifungal agents include, but are not limited to, azoles (e.g., butoconazole, econazole, fluconazole, isavuconazole, itraconazole, ketoconazole, miconazole, clortrimazole, voriconazole, posaconazole, ravuconazole, tercoconazole, tioconazole, voriconazole, ciclopirox, etc.), polyenes (e.g., natamycin, lucensomycin, nystatin, amphotericin B, etc.), echinocandins (e.g., Cancidas), pradimicins (e.g., beanomicins, nikkomycins, sordarins, allylamines, etc.), Triclosan, Piroctone and its olamine salt, fenpropimorph, terbinafine, and derivatives and analogs thereof. Additional antifungal agents include those described, for example, in Int. Pat. Pub. No. WO2001/066551, No. WO2002/090354, No. WO2000/043390, No. WO2010/032652, No. WO2003/008391, No. WO2004/018485, No. WO2005/006860, No. WO2003/086271, No. WO2002/067880; in U.S. Pat. App. Pub. No. 2008/0194661, No. 2008/0287440, No. 2005/0130940, No. 2010/0063285, No. 2008/0032994, No. 2006/0047135, No. 2008/0182885; and in U.S. Pat. Nos. 6,812,238; 4,588,525; 6,235,728; 6,265,584; 4,942,162; and 6,362,172, content of all of which is incorporated herein by reference.

In some embodiments of any one of the aspects, the antifungal agent is an azole antifungal agent. Azole antifungals are compounds that contain an azole ring and inhibit the growth of a wide range of fungi. Exemplary azole antifungals include, but are not limited to, butoconazole, econazole, fluconazole, isavuconazole, itraconazole, ketoconazole, miconazole, clortrimazole, voriconazole, posaconazole, ravuconazole, tercocnazole, tioconazole, voriconazole, and ciclopirox.

In some embodiments of any one of the aspects, the antimicrobial agent is a bacterial agent. For example, the composition comprises a compound of Formula (I) and an antibacterial agent, wherein the antibacterial agent is an efflux pump substrate. Exemplary antibacterial agents include, but are not limited to, acrosoxacin, amifloxacin, amoxycillin, ampicillin, aspoxicillin, azidocillin, azithromycin, aztreonam, balofloxacin, lc benzylpenicillin, biapenem, brodimoprim, cefaclor, cefadroxil, cefatrizine, cefcapene, cefdinir, cefetamet, cefmetazole, cefprozil, cefroxadine, ceftibuten, cefuroxime, cephalexin, cephalonium, cephaloridine, cephamandole, cephazolin, cephradine, chlorquinaldol, chlortetracycline, ciclacillin, cinoxacin, ciprofloxacin, clarithromycin, clavulanic acid, clindamycin, clofazimine, cloxacillin, danofloxacin, dapsone, demeclocycline, dicloxacillin, difloxacin, doxycycline, enoxacin, enrofloxacin, erythromycin, fleroxacin, flomoxef, flucloxacillin, flumequine, fosfomycin, isoniazid, levofloxacin, mandelic acid, mecillinam, metronidazole, minocycline, mupirocin, nadifloxacin, nalidixic acid, nifuirtoinol, nitrofurantoin, nitroxoline, norfloxacin, ofloxacin, oxytetracycline, panipenem, pefloxacin, phenoxymethylpenicillin, pipemidic acid, piromidic acid, pivampicillin, pivmecillinam, prulifloxacin, rufloxacin, sparfloxacin, sulbactam, sulfabenzamide, sulfacytine, sulfametopyrazine, sulphacetamide, sulphadiazine, sulphadimidine, sulphamethizole, sulphamethoxazole, sulphanilamide, sulphasomidine, sulphathiazole, temafloxacin, tetracycline, tetroxoprim, tinidazole, tosufloxacin, trimethoprim, doramectin, ivermectin, milbemycin, moxidectin, and selamectin.

In some embodiments of any one of the aspects, the antimicrobial agent is an antiprotozoal agent. Exemplary antiprotozoal agents include, but are not limited to, acetarsol, azanidazole, chloroquine, metronidazole, nifuratel, nimorazole, omidazole, propenidazole, secnidazole, sinefingin, tenonitrozole, temidazole, and tinidazole.

In some embodiments of any one of the aspects, the antimicrobial agent is an antiviral agent. Exemplary antiviral agents include, but are not limited to, acyclovir, brivudine, cidofovir, curcumin, desciclovir, 1-docosanol, edoxudine, gq fameyclovir, fiacitabine, ibacitabine, imiquimod, lamivudine, penciclovir, valacyclovir, and valganciclovir.

In some embodiments, the antimicrobial agent can be an antimicrobial peptide. Antimicrobial peptides are ubiquitous in nature and play an important role in the innate immune system of many species (Zasloff et al., 2002; and Epand et al., 1999). The antimicrobial peptide can be a naturally occurring peptide or an analog thereof, or it can be a synthetic peptide. As used herein an "analog" in reference to antimicrobial peptide refers to a naturally-occurring antimicrobial peptide that has been chemically modified to improve its effectiveness and/or reduce its toxic side effects. Non-limiting examples include lantibiotics, such as nisin, subtilin, epidermin and gallidermin; defensins; attacins, such as sarcotoxin; cecropins, such as cecropin A, bactericidin, and lepidopteran; magainins; melittins; histatins; brevinins; and combinations thereof.

In some embodiments of any one of the aspects, the antimicrobial agent is fluconazole, gepinacin, cerulenin, cycloheximide, itraconazole, econazole, tercocnazole, butoconazole, tioconazole, voriconazole, posaconazole, ravuconazole, erythromycin, tetracycline, doxycycline, levofloxacin, ofloxacin, sparfloxacin, doramectin, ivermectin, milbemycin, moxidectin, or selamectin. For example, the antimicrobial agent is fluconazole.

Drug resistance in the field of cancer, is discussed in greater detail in "Detoxification Mechanisms and Tumor Cell Resistance to Anticancer Drugs," by Kuzmich and Tew, particularly section VII "The Multidrug-Resistant Phenotype (MDR)," Medical Research Reviews, Vol. 11, No. 2, 185-217, (Section VII is at pp. 208-213) (1991); and in "Multidrug Resistance and Chemosensitization Therapeutic Implications for Cancer Chemotherapy," by Georges, Sharom and Ling, Advances in Pharmacology, Vol. 21, 185-220 (1990). P-glycoprotein, an energy-dependent efflux pump encoded by MDR-1 gene (Enudicott J A, Annu Rev Biochem 1989), has been shown to play a major role in the intrinsic and acquired resistance of a number of human tumors. Anticancer agents that act as substrates for and are consequently detoxified by P-gp include the vinca alkaloids (vincristine and vinblastine), anthracyclines (Adriamycin), and epipodophyllotoxins (etoposide).

It has been discovered that compounds of Formula (I) described herein are capable of inhibiting efflux pumps including P-gp (MDR1). Without wising to be bound by a theory, compounds of Formula (I) can be useful for treating cancer when administered with an anticancer agent. Accordingly, in some embodiments of any one of the aspects, the therapeutic agent is an anticancer agent. In other words, the composition comprises a compound of Formula (I) and an anticancer agent. For example, the composition comprises a compound of Formula (I) and an anticancer agent, wherein the anticancer agent is an efflux pump substrate.

As used herein, the term "anti-cancer agent" is refers to any compound (including its analogs, derivatives, prodrugs and pharmaceutically salts) or composition which can be used to treat cancer Anti-cancer compounds for use in the present invention include, but are not limited to, inhibitors of topoisomerase I and II, alkylating agents, microtubule inhibitors (e.g., taxol), and angiogenesis inhibitors. Exemplary anti-cancer compounds include, but are not limited to, paclitaxel (taxol); docetaxel: gemicitabine; Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfanoral; calusterone; capecitabine; carboplatin; carmustine; carmustine with Polifeprosan Implant; celecoxib; chlorambucil; cisplatin: cladribine; cyclophosphamide; cytarabine: cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliot's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin: goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogenmustard);

megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; pamidronate; pegademase; Pegaspargase: Pegfilgrastim; pentostatin: pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone: thioguanine (6-TG); thiotepa; topotecan; toremifene; Tositumomab; Trastuzumab; tretinoin (ATRA); Uracil Mustard; valrubicin; valtorcitabine (monoval LDC) vinblastine; vinorelbine; zoledronate; and any mixtures thereof.

In some embodiments, the anticancer agent is selected from the group consisting of gemcitabine, cisplatin, paclitaxel, carboplatin, bortezomib, AMG479, vorinostat, rituximab, temozolomide, rapamycin, ABT-737, PI-103; alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Angew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE™ vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin; lapatinib (Tykerb™); inhibitors of PKC-alpha, Raf, H-Ras, EGFR (e.g., erlotinib (Tarceva®)) and VEGF-A.

In some embodiments of any one of the aspects, the anticancer agent is selected from the group consisting of doxorubicin, daunorubicin, actinomycin, camptothecins (e.g., such as irinotecan and topotecan), epipodophyllotoxins (such as etoposide and teniposide), taxane (e.g., such as paclitaxel and docetaxel), tyrosine kinase inhibitors (e.g., such as, rucaparib, olaparib, imatinib, masitinib, nilotinib and toceranib), and vinca alkaloids (e.g., such as vinblastine, vincristine, and vinorelbine).

Pharmaceutical Compositions

For administration to a subject, the compositions described herein can be formulated as a pharmaceutical composition. These pharmaceutically acceptable compositions comprise a compound of Formula (I), and optionally a therapeutic agent, formulated together with one or more pharmaceutically acceptable carriers (additives) and/or diluents. As described in detail below, the pharmaceutical compositions described herein can be specially formulated for administration in solid or liquid form, including those adapted for the following: (1) oral administration, for example, drenches (aqueous or non-aqueous solutions or suspensions), gavages, lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 3,270,960, content of all of which is herein incorporated by reference.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Examples of solid carriers include starch, sugar, bentonite, silica, and other commonly used carriers. Further non-limiting examples of carriers and diluents which can be used in the formulations comprising a compound of Formula (I) as disclosed herein of the present invention include saline, syrup, dextrose, and water.

Pharmaceutically-acceptable antioxidants include, but are not limited to, (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acids, and the like.

The phrase "therapeutically-effective amount" as used herein means that amount of a compound, material, or composition which is effective for producing some desired therapeutic effect in at least a sub-population of cells in an animal at a reasonable benefit/risk ratio applicable to any medical treatment. According, a "therapeutically effective amount" refers to an amount effective, at dosage and periods of time necessary, to achieve a desired therapeutic result. A therapeutic result can be, e.g., lessening of symptoms, prolonged survival, improved mobility, and the like. A therapeutic result need not be a "cure."

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

The compounds can be formulated in a gelatin capsule, in tablet form, dragee, syrup, suspension, topical cream, suppository, injectable solution, or kits for the preparation of syrups, suspension, topical cream, suppository or injectable solution just prior to use. Also, compounds can be included in composites, which facilitate its slow release into the blood stream, e.g., silicon disc, polymer beads.

The formulations can conveniently be presented in unit dosage form and may be prepared by any of the methods well known in the art of pharmacy. Techniques, excipients and formulations generally are found in, e.g., *Remington's Pharmaceutical Sciences*, Mack Publishing Co., Easton, Pa. 1985, 17th edition, Nema et al., *PDA J Pharm. Sci. Tech.* 1997 51:166-171. Methods to make invention formulations include the step of bringing into association or contacting compounds of Formula (I), and optionally a therapeutic agent, with one or more excipients or carriers. In general, the formulations are prepared by uniformly and intimately bringing into association one or more compounds with liquid excipients or finely divided solid excipients or both, and then, if appropriate, shaping the product.

The preparative procedure may include the sterilization of the pharmaceutical preparations. The compounds may be mixed with auxiliary agents such as lubricants, preservatives, stabilizers, salts for influencing osmotic pressure, etc., which do not react deleteriously with the compounds.

Examples of injectable form include solutions, suspensions and emulsions. Injectable forms also include sterile powders for extemporaneous preparation of injectable solutions, suspensions or emulsions. The compounds of the present invention can be injected in association with a pharmaceutical carrier such as normal saline, physiological saline, bacteriostatic water, Cremophor™ EL (BASF, Parsippany, N.J.), phosphate buffered saline (PBS), Ringer's solution, dextrose solution, ethanol, polyol (e.g., glycerol, propylene glycol, and liquid polyethylene glycol), vegetable oils, and suitable mixtures thereof, and other aqueous carriers known in the art. Appropriate non-aqueous carriers may also be used and examples include fixed oils and ethyl oleate. In all cases, the composition must be sterile and should be fluid to the extent that easy syringability exists. It must be stable under the conditions of manufacture and storage and must be preserved against the contaminating action of microorganisms such as bacteria and fungi. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin. A suitable carrier is 5% dextrose in saline. Frequently, it is desirable to include additives in the carrier such as buffers and preservatives or other substances to enhance isotonicity and chemical stability.

In some embodiments, compounds can be administrated encapsulated within liposomes. The manufacture of such liposomes and insertion of molecules into such liposomes being well known in the art, for example, as described in U.S. Pat. No. 4,522,811. Liposomal suspensions (including liposomes targeted to particular cells, e.g., a pituitary cell) can also be used as pharmaceutically acceptable carriers.

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the composition can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185; content of each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

In some embodiments, the compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

In the case of oral ingestion, excipients useful for solid preparations for oral administration are those generally used in the art, and the useful examples are excipients such as lactose, sucrose, sodium chloride, starches, calcium carbonate, kaolin, crystalline cellulose, methyl cellulose, glycerin, sodium alginate, gum arabic and the like, binders such as polyvinyl alcohol, polyvinyl ether, polyvinyl pyrrolidone, ethyl cellulose, gum arabic, shellac, sucrose, water, ethanol, propanol, carboxymethyl cellulose, potassium phosphate and the like, lubricants such as magnesium stearate, talc and the like, and further include additives such as usual known coloring agents, disintegrators such as alginic acid and Primogel™, and the like. The compounds can be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these compounds may be incorporated with excipients and used in the form of tablets, capsules, elixirs, suspensions, syrups, and the like. Such compositions and preparations should contain at least 0.1% of compound. The percentage of the agent in these compositions may, of course, be varied and may conveniently be between about 2% to about 60% of the weight of the unit. The amount of compound in such therapeutically useful compositions is such that a suitable dosage will be obtained. Preferred compositions according to the present invention are prepared so that an oral dosage unit contains between about 100 and 2000 mg of compound. Examples of bases useful for formulation of suppositories are oleaginous bases such as cacao butter, polyethylene glycol, lanolin, fatty acid triglycerides, witepsol (trademark, Dynamite Nobel Co. Ltd.) and the like. Liquid preparations may be in the form of aqueous or oleaginous suspension, solution, syrup, elixir and the like, which can be prepared by a conventional way using additives. The compositions can be given as a bolus dose, to maximize the circulating levels for the greatest length of time after the dose. Continuous infusion may also be used after the bolus dose.

The compounds can also be administrated directly to the airways in the form of an aerosol. For administration by inhalation, the compounds in solution or suspension can be delivered in the form of an aerosol spray from pressured container or dispenser which contains a suitable propellant, e.g., a gas such as carbon dioxide, or hydrocarbon propellant like propane, butane or isobutene. The compounds can also be administrated in a no-pressurized form such as in an atomizer or nebulizer.

In the case of a pressurized aerosol, the dosage unit may be determined by providing a valve to deliver a metered amount. Capsules and cartridges of, such as, by way of example only, gelatin for use in an inhaler or insufflator may be formulated containing a powder mix of the compound described herein and a suitable powder base such as lactose or starch.

Representative intranasal formulations are described in, for example, U.S. Pat. Nos. 4,476,116, 5,116,817 and 6,391,452. Formulations that include a compound of Formula (I) are prepared as solutions in saline, employing benzyl alcohol or other suitable preservatives, fluorocarbons, and/or other solubilizing or dispersing agents known in the art. See, for example, Ansel, H. C. et al., Pharmaceutical Dosage Forms and Drug Delivery Systems, Sixth Ed. (1995). Preferably these compositions and formulations are prepared with suitable nontoxic pharmaceutically acceptable ingredients. These ingredients are known to those skilled in the preparation of nasal dosage forms and some of these can be found in REMINGTON: THE SCIENCE AND PRACTICE OF PHARMACY, 21st edition, 2005. The choice of suitable carriers is dependent upon the exact nature of the nasal dosage form desired, e.g., solutions, suspensions, ointments, or gels. Nasal dosage forms generally contain large amounts of water in addition to the active ingredient. Minor amounts of other ingredients such as pH adjusters, emulsifiers or dispersing agents, preservatives, surfactants, gelling agents, or buffering and other stabilizing and solubilizing agents are optionally present. Preferably, the nasal dosage form should be isotonic with nasal secretions The compounds can also be administered parenterally. Solutions or suspensions of these compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

It may be advantageous to formulate oral or parenteral compositions in dosage unit form for ease of administration and uniformity of dosage. As used herein, "dosage unit" refers to physically discrete units suited as unitary dosages for the subject to be treated; each unit containing a predetermined quantity of compound calculated to produce the desired therapeutic effect in association with the required pharmaceutical carrier.

Administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the compounds are formulated into ointments, salves, gels, or creams as generally known in the art.

For oral or enteral formulations as disclosed herein for use with the present invention, tablets can be formulated in accordance with conventional procedures employing solid carriers well-known in the art. Capsules employed for oral formulations to be used with the methods of the present invention can be made from any pharmaceutically acceptable material, such as gelatin or cellulose derivatives. Sustained release oral delivery systems and/or enteric coatings for orally administered dosage forms are also contemplated, such as those described in U.S. Pat. No. 4,704,295, "Enteric Film-Coating Compositions," issued Nov. 3, 1987; U.S. Pat. No. 4,556,552, "Enteric Film-Coating Compositions," issued Dec. 3, 1985; U.S. Pat. No. 4,309,404, "Sustained Release Pharmaceutical Compositions," issued Jan. 5, 1982; and U.S. Pat. No. 4,309,406, "Sustained Release Pharmaceutical Compositions," issued Jan. 5, 1982. As regards formulations for administering a compound of Formula I as disclosed herein, one particularly useful embodiment Also provided herein is a tablet formulation comprising a compound of Formula I with an enteric polymer casing. An example of such a preparation can be found in WO2005/021002. The active material in the core can be present in a micronised or solubilised form. In addition to active materials the core can contain additives conventional to the art of compressed tablets. Appropriate additives in such a tablet can comprise diluents such as anhydrous lactose, lactose monohydrate, calcium carbonate, magnesium carbonate, dicalcium phosphate or mixtures thereof; binders such as microcrystalline cellulose, hydroxypropylmethylcellulose, hydroxypropylcellulose, polyvinylpyrrolidone, pre-gelatinised starch or gum acacia or mixtures thereof; disintegrants such as microcrystalline cellulose (fulfilling both binder and disintegrant functions) cross-linked polyvinylpyrrolidone, sodium starch glycollate, croscarmellose sodium or mixtures thereof; lubricants, such as magnesium stearate or stearic acid, glidants or flow aids, such as colloidal silica, talc or starch, and stabilisers such as desiccating amorphous silica, colouring agents, flavours etc. Preferably the tablet comprises lactose as diluent. When a binder is present, it is preferably hydroxypropylmethyl cellulose. Preferably, the tablet comprises magnesium stearate as lubricant. Preferably the tablet comprises croscarmellose sodium as disintegrant. Preferably, the tablet comprises microcrystalline cellulose.

The diluent can be present in a range of 10-80% by weight of the core. The lubricant can be present in a range of 0.25-2% by weight of the core. The disintegrant can be present in a range of 1-10% by weight of the core. Microcrystalline cellulose, if present, can be present in a range of 10-80% by weight of the core.

The active ingredient, e.g., compound of Formula I, and optionally a therapeutic agent, preferably comprises between 10 and 50% of the weight of the core, more preferably between 15 and 35% of the weight of the core (calculated as free base equivalent). The core can contain any therapeutically suitable dosage level of the active ingredient, but preferably contains up to 150 mg of the active ingredient. Particularly preferably, the core contains 20, 30, 40, 50, 60, 80 or 100 mg of the active ingredient. The active ingredient can be present as is or as any pharmaceutically acceptable salt. If the active ingredient is present as a salt, the weight is adjusted such that the tablet contains the desired amount of active ingredient, calculated as free base or free acid of the salt.

The core can be made from a compacted mixture of its components. The components can be directly compressed, or can be granulated before compression. Such granules can be formed by a conventional granulating process as known in the art. In an alternative embodiment, the granules can be individually coated with an enteric casing, and then enclosed in a standard capsule casing.

The core is surrounded by a casing which comprises an enteric polymer. Examples of enteric polymers are cellulose acetate phthalate, cellulose acetate succinate, methylcellulose phthalate, ethylhydroxycellulose phthalate, polyvinylacetate pthalate, polyvinylbutyrate acetate, vinyl acetate-maleic anhydride copolymer, styrene-maleic mono-ester copolymer, methyl acrylate-methacrylic acid copolymer or methacrylate-methacrylic acid-octyl acrylate copolymer. These can be used either alone or in combination, or together with other polymers than those mentioned above. The casing can also include insoluble substances which are neither decomposed nor solubilised in living bodies, such as alkyl cellulose derivatives such as ethyl cellulose, crosslinked polymers such as styrene-divinylbenzene copolymer, polysaccharides having hydroxyl groups such as dextran, cellulose derivatives which are treated with bifunctional cross-linking agents such as epichlorohydrin, dichlorohydrin or 1, 2-, 3, 4-diepoxybutane. The casing can also include starch and/or dextrin.

In some embodiments, an entericcoating materials are the commercially available Eudragit® enteric polymers such as Eudragit® L, Eudragit® S and Eudragit® NE used alone or with a plasticiser. Such coatings are normally applied using a liquid medium, and the nature of the plasticiser depends upon whether the medium is aqueous or non-aqueous. Plasticisers for use with aqueous medium include propylene glycol, triethyl citrate, acetyl triethyl citrate or Citroflex® or Citroflex® A2. Non-aqueous plasticisers include these, and also diethyl and dibutyl phthalate and dibutyl sebacate. A preferred plasticiser is Triethyl citrate. The quantity of plasticiser included will be apparent to those skilled in the art.

The casing can also include an anti-tack agent such as talc, silica or glyceryl monostearate. Preferably the anti-tack agent is glyceryl monostearate. Typically, the casing can include around 5-25 wt % Plasticizers and up to around 50 wt % of anti-tack agent, preferably 1-10 wt % of anti-tack agent.

If desired, a surfactant can be included to aid with forming an aqueous suspension of the polymer. Many examples of possible surfactants are known to the person skilled in the art. Preferred examples of surfactants are polysorbate 80, polysorbate 20, or sodium lauryl sulphate. If present, a surfactant can form 0.1-10% of the casing, preferably 0.2-5% and particularly preferably 0.5-2%.

A seal coat can also be included between the core and the enteric coating. A seal coat is a coating material which can be used to protect the enteric casing from possible chemical attack by any alkaline ingredients in the core. The seal coat can also provide a smoother surface, thereby allowing easier attachment of the enteric casing. A person skilled in the art would be aware of suitable coatings. Preferably the seal coat is made of an Opadry coating, and particularly preferably it is Opadry White OY-S-28876. Other enteric-coated preparations of this sort can be prepared by one skilled in the art, using these materials or their equivalents.

For intravenous injections or drips or infusions, compounds described herein are formulated in aqueous solutions, preferably in physiologically compatible buffers such as Hank's solution, Ringer's solution, or physiological saline buffer. For transmucosal administration, penetrants appropriate to the barrier to be permeated are used in the formulation. Such penetrants are generally known in the art. For other parenteral injections, appropriate formulations include aqueous or nonaqueous solutions, preferably with physiologically compatible buffers or excipients. Such excipients are known.

Parenteral injections may involve bolus injection or continuous infusion. Formulations for injection may be presented in unit dosage form, e.g., in ampoules or in multi-dose containers, with an added preservative. The pharmaceutical composition described herein may be in a form suitable for parenteral injection as a sterile suspension, solutions or emulsions in oily or aqueous vehicles, and may contain formulatory agents such as suspending, stabilizing and/or dispersing agents. In one aspect, the active ingredient is in powder form for constitution with a suitable vehicle, e.g., sterile pyrogen-free water, before use.

The compositions described herein, e.g., pharmaceutical compositions described herein, can be formulated for topical administration. For example, the composition can be formulated as a cream, gel, lotion, oil or spray.

Amount of compound of Formula (I) in the composition, e.g., pharmaceutical composition can be based on weight, moles, or volume. For example, the amount of compound of Formula (I) in the composition is based on weight. In some other non-limiting example, the amount of compound of Formula (I) in the composition is based on volume.

In some embodiments, the composition, e.g., pharmaceutical composition comprises at least 0.0001% of compound of Formula (I). In some embodiments, the composition, e.g., pharmaceutical composition comprises at least 0.1% of compound of Formula (I). In some embodiments, the composition, e.g., pharmaceutical composition comprises at least 0.5% of compound of Formula (I). In some embodiments, the composition, e.g., pharmaceutical composition comprises at least 1% of compound of Formula (I). In some embodiments, the composition, e.g., pharmaceutical composition comprises at least 2% of compound of Formula (I). In some embodiments, the composition, e.g., pharmaceutical composition comprises at least 3% of compound of Formula (I). In some embodiments, the composition, e.g., pharmaceutical composition comprises at least 4% of compound of Formula (I). In some embodiments, the composition, e.g., pharmaceutical composition comprises at least 5% of compound of Formula (I). In some embodiments, the composition, e.g., pharmaceutical composition comprises at least 10% of compound of Formula (I). In some embodiments, the composition, e.g., pharmaceutical composition comprises 0.01%-99% of The compound of Formula (I). In some embodiments, the composition, e.g., pharmaceutical composition comprises 0.05%-90% of The compound of Formula (I). In some embodiments, the composition, e.g., pharmaceutical composition comprises 0.1%-85% of The compound of Formula (I). In some embodiments, the composition, e.g., pharmaceutical composition comprises 0.5%-80% of The compound of Formula (I). In some embodiments, the composition, e.g., pharmaceutical composition comprises 1%-75% of The compound of Formula (I). In some embodiments, the composition, e.g., pharmaceutical composition comprises 2%-70% of The compound of Formula (I). In some embodiments, the composition, e.g., pharmaceutical composition comprises 3%-65% of The compound of Formula (I). In some embodiments, the composition, e.g., pharmaceutical composition comprises 4%-60% of The compound of Formula (I). In some embodiments, the composition, e.g., pharmaceutical composition comprises 5%-50% of The compound of Formula (I).

When present, amount of therapeutic agent, e.g., antimicrobial agent or anticancer agent, in the composition, e.g., pharmaceutical composition can be based on weight, moles, or volume. For example, the amount of therapeutic agent, e.g., antimicrobial agent or anticancer agent, in the composition is based on weight. In some other non-limiting example, the amount of therapeutic agent, e.g., antimicrobial agent or anticancer agent, in the composition is based on volume.

In some embodiments, the composition, e.g., pharmaceutical composition comprises at least 0.0001% of therapeutic agent, e.g., antimicrobial agent or anticancer agent. In some embodiments, the composition, e.g., pharmaceutical composition comprises at least 0.1% of therapeutic agent, e.g., antimicrobial agent or anticancer agent. In some embodiments, the composition, e.g., pharmaceutical composition comprises at least 0.5% of therapeutic agent, e.g., antimicrobial agent or anticancer agent. In some embodiments, the composition, e.g., pharmaceutical composition comprises at least 1% of therapeutic agent, e.g., antimicrobial agent or anticancer agent. In some embodiments, the composition, e.g., pharmaceutical composition comprises at least 2% of therapeutic agent, e.g., antimicrobial agent or anticancer agent. In some embodiments, the composition, e.g., pharmaceutical composition comprises at least 3% of therapeutic agent, e.g., antimicrobial agent or anticancer agent. In some embodiments, the composition, e.g., pharmaceutical composition comprises at least 4% of therapeutic agent, e.g., antimicrobial agent or anticancer agent. In some embodiments, the composition, e.g., pharmaceutical composition comprises at least 5% of therapeutic agent, e.g., antimicrobial agent or anticancer agent. In some embodiments, the composition, e.g., pharmaceutical composition comprises at least 10% of therapeutic agent, e.g., antimicrobial agent or anticancer agent. In some embodiments, the composition, e.g., pharmaceutical composition comprises 0.01%-99% of the therapeutic agent, e.g., antimicrobial agent or anticancer agent. In some embodiments, the composition, e.g., pharmaceutical composition comprises 0.05%-90% of the therapeutic agent, e.g., antimicrobial agent or anticancer agent. In some embodiments, the composition, e.g., pharmaceutical composition comprises 0.1%-85% of the therapeutic agent, e.g., antimicrobial agent or anticancer agent. In some embodiments, the composition, e.g., pharmaceutical composition comprises 0.5%-80% of the therapeutic agent, e.g., antimicrobial agent or anticancer agent. In some embodiments, the composition, e.g., pharmaceutical composition comprises 1%-75% of the therapeutic agent, e.g., antimicrobial agent or anticancer agent. In some embodiments, the composition, e.g., pharmaceutical composition comprises 2%-70% of the therapeutic agent, e.g., antimicrobial agent or anticancer agent. In some embodiments, the composition, e.g., pharmaceutical composition comprises 3%-65% of the therapeutic agent, e.g., antimicrobial agent or anticancer agent. In some embodiments, the composition, e.g., pharmaceutical composition comprises 4%-60% of the therapeutic agent, e.g., antimicrobial agent or anticancer agent. In some embodiments, the composition, e.g., pharmaceutical composition comprises 5%-50% of the therapeutic agent, e.g., antimicrobial agent or anticancer agent.

In some embodiments, the amount of the therapeutic agent in the composition, e.g., pharmaceutical composition is less than the therapeutically effective amount of the therapeutic agent. In other words, the amount of the therapeutic agent in the composition, e.g., pharmaceutical composition is less than the amount required for therapeutic efficacy when the therapeutic agent is used alone.

Synergistic Compositions

The data presented herein show that therapeutic agents, such as the therapeutic agents that are efflux pump substrates, demonstrate synergistic therapeutic activity in combination with compounds of Formula (I). Moreover, the data demonstrate therapeutic agents, such as the therapeutic agents that are efflux pump substrates, in combination with compounds of Formula (I) demonstrate synergistic therapeutic activity against drug-resistant pathogens and diseases.

As used herein, the term "synergistic" or "synergy" means that the therapeutic effect achieved with combinations of therapeutic agents and compounds of Formula (I) is greater than the sum of the effects that results from using the therapeutic agent and compounds of Formula (I) individually. In the present disclosure, "synergy" is being achieved by the combination of therapeutic agents and compounds of Formula (I), a term, which is therefore also applicable to compositions comprising the said combinations, with or without any additional component. Accordingly, the terms "synergistic composition" or "synergistic combination" may be used interchangeably in the present disclosure and refer to the compositions/combinations of the disclosure comprising at least one therapeutic agent, e.g., a therapeutic agent that is an efflux pump substrate, and at least one compound of Formula (I).

Generally, the synergy is measured by determining the fractional inhibitory concentration (FIC) value of the combination. This experimental set up, called checkerboard method, allows measurement of a desired effect (inhibition of microbial growth) at different combinations of various concentrations of the two agents (e.g., compound of Formula (I) and the antimicrobial agent) FIC value for each agent in a particular square/well of the checkerboard layout is calculated by dividing the agent concentration in that square/well by the established MIC value of the agent against the test organism (Hsieh et al, Synergy assessed by checkerboard: A critical Analysis, Diagn. Microbiol. Infect Dis. (1993) 16:343-349, content of which is incorporated herein by reference in its entirety). FIC values for both agents in a particular square/well are calculated in this way followed by determination of the FIC index (sum of the FICs of each agent in the particular square/well). Combinations that give FIC indices less than 1 are designated as "synergistic" based on the guidelines from the literature (Zhang et al., Synthesis of novel sulfonamide azoles via C—N cleavage of sulfonamides by azole ring and relational antimicrobial study, *New J Chem.* (2015) 39:5776-5796 and Meletiadis et al., Defining Fractional Inhibitory Concentration Index Cutoffs for Additive Interactions based on self-drug combinations, *Antimicrob. Agents Chemother.* (2010) 54(2): 602-609, contents of both of which are incorporated herein by reference in their entirety).

In some embodiments, a composition described herein, e.g., a composition comprising a compound of Formula (I) and a therapeutic agent, such as a therapeutic agent that is an efflux pump substrate, is a synergistic composition. In other words, the composition comprising a compound of Formula (I) and a therapeutic agent, such as a therapeutic agent that is an efflux pump substrate, has synergistic therapeutic activity. For example, when the therapeutic agent is an antimicrobial agent (e.g., an antifungal agent), the composition comprising a compound of Formula (I) and the antimicrobial agent (e.g., the antifungal agent) has synergistic antimicrobial (e.g., antifungal) activity. When the therapeutic agent is an anticancer agent, the composition comprising a compound of Formula (I) and the anticancer agent has synergistic anticancer activity.

Methods of Use

It has been discovered inter alia that compounds of Formula (T) described herein are capable of inhibiting efflux pumps. The compounds described herein, e.g., compounds of Formula (I) can inhibit efflux pumps. Thus, the compounds can be used in methods for inhibiting an efflux pump in a cell. For example, a compound of Formula (I) can be administered to a cell, e.g., a cell expressing an efflux pump, for inhibiting the efflux pump. In some embodiments, the method further comprises administering an efflux pump substrate, e.g., a therapeutic agent to the cell.

It is noted that administering to the cell can be in vitro or in-vivo. Methods for administering a compound to a cell are well known and available to one of skill in the art. As used herein, administering the compound to the cell means contacting the cell with the compound so that the compound is taken up by the cell. Generally, the cell can be contacted with the compound in a cell culture e.g., in vitro or ex vivo, or the compound can be administrated to a subject, e.g., in vivo. The term "contacting" or "contact" as used herein in connection with contacting a cell includes subjecting the cells to an appropriate culture media, which comprises a compound of Formula (I). Where the cell is in vivo, "contacting" or "contact" includes administering the compound, e.g., in a pharmaceutical composition to a subject via an appropriate administration route such that the compound contacts the cell in vivo.

For example, when the cell is in vitro, said administering to the cell can include subjecting the cell to an appropriate culture media which comprises the indicated compound. Where the cell is in vivo, said administering to the cell includes administering the compound to a subject via an appropriate administration route such that the compound is administered to the cell in vivo.

The cell to be administered a compound of Formula (I) can be any desired cell. For example, the cell is a cell expressing an efflux pump. Further, the cell can be a microbial cell or a mammalian cell. In some embodiments, the cell is a microbial cell. For example, the microbial cell is a fungal cell.

In some embodiments of any of the aspects described herein, the microbial cell is from a microbial pathogen that is resistant to one or more antimicrobial agents. For example, the microbial pathogen is a fungal pathogen and resistant to an antifungal agent.

In some embodiments, the cell is from a fungal pathogen described herein. For example, the cell is from a fungal pathogen described herein and the fungal pathogen is resistant to an antifungal agent described herein.

In some embodiments, the cell is from a fungal pathogen which is of the genus *Candida* spp., *Cryptococcus* spp., or *Aspergillus* spp. For example, the cell is from the genus *Candida* spp. In some embodiments, the cell is from *C. auris, C. albicans, C. tropicalis, C. gglabrata, C. parapsilosis, C. krusei, C. zeylanoides, C. guillermondii, C. pelliculosa, C. kefyr* or *C. dubliniensis*. For example, the cell is from *C. auris*.

In some embodiments of any one of the aspects, the cell is from a fungal pathogen and the fungal pathogen is resistant an azole antifungal agent. For example, the fungal pathogen is resistant to an antifungal agent selected from the group consisting of butoconazole, econazole, fluconazole, isavuconazole, itraconazole, ketoconazole, miconazole, clortrimazole, voriconazole, posaconazole, ravuconazole, tercocnazole, tioconazole, voriconazole, and ciclopirox. In some embodiments, the cell is from fluconazole resistant *C. auris*.

In some embodiments of any one of the aspects, the cell is a mammalian cell. For example, the cell is a mammalian cell from a subject having a drug resistant disease. In some embodiments, the cell is the cell is a cancer cell. For example, the cancer cell is a drug resistant cancer cell.

Without wishing to be bound by a theory, inhibiting the efflux pump in a cell can enhance efficacy of therapeutic agent in the cell. For example, inhibiting the efflux pump in a drug resistant pathogen can re-sensitize the pathogen to the drug.

This disclosure also features a method of enhancing the antimicrobial activity of an antimicrobial agent against a microbe, e.g., a microbial pathogen. The method comprises contacting a microbe is contacted with a compound of Formula (I), and optionally an antimicrobial agent.

Methods of Treatment

Without wishing to be bound by a theory, when administered to a subject suffering from a microbial infection that employs efflux pump(s) as a resistance mechanism, compounds of Formula (I) can inhibit the activity of the efflux pump(s) allowing a co-administrated drug to accumulate in sufficient concentration to treat the infection. Thus, in one aspect the present invention relates to a method for treating a microbial infection Generally, the method comprises administering to a subject in need thereof a compound of Formula (I), optionally in combination with an antimicrobial agent. In some embodiments of any one of the aspects, the microbial infection is a microbial infection that employs an efflux pump resistance mechanism.

By "microbial infection" is meant an infection caused by a fungal, bacterial, parasitic, protozoan or viral pathogen. A "pathogen" is generally defined as any disease-causing organism.

A fungal pathogen can be derived from a fungal pathogen which is of the genus *Candida* spp., (e.g., *C. auris, C. albicans, C. tropicalis. C. gglabrata, C. parapsilosis, C. krusei, C. zeylanoides, C. guillermondii, C. pelliculosa, C. kefyr* and *C. dubliniensis*), *Epidermophyton* spp., *Exophiala* spp., *Microsporum* spp., *Trichophyton* spp., (e.g. *T. rubrum* and *T. interdigitale*), *Tinea* spp., *Aspergillus* spp. (e.g., *A. fumigatus*), *Blastomyces* spp., *Blastoschizomyces* spp., *Coccidioides* spp., *Cryptococcus* spp. (e.g., *C. neoformans*), *Histoplasma* spp., *Paracoccidiomyces* spp., *Sporotrix* spp., *Absidia* spp., *Cladophialophora* spp., *Fonsecaea* spp., *Phialophora* spp., *Lacazia* spp., *Arthrographis* spp., *Acremonium* spp., *Actinomadura* spp., *Apophysomyces* spp., *Emmonsia* spp., *Basidiobolus* spp., *Beauveria* spp., *Chrysosporium* spp., *Conidiobolus* spp., *Cunninghamella* spp., *Fusarium* spp., *Geotrichum* spp., *Graphium* spp., *Leptosphaeria* spp., *Malassezia* spp., *Mucor* spp., *Neotestudina* spp., *Nocardia* spp., *Nocardiopsis* spp., *Paecilomyces* spp., *Phoma* spp., *Piedraia* spp., *Pneumocystis* spp., *Pseudallescheria* spp., *Pyrenochaeta* spp., *Rhizomucor* spp., *Rhizopus* spp., *Rhodotorula* spp., *Saccharomyces* spp., *Scedosporium* spp., *Scopulariopsis* spp., *Sporobolomyces* spp., *Syncephalastrum* spp., *Trichoderma* spp., *Trichosporon* spp., *Ulocladium* spp., *Ustilago* spp., *Vericillium* spp. or, *Wangiella* spp.

In some embodiments, the fungal pathogen is of the genus *Candida* spp., *Cryptococcus* spp., or *Aspergillus* spp.

In some embodiments of any one of the aspects, the fugal pathogen is *C. auris. C albicans, C. tropicalis, C. glabrata, C. parapsilosis, C. krusei, C. zeylanoides, C. guillermondii,*

*C. pelliculosa, C. kefyr, C. dubliniensis, A. corymbifera, A. falciforme, A. kiliensis, A. recifei, A. elegans, A. dermatitidis, A. capsulatus, A. alternata, A. vanbreuseghenii, A. kalrae, A. grisea, A. fumigatus, A. ochracens, A. versicolor, A. flavus, A. terreus, A. glaucus, A. nidulans, A. niger, A. oryzae, A. flavatus, A. ustus, B. ranarum, B. meristosporus, B. haptosporus, B. bassiana, B. spicifera, B. australiensis, B. hawaiiensis, B. dermatitidis, B. brasiliensis, B. capitatum, C. keratinophilum, C. tropicum, C. merdarium, C. inops, C. pannicola, C. queenslandicum, C. zonatum, C. parvum, C. bantiana, C. carrionii, C. bantianum, C. caldosporiodes, C. immitis, C. coronatus, C. fuckelii, C. neoformans, C. albidus, C. laurentii, C. bertholletiae, C. brachyspora, C. clavata, C. geniculata, C. lunata, C. pallescens, C. senegalensis, C. verruculosis, F. parva, E. floccosum, E. rubrum, L. stockdaleae, E. gallinae, E. jeanselmiae, E. dermatitidis, E. rostratum, E. halodes, E. meginnisii, E. longirostratum, F. neoformans, F. compacta, F. pedrosoi, F. oxyporum, F. solani, G. candidum, H. capsulatum, L. loboi, L, theobromae, L. senegalensis. L. loboi, M. grisea, M. mycetomatis, M. furfur, M. gypseum, M. audoinii, M. canis, M. nanum, M. Fulvum, M. ferrugineum, M. distortum, M. ramosissinus, M. indicus, M. circinneloides, M. hiernalis, N. rosatii, N. dassonvillei, O. gallopava, O. canadiensis, P. crutstaceus, P. variotii, P. brasilensis, P. brasiliensis, P. marneffei, P. verrucosum, P. werneckii, P. verrucosa, P. repens, P. parasitica, P. cruris-hominis, P. hortae, P. carinii, P. jiroveci(i), P. boydii, P. romeroi, R. seeberi, R. pusillus, R. arrhizus, R. rubra, R. minuta, R. glutinis, R. muclaginosa, S. cerevisiae, S. boulardii, S. apiospermum, S. proliferans, S. inflatum, S. brevicaulis, S. commune, S. dimidiatum, S. hyalinum, S. salmonicolor, S. schenckii, S. chartarum, S. atra, S. alternans, S. racemosum, T. longibrachiatum, T. rubrum, T. interdigitale, T. mentagrophytes, T. violaceum, T. tonsurans, T. schoenleinii, T. megninii, T. concentricum, T. sourdanense, T. gourvilii, T. verrucosum, T. terrestre, T. beigleii, T. botyris, T. chartarum, U. maydis, V. affinae, V. albo-atrum, V. fusisporum, V. luteoalbum, W. dermatitidis,* or *X. bantiana.*

In some embodiments of any of the aspects, the fungal pathogen is *C. auris, C. albicans, C. neoformans* or *A. fumigatus.* For example, the fungal pathogen is *C. auris.*

A bacterial pathogen can be derived from a bacterial species selected from the group consisting of: *Staphylococcus* spp., e.g. *Staphylococcus aureus, Staphylococcus epidermidis; Enterococcus* spp., e.g. *Enterococcus faecalis; Streptococcus pyogenes; Listeria* spp. *Pseudomonas* spp.; *Mycobacterium* spp., e.g. *Mycobacterium tuberculosis; Enterobacter* spp.; *Campylobacter* spp.; *Salmonella* spp.; *Streptococcus* spp., e.g. *Streptococcus* Group A or B, *Streptococcus pneumoniae: Helicobacter* spp., e.g. *Helicobacter pylori; Neisseria* spp., e.g. *Neisseria gonorrhea, Neisseria meningitidis; Borrelia burgdorferi; Shigella* spp., e.g. *Shigella* flexneri; *Escherichia coli; Haemophilus* spp., e.g. *Haemophilus influenzae; Chlamydia* spp., e.g. *Chlamydia* trachomatis, *Chlamydia pneumoniae, Chlamydia psittaci; Francisella tularensis; Bacillus* spp., e.g. *Bacillus anthracia; Clostridia* spp., e.g. *Clostridium botulinum; Yersinia* spp., e.g. *Yersinia pestis; Treponema* spp.; and *Burkholderia* spp.; e.g. *Burkholderia mallei* and *Burkholderia pseudomallei.*

In some embodiments of any one of the aspects, the bacterial pathogen is a Gram-negative bacterial strain. Exemplary Gram-negative bacterial strains include, but are not limited to, *Acinetobacter baumannii, Acinetobacter calcoaceticus, Acinetobacter haemolyticus, Acinetobacter lwoffi, Actinobacillus actinomycetemcomitans, Aeromonas hydrophilia, Aggregatibacter actinomycetemcomitans, Agrobacterium tumefaciens, Bacteroides distasonis, Bacteroides eggerthii, Bacteroides forsythus, Bacteroides fragilis, Bacteroides ovalus, Bacteroides splanchnicus, Bacteroides thetaiotaomicron, Bacteroides uniformis, Bacteroides vulgatus, Bordetella bronchiseptica, Bordetella parapertussis, Bordetella pertussis, Borrelia burgdorferi, Branhamella catarrhalis, Burkholderia cepacia, Campylobacter coli, Campylobacter fetus, Campylobacter jejuni, Caulobacter crescentus, Chlamydia trachomatis, Citrobacter diversus, Citrobacter freundii, Enterobacter aerogenes, Enterobacter asburiae, Enterobacter cloacae, Enterobacter sakazakii, Escherichia coli, Francisella tularensis, Fusobacterium nucleatum, Gardnerella vaginalis, Haemophilus ducreyi, Haemophilus haemolyticus, Haemophilus influenzae, Haemophilus parahaemolyticus, Haemophilus parainfluenzae, Helicobacter pylori, Kingella denitrificans, Kingella indologenes, Kingella kingae, Kingella oralis, Klebsiclla oaytoca, Klebsiella pneumoniae, Klebsiella rhinoscleromatis, Legionella pneunophila, Listeria monocytogenes, Moraxella bovis, Moraxella catarrhalis, Moraxella lacunata, Morganella morganii, Neisseria gonorrhoeae, Neisseria meningitidis, Pantoea agglomerans, Pasteurella canis, Pasteurella haemolytica, Pasteurella multocida, Pasteurella tularensis, Porphyromonas gingivalis, Proteus mirabilis, Proteus vulgaris, Providencia alcalifaciens, Providencia rettgeri, Providencia stuartii, Pseudomonas acidovorans, Pseudomonas aeruginosa, Pseudomonas alcaligenes, Pseudomonas fluorescens, Pseudomonas putida, Salmonella enteriditis, Salmonella paratyphi, Salmonella typhi, Salmonella typhimurium, Serratia marcescens, Shigella dysenteriae, Shigella jlexneri, Shigella sonnei, Stenotrophomonas maltophilla, Veillonella parvula, Vibrio cholerae, Vibrio parahaemolyticus, Yersinia enterocolitica, Yersinia intermedia, Yersinia pestis* and *Yersinia pseudotuberculosis.*

In some embodiments of any one of the aspects, the bacterial pathogen is a Gram-negative bacterial strain. Exemplary Gram-positive bacterial strains include, but are not limited to, *Actinomyces naeslundii, Actinorvces viscosus, Bacillus anthracis, Bacillus cereus, Bacillus subtilis, Clostridium difficile, Corynebacterium diphtheriae, Corynebacterium ulcerans, Enterococcus faecalis, Enterococcus faecium, Micrococcus lutens, Mycobacterium avium, Mycobacterium intracellulare, Mycobacterium leprae, Mycobacterium tuberculosis, Propionibacterium acnes, Staphylococcus aureus, Staphylococcus epidermidis, Staphylococcus haemolyticus, Staphylococcus hominis, Staphylococcus hyicus, Staphylococcus intermedius, Staphylococcus saccharolyticus, Staphylococcus saprophyticus, Streptococcus agalactiae, Streptococcus mutans, Streptococcus pneumoniae, Streptococcus pyrogenes, Streptococcus salivarius* and *Streptococcus sanguis.*

A parasitic pathogen may be derived from a parasitic pathogen selected from the group consisting of *Trypanosoma* spp. (*Trypanosoma cruzi, Trypanosoma brucei*), *Leishmania* spp., *Giardia* spp., *Trichomonas* spp., *Entamoeba* spp., *Naegleria* spp., *Acanthamoeba* spp., *Schistosoma* spp., *Plasmodium* spp., *Cryptosporidium* spp., *Isospora* spp., *Balantidium* spp., *Loa loa, Ascaris lumbricoides, Dirofilaria immitis,* and *Toxoplasma* ssp., e.g. *Toxoplasma gondii.*

A viral pathogen may be derived from a virus selected from the group consisting of: Human Immunodeficiency Virus (HIV1 & 2): Human T Cell Leukaemia Virus (HTLV 1 & 2); Ebola virus; human papilloma virus (e.g. HPV-2, HPV-5, HPV-8 HPV-16, HPV-18, HPV-31, HPV-33, HPV-52, HPV-54 and HPV-56); papovavirus; rhinovirus; poliovirus; herpesvirus; adenovirus; Epstein Barr virus; influenza virus; hepatitis B and C viruses; Variola virus, rotavirus; and SARS coronavirus.

In some embodiments of any one of the aspects, the microbial pathogen is resistant to one or more antimicrobial agents. For example, the microbial pathogen is resistant to one or more antimicrobial agents and wherein the resistance is at least partly efflux pump-mediated.

Accordingly, in some embodiments of any one of the aspects, the method comprises a step of identifying the subject as a subject infected with a microbe that is resistant to the antimicrobial agent. In some embodiments of any one of the aspects, the method comprises a step of identifying the subject as a subject infected with a microbe that is capable of developing resistance to the antimicrobial agent. In some embodiments, the resistance is at least partly efflux pump-mediated.

In some embodiments of any one of the aspects, the microbial pathogen is resistant to the antimicrobial agent co-administered with The compound of Formula (I).

In yet another aspect, provided herein is a method of treating a cancer in a subject. The method comprises administering to a subject in need thereof a compound of Formula (I) optionally in combination with an anticancer agent. In some embodiments of any one of the aspects, the cancer is a drug resistant cancer that employs an efflux pump resistance mechanism. For example, the cancer is resistant to the anticancer agent co-administered with The compound of Formula (I).

Routes of Administration

It is noted that the terms "administered" and "subjected" are used interchangeably in the context of treatment of a disease or disorder. In jurisdictions that forbid the patenting of methods that are practiced on the human body, the meaning of "administering" of a composition to a human subject shall be restricted to prescribing a controlled substance that a human subject will be administer to the subject by any technique (e.g., orally, inhalation, topical application, injection, insertion, etc.). The broadest reasonable interpretation that is consistent with laws or regulations defining patentable subject matter is intended. In jurisdictions that do not forbid the patenting of methods that are practiced on the human body, the "administering" of compositions includes both methods practiced on the human body and also the foregoing activities.

As used herein, the term "administer" refers to the placement of a composition into a subject by a method or route which results in at least partial localization of the composition at a desired site such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebrospinal, and intrasternal injection and infusion. In some embodiments, administration will generally be systemic. In some embodiments, administration can be local.

In some embodiments, a compound of Formula (I) or a composition comprising same is orally administered. Without limitations, oral administration can be in the form of solutions, suspensions, tablets, pills, capsules, sustained-release formulations, oral rinses, powders and the like.

In some embodiments, a compound of Formula (I) or a composition comprising same is administered in a local rather than systemic manner, for example, via topical application of the compound directly on to skin, or intravenously, or subcutaneously, often in a depot preparation or sustained release formulation. In specific embodiments, long-acting formulations are administered by implantation (for example subcutaneously or intramuscularly) or by intramuscular injection. In yet other embodiments, the compound as described herein is provided in the form of a rapid release formulation, in the form of an extended-release formulation, or in the form of an intermediate release formulation. In yet other embodiments, the compound described herein is administered topically (e.g., as a patch, an ointment, or in combination with a wound dressing, or as a wash or a spray). In alternative embodiments, a formulation is administered systemically (e.g., by injection, or as a pill).

The phrase "therapeutically-effective amount" as used herein means that amount of a compound, material, or composition comprising a compound described herein which is effective for producing some desired therapeutic effect in at least a sub-population of cells in a subject at a reasonable benefit/risk ratio applicable to any medical treatment. Thus, "therapeutically effective amount" means that amount which, when administered to a subject for treating a disease or di, is sufficient to affect such treatment for the disease or disorder, e.g., a microbial infection.

Depending on the route of administration, effective doses can be calculated according to the body weight, body surface area, or organ size of the subject to be treated. Optimization of the appropriate dosages can readily be made by one skilled in the art in light of pharmacokinetic data observed in human clinical trials. Alternatively, or additionally, the dosage to be administered can be determined from studies using animal models for the particular type of condition to be treated, and/or from animal or human data obtained from agents which are known to exhibit similar pharmacological activities. The final dosage regimen will be determined by the attending surgeon or physician, considering various factors which modify the action of active agent, e.g., the agent's specific activity, the agent's specific half-life in vivo, the severity of the condition and the responsiveness of the patient, the age, condition, body weight, sex and diet of the patient, the severity of any present infection, time of administration, the use (or not) of other concomitant therapies, and other clinical factors.

Determination of an effective amount is well within the capability of those skilled in the art. Generally, the actual effective amount can vary with the specific compound, the use or application technique, the desired effect, the duration of the effect and side effects, the subject's history, age, condition, sex, as well as the severity and type of the medical condition in the subject, and administration of other pharmaceutically active agents. Accordingly, an effective dose of compound described herein is an amount sufficient to produce at least some desired therapeutic effect in a subject.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of use or administration utilized.

The effective dose can be estimated initially from cell culture assays. A dose can be formulated in animal models to achieve a circulating plasma concentration range that includes the IC50 (i.e., the concentration of the therapeutic which achieves a half-maximal inhibition of symptoms) as determined in cell culture. Levels in plasma can be measured, for example, by high performance liquid chromatography. The effects of any particular dosage can be monitored by a suitable bioassay. The effective plasma concentration for a compound as disclosed herein can be about 0.01 µM to about 10 µM, about 0.2 µM to about 5 µM, or about 0.8 to about 3 µM in a subject, such as a rat, dog, or human.

Generally, the compositions are administered so that a compound of Formula (I) and/or a the therapeutic agent is used or given at a dose from 1 µg/kg to 1000 mg/kg; 1 µg/kg to 500 mg/kg; 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. Further contemplated is a dose (either as a bolus or continuous infusion) of about 0.1 mg/kg to about 10 mg/kg, about 0.3 mg/kg to about 5 mg/kg, or 0.5 mg/kg to about 3 mg/kg. It is to be further understood that the ranges intermediate to those given above are also within the scope of this disclosure, for example, in the range 1 mg/kg to 10 mg/kg, for example use or dose ranges such as 2 mg/kg to 8 mg/kg, 3 mg/kg to 7 mg/kg, 4 mg/kg to 6 mg/kg, and the like.

The compounds described herein, e.g., a compound of Formula (I) and/or the therapeutic agent can be administered at once, or can be divided into a number of smaller doses to be administered at intervals of time. Thus, in some embodiments, the compound, e.g., a compound of Formula (I) and/or the therapeutic agent, is administered once a day. In some other embodiments, the compound, e.g., a compound of Formula (I) and/or the therapeutic agent, is administered multiple times, e.g., two, three, four, five or more times a day.

It is understood that the precise dosage and duration of treatment will be a function of the location of where the composition is parenterally administered, the carrier and other variables that can be determined empirically using known testing protocols or by extrapolation from in vivo or in vitro test data. It is to be noted that concentrations and dosage values can also vary with the age of the individual treated. It is to be further understood that for any particular subject, specific dosage regimens can need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The compound, e.g., a compound of Formula (I) and/or the therapeutic agent, can be administered as a single bolus or multiple boluses, as a continuous infusion, or a combination thereof. For example, the compound, e.g., a compound of Formula (I) and/or the therapeutic agent, can be administered as a single bolus initially, and then administered as a continuous infusion following the bolus. The rate of the infusion can be any rate sufficient to maintain effective concentration, for example, to maintain effective plasma concentration. Some contemplated infusion rates include from 1 µg/kg/min to 100 mg/kg/min, or from 1 µg/kg/hr to 1000 mg/kg/hr. Rates of infusion can include 0.2 to 1.5 mg/kg/min, or more specifically 0.25 to 1 mg/kg/min, or even more specifically 0.25 to 0.5 mg/kg/min. It will be appreciated that the rate of infusion can be determined based upon the dose necessary to maintain effective plasma concentration and the rate of elimination of the compound, such that the compound is administered via infusion at a rate sufficient to safely maintain a sufficient effective plasma concentration of compound, e.g., a compound of Formula (I) and/or the therapeutic agent in the bloodstream.

Co-Administering

In some embodiments of any one of the aspects described herein, the method comprises co-administering a compound of Formula (I) and therapeutic agent to a cell or a subject. The terms "co-administering", "co-administration" and the like, as used herein, are meant to encompass administration of The compound of Formula I and the selected therapeutic agents to a single patient and are intended to include treatment regimens in which The compound of Formula (I) and the therapeutic agent are administered by the same or different route of administration or at the same or different time. The particular combination of therapies (therapeutics or procedures) to employ in such a combination regimen will take into account compatibility of the desired therapeutics and/or procedures and the desired therapeutic effect to be achieved.

Exemplary embodiments of the various aspects disclosed herein can be described by the following numbered embodiments:

Embodiment 1: A compound of Formula (I),

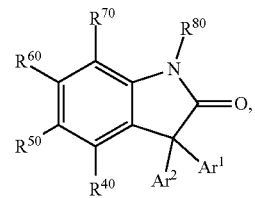

or enantiomers, prodrugs, derivatives, and pharmaceutically acceptable salts thereof, wherein: each of $R^{40}$, $R^{50}$, $R^{60}$, $R^{70}$, and $R^{80}$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted; $Ar^1$ and $Ar^2$ are each independently optionally substituted aryl or optionally substituted heteroaryl; and provided that the compound is not oxyphenisatin, isatin bis-cresol or MS-8396.

Embodiment 2: The compound of Embodiment 1, wherein each of $R^{40}$, $R^{50}$, $R^{60}$, $R^{70}$, and $R^{80}$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted.

Embodiment 3: The compound of any one of Embodiments 1-3, wherein each of $R^{40}$, $R^{50}$, $R^{60}$, $R^{70}$, and $R^{80}$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, $C_2$-$C_8$ alkynyl, sulfinyl, sulfonyl, thiocarbonyl, carbamoyl, cycloalkyl, heterocyclyl, aryl or heteroaryl, and each of which can be optionally substituted.

Embodiment 4: The compound of any one of Embodiments 1-3, wherein each of $R^{40}$, $R^{50}$, $R^{60}$, $R^{70}$, and $R^{80}$ independently are hydrogen, halogen, hydroxyl, amino, alkylamino, dialkylamino, thiol, alkylthio, carboxyl, nitro, acyl, acyloxy, alkyl, haloalkyl, heteroalkyl, or alkoxy, and each of which can be optionally substituted.

Embodiment 5: The compound of any one of Embodiments 1-4, wherein each of $R^{40}$, $R^{50}$, $R^{60}$, $R^{70}$, and $R^{80}$ independently are hydrogen, halogen, hydroxyl, amino, alkylamino, dialkylamino, thiol, alkylthio, carboxyl, nitro, acyl, acyloxy, $C_1$-$C_6$ alkyl, $C_1$-$C_6$ haloalkyl, $C_1$-$C_6$ heteroalkyl or $C_1$-$C_6$ alkoxy, and each of which can be optionally substituted.

Embodiment 6: The compound of any one of Embodiments 1-5, wherein each of $R^{40}$, $R^{50}$, $R^{60}$, $R^{70}$, and $R^{80}$ independently are hydrogen, halogen, optionally substituted $C_1$-$C_6$ alkyl, optionally substituted $C_1$-$C_6$ alkoxy.

Embodiment 7: The compound of any one of Embodiments 1-6, wherein each of $R^{40}$, $R^{50}$, $R^{60}$, $R^{70}$, and $R^{80}$ independently are hydrogen, halogen or optionally substituted $C_1$-$C_6$ alkyl.

Embodiment 8: The compound of any one of Embodiments 1-7, wherein each of $R^{40}$, $R^{50}$, $R^{60}$, $R^{70}$, and $R^{80}$ independently are hydrogen, F, Cl, Br, methyl, trifluoromethyl, ethyl, propyl, i-propyl, n-butyl, t-butyl, n-pentyl or hexyl.

Embodiment 9: The compound of any one of Embodiments 1-8, wherein at least one of $R^{40}$, $R^{50}$, $R^{60}$, $R^{70}$, and $R^{80}$ is not H.

Embodiment 10: The compound of any one of Embodiments 1-9, wherein one of $R^{40}$, $R^{50}$, $R^{60}$, $R^{70}$, and $R^{80}$ is not hydrogen and the remaining of $R^{40}$, $R^{50}$, $R^{60}$ and $R^{70}$ are H.

Embodiment 11: The compound of any one of Embodiments 1-10, wherein at least one of $R^{40}$, $R^{50}$, $R^{60}$, $R^{70}$, and $R^{80}$ is halogen, hydroxyl, amino, alkylamino, dialkylamino, thiol, alkylthio, carboxyl, nitro, acyl, acyloxy, alkyl, haloalkyl, heteroalkyl, or alkoxy, each of which can be optionally substituted; and the remaining of $R^{40}$, $R^{50}$, $R^{60}$ and $R^{70}$ are H.

Embodiment 12: The compound of any one of Embodiments 1-11, wherein one of $R^{40}$, $R^{50}$, $R^{60}$, $R^{70}$, and $R^{80}$ is halogen or $C_1$-$C_6$alkyl and the remaining of $R^{40}$, $R^{50}$, $R^{60}$ and $R^{70}$ are H.

Embodiment 13: The compound of any one of Embodiments 1-12, wherein one of $R^{40}$, $R^{50}$, $R^{60}$, $R^{70}$, and $R^{80}$ is F, Cl, Br, methyl, trifluoromethyl, ethyl, propyl, i-propyl, n-butyl, t-butyl, n-pentyl or hexyl; and the remaining of $R^{40}$, $R^{40}$, $R^{60}$ and $R^{70}$ are H.

Embodiment 14: The compound of any one of Embodiments 1-13, wherein one of $R^{40}$, $R^{50}$, $R^{60}$, $R^{70}$, and $R^{80}$ is F, Cl, Br or methyl, and the remaining of $R^{40}$, $R^{50}$, $R^{60}$ and $R^{70}$ are H Embodiment 15: The compound of any one of Embodiments 1-14, wherein $R^{40}$ is not H and each of $R^{50}$, $R^{60}$ and $R^{70}$ are H.

Embodiment 16: The compound of any one of Embodiments 1-15, wherein $R^{40}$ is halogen, hydroxyl, amino, alkylamino, dialkylamino, thiol, alkylthio, carboxyl, nitro, acyl, acyloxy, alkyl, haloalkyl, heteroalkyl, or alkoxy, each of which can be optionally substituted; and each of $R^{40}$, $R^{60}$ and $R^{70}$ are H.

Embodiment 17: The compound of any one of Embodiments 1-16, wherein $R^{40}$ is halogen or $C_1$-$C_6$ alkyl, and each of $R^{40}$, $R^{60}$ and $R^{70}$ are H.

Embodiment 18: The compound of any one of Embodiments 1-17, wherein $R^{40}$ is F, Cl, Br, methyl, trifluoromethyl, ethyl, propyl, i-propyl, n-butyl, t-butyl, n-pentyl or hexyl, and each of $R^{40}$, $R^{60}$ and $R^{70}$ are H.

Embodiment 19: The compound of any one of Embodiments 1-18, wherein $R^{40}$ is F, Cl, Br or methyl, and each of $R^{40}$, $R^{60}$ and $R^{70}$ are H.

Embodiment 20: The compound of any one of Embodiments 1-19, wherein $R^{50}$ is not H and each of $R^{40}$, $R^{60}$ and $R^{70}$ are H.

Embodiment 21: The compound of any one of Embodiments 1-20, wherein $R^{50}$ is halogen, hydroxyl, amino, alkylamino, dialkylamino, thiol, alkylthio, carboxyl, nitro, acyl, acyloxy, alkyl, haloalkyl, heteroalkyl, or alkoxy, each of which can be optionally substituted; and each of $R^{40}$, $R^{60}$ and $R^{70}$ are H.

Embodiment 22: The compound of any one of Embodiments 1-21, wherein $R^{50}$ is halogen or $C_1$-$C_6$ alkyl, and each of $R^{40}$, $R^{60}$ and $R^{70}$ are H.

Embodiment 23: The compound of any one of Embodiments 1-22, wherein $R^{50}$ is F, Cl, Br, methyl, trifluoromethyl, ethyl, propyl, i-propyl, n-butyl, t-butyl, n-pentyl or hexyl, and each of $R^{40}$, $R^{60}$ and $R^{70}$ are H.

Embodiment 24: The compound of any one of Embodiments 1-23, wherein $R^{50}$ is F, Cl, Br or methyl, and each of $R^{40}$, $R^{60}$ and $R^{70}$ are H.

Embodiment 25: The compound of any one of Embodiments 1-24, wherein $R^{60}$ is not H and each of $R^{40}$, $R^{50}$ and $R^{70}$ are H.

Embodiment 26: The compound of any one of Embodiments 1-25, wherein $R^{60}$ is halogen, hydroxyl, amino, alkylamino, dialkylamino, thiol, alkylthio, carboxyl, nitro, acyl, acyloxy, alkyl, haloalkyl, heteroalkyl, or alkoxy, each of which can be optionally substituted; and each of $R^{40}$, $R^{50}$ and $R^{70}$ are H.

Embodiment 27: The compound of any one of Embodiments 1-26, wherein $R^{60}$ is halogen or $C_1$-$C_6$ alkyl, and each of $R^{40}$, $R^{50}$ and $R^{70}$ are H.

Embodiment 28: The compound of any one of Embodiments 1-27, wherein $R^{60}$ is F, Cl, Br, methyl, trifluoromethyl, ethyl, propyl, i-propyl, n-butyl, t-butyl, n-pentyl or hexyl, and each of $R^{40}$, $R^{50}$ and $R^{70}$ are H.

Embodiment 29: The compound of any one of Embodiments 1-28, wherein $R^{60}$ is F, Cl, Br or methyl, and each of $R^{40}$, $R^{50}$ and $R^{70}$ are H.

Embodiment 30: The compound of any one of Embodiments 1-29, wherein $R^{70}$ is not H and each of $R^{40}$, $R^{50}$ and $R^{60}$ are H.

Embodiment 31: The compound of any one of Embodiments 1-30, wherein $R^{70}$ is halogen, hydroxyl, amino, alkylamino, dialkylamino, thiol, alkylthio, carboxyl, nitro, acyl, acyloxy, alkyl, haloalkyl, heteroalkyl, or alkoxy, each of which can be optionally substituted; and each of $R^{40}$, $R^{50}$ and $R^{60}$ are H.

Embodiment 32: The compound of any one of Embodiments 1-31, wherein $R^{70}$ is halogen or $C_1$-$C_6$ alkyl, and each of $R^{40}$, $R^{50}$ and $R^{60}$ are H.

Embodiment 33: The compound of any one of Embodiments 1-32, wherein $R^{70}$ is F, Cl, Br, methyl, trifluoromethyl, ethyl, propyl, i-propyl, n-butyl, t-butyl, n-pentyl or hexyl, and each of $R^{40}$, $R^{50}$ and $R^{60}$ are H.

Embodiment 34: The compound of any one of Embodiments 1-33, wherein $R^{70}$ is F, Cl, Br or methyl, and each of $R^{40}$, $R^{50}$ and $R^{60}$ are H.

Embodiment 35: The compound of any one of Embodiments 1-34, wherein each of $R^{40}$, $R^{40}$, $R^{60}$ and $R^{70}$ are H.

Embodiment 36: The compound of any one of Embodiments 1-35, wherein $R^{80}$ can be hydrogen, alkyl, alkenyl, alkynyl, cycloalkyl, heterocyclyl, aryl or heteroaryl, each of which can be optionally substituted.

Embodiment 37: The compound of any one of Embodiments 1-36, wherein $R^{80}$ can be hydrogen, optionally substituted $C_1$-$C_6$alkyl, optionally substituted $C_2$-$C_8$alkenyl, or optionally substituted $C_2$-$C_8$alkynyl.

Embodiment 38: The compound of any one of Embodiments 1-37, wherein $R^{80}$ is H, methyl, trifluoromethyl, ethyl, propyl, i-propyl, n-butyl, t-butyl, n-pentyl or hexyl.

Embodiment 39: The compound of any one of Embodiments 1-38, wherein $R^{80}$ is H, methyl, ethyl, propyl or i-propyl, optionally, $R^{80}$ is H.

Embodiment 40: The compound of any one of Embodiments 1-39, wherein $Ar^1$ and $Ar^2$ are each independently an optionally substituted aryl or optionally substituted heteroaryl.

Embodiment 41: The compound of any one of claims 1-40, wherein $Ar^1$ and $Ar^2$ are the same.

Embodiment 42: The compound of any one of Embodiments 1-40, wherein $Ar^1$ and $Ar^2$ are different.

Embodiment 43: The compound of any one of Embodiments 1-42, wherein at least one of $Ar^1$ and $Ar^2$ is of the structure (Ar'):

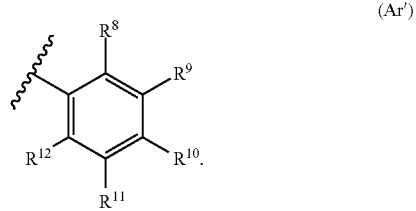

Embodiment 44: The compound of Embodiment 43, wherein each of $R^8$, $R^9$, $R^{10}$, $R^{11}$, and $R^{12}$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted.

Embodiment 45: The compound of any one of Embodiments 43-44, wherein each of $R^8$, $R^9$, $R^{10}$, $R^{11}$, and $R^{12}$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, $C_2$-$C_8$ alkynyl, sulfinyl, sulfonyl, thiocarbonyl, carbamoyl, cycloalkyl, heterocyclyl, aryl or heteroaryl, and each of which can be optionally substituted.

Embodiment 46: The compound of any one of Embodiments 43-45, wherein each of $R^8$, $R^9$, $R^{10}$, $R^{11}$, and $R^{12}$ independently are hydrogen, halogen, $C_1$-$C_6$alkyl, or $C_1$-$C_6$alkoxy.

Embodiment 47: The compound of any one of Embodiments 43-46, wherein $R^8$ is hydrogen, halogen, hydroxyl, amino, alkylamino, dialkylamino, acylamino, thiol, alkylthio, cyano, carbonyl, carboxyl, alkoxycarbonyl, nitro, acyl, acyloxy, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, $C_2$-$C_8$ alkynyl, sulfinyl, sulfonyl, thiocarbonyl, carbamoyl, cycloalkyl, heterocyclyl, aryl or heteroaryl, and each of which can be optionally substituted.

Embodiment 48: The compound of any one of Embodiments 43-47, wherein $R^8$ is hydrogen, halogen, hydroxyl, amino, alkylamino, dialkylamino, thiol, alkylthio, carboxyl, alkoxycarbonyl, acyl, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl or $C_2$-$C_8$ alkynyl, each of which can be optionally substituted.

Embodiment 49: The compound of any one of Embodiments 43-48, wherein $R^8$ is an optionally substituted alkoxy.

Embodiment 50: The compound of any one of Embodiments 43-49, wherein $R^8$ is an optionally substituted $C_1$-$C_{10}$ alkoxy.

Embodiment 51: The compound of any one of Embodiments 43-50, wherein $R^8$ is methoxy, ethoxy, —O-n-propyl, —O-isopropyl, —O-sec-butyl, —O-tert-butyl, —O-n-butyl, O-isobutyl, —O-neopentyl, —O-isopropenyl, —O-n-propenyl, or —O-n-butenyl.

Embodiment 52: The compound of any one of Embodiments 43-51, wherein $R^8$ is

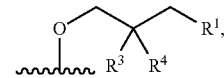

wherein each of $R^1$, $R^3$ and $R^4$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted.

Embodiment 53: The compound of Embodiment 52, wherein $R^1$ is hydrogen, halogen, hydroxyl, amino, alkylamino, dialkylamino, acylamino, thiol, alkylthio, cyano, carbonyl, carboxyl, alkoxycarbonyl, nitro, acyl, acyloxy, $C_1$-$C_6$ alkyl, $C_1$-$C_6$haloalkyl, $C_1$-$C_6$ heteroalkyl, $C_1$-$C_6$ alkoxy, $C_2$-$C_8$ alkenyl, $C_2$-$C_8$ alkynyl, sulfinyl, sulfonyl, thiocarbonyl, carbamoyl, cycloalkyl, heterocyclyl, aryl or heteroaryl, and each of which can be optionally substituted.

Embodiment 54: The compound of any one of Embodiments 52-53, wherein $R^1$ is hydrogen, optionally substituted $C_1$-$C_6$ alkyl, optionally substituted $C_2$-$C_8$ alkenyl or optionally substituted $C_2$-$C_8$ alkynyl.

Embodiment 55: The compound of any one of Embodiments 52-54, wherein $R^1$ is optionally substituted $C_1$-$C_6$ alkyl, optionally substituted $C_2$-$C_8$ alkenyl or optionally substituted $C_2$-$C_8$ alkynyl.

Embodiment 56: The compound of any one of Embodiments 52-55, wherein $R^1$ is methyl, ethyl, n-propyl, isopropyl, sec-butyl, tert-butyl, n-butyl, isobutyl, neopentyl (—CH$_2$C(CH$_3$)$_3$), vinyl (—CH=CH$_2$), isopropenyl (—C(=CH$_2$)CH$_3$), 1-propenyl, 2-propenyl (—CH$_2$C=CH$_2$), propargyl (—CH$_2$C≡CH), or n-butenyl.

Embodiment 57: The compound of any one of Embodiments 52-56, wherein $R^3$ is hydrogen, halogen, hydroxyl, amino, alkylamino, dialkylamino, acylamino, thiol, alkylthio, cyano, carbonyl, carboxyl, alkoxycarbonyl, nitro, acyl, acyloxy, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, $C_2$-$C_8$ alkynyl, sulfinyl, sulfonyl, thiocarbonyl, carbamoyl, cycloalkyl, heterocyclyl, aryl or heteroaryl, and each of which can be optionally substituted.

Embodiment 58: The compound of any one of Embodiments 52-57, wherein $R^3$ is hydrogen, halogen, hydroxyl, amino, or $C_1$-$C_6$ alkoxy.

Embodiment 59: The compound of any one of Embodiments 52-58, wherein $R^3$ is hydrogen or halogen.

Embodiment 60: The compound of any one of Embodiments 52-59, wherein $R^3$ is H, F, Cl or Br.

Embodiment 61: The compound of any one of Embodiments 52-60, wherein $R^3$ is H or F.

Embodiment 62: The compound of any one of Embodiments 52-61, wherein $R^4$ is hydrogen, halogen, hydroxyl, amino, alkylamino, dialkylamino, acylamino, thiol, alkylthio, cyano, carbonyl, carboxyl, alkoxycarbonyl, nitro, acyl, acyloxy, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, $C_2$-$C_8$ alkynyl, sulfinyl, sulfonyl, thiocarbonyl, carbamoyl, cycloalkyl, heterocyclyl, aryl or heteroaryl, and each of which can be optionally substituted.

Embodiment 63: The compound of any one of Embodiments 52-62, wherein $R^4$ is hydrogen, halogen, hydroxyl, amino, or $C_1$-$C_6$ alkoxy.

Embodiment 64: The compound of any one of Embodiments 52-63, wherein $R^4$ is hydrogen, amino or $C_1$-$C_6$ alkoxy halogen.

Embodiment 65: The compound of any one of Embodiments 52-64, wherein $R^4$ is H, F, Cl, Br, amino, methoxy, ethoxy, —O-n-propyl, —O-isopropyl, —O-sec-butyl, —O-tert-butyl, —O-n-butyl, O-isobutyl, —O-neopentyl, —O-n-propenyl, or —O-n-butenyl.

Embodiment 66: The compound of any one of Embodiments 52-65, wherein $R^4$ is H, F, amino or methoxy.

Embodiment 67: The compound of any one of Embodiments 52-66, wherein each of $R^3$ and $R^4$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, $C_2$-$C_8$ alkynyl, sulfinyl, sulfonyl, thiocarbonyl, carbamoyl, cycloalkyl, heterocyclyl, aryl or heteroaryl, and each of which can be optionally substituted.

Embodiment 68: The compound of any one of Embodiments 52-67, wherein $R^3$ is hydrogen, halogen, hydroxyl, amino, or $C_1$-$C_6$ alkoxy; and $R^4$ is hydrogen, halogen, hydroxyl, amino, or $C_1$-$C_6$ alkoxy.

Embodiment 69: The compound of any one of Embodiments 53-68, wherein $R^3$ is hydrogen or halogen, and $R^4$ is hydrogen, amino or $C_1$-$C_6$ alkoxy halogen.

Embodiment 70: The compound of any one of Embodiments 52-69, wherein $R^3$ is H, F, Cl or Br, and $R^4$ is H, F, Cl, Br, amino, methoxy, ethoxy, —O-n-propyl, —O-isopropyl, —O-sec-butyl, —O-tert-butyl, —O-n-butyl, O-isobutyl, —O-neopentyl, —O-n-propenyl, or —O-n-butenyl.

Embodiment 71: The compound of Embodiment 70, wherein $R^4$ is H, F, amino or methoxy.

Embodiment 72: The compound of any one of Embodiments 70 or 71, wherein $R^3$ is H or F and $R^4$ is H, F, amino or methoxy.

Embodiment 73: The compound of any one of Embodiments 70-72, wherein $R^3$ and $R^4$ are H.

Embodiment 74: The compound of any one of Embodiments 52-73, wherein the carbon to which $R^3$ and $R^4$ are attached has the R configuration.

Embodiment 75: The compound of any one of Embodiments 52-73, wherein the carbon to which $R^3$ and $R^4$ are attached has the S configuration.

Embodiment 76: The compound of any one of Embodiments 52-75, wherein $R^8$ is

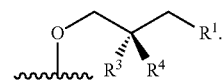

Embodiment 77: The compound of any one of Embodiments 52-76, wherein $R^8$ is

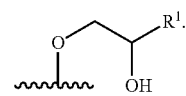

Embodiment 78: The compound of any one of Embodiments 52-77, wherein $R^8$ is

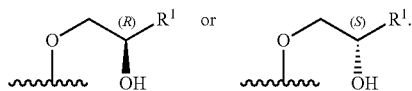

Embodiment 79: The compound of any one of Embodiments 52-78, wherein each $R^8$ is independently

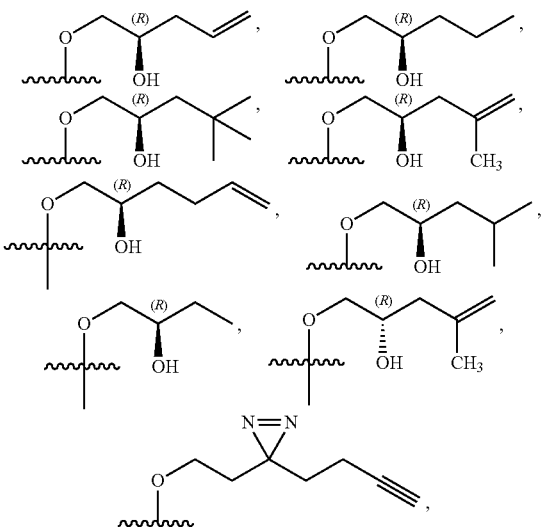

methoxy, ethoxy, —O-n-propyl, —O-isopropyl, —O-sec-butyl, —O-tert-butyl, —O-n-butyl, O-isobutyl, —O-neopentyl, —O-isopropenyl, —O-n-propenyl, and —O-n-butenyl.

Embodiment 80: The compound of any one of Embodiments 52-79, wherein $R^8$ is ethoxy, —O-n-propyl, —O-isopropyl, —O-sec-butyl, —O-tert-butyl, —O-n-butyl, O-isobutyl, —O-neopentyl, —O-isopropenyl, —O-n-propenyl, or —O-n-butenyl.

Embodiment 81: The compound of any one of Embodiments 43-80, wherein each $R^9$ can be hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted.

Embodiment 82: The compound of any one of Embodiments 43-81, wherein each $R^9$ independently is hydrogen, halogen, hydroxyl, amino, alkylamino, dialkylamino, acylamino, thiol, alkylthio, cyano, carbonyl, carboxyl, alkoxycarbonyl, nitro, acyl, acyloxy, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, $C_2$-$C_8$ alkynyl, sulfinyl, sulfonyl, thiocarbonyl, carbamoyl, cycloalkyl, heterocyclyl, aryl or heteroaryl, and each of which can be optionally substituted.

Embodiment 83: The compound of any one of Embodiments 43-82, wherein each $R^9$ independently is hydrogen, halogen, $C_1$-$C_6$ alkyl, or $C_1$-$C_6$alkoxy.

Embodiment 84: The compound of any one of Embodiments 43-83, wherein each $R^9$ is H.

Embodiment 85: The compound of any one of Embodiments 43-84, wherein each $R^{10}$ can be hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted.

Embodiment 86: The compound of any one of Embodiments 43-85, wherein each $R^{10}$ independently is hydrogen, halogen, hydroxyl, amino, alkylamino, dialkylamino, acylamino, thiol, alkylthio, cyano, carbonyl, carboxyl, alkoxycarbonyl, nitro, acyl, acyloxy, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, $C_2$-$C_8$ alkynyl, sulfinyl, sulfonyl, thiocarbonyl, carbamoyl, cycloalkyl, heterocyclyl, aryl or heteroaryl, and each of which can be optionally substituted.

Embodiment 87: The compound of any one of Embodiments 43-86, wherein each $R^{10}$ independently is hydrogen, halogen, $C_1$-$C_6$ alkyl, or $C_1$-$C_6$alkoxy.

Embodiment 88: The compound of any one of Embodiments 43-87, wherein each $R^{10}$ independently is H, F, Cl, Br, methyl, trifluoromethyl, ethyl, propyl, i-propyl, n-butyl, t-butyl, n-pentyl, hexyl, methoxy, ethoxy, —O-n-propyl, —O-isopropyl, —O-sec-butyl, —O-tert-butyl, —O-n-butyl, O-isobutyl, —O-neopentyl, —O-n-propenyl, or —O-n-butenyl.

Embodiment 89: The compound of any one of Embodiments 43-88, wherein each $R^{10}$ independently is H, F, Cl, Br, methyl or methoxy.

Embodiment 90: The compound of any one of Embodiments 43-89, wherein each $R^{11}$ can be hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted.

Embodiment 91: The compound of any one of Embodiments 43-90, wherein each $R^{11}$ independently is hydrogen, halogen, hydroxyl, amino, alkylamino, dialkylamino, acylamino, thiol, alkylthio, cyano, carbonyl, carboxyl, alkoxycarbonyl, nitro, acyl, acyloxy, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, $C_2$-$C_8$ alkynyl, sulfinyl, sulfonyl, thiocarbonyl, carbamoyl, cycloalkyl, heterocyclyl, aryl or heteroaryl, and each of which can be optionally substituted.

Embodiment 92: The compound of any one of Embodiments 43-91, wherein each $R^{11}$ independently is hydrogen, halogen, $C_1$-$C_6$ alkyl, or $C_1$-$C_6$alkoxy.

Embodiment 93: The compound of any one of Embodiments 43-92, wherein each $R^{11}$ independently is H, F, Cl, Br, methyl, trifluoromethyl, ethyl, propyl, i-propyl, n-butyl, t-butyl, n-pentyl, hexyl, methoxy, ethoxy, —O-n-propyl, —O-isopropyl, —O-sec-butyl, —O-tert-butyl, —O-n-butyl, 0-isobutyl, —O-neopentyl, —O-n-propenyl, or —O-n-butenyl.

Embodiment 94: The compound of any one of Embodiments 43-93, wherein each $R^{11}$ independently is H, F, Cl, Br, methyl or methoxy.

Embodiment 95: The compound of any one of Embodiments 43-94, wherein each of $R^{10}$ and $R^{11}$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted.

Embodiment 96: The compound of any one of Embodiments 43-95, wherein each of $R^{10}$ and $R^{11}$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, $C_2$-$C_8$ alkynyl, sulfinyl, sulfonyl, thiocarbonyl, carbamoyl, cycloalkyl, heterocyclyl, aryl or heteroaryl, and each of which can be optionally substituted.

Embodiment 97: The compound of any one of Embodiments 43-96, wherein each of $R^{10}$ and $R^{11}$ independently are hydrogen, halogen, $C_1$-$C_6$ alkyl, or $C_1$-$C_6$alkoxy.

Embodiment 98: The compound of any one of Embodiments 43-97, wherein each of $R^{10}$ and $R^{11}$ independently are H, F, Cl, Br, methyl, trifluoromethyl, ethyl, propyl, i-propyl, n-butyl, t-butyl, n-pentyl, hexyl, methoxy, ethoxy, —O-n-propyl, —O-isopropyl, —O-sec-butyl, —O-tert-butyl, —O-n-butyl, O-isobutyl, —O-neopentyl, —O-n-propenyl, or —O-n-butenyl.

Embodiment 99: The compound of any one of Embodiments 43-98, wherein each of $R^{10}$ and $R^{11}$ independently are H, F, Cl, Br, methyl or methoxy.

Embodiment 100: The compound of any one of Embodiments 43-99, wherein each $R^2$ can be hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted.

Embodiment 101: The compound of any one of Embodiments 43-100, wherein each $R^{12}$ independently is hydrogen, halogen, hydroxyl, amino, alkylamino, dialkylamino, acylamino, thiol, alkylthio, cyano, carbonyl, carboxyl, alkoxycarbonyl, nitro, acyl, acyloxy, $C_1$-$C_6$ alkyl, $C_1$-$C_6$ haloalkyl, $C_1$-$C_6$ heteroalkyl, $C_1$-$C_6$ alkoxy, $C_2$-$C_8$ alkenyl, $C_2$-$C_8$ alkynyl, sulfinyl, sulfonyl, thiocarbonyl, carbamoyl, cycloalkyl, heterocyclyl, aryl or heteroaryl, and each of which can be optionally substituted.

Embodiment 102: The compound of any one of Embodiments 43-101, wherein each $R^{12}$ independently is hydrogen, halogen, $C_1$-$C_6$ alkyl, or $C_1$-$C_6$alkoxy.

Embodiment 103: The compound of any one of Embodiments 43-102, wherein each $R^{12}$ is H.

Embodiment 104: The compound of any one of Embodiments 43-103, wherein $R^9$ and $R^2$ are H.

Embodiment 105: The compound of any one of Embodiments 43-104, wherein at least a vicinal pair formed from selecting two of $R^8$, $R^9$, $R^{10}$, $R^{11}$, or $R^{12}$ and the carbons to which they are attached form an optionally substituted 5- or 6-member cycloalkyl or an optionally substituted 5- or 6-member heterocycle, and the remaining $R^8$, $R^9$, $R^{10}$, $R^{11}$, or $R^{12}$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted.

Embodiment 106: The compound of Embodiment 105, wherein $R^8$ and $R^9$ and the carbons to which they are attached form an optionally substituted 5- or 6-member cycloalkyl or an optionally substituted 5- or 6-member heterocycle.

Embodiment 107: The compound of Embodiment 105, wherein $R^9$ and $R^{10}$ and the carbons to which they are attached form an optionally substituted 5- or 6-member cycloalkyl or an optionally substituted 5- or 6-member heterocycle.

Embodiment 108: The compound of Embodiment 105, wherein $R^{11}$ and $R^{12}$ and the carbons to which they are attached form an optionally substituted 5- or 6-member cycloalkyl or an optionally substituted 5- or 6-member heterocycle.

Embodiment 109: The compound of Embodiment 105, wherein $R^{11}$ and $R^{12}$ and the carbons to which they are attached form an optionally substituted 5- or 6-member cycloalkyl.

Embodiment 110: The compound of Embodiment 105, wherein $R^{10}$ and $R^{11}$ and the carbons to which they are attached form an optionally substituted 5- or 6-member heterocycle.

Embodiment 111: The compound of Embodiment 110, wherein at least one of $Ar^1$ and $Ar^2$ is of the structure

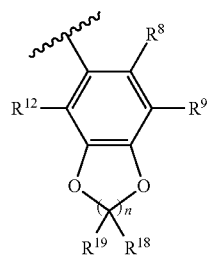

(Ar″), wherein: n is 1 or 2; and each of $R^{18}$ and $R^{19}$ independently are hydrogen or halogen.

Embodiment 112: The compound of Embodiment 111, wherein each of $R^{18}$ and $R^{19}$ are H. In some other embodiments, each of $R^{18}$ and $R^{19}$ halogen.

Embodiment 113: The compound of Embodiment 111, wherein each of $R^{18}$ and $R^{19}$ are F, Cl or Br.

Embodiment 114: The compound of Embodiment 113, wherein each of $R^{18}$ and $R^{19}$ are F.

Embodiment 115: The compound of any one of Embodiments 1-114, wherein at least one of $Ar^1$ and $Ar^2$ is selected from the group consisting of:

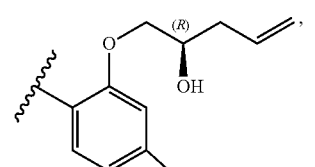

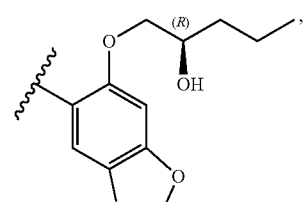

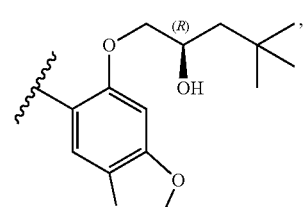

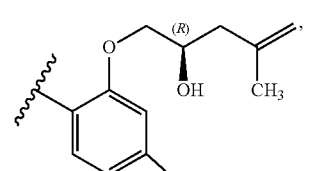

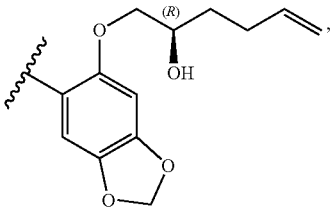

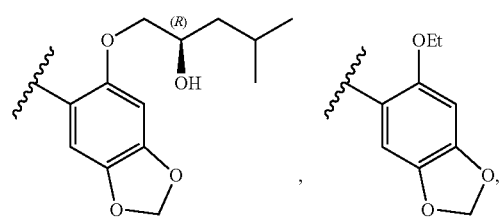

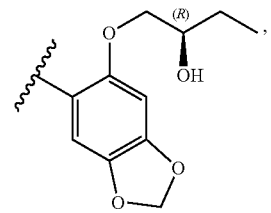

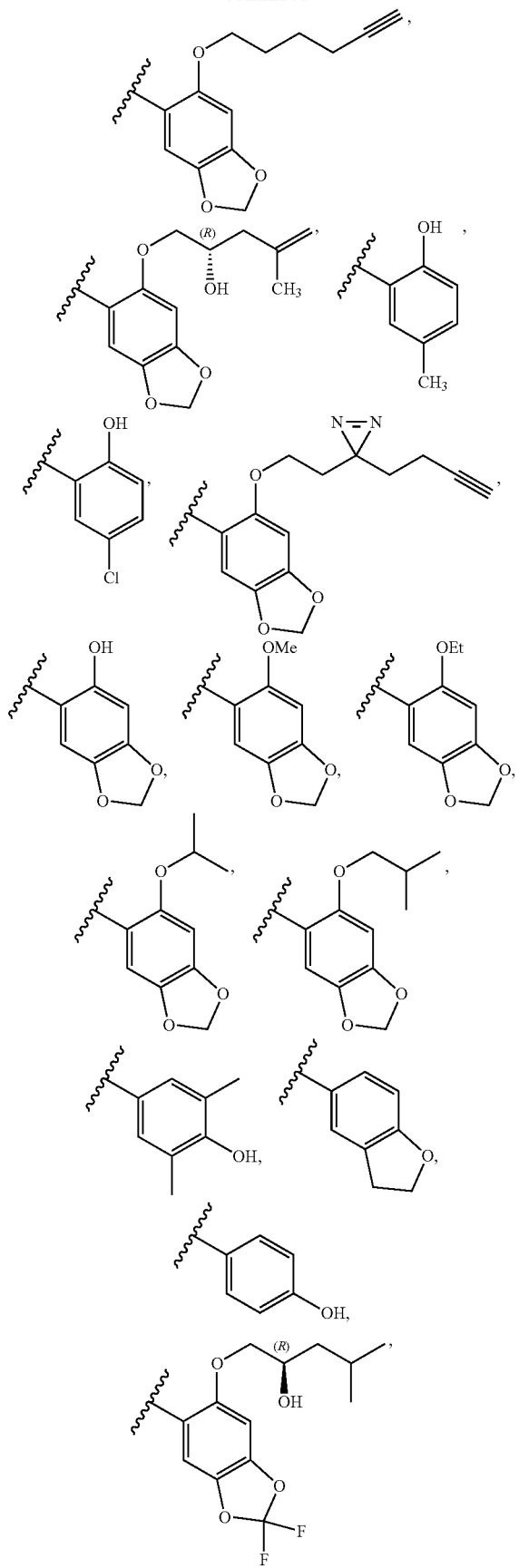

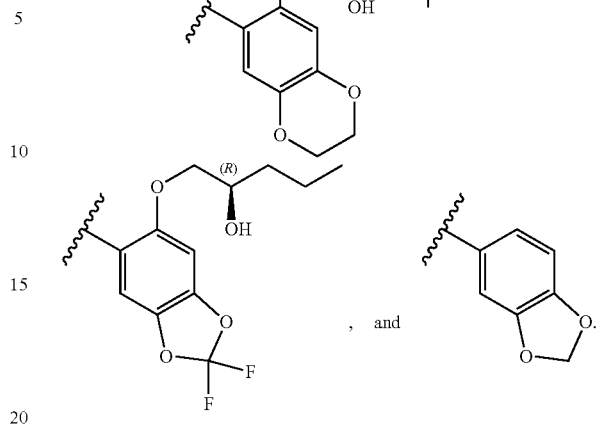

Embodiment 116: The compound of any one of Embodiments 1-115, wherein the compound inhibits an efflux pump.

Embodiment 117: The compound of Embodiment 116, wherein the efflux pump is a microbial or mammalian efflux pump.

Embodiment 118: The compound of Embodiment 116 or 117, wherein the efflux pump is from the major facilitator superfamily (MFS); the ATP-binding cassette superfamily (ABC); the small multidrug resistance family (SMR); the resistance-nodulation-cell division superfamily (RND); or the multi antimicrobial extrusion protein family (MATE).

Embodiment 119: The compound of any one of Embodiments 116-118, wherein the efflux pump is selected from the group consisting of Cdr1, ABCB1(MDR1/Pgp), ABCC1 (MRP1), and ABCG2 (BCRP).

Embodiment 120: The compound of any one of Embodiments 116-119, wherein the efflux pump is Cdr1 or MDR1/Pgp.

Embodiment 121: A composition comprising a compound of any one of Embodiments 1-120.

Embodiment 122: The composition of Embodiment 121, further comprising a therapeutic agent.

Embodiment 123: The composition of Embodiment 122, wherein the therapeutic agent is an efflux pump substrate.

Embodiment 124: The composition of Embodiment 122 or 123, wherein the therapeutic agent is an antimicrobial agent or an anticancer agent.

Embodiment 125: The composition of Embodiment 124, wherein the antimicrobial agent is selected from the group consisting of antifungal agents, antibacterial agents, antiprotozoal agents, and antiviral agents.

Embodiment 126: The composition of Embodiment 124 or 125, wherein the antimicrobial agent is an antifungal agent.

Embodiment 127: The composition of Embodiment 126, wherein the antifungal agent is selected from the group consisting of azoles, polyenes, echinocandins, pradimicins, triclosan, piroctone and its olamine salt, fenpropimorph, and terbinafine.

Embodiment 128: The composition of Embodiment 127, wherein the antifungal agent is an azole.

Embodiment 129: The composition of any one of Embodiments 125-128, wherein the antifungal agent is selected from the group consisting of fluconazole, gepinacin, cerulenin, cycloheximide, itraconazole, econazole, tercoconazole, butoconazole, tioconazole, voriconazole, posaconazole, ravuconazole.

Embodiment 130: The composition of Embodiment 124 or 125, wherein the antimicrobial agent is selected from the group consisting of erythromycin, tetracycline, doxycycline, levofloxacin, ofloxacin, sparfloxacin, doramectin, ivermectin, milbemycin, moxidectin, and selamectin.

Embodiment 131: The composition of Embodiment 124, wherein the anticancer agent is selected from the group consisting of doxorubicin, daunorubicin, actinomycin, camptothecins, epipodophyllotoxins, taxanes, tyrosine kinase inhibitors, and vinca alkaloids.

Embodiment 131: The composition of embodiment 124 or 131, wherein the anticancer agent is selected from the group consisting of doxorubicin, daunorubicin, actinomycin, irinotecan, topotecan, etoposide, teniposide, paclitaxel, docetaxel, rucaparib, olaparib, imatinib, masitinib, nilotinib, toceranib, taxol, gemicitabine, Aldesleukin, Alemtuzumab, alitretinoin, allopurinol, altretamine, amifostine, anastrozole, arsenic trioxide, Asparaginase, BCG Live, bexarotene capsules, bexarotene gel, bleomycin, busulfan intravenous, busulfanoral, calusterone, capecitabine, carboplatin, carmustine, celecoxib, chlorambucil, cisplatin, cladribine, cyclophosphamide, cytarabine, cytarabine liposomal, dacarbazine, dactinomycin, actinomycin D, Darbepoetin alfa, daunorubicin liposomal, daunorubicin, daunomycin, Denileukin diftitox, dexrazoxane, docetaxel, doxorubicin, doxorubicin liposomal, Dromostanolone propionate, Elliott's B Solution, epirubicin, Epoetin alfa estramustine, etoposide phosphate, etoposide (VP-16), exemestane, Filgrastim, floxuridine (intraarterial), fludarabine, fluorouracil (5-FU), fulvestrant, gemtuzumab ozogamicin, goserelin acetate, hydroxyurea, Ibritumomab Tiuxetan, idarubicin, ifosfamide, imatinib mesylate, Interferon alfa-2a, Interferon alfa-2b, irinotecan, letrozole, leucovorin, levamisole, lomustine (CCNU), mechlorethamine (nitrogenmustard), megestrol acetate, melphalan (L-PAM), mercaptopurine (6-MP), mesna, methotrexate, methoxsalen, mitomycin C, mitotane, mitoxantrone, nandrolone phenpropionate, Nofetumomab, LOddC, Oprelvekin, oxaliplatin, pamidronate, pegademase, Pegaspargase, Pegfilgrastim, pentostatin, pipobroman, plicamycin, mithramycin, porfimer sodium, procarbazine, quinacrine, Rasburicase, Rituximab, Sargramostim, streptozocin, talbuvidine (LDT), talc, tamoxifen, temozolomide, teniposide (VM-26), testolactone, thioguanine (6-TG), thiotepa, topotecan, toremifene, Tositumomab, Trastuzumab, tretinoin (ATRA), Uracil Mustard, valrubicin, valtorcitabine (monoval LDC), vinblastine, vinorelbine, and zoledronate.

Embodiment 133: The composition of any one of Embodiments 121-132, wherein the composition is a pharmaceutical composition.

Embodiment 134: A method of inhibiting an efflux pump in a cell, the method comprising administering to the cell a compound of any one of Embodiments 1-120.

Embodiment 135: The method of Embodiment 134, wherein the cell is a drug-resistant cell.

Embodiment 13: The method of Embodiment 135, wherein the drug resistance is at least partly efflux pump-mediated Embodiment 137: The method of any one of Embodiments 134-136, wherein the cell is a microbial cell, optionally the microbial cell is a microbial pathogen that is resistant to one or more antimicrobial agents.

Embodiment 138: The method of any one of Embodiments 134-137, wherein the cell is a fungal cell.

Embodiment 139: The method of any one of Embodiments 134-138, wherein the cell is a fungal cell from the genus Candida spp., Cryptococcus spp., or Aspergillus spp.

Embodiment 140: The method of any one of Embodiments 134-140, wherein cell is a fungal cell from C. auris, C. albicans, C. neoformans or A. fumigatus, optionally, the fungal cell is from C. auris.

Embodiment 141: The method of any one of Embodiments 134-136, wherein the cell is a cancer cell, optionally, the cancer cell is from a drug-resistant cancer.

Embodiment 142: A method of enhancing the efficacy of an antimicrobial agent against a microbial pathogen, the method comprising contacting the microbial pathogen with a compound of any one of Embodiments 1-120, and optionally with the antimicrobial agent.

Embodiment 143: A method of re-sensitizing a microbial pathogen to an antimicrobial agent, the method comprising the method comprising contacting the microbial pathogen with a compound of any one of Embodiments 1-120, and optionally with the antimicrobial agent.

Embodiment 144: A method of treating a microbial infection in a subject, the method comprising administering to a subject in need thereof a compound of any one of Embodiments 1-120 and, optionally co-administering an antimicrobial agent.

Embodiment 145: The method of any one of Embodiments 142-143, the microbial pathogen is resistant to the therapeutic agent.

Embodiment 146: The method of Embodiment 145, wherein the resistance is at least partly efflux pump-mediated.

Embodiment 147: The method of any one of Embodiments 142-146, wherein the microbial pathogen is selected from the group consisting of a fungal, bacterial, parasitic, protozoan or viral pathogen.

Embodiment 148: The method of any one of Embodiments 142-147, wherein the microbial pathogen is a fungal pathogen.

Embodiment 149: The method of any one of Embodiments 142-148, wherein the microbial pathogen is selected from the group consisting of Candida spp., Cryptococcus spp., and Aspergillus spp.

Embodiment 150: The method of any one of Embodiments 142-149, wherein the microbial pathogen is C. auris, C. albicans, C. neoformans or A. fumigatus, optionally, the microbial pathogen is C. auris.

Embodiment 151: The method of any one of Embodiments 142-151, wherein the antimicrobial agent is selected from the group consisting of azoles, polyenes, echinocandins, pradimicins, triclosan, piroctone and its olamine salt, fenpropimorph, and terbinafine.

Embodiment 152: The composition of Embodiment 151, wherein the antifungal agent is an azole.

Embodiment 153: The composition of any one of Embodiments 151 or 152, wherein the antifungal agent is selected from the group consisting of fluconazole, gepinacin, cerulenin, cycloheximide, itraconazole, econazole, tercoconazole, butoconazole, tioconazole, voriconazole, posaconazole, ravuconazole.

Embodiment 154: The composition of any one of Embodiments 142-147, wherein the antimicrobial agent is selected from the group consisting of erythromycin, tetracycline, doxycycline, levofloxacin, ofloxacin, sparfloxacin, doramectin, ivermectin, milbemycin, moxidectin, and selamectin.

Embodiment 155: A method of enhancing the efficacy of a therapeutic agent against disease or disorder in a subject, the method comprising administering to a subject in need thereof, a compound of any one of Embodiments 1-120, and optionally co-administering the therapeutic agent.

Embodiment 156: A method of re-sensitizing a disease or disorder in a subject to a therapeutic agent the method comprising administering to a subject in need thereof, a compound of any one of Embodiments 1-120, and optionally co-administering the therapeutic agent.

Embodiment 157: A method of treating a disease or disorder in a subject, the method comprising administering to a subject in need thereof a compound of any one of Embodiments 1-120 and, optionally co-administering a therapeutic agent.

Embodiment 158: The method of any one of Embodiments 155-157, wherein the disease or disorder is resistant to the therapeutic agent.

Embodiment 159: The method of Embodiment 158, wherein the resistance is at least partly efflux pump-mediated.

Embodiment 160: The method of any one of Embodiment 155-159, wherein the disease or disorder is cancer.

Embodiment 161: The method of Embodiment 160, wherein the therapeutic agent is an anticancer agent.

Embodiment 162: The method of Embodiment 161, wherein the anticancer agent is selected from the group consisting of doxorubicin, daunorubicin, actinomycin, camptothecins, epipodophyllotoxins, taxanes, tyrosine kinase inhibitors, and vinca alkaloids.

Embodiment 163: The composition of Embodiment 161 or 162, wherein the anticancer agent is selected from the group consisting of doxorubicin, daunorubicin, actinomycin, irinotecan, topotecan, etoposide, teniposide, paclitaxel, docetaxel, rucaparib, olaparib, imatinib, masitinib, nilotinib, toceranib, taxol, gemicitabine, Aldesleukin, Alemtuzumab, alitretinoin, allopurinol, altretamine, amifostine, anastrozole, arsenic trioxide, Asparaginase, BCG Live, bexarotene capsules, bexarotene gel, bleomycin, busulfan intravenous, busulfanoral, calusterone, capecitabine, carboplatin, carmustine, celecoxib, chlorambucil, cisplatin, cladribine, cyclophosphamide, cytarabine, cytarabine liposomal, dacarbazine, dactinomycin, actinomycin D, Darbepoetin alfa, daunorubicin liposomal, daunorubicin, daunomycin, Denileukin diftitox, dexrazoxane, docetaxel, doxorubicin, doxorubicin liposomal, Dromostanolone propionate, Elliott's B Solution, epirubicin, Epoetin alfa estramustine, etoposide phosphate, etoposide (VP-16), exemestane, Filgrastim, floxuridine (intraarterial), fludarabine, fluorouracil (5-FU), fulvestrant, gemtuzumab ozogamicin, goserelin acetate, hydroxyurea, Ibritumomab Tiuxetan, idarubicin, ifosfamide, imatinib mesylate, Interferon alfa-2a, Interferon alfa-2b, irinotecan, letrozole, leucovorin, levamisole, lomustine (CCNU), mechlorethamine (nitrogenmustard), megestrol acetate, melphalan (L-PAM), mercaptopurine (6-MP), mesna, methotrexate, methoxsalen, mitomycin C, mitotane, mitoxantrone, nandrolone phenpropionate, Nofetumomab, LOddC, Oprelvekin, oxaliplatin, pamidronate, pegademase, Pegaspargase, Pegfilgrastim, pentostatin, pipobroman, plicamycin, mithramycin, porfimer sodium, procarbazine, quinacrine, Rasburicase, Rituximab, Sargramostim, streptozocin, talbuvidine (LDT), talc, tamoxifen, temozolomide, teniposide (VM-26), testolactone, thioguanine (6-TG), thiotepa, topotecan, toremifene, Tositumomab, Trastuzumab, tretinoin (ATRA), Uracil Mustard, valrubicin, valtorcitabine (monoval LDC), vinblastine, vinorelbine, and zoledronate.

Some Selected Definitions

For convenience, certain terms employed herein, in the specification, examples and appended claims are collected herein. Unless stated otherwise, or implicit from context, the following terms and phrases include the meanings provided below Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and *Current Protocols in Protein Sciences* 2009, Wiley Intersciences, Coligan et al., eds.

Other than in the operating examples, or where otherwise indicated, all numbers expressing quantities of ingredients or reaction conditions used herein should be understood as modified in all instances by the term "about." The term "about" when used to described the present invention, in connection with percentages means ±1%, ±1.5%, ±2%, ±2.5%, ±3%, ±3.5%, ±4%, +4.5%, or +5%.

The singular terms "a," "an," and "the" include plural referents unless context clearly indicates otherwise. Similarly, the word "or" is intended to include "and" unless the context clearly indicates otherwise.

As used herein the terms "comprising" or "comprises" means "including" or "includes" and are used in reference to compositions, methods, systems, and respective component(s) thereof, that are useful to the invention, yet open to the inclusion of unspecified elements, whether useful or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, systems, and respective components thereof as described herein, which are exclusive of any element not recited in that description of the embodiment.

The abbreviation, "e.g." is derived from the Latin exempli gratia, and is used herein to indicate a non-limiting example. Thus, the abbreviation "e.g." is synonymous with the term "for example."

The terms "significantly different than,", "statistically significant," and similar phrases refer to comparisons between data or other measurements, wherein the differences between two compared data or other measurements are evidently or reasonably different to the trained observer, or statistically significant (if the phrase includes the term "statistically" or if there is some indication of statistical test, such as a p-value, or if the data, when analyzed, produce a statistical difference by standard statistical tests known in the art).

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g. absent level as compared to a reference sample), or any decrease between 10-100% as compared to a reference level.

The term "a reference level" as used herein refer to a negative control. For example, in the context of treatment, a reference level is the level if a subject is not treated. In some embodiments, a reference level in the context of diagnosis is the level present in a normal healthy subject. The term "normal healthy subject" refers to a subject who has no symptoms of any diseases or disorders, or who is not identified with any diseases or disorders, or who is not on any medication treatment, or a subject who is identified as healthy by physicians based on medical examinations. In some embodiments, a reference level used herein refers to the level measured prior to onset of treatment.

As used herein, the terms "treat," "treatment," "treating," or "amelioration" are used herein to characterize a method or process that is aimed at (1) delaying or preventing the onset of a disease or condition; (2) slowing down or stopping the progression, aggravation, or deterioration of the symptoms of the disease or condition; (3) bringing about ameliorations of the symptoms of the disease or condition; or (4) curing the disease or condition. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased morbidity or mortality. The term "treatment" of a disease also includes providing relief from the symptoms or side-effects of the disease (including palliative treatment). A treatment can be administered prior to the onset of the disease, for a prophylactic or preventive action. Alternatively, or additionally, the treatment can be administered after initiation of the disease or condition, for a therapeutic action.

In some embodiments, treatment is therapeutic and does not include prophylactic treatment.

As used herein, the term "subject" refers to any living organism which can be administered compound and/or pharmaceutical compositions of the present invention. The term includes, but is not limited to, humans, non-human primates such as chimpanzees and other apes and monkey species; farm animals such as cattle, sheep, pigs, goats and horses, domestic subjects such as dogs and cats, laboratory animals including rodents such as mice, rats and guinea pigs, and the like. The term does not denote a particular age or sex. Thus, adult, child and newborn subjects, whether male or female, are intended to be covered. The term "subject" is also intended to include living organisms susceptible to conditions or disease states as generally disclosed, but not limited to, throughout this specification. Examples of subjects include humans, dogs, cats, cows, goats, and mice. The term subject is further intended to include transgenic species. The term "subject" and "individual" are used interchangeably herein, and refer to an animal, for example a human or non-human mammals/animals, to whom treatment, including prophylactic treatment, with the compounds and compositions according to the present invention, is provided. The term "non-human animals" and "non-human mammals" are used interchangeably herein and include all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc.

In some embodiments, the subject is a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used as subjects that represent animal models of a fibrotic disease or disorder.

It is noted that a human subject can be of any age, gender, race or ethnic group, e.g., Caucasian (white), Asian, African, black, African American, African European, Hispanic, Middle eastern, etc. . . . . .

In addition, the methods described herein can be used to treat domesticated animals and/or pets. A subject can be male or female. A subject can be one who has been previously diagnosed with or identified as suffering from or having a disease or disorder needing treatment, but need not have already undergone treatment. For example, the subject can be one who has been previously diagnosed with or identified as suffering from or having a microbial infection, e.g., a fungal infection.

In some embodiments of any one of the aspects, the subject is human.

The term "disorder" or "disease" used interchangeably herein, refers to any alteration in the state of the body or of some of its organs, interrupting or disturbing the performance of the functions and/or causing symptoms such as discomfort, dysfunction, distress, or even death to the person afflicted or those in contact with the person. A disease or disorder can also relate to distemper, ailing, ailment, malady, disorder, sickness, illness, complaint, indisposition, affection. In some embodiments of any one of the aspects, the disorder or disease is a microbial infection. For example, a drug resistant microbial infection, such as a drug resistant microbial infection where the resistance is at least partly efflux pump-mediated. In some embodiments of any one of the aspects, the disorder or disease is a cancer. For example, a drug resistant cancer, such as a drug resistant cancer where the resistance is at least partly efflux pump-mediated.

The term "cancer" and "malignancy" are used interchangeably herein, and refer to a disease that is characterized by uncontrolled, abnormal growth of cells. Cancer cells can spread locally or through the bloodstream and lymphatic system to other parts of the body. The term is also intended to include any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer. The term cancer also includes metastases which are cancer cells (e.g. a primary tumor, or a metastasis tumor) which has migrated to other locations in the subject and to establish new tumors at such locations.

Exemplary cancers include, but are not limited to acoustic neuroma, acute lymphoblastic leukemia (ALL), adenocarcinoma, angiosarcoma, astrocytoma, basal cell carcinoma, B-cell lymphoma, bile duct carcinoma, bladder cancer, bone cancer, brain tumor, breast cancer, bronchogenic carcinoma, cancer of the peritoneum, cervical cancer, chondrosarcoma, chordoma, choriocarcinoma, chronic lymphocytic leukemia (CLL), colon carcinoma, colorectal cancer, craniopharyngioma, cystadenocarcinoma, embryonal carcinoma, endometrial or uterine carcinoma, endotheliosarcoma, ependymoma, epithelial carcinoma, Ewing's tumor, fibrosarcoma, gastric cancer, glioblastoma, Hairy cell leukemia, head and neck cancer, heavy chain disease, hemangioblastoma, hepatocellular cancer, kidney or renal cancer, leiomyosarcoma, liposarcoma, liver cancer, lung carcinoma, lymphangioendothelial sarcoma, lymphangiosarcoma, lymphoma (Hodgkin's disease and non-Hodgkin's disease), medullary carcinoma, medulloblastoma, melanoma, meningioma, mesothelioma, multiple myeloma, myeloblastic leukemia, myxosarcoma, neuroblastoma, oligodendroglioma, osteogenic sarcoma, ovarian cancer, pancreatic cancer, papillary adenocarcinomas, papillary carcinoma, pinealoma, polycythemia vera, prostate cancer, renal cell carcinoma, retinoblastoma; leukemia (e.g. acute lymphocytic leukemia, chronic lymphocytic leukemia (CLL) and acute myeloid leukemia (myeloblastic; promyelocytic, myelomonocytic, monocytic and erythroleukemia), chronic leukemia (chronic myelocytic (granulocytic) leukemia and chronic lymphocytic leukemia)), rhabdomyosarcoma, salivary gland carcinoma, sebaceous gland carcinoma, seminoma, small cell lung carcinoma, squamous cell carcinoma, sweat gland carcinoma, synovial sarcoma, synovioma, testicular cancer, thyroid cancer, vulvar cancer, Waldenstrom macroglobulinemia, and Wilms' tumor.

A "cancer cell" refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage dependence, proliferation, malignancy, lack of contact inhibition and density limitation of growth, lack of growth factor or serum dependence, tumor specific markers levels, invasiveness, tumor growth in suitable animal hosts such as nude mice, and the like, in vitro, in vivo, and ex vivo (see also Freshney, Culture of Animal Cells: A Manual of Basic Technique (3rd ed. 1994)).

As used herein, the term "alkyl" refers to an aliphatic hydrocarbon group which can be straight or branched having 1 to about 60 carbon atoms in the chain, and which preferably have about 6 to about 50 carbons in the chain. "Lower alkyl" refers to an alkyl group having 1 to about 8 carbon atoms. "Higher alkyl" refers to an alkyl group having about 10 to about 20 carbon atoms. The alkyl group can be optionally substituted with one or more alkyl group substituents which can be the same or different, where "alkyl group substituent" includes halo, amino, aryl, hydroxy, alkoxy, aryloxy, alkyloxy, alkylthio, arylthio, aralkyloxy, aralkylthio, carboxy, alkoxycarbonyl, oxo and cycloalkyl. "Branched" refers to an alkyl group in which a lower alkyl group, such as methyl, ethyl or propyl, is attached to a linear alkyl chain. Exemplary alkyl groups include methyl, ethyl, propyl, i-propyl, n-butyl, t-butyl, n-pentyl, hexyl, heptyl, octyl, decyl, dodecyl, tridecyl, tetradecyl, pentadecyl and hexadecyl. Useful alkyl groups include branched or straight chain alkyl groups of 6 to 50 carbon, and also include the lower alkyl groups of 1 to about 4 carbons and the higher alkyl groups of about 12 to about 16 carbons.

A "heteroalkyl" group substitutes any one of the carbons of the alkyl group with a heteroatom having the appropriate number of hydrogen atoms attached (e.g., a $CH_2$ group to an NH group or an O group). The term "heteroalkyl" include optionally substituted alkyl, alkenyl and alkynyl radicals which have one or more skeletal chain atoms selected from an atom other than carbon, e.g., oxygen, nitrogen, sulfur, phosphorus, silicon, or combinations thereof. In certain embodiments, the heteroatom(s) is placed at any interior position of the heteroalkyl group. Examples include, but are not limited to, $—CH_2—O—CH_3$, $—CH_2—CH_2—O—CH_3$, $—CH_2—NH—CH_3$, $—CH_2—CH_2—NH—CH_3$, $—CH_2—N(CH_3)—CH_3$, $—CH_2—CH_2—NH—CH_3$, $—CH_2—CH_2—N(CH_3)—CH_3$, $—CH_2—S—CH_2—CH_3$, $—CH_2—CH_2$, $—S(O)—CH_3$, $—CH_2—CH_2—S(O)_2—CH_3$, $—CH=CH—O—CH_3$, $—Si(CH_3)_3$, $—CH_2—CH=N—OCH_3$, and $—CH=CH—N(CH_3)—CH_3$. In some embodiments, up to two heteroatoms are consecutive, such as, by way of example, $—CH_2—NH—OCH_3$ and $—CH_2—O—Si(CH_3)_3$ As used herein, the term "alkenyl" refers to an alkyl group containing at least one carbon-carbon double bond. The alkenyl group can be optionally substituted with one or more "alkyl group substituents." Exemplary alkenyl groups include vinyl, allyl, n-pentenyl, decenyl, dodecenyl, tetradecadienyl, heptadec-8-en-1-yl and heptadec-8,11-dien-1-yl.

As used herein, the term "alkynyl" refers to an alkyl group containing a carbon-carbon triple bond. The alkynyl group can be optionally substituted with one or more "alkyl group substituents." Exemplary alkynyl groups include ethynyl, propargyl, n-pentynyl, decynyl and dodecynyl. Useful alkynyl groups include the lower alkynyl groups.

As used herein, the term "cycloalkyl" refers to a non-aromatic mono- or multicyclic ring system of about 3 to about 12 carbon atoms. The cycloalkyl group can be optionally partially unsaturated. The cycloalkyl group can be also optionally substituted with an aryl group substituent, oxo and/or alkylene. Representative monocyclic cycloalkyl rings include cyclopentyl, cyclohexyl and cycloheptyl. Useful multicyclic cycloalkyl rings include adamantyl, octahydronaphthyl, decalin, camphor, camphane, and noradamantyl.

"Heterocyclyl" refers to a nonaromatic 3-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$heterocyclyl and $C_x$-$C_y$heterocyclyl are typically used where X and Y indicate the number of carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like.

"Aryl" refers to an aromatic carbocyclic radical containing about 3 to about 13 carbon atoms. The aryl group can be optionally substituted with one or more aryl group substituents, which can be the same or different, where "aryl group substituent" includes alkyl, alkenyl, alkynyl, aryl, aralkyl, hydroxy, alkoxy, aryloxy, aralkoxy, carboxy, aroyl, halo, nitro, trihalomethyl, cyano, alkoxycarbonyl, aryloxycarbonyl, aralkoxycarbonyl, acyloxy, acylamino, aroylamino, carbamoyl, alkylcarbamoyl, dialkylcarbamoyl, arylthio, alkylthio, alkylene and —NRR', where R and R' are each independently hydrogen, alkyl, aryl and aralkyl. Exemplary aryl groups include substituted or unsubstituted phenyl and substituted or unsubstituted naphthyl.

"Heteroaryl" refers to an aromatic 3-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively.

Exemplary aryl and heteroaryls include, but are not limited to, phenyl, pyridinyl, pyrimidinyl, furanyl, thienyl, imidazolyl, thiazolyl, pyrazolyl, pyridazinyl, pyrazinyl, triazinyl, tetrazolyl, indolyl, benzyl, naphthyl, anthracenyl, azulenyl, fluorenyl, indanyl, indenyl, naphthyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a substituent.

As used herein, the term "halogen" or "halo" refers to an atom selected from fluorine, chlorine, bromine and iodine. The term "halogen radioisotope" or "halo isotope" refers to a radionuclide of an atom selected from fluorine, chlorine, bromine and iodine.

A "halogen-substituted moiety" or "halo-substituted moiety", as an isolated group or part of a larger group, means an aliphatic, alicyclic, or aromatic moiety, as described herein, substituted by one or more "halo" atoms, as such terms are defined in this application.

The term "haloalkyl" as used herein refers to alkyl and alkoxy structures structure with at least one substituent of fluorine, chorine, bromine or iodine, or with combinations thereof. In embodiments, where more than one halogen is included in the group, the halogens are the same or they are different. The terms "fluoroalkyl" and "fluoroalkoxy" include haloalkyl and haloalkoxy groups, respectively, in which the halo is fluorine. Exemplary halo-substituted alkyl includes haloalkyl, dihaloalkyl, trihaloalkyl, perhaloalkyl and the like (e.g. halosubstituted ($C_1$-$C_3$)alkyl includes chloromethyl, dichloromethyl, difluoromethyl, trifluoromethyl ($CF_3$), perfluoroethyl, 2,2,2-trifluoroethyl, 2,2,2-trifluoro-1,1-dichloroethyl, and the like).

As used herein, the term "amino" means —$NH_2$. The term "alkylamino" means a nitrogen moiety having one straight or branched unsaturated aliphatic, cyclyl, or heterocyclyl radicals attached to the nitrogen, e.g., —NH(alkyl). The term "dialkylamino" means a nitrogen moiety having at two straight or branched unsaturated aliphatic, cyclyl, or heterocyclyl radicals attached to the nitrogen, e.g., —N(alkyl)(alkyl). The term "alkylamino" includes "alkenylamino," "alkynylamino," "cyclylamino," and "heterocyclylamino." The term "arylamino" means a nitrogen moiety having at least one aryl radical attached to the nitrogen. For example, —NHaryl, and N(aryl)$_2$. The term "heteroarylamino" means a nitrogen moiety having at least one heteroaryl radical attached to the nitrogen. For example —NHheteroaryl, and —N(heteroaryl)$_2$. Optionally, two substituents together with the nitrogen can also form a ring. Unless indicated otherwise, the compounds described herein containing amino moieties can include protected derivatives thereof. Suitable protecting groups for amino moieties include acetyl, tertbutoxycarbonyl, benzyloxycarbonyl, and the like. Exemplary alkylamino includes, but is not limited to, NH($C_1$-$C_{10}$alkyl), such as —$NHCH_3$, —$NHCH_2CH_3$, —$NHCH_2CH_2CH_3$, and —$NHCH(CH_3)_2$. Exemplary dialkylamino includes, but is not limited to, —N($C_1$-$C_{10}$alkyl)$_2$, such as N($CH_3$)$_2$, —N($CH_2CH_3$)$_2$, —N($CH_2CH_2CH_3$)$_2$, and —N(CH($CH_3$)$_2$)$_2$.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an ($C_2$-$C_6$) aminoalkyl refers to a chain comprising between 2 and 6 carbons and one or more nitrogen atoms positioned between the carbon atoms.

The terms "hydroxy" and "hydroxyl" mean the radical —OH.

The terms "alkoxyl" or "alkoxy" as used herein refers to an alkyl group, as defined above, having an oxygen radical attached thereto, and can be represented by one of —O- alkyl, —O-alkenyl, and —O-alkynyl. Aroxy can be represented by —O-aryl or O-heteroaryl, wherein aryl and heteroaryl are as defined herein. The alkoxy and aroxy groups can be substituted as described above for alkyl. Exemplary alkoxy groups include, but are not limited to O-methyl, O-ethyl, O-n-propyl, O-isopropyl, O-n-butyl, O-isobutyl, O-sec-butyl, O-tert-butyl, O-pentyl, O-hexyl, O-cyclopropyl, O-cyclobutyl, O-cyclopentyl, O-cyclohexyl and the like.

As used herein, the term "carbonyl" means the radical —C(O)—. It is noted that the carbonyl radical can be further substituted with a variety of substituents to form different carbonyl groups including acids, acid halides, amides, esters, ketones, and the like.

The term "carboxy" means the radical —C(O)O—. It is noted that compounds described herein containing carboxy moieties can include protected derivatives thereof, i.e., where the oxygen is substituted with a protecting group. Suitable protecting groups for carboxy moieties include benzyl, tert-butyl, and the like. As used herein, a carboxy group includes —COOH, i.e., carboxyl group.

The term "ester" refers to a chemical moiety with formula —C(=O)OR, where R is selected from the group consisting of alkyl, cycloalkyl, aryl, heteroaryl and heterocycloalkyl.

The term "cyano" means the radical —CN.

The term "nitro" means the radical —NO$_2$.

The term, "heteroatom" refers to an atom that is not a carbon atom. Particular examples of heteroatoms include, but are not limited to nitrogen, oxygen, sulfur and halogens. A "heteroatom moiety" includes a moiety where the atom by which the moiety is attached is not a carbon. Examples of heteroatom moieties include —N=, —NR$^N$—, —N$^+$(O$^-$)=, —O—, —S— or —S(O)$_2$—, —OS(O)$_2$—, and —SS—, wherein R$^N$ is H or a further substituent.

The terms "alkylthio" and "thioalkoxy" refer to an alkoxy group, as defined above, where the oxygen atom is replaced with a sulfur. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

The term "sulfinyl" means the radical —SO—. It is noted that the sulfinyl radical can be further substituted with a variety of substituents to form different sulfinyl groups including sulfinic acids, sulfinamides, sulfinyl esters, sulfoxides, and the like.

The term "sulfonyl" means the radical —SO$_2$—. It is noted that the sulfonyl radical can be further substituted with a variety of substituents to form different sulfonyl groups including sulfonic acids (—SO$_3$H), sulfonamides, sulfonate esters, sulfones, and the like.

The term "thiocarbonyl" means the radical —C(S)—. It is noted that the thiocarbonyl radical can be further substituted with a variety of substituents to form different thiocarbonyl groups including thioacids, thioamides, thioesters, thioketones, and the like.

"Acyl" refers to an alkyl-CO— group, wherein alkyl is as previously described. Exemplary acyl groups comprise alkyl of 1 to about 30 carbon atoms. Exemplary acyl groups also include acetyl, propanoyl, 2-methylpropanoyl, butanoyl and palmitoyl.

"Aroyl" means an aryl-CO— group, wherein aryl is as previously described. Exemplary aroyl groups include benzoyl and 1- and 2-naphthoyl.

"Arylthio" refers to an aryl-S— group, wherein the aryl group is as previously described. Exemplary arylthio groups include phenylthio and naphthylthio.

"Aralkyl" refers to an aryl-alkyl- group, wherein aryl and alkyl are as previously described. Exemplary aralkyl groups include benzyl, phenylethyl and naphthylmethyl.

"Aralkyloxy" refers to an aralkyl-O— group, wherein the aralkyl group is as previously described. An exemplary aralkyloxy group is benzyloxy.

"Aralkylthio" refers to an aralkyl-S— group, wherein the aralkyl group is as previously described. An exemplary aralkylthio group is benzylthio.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an H$_2$N—CO— group.

"Alkylcarbamoyl" refers to a R'RN—CO— group, wherein one of R and R' is hydrogen and the other of R and R' is alkyl as previously described.

"Dialkylcarbamoyl" refers to R'RN—CO— group, wherein each of R and R' is independently alkyl as previously described.

"Acyloxy" refers to an acyl-O— group, wherein acyl is as previously described. "Acylamino" refers to an acyl-NH— group, wherein acyl is as previously described. "Aroylamino" refers to an aroyl-NH— group, wherein aroyl is as previously described.

The term "optionally substituted" means that the specified group or moiety is unsubstituted or is substituted with one or more (typically 1, 2, 3, 4, 5 or 6 substituents) independently selected from the group of substituents listed below in the definition for "substituents" or otherwise specified. The term "substituents" refers to a group "substituted" on a substituted group at any atom of the substituted group. Suitable substituents include, without limitation, halogen, hydroxy, caboxy, oxo, nitro, haloalkyl, alkyl, alkenyl, alkynyl, alkaryl, aryl, heteroaryl, cyclyl, heterocyclyl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano or ureido. In some cases, two substituents, together with the carbons to which they are attached to can form a ring.

For example, any alkyl, alkenyl, cycloalkyl, heterocyclyl, heteroaryl or aryl is optionally substituted with 1, 2, 3, 4 or 5 groups selected from OH, CN, SH, SO$_2$NH$_2$, SO$_2$(C$_1$-C$_4$) alkyl, SO$_2$NH(C$_1$-C$_4$)alkyl, halogen, carbonyl, thiol, cyano, NH$_2$, NH(C$_1$-C$_4$)alkyl, N[(C$_1$-C$_4$)alkyl]$_2$, C(O)NH$_2$, COOH, COOMe, acetyl, (C$_1$-C$_8$)alkyl, O(C$_1$-C$_8$)alkyl, O(C$_1$-C$_8$)haloalkyl, (C$_2$-C$_8$)alkenyl, (C$_2$-C$_8$)alkynyl, haloalkyl, thioalkyl, cyanomethylene, alkylaminyl, aryl, heteroaryl, substituted aryl, NH$_2$—C(O)-alkylene, NH(Me)-C(O)-alkylene, CH$_2$—C(O)-alkyl, C(O)-alkyl, alkylcarbonylaminyl, CH$_2$—[CH(OH)]$_m$—(CH$_2$)$_p$—OH, CH$_2$—[CH(OH)]$_m$—(CH$_2$)$_p$ NH$_2$ or CH$_2$-aryl-alkoxy; or wherein any alkyl, cycloalkyl or heterocyclyl is optionally substituted with oxo; "m" and "p" are independently 1, 2, 3, 4, 5 or 6.

In some embodiments, an optionally substituted group is substituted with 1 substituent. In some other embodiments, an optionally substituted group is substituted with 2 independently selected substituents, which can be same or different. In some other embodiments, an optionally substituted group is substituted with 3 independently selected substituents, which can be same, different or any combination of same and different. In still some other embodiments, an optionally substituted group is substituted with 4 independently selected substituents, which can be same, different or any combination of same and different. In yet some other embodiments, an optionally substituted group is substituted with 5 independently selected substituents, which can be same, different or any combination of same and different.

An "isocyanato" group refers to a NCO group.
A "thiocyanato" group refers to a CNS group.
An "isothiocyanato" group refers to a NCS group.
"Alkoyloxy" refers to a RC(=O)O— group.
"Alkoyl" refers to a RC(=O)— group.

The phrase "racemic mixture" refers to a mixture of the two enantiomers of one compound. An ideal racemic mixture is one wherein there is a 50:50 mixture of both enantiomers of a compound such that the optical rotation of the (+) enantiomers cancels out the optical rotation of the (−) enantiomers.

It should be understood that this disclosure is not limited to the particular methodology, protocols, and reagents, etc., provided herein and as such may vary. The terminology used herein is for the purpose of describing particular embodiments only, and is not intended to limit the scope of the present disclosure, which is defined solely by the claims. The invention is further illustrated by the following example, which should not be construed as further limiting.

EXAMPLES

Example 1: An Oxindole Efflux Inhibitor Potentiates Azoles and Impairs Virulence in the Fungal Pathogen *Candida auris*

Rapidly increasing antimicrobial resistance is threating human health world-wide. This threat is amplified by the emergence and spread of novel multidrug-resistant organisms, exemplified by the human fungal pathogen *Candida auris*. Concern regarding *C. auris* is driven by widespread drug resistance amongst isolates of this recently discovered pathogen, specifically resistance to the most commonly prescribed antifungal fluconazole. Particularly alarming is the propensity of *C. auris* to cause outbreaks due to its capacity to persist on surfaces and spread through health care settings serving vulnerable patient populations. To address the urgent need for new strategies to combat *C. auris* drug-resistance, a diversity-oriented synthetic compound library in combination with fluconazole was screened. Through this screen, bis-benzodioxolylindolinone (azoffluxin, CMLD012336) was identified to potently synergized with fluconazole against *C. auris*. Using biochemical and genetic approaches, it was determined that azoffluxin enhanced fluconazole bioactivity through the inhibition of the major efflux pump Cdr1, which increased intracellular fluconazole accumulation. Although this activity was conserved across most *C. auris* clades, isolates from Clade III were recalcitrant to azoffluxin, implicating Cdr1-independent molecular mechanisms in the azole-resistance of these strains. Azoffluxin also inhibited efflux in a highly azole-resistant strain of *Candida albicans*, the most common human fungal pathogen, causing increased susceptibility to fluconazole. Finally, azoffluxin transformed fluconazole from ineffective to highly active in rescuing mammalian cell growth in co-culture with drug-resistant fungus. Collectively, our findings demonstrate the promising therapeutic potential of pairing an existing antifungal agent with a compound that targets a powerful resistance mechanism that frequently undermines antifungal efficacy.

*C. auris* has an enigmatic history. Since it was first identified in 2009 in Japan genomic analysis has revealed the near simultaneous emergence of distinct lineages across six continents, encompassing over 30 countries within the past ~400 years. Currently, the majority of *C. auris* isolates fall into four major geographical clades: South Asian (I), East Asian (II), African (III), and South American (IV). This species has a remarkable ability to persist on human skin and other surfaces for extended periods of time, which facilitates hospital transmission amongst patients who are already vulnerable to infection. Additionally, the prevalence of drug resistance amongst *C. auris* isolates has caused considerable concern. Recent studies have shown that over 80% of clinical isolates are resistant to the azole antifungal fluconazole, however, resistance levels vary significantly between clades, and some isolates are resistant to all three major antifungal drug classes available to treat systemic infections.

Figure 1:
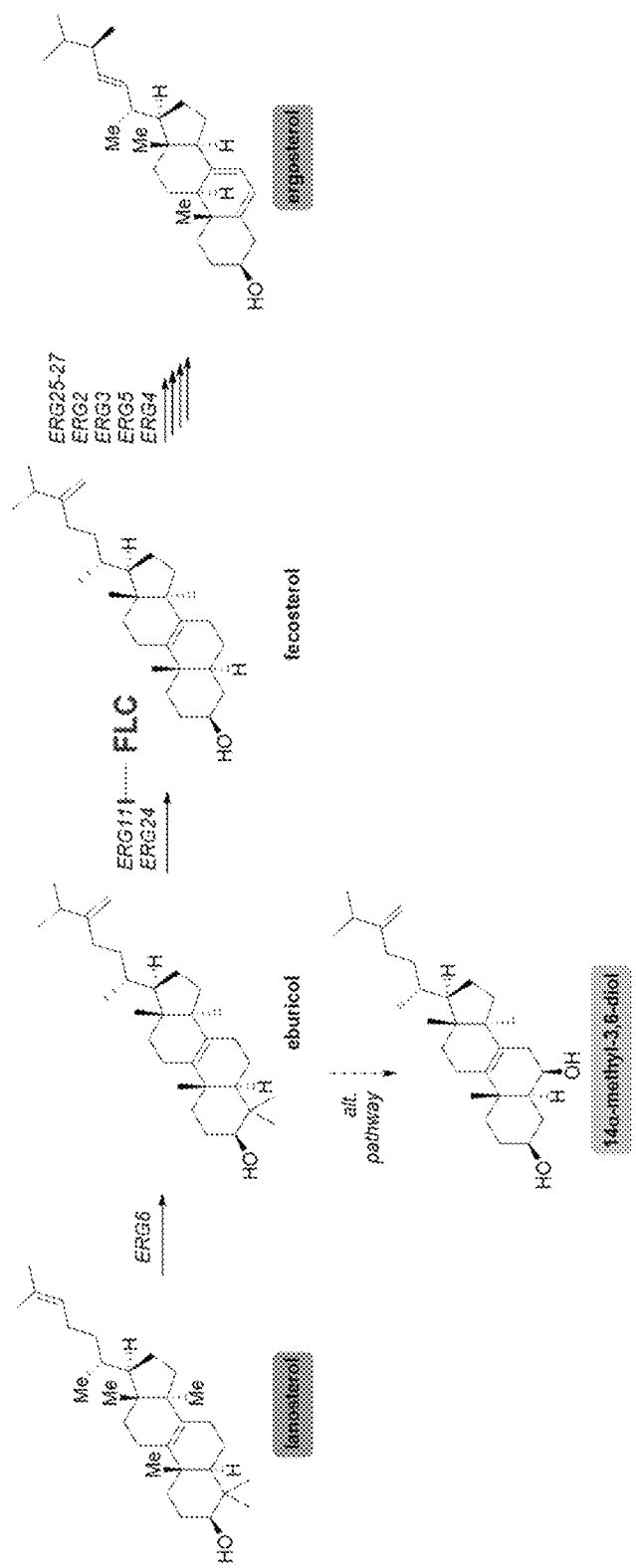
FIG. 1 shows the general mechanism of fluconazole (FLC) sterol synthesis modulation.

The prevalence of fluconazole resistance in *C. auris* is of particular concern. Fluconazole is the most widely administered antifungal due to its oral bioavailability, broad spectrum of activity, and favorable safety profile. Fluconazole inhibits the biosynthesis of ergosterol, the major sterol in fungal cell membranes, through inhibition of lanosterol demethylase, which is encoded by ERG11. Inhibition leads to an increase in the Erg11 substrate lanosterol, and the production of other toxic sterol intermediates, including 14-α-methyl-3,6-diol. The general mechanism and sterol intermediates are shown in FIG. 1. Mechanisms of fluconazole resistance amongst *C. auris* isolates are highly variable and often clade specific, the nuances of which are still being elucidated. One major mechanism of fluconazole resistance involves point mutations in hot spot regions in its target ERG11, which are known to confer resistance in other fungi. In addition to ERG11 mutations that are shared across all clades, the most common substitutions found in Clade I and IV are $Erg11^{Y132F}$ or $Erg11^{K143R}$ whilst Clade III isolates commonly have an $Erg11^{F126L}$ substitution. Notably, strains from Clade II generally have no ERG11 mutations and include the most sensitive isolates. In addition to target alteration, *C. auris* encodes an array of multidrug transporters, several of which are strongly induced under various conditions, including fluconazole treatment. Finally, *C. auris* isolates possess other genetic alterations that could confer fluconazole resistance, such as gene duplication leading to a higher copy number of ERG11 or transcriptional upregulation of ERG11. Overall, the diversity of *C. auris* resistance mechanisms is extensive, and the prevalence of fluconazole resistance threatens to render this important therapeutic obsolete in treatment of the rising number of *C. auris* infections worldwide.

A prominent strategy to thwart drug resistance and restore antimicrobial efficacy is the use of combination therapy, which has been successfully implemented to manage refractory diseases such as AIDS, tuberculosis, and malaria. By identifying agents that re-sensitize pathogens to existing therapeutics, the lifespan of existing antifungals can be extended. An excellent example of this tactic is iKIX1, a compound that inhibits the interaction of the transcription factor Pdr1 with the Mediator complex in the fungal pathogen *Candida glabrata*, thus preventing upregulation of the multidrug transporter Pdr5. Combination treatment with iKIX1 and fluconazole abrogated intrinsic azole resistance and improved survival in a murine model of *C. glabrata* infection. Clearly, the inclusion of agents capable of impairing the most common, readily anticipated modes of antifungal resistance provides a rational, readily implemented strategy in the development of more effective combination treatment regimens.

A combinatorial approach was used to screen a chemically diverse library against an azole-resistant strain of *C. auris* to identify molecules that specifically enhanced the activity of fluconazole. Azoffluxin was identified as a compound that potently synergized with fluconazole by increasing intracellular fluconazole accumulation through inhibition of the major multidrug efflux transporter Cdr1. Using azoffluxin as a chemical probe, we established that efflux is a major mechanism of resistance in isolates of three of the four major *C. auris* clades. Notably, Clade III isolates carrying specific mutations in ERG11, in addition to upregulating the multi-drug transporter Mdr1, remained resistant to fluconazole in the presence of azoffluxin, even though the compound was capable of blocking efflux of Nile red in these isolates. Azoffluxin showed cross-species activity by potentiating fluconazole against a resistant isolate of *Candida albicans*, currently the most common human fungal pathogen. Importantly, the combination of fluconazole with azoffluxin rescued mammalian cell growth in co-culture experiments with drug-resistant *C. auris*, highlighting the promise of pairing an existing antifungal with a compound that blocks drug efflux, a resistance mechanism that very frequently undermines antifungal efficacy.

Results

Figure 2A:
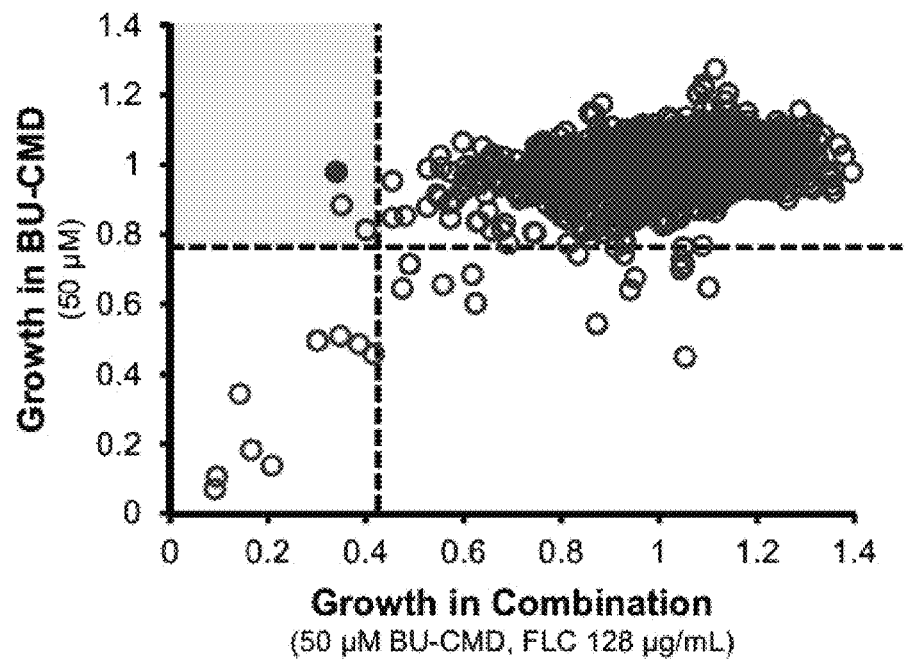
FIG. 2A shows a plot of a screened library of compounds in the presence or absence of FLC in RPMI medium at 30° C. for 48 hours.
Figure 2B:
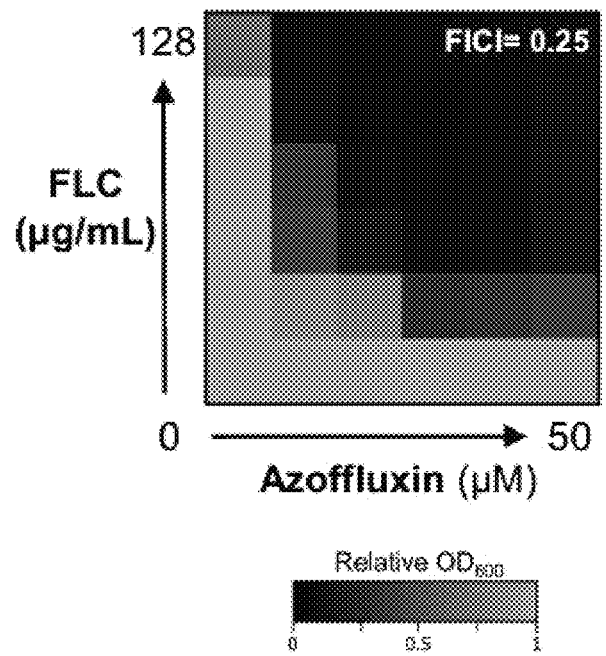
FIG. 2B shows a checkerboard assay which depicts the synergistic interactions. The columns contain two-fold serial dilutions of fluconazole, and the rows contain two-fold serial dilutions of azoffluxin. In this illustration, growth is represented by green color and no growth is represented by black color (see color bar).
Figure 2C:
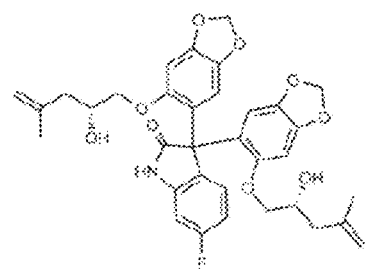
FIG. 2C shows the structure of CMLD012336 (azoffluxin).
Figure 2D:
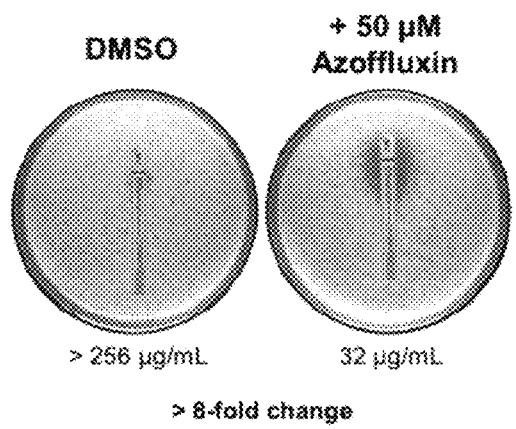
FIG. 2D depicts FLC Etest strips in the presence and absence of azoffluxin.
Figure 2E:
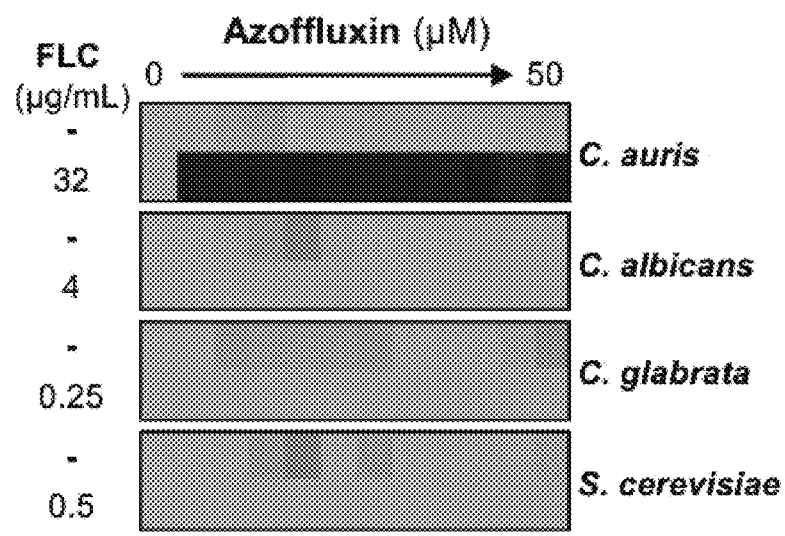
FIG. 2E shows a dose-response assay for several organisms.

To identify novel chemical matter that enhances the activity of fluconazole against the emerging multidrug-resistant pathogen *C. auris*, a diversity-oriented library created by Boston University's Center for Molecular Discovery (BU-CMD) was used. This library of 2,456 molecules, many natural product-inspired, has been curated to encompass greater structural complexity than conventional chemical libraries, which is a feature that increases the likelihood of identifying compounds with bioactivity against microorganisms. The BU-CMD library was screened at 50 µM in the absence or presence of a concentration of fluconazole that inhibited growth of the fluconazole-resistant Clade I *C. auris* strain VPCI 673/P/12 by ~20%. Compounds that reduced growth after 48 hours compared to the control by 7-median absolute deviations from the median alone were classified as single agent antifungals, and their mechanism of action has been explored elsewhere. Compounds for which antifungal activity was only observed in combination with fluconazole were classified as fluconazole potentiators (FIG. 2A). Of three fluconazole potentiators identified, the bis-benzodioxolylindolinone compound CMLD012336, a 3,3-diarylated oxindole herein referred to as azoffluxin, was prioritized due to its strong synergistic interaction with fluconazole against a resistant strain of *C. auris* Ci6684 (Erg11$^{Y132F}$) as determined by a standard dose-response matrix (checkerboard) involving gradients of fluconazole and azoffluxin (FIG. 2B and FIG. 2C). The fractional inhibitory concentration index (FICI) calculated for the combination was 0.25, with values less than 0.5 indicating a synergistic interaction (FIG. 2B). As a complementary approach, fluconazole E-test strips were used to assess whether this synergy could also be observed on solid medium. In the absence of azoffluxin, *C. auris* grew up to the highest concentration of fluconazole present on the E-test strip. However, 50 µM of azoffluxin reduced the fluconazole minimum inhibitory concentration (MIC) >16-fold, from >256 µg/mL to 16 µg/mL (FIG. 2D). Finally, given the potent synergy against *C. auris*, fluconazole-sensitive laboratory strains of *C. albicans* (SN95), *C. glabrata* (BG2) and *Saccharomyces cerevisiae* (BY4741), were tested to represent diverse fungi. Interestingly, azoffluxin did not enhance the activity of fluconazole against any of these species even in the presence of the highest concentration of fluconazole that did not impair growth in each respective species on its own (FIG. 2E). Thus, either azoffluxin exerts species-selective activity or it only enhances fluconazole activity in the context of pre-existing resistance, not in fluconazole-sensitive organisms.

FIGS. 2A-2E illustrate the above-described screening of the BU-CMD which identified azoffluxin as a fluconazole (FLC) potentiator against *C. auris*. FIG. 2A shows a plot of the BU-CMD library screened at 50 µM in the presence or absence of 128 µg/mL of FLC in RPMI medium at 30° C. for 48 hours. Growth, as determined by optical density at 600 nm ($OD_{600}$), is plotted in the presence of each CMD compound alone on the y-axis and in combination with FLC on the x-axis. Dotted lines represent 7-median absolute deviations from the median for each condition. Red circles indicate those compounds that showed significant bioactivity. The shaded quadrant indicates compounds that show significantly enhanced activity in the presence of fluconazole, with azoffluxin shown as a filled red circle. FIG. 2B depicts the synergistic interactions. Of the three potentiating hits, one compound (CMLD012336, Azoffluxin) showed a synergistic interaction with FLC when checkerboard assays were performed by titering a two-fold dilution of azoffluxin and FLC across the x- and y-axes, respectively. Growth was measured by the OD600 and normalized to the no drug control (see color bar). The fractional inhibitory concentration index (FICI) was calculated to determine the chemical interaction, with a value below 0.5 indicating synergy. FIG. 2C shows the structure of CMLD012336 (azoffluxin). FIG. 2D depicts FLC Etest strips in the presence and absence of 50 µM azoffluxin. A total of 1×10$^6$ *C. auris* cells were added to YPD agar plates, the E-test strip was added, and plates were incubated at 30° C. for 24 hours prior to imaging. FIG. 2. E shows a dose-response assay for several organisms. Dose-response assay where a two-fold dilution of azoffluxin was titered starting from 50 µM. Indicated titrations have a background concentration of FLC of 32 µg/mL, 4 µg/mL, 0.25 µg/mL, and 0.5 µg/mL for *C. auris* Ci6684 (Erg11Y132F), *C. albicans* (SN95), *C. glabrata* (BG2) or *S. cerevisiae* (BY4741), respectively. These were the highest FLC concentrations that alone did not affect growth for each species. Dose response assays were incubated for 48 hours at 30° C. in RPMI. Growth in each well was plotted by the relative optical density to the respective no drug control (See color bar in FIG. 2B).

Azoffluxin Enhances Fluconazole Activity and Intracellular Accumulation in a Cdr1-Dependent Manner.

Of the many ways in which drug combinations can exert a synergistic effect, a common mechanism involves one compound enhancing the biological effect of another agent through targeting parallel pathways or improving bioavailability. To investigate this potential mode of action for azoffluxin, the sterol composition of *C. auris* with or without prior exposure to compounds was profiled. A hypothesis was that if azoffluxin heightens the effects resulting from fluconazole-mediated Erg11 inhibition, a low concentration of fluconazole combined with azoffluxin would have an equally profound impact on sterol composition as a high concentration of fluconazole alone. Using LC-MS, how exposure of *C.*

Figure 3A:
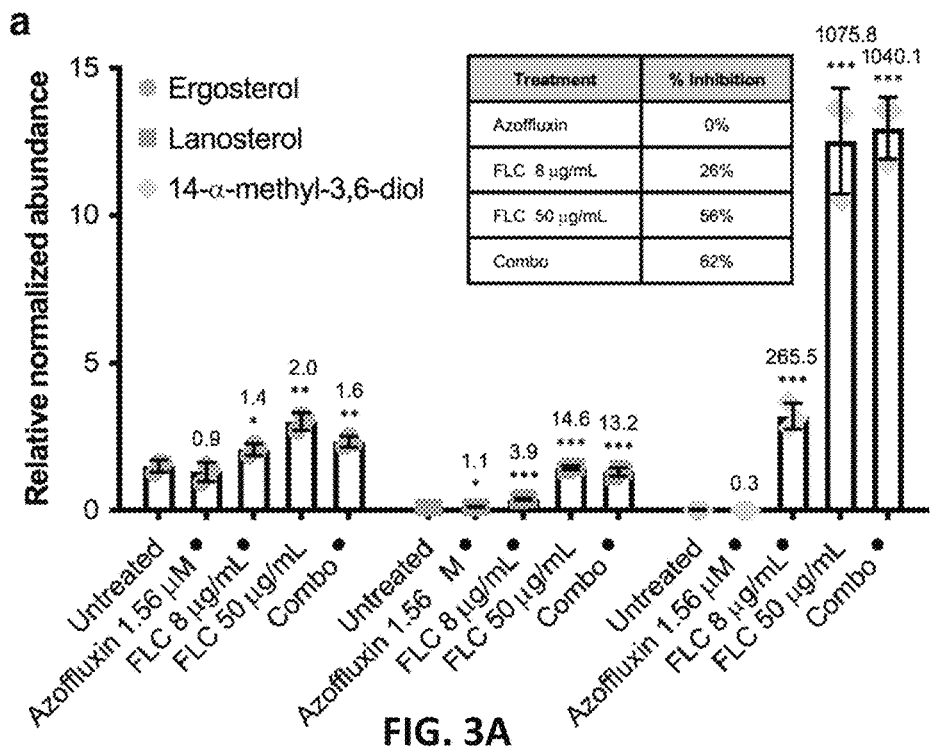
FIG. 3A depicts the relative abundance of specific sterols determined in C. auris after a treatment with FLC and azoffluxin in various combinations.
Figure 3B:
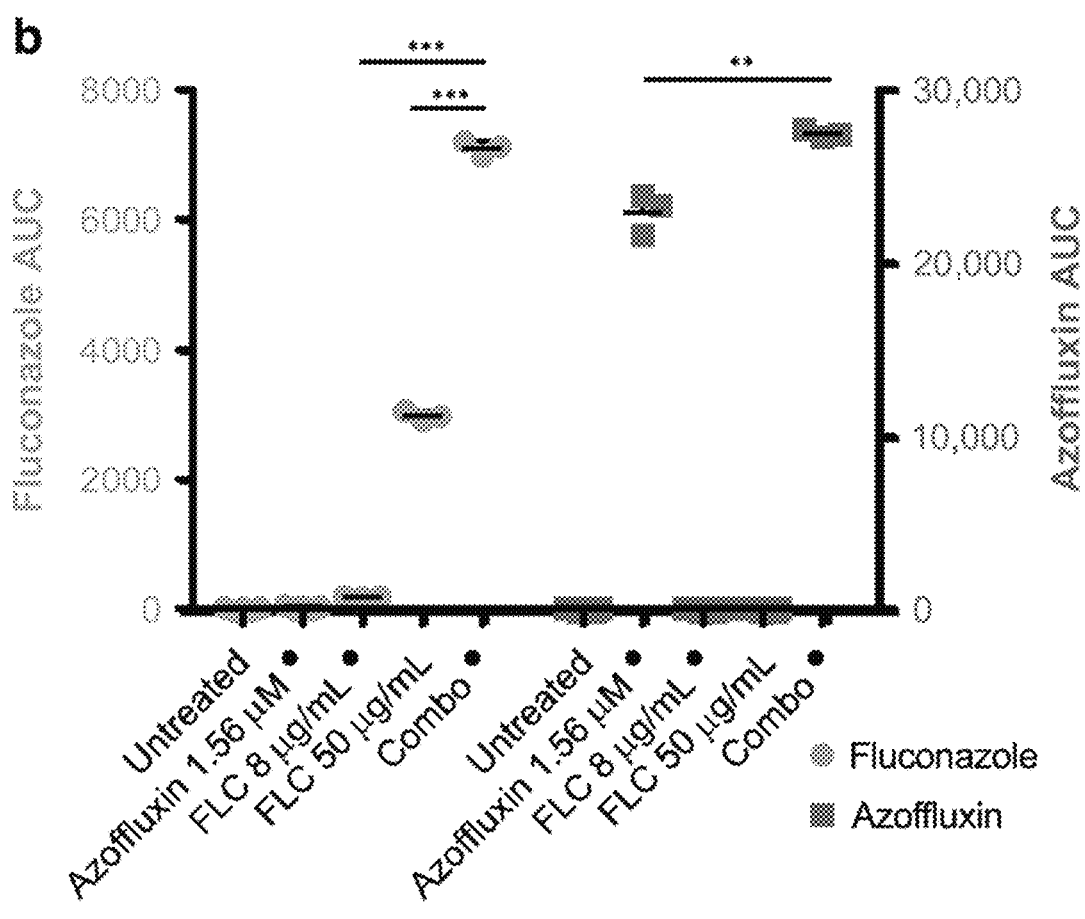
FIG. 3B depicts the intracellular concentrations of FLC and azoffluxin measured after treatment depicted in FIG. 3A.

*auris* to a combination of azoffluxin and fluconazole for 18 hours affected the abundance of three membrane sterols: ergosterol, lanosterol, and the azole-induced aberrant sterol intermediate 14-α-methyl-3,6-diol, was evaluated. No significant increases in abundance for these sterols were detected between untreated and azoffluxin-treated cells. Compared to untreated cells, low-concentration fluconazole resulted in a slight but significant (p<0.05) increase in ergosterol and lanosterol, and a larger increase in 14-α-methyl-3,6-diol (FIG. 3A). This result suggested that while exerting a minimal effect on growth, the low fluconazole concentration partially inhibited Erg11, causing a compensatory upregulation in ergosterol biosynthesis. However, azoffluxin dramatically amplified the impact of the low fluconazole concentration on sterol composition. Most notable was a 4-fold increase in 14-α-methyl-3,6-diol compared to low fluconazole alone (FIG. 3A). The relative abundance of this toxic metabolite was similar to that seen in the sterol profile found upon treatment of cells with a higher concentration fluconazole alone, which resulted in a similar level of growth inhibition as the combination (50%) (FIG. 3A). Next, to determine if azoffluxin enhances the effect of fluconazole treatment by increasing intracellular fluconazole abundance, intracellular levels of fluconazole using LC-MS were measured after 1 hour of treatment. Significantly more intracellular fluconazole in the combination treatment group compared to treatment with either a high or low fluconazole concentration alone (p<0.001; FIG. 3B) was detected. The discrepancy between the combination treatment and high fluconazole alone resulting in equivalent growth inhibition in the previously described sterol experiment, despite a ~2.5-fold increase in intracellular fluconazole found here, is likely due to the different time points at which these assays were performed. Furthermore, intracellular levels of azoffluxin was detected, indicating that this compound is able to cross the fungal cell wall and plasma membrane (FIG. 3B). Overall, these LC-MS profiles suggest that azoffluxin synergizes with fluconazole by increasing the intracellular accumulation of fluconazole through an undetermined mechanism that we next sought to define.

Figure 4A:
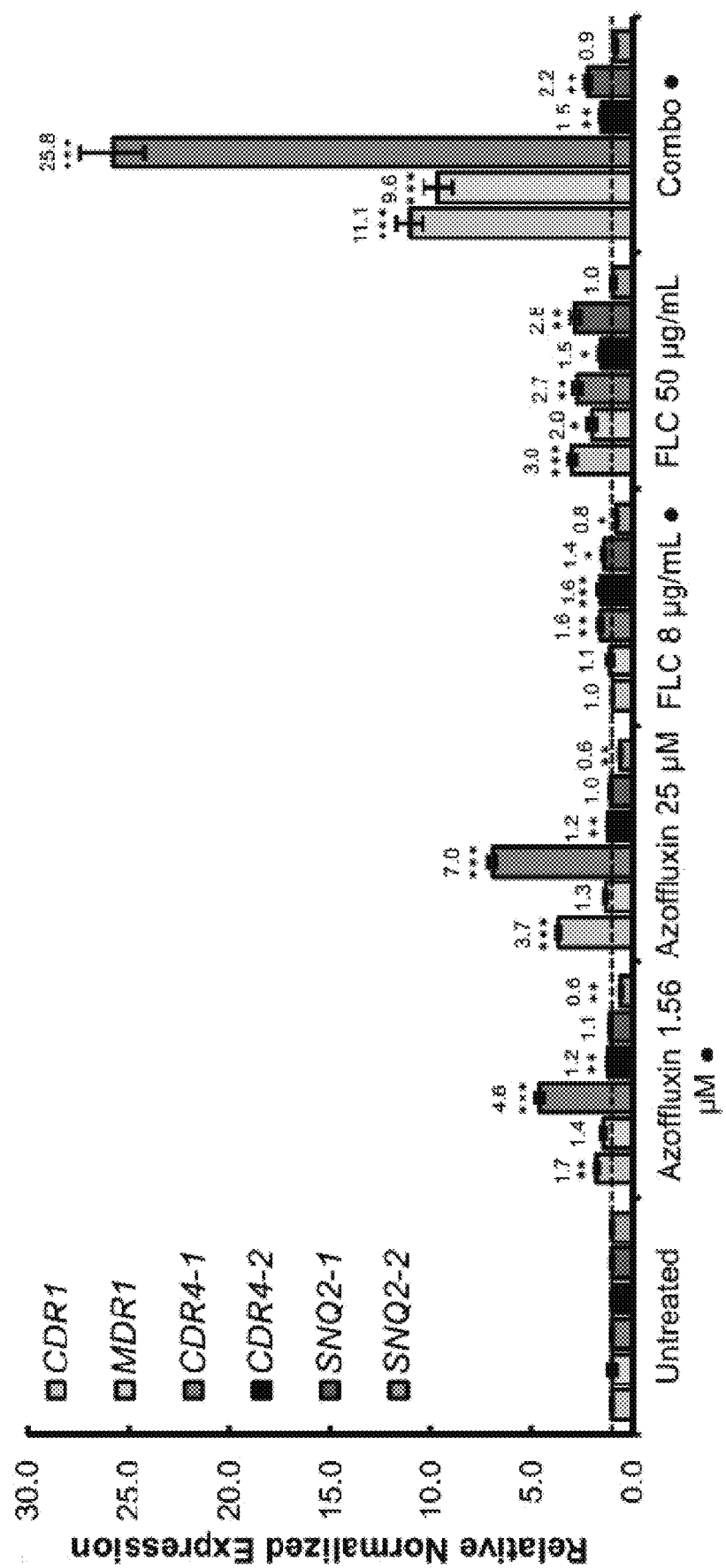
FIG. 4A depicts the quantified relative expression of a panel of putative efflux pumps in C. auris Ci6684.
Figure 4B:
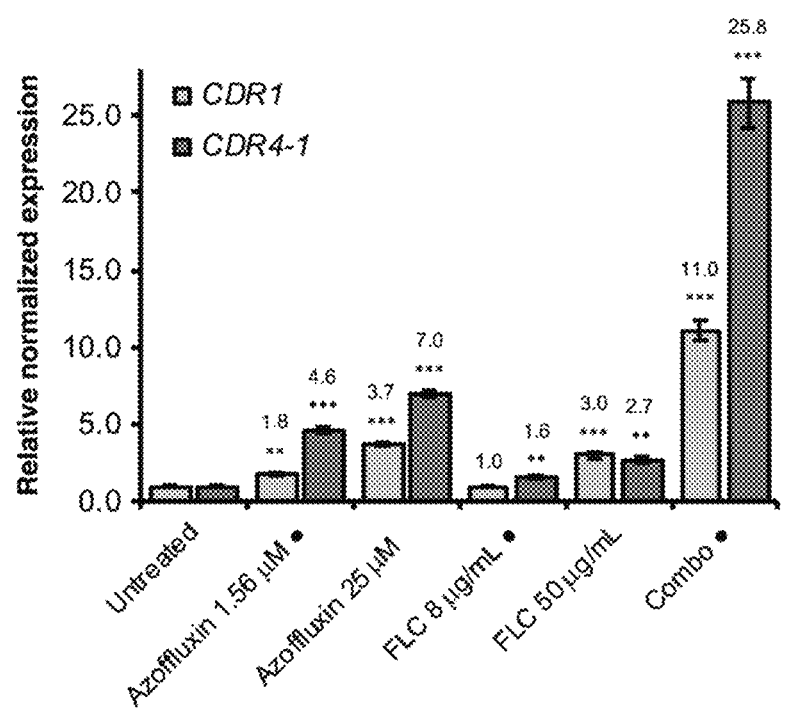
FIG. 4B depicts expression of CDR1 (B9J08_000164) and CDR4-1 (B9J08_000479) measured by quantitative real-time PCR (RT-qPCR).

In pursuing mechanistic studies, it was reasoned that an increase in intracellular azole accumulation could be caused either by enhancing permeability or by impeding drug efflux. To discriminate between these two models, we first tested the hypothesis that the increase in intracellular fluconazole caused by azoffluxin treatment resulted from impairment of multidrug efflux transporter activity. Impairment could be achieved by either a transcriptional mechanism that reduces the expression of genes encoding transporters or through a post-transcriptional mechanism. In order to evaluate potential transcriptional effects, the relative expression of six putative *C. auris* efflux genes, identified by Muñoz et al., following treatment with azoffluxin, fluconazole, or a combination of the two compounds, were profiled (FIG. 4A). Of the six transporter genes assessed, those encoding the putative ABC transporters Cdr1 (B9J08_000164) and Cdr4-1 (B9J08_000479) demonstrated similar expression profiles. At exposures to azoffluxin alone which had no effect on growth, a concentration-dependent increase in CDR1 and CDR4-1 transcript levels was seen, which was greater than the induction observed upon treatment with fluconazole (FIG. 4B and FIG. 4A). Furthermore, a greater increase in CDR1 and CDR4-1 expression upon combination treatment was seen than the increase seen with any individual compound treatment (FIG. 4B). The observation that azoffluxin causes an increase in transcript level of two efflux genes but increases intracellular accumulation of fluconazole, suggests a model where azoffluxin directly inhibits efflux transporter function post-transcriptionally, resulting in the compensatory upregulation of efflux gene expression.

FIGS. 3A-3B, and 4A-4B illustrate azoffluxin increases fluconazole (FLC) bioavailability by inhibiting Cdr1-mediated efflux in *C. auris*, as described above. FIG. 3A depicts the relative abundance of specific sterols determined in *C. auris* after an 18-hour treatment with the respective compounds (• indicates combo treatment concentrations) using LC-MS. Values are plotted relative to the internal standard of cholesterol and error bars indicate standard deviation between technical triplicates. Significance was determined by an unpaired student t-test of each condition to untreated, (*) indicates a p-value<0.05 and () indicates a p-value<0.01. FIG. 3B depicts the intracellular concentrations of FLC and azoffluxin measured after treatment for 1 hour (conditions as in FIG. 3A) Error bars indicate standard deviation between technical triplicates. Significance was determined by an unpaired student t-test, () indicates a p-value<0.01. FIG. 4A depicts the quantified relative expression of a panel of putative efflux pumps in *C. auris* Ci6684. Expression of CDR1 (B9J08_000164), MDR1 (B9J08_003981), CDR4-1 (B9J08_000479), CDR4-2 (B9J08_002451), SNQ2-1 (B9J08_001125), and SNQ2-2 (B9J08_004452) was measured by RT-qPCR. Cells were treated for 3 hours (• indicates combo treatment concentrations) and RNA was extracted. Expression is plotted normalized to ACT1 and GPD1 and relative to the untreated control. Error bars represent standard error of the mean between technical triplicates, (*) indicates a p-value<0.05, () a p-value<0.01, and (*) a p-value<0.001 compared to respective untreated control. FIG. 4B depicts expression of CDR1 (B9J08_000164) and CDR4-1 (B9J08_000479) measured by quantitative real-time PCR (RT-qPCR). Cells were treated for 3 hours with indicated concentrations of compound (• indicates combo treatment concentrations) and RNA was extracted. Expression is normalized to ACT1 and GPD1 and subsequently normalized to the untreated control. Error bars represent standard error of the mean between three technical triplicates, (*) indicates a p-value<0.05, () a p-value<0.01, and (*) a p-value<0.001 compared to respective untreated control.

Figure 5A:
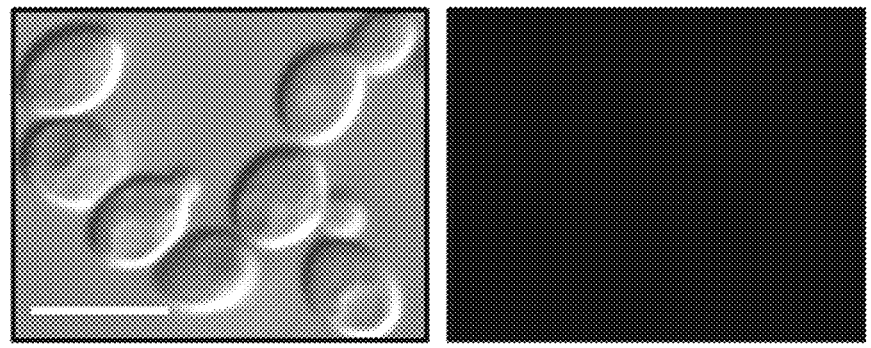
FIG. 5A shows C. auris strains grown to exponential phase and either treated with azoffluxin or untreated, followed by addition of the dye Nile red.
Figure 5A:
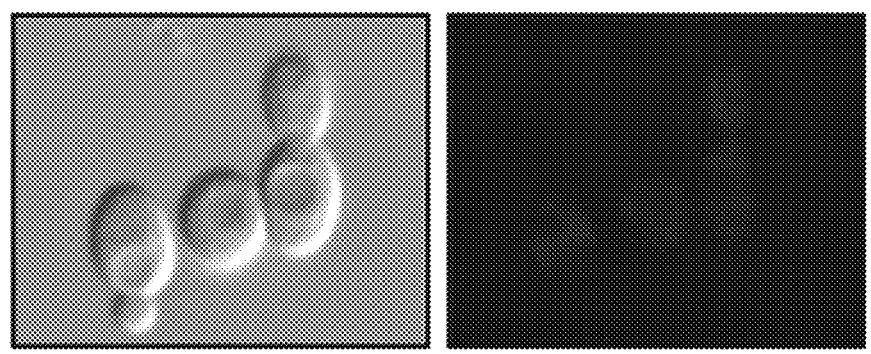
Figure 5B:
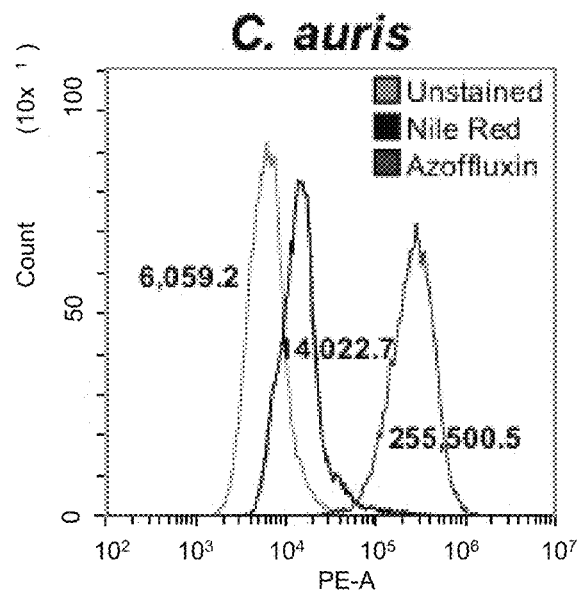
FIG. 5B: depicts flow cytometric measurements of relative efflux inhibition in C. auris as monitored by intracellular accumulation of the dye Nile red
Figure 5B:
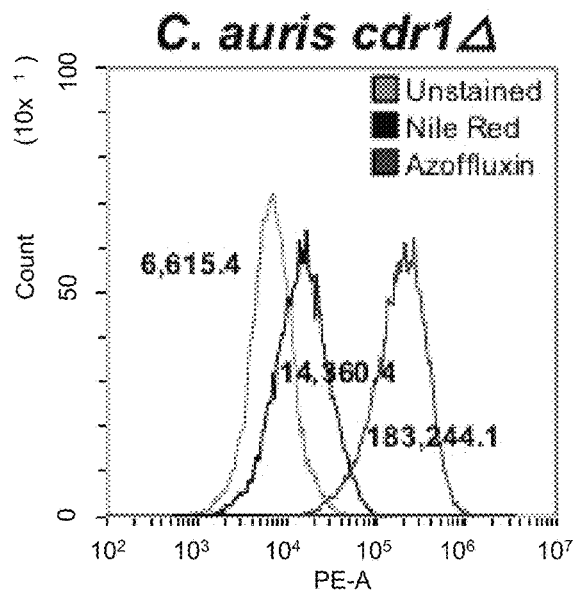
Figure 5B:
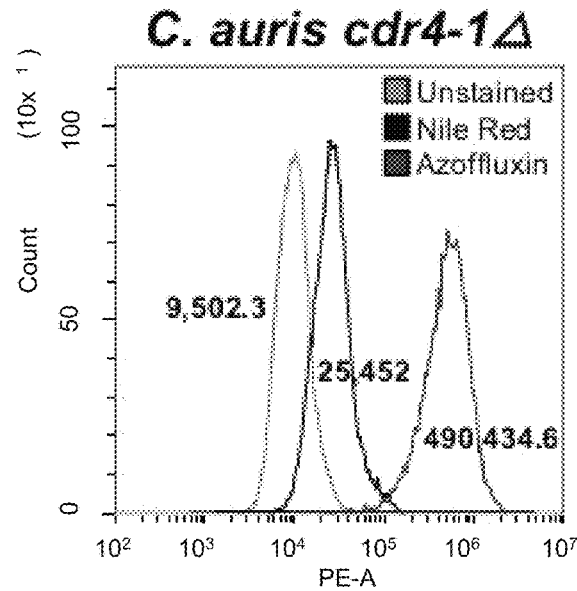

To test the proposed model experimentally, it was determined whether azoffluxin directly inhibited transporter function by monitoring the impact of a on accumulation within *C. auris* of the relatively promiscuous efflux pump substrate Nile red. Flow cytometry revealed a 42-fold increase in relative cell-associated Nile red signal caused by treatment with 50 μM azoffluxin (FIGS. 5A and 5B). To determine if Cdr1 and/or Cdr4-1 were relevant targets of azoffluxin, a *C. auris* strain in which CDR1 had been deleted and also a generated CDR4-1 deletion strain were used. If azoffluxin acts by inhibiting the activity of either transporter, then deletion of that transporter should reduce or eliminate the increase in Nile red accumulation caused by azoffluxin treatment. Although deletion of these efflux genes did not block the increase in Nile red accumulation caused by azoffluxin treatment, the magnitude of the increase was diminished in the cdr1Δ strain (FIG. 5B), implicating Cdr1 as a target of azoffluxin in *C. auris*. This result also implicated other *C. auris* transporters as targets of azoffluxin because the compound still increased Nile red signal in the absence of CDR1, albeit to a lesser extent. Cdr4-1 is unlikely to be a relevant target given that loss of this transporter actually enhanced rather than diminished the increase in Nile Red staining caused by azoffluxin. In *C. albicans* Cdr4, despite being a homolog to Cdr1, is involved in translocation of phosphoglycerides and therefore, deletion could disrupt plasma membrane homeostasis leading to enhanced Nile Red accumulation. Alternatively, given the interdependent regulatory network reported for efflux transporters, deletion of CDR4-1 could well have driven compensatory upregulation of additional azoffluxin-sensitive transporters capable of effluxing Nile red.

Figure 6:
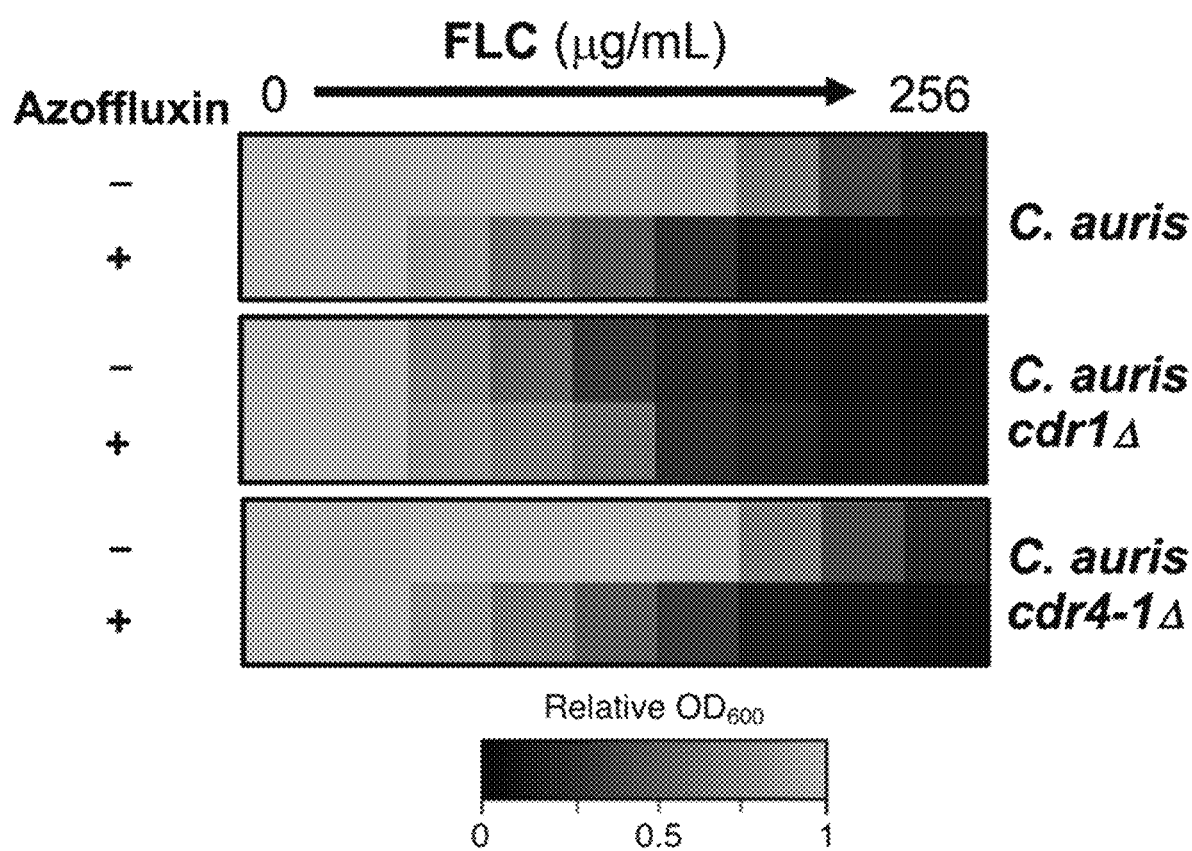
FIG. 6 illustrates azoffluxin effect on fluconazole (FLC) antifungal activity.

Encouraged by the effects seen on Nile red as a model efflux substrate, the functional relevance of Cdr1 for potentiation of fluconazole activity by azoffluxin was assessed. As would be expected if azoffluxin enhances fluconazole activity via inhibition of Cdr1, it was found that deletion of CDR1 abolished the ability of azoffluxin to potentiate the antifungal activity of fluconazole (FIG. 6). In dose-response assays, deletion of CDR1 reduced the fluconazole MIC to that observed upon combination with azoffluxin in a wild-type background (FIG. 6). In contrast, deletion of CDR4-1 did not alter fluconazole sensitivity nor the ability of azoffluxin to potentiate fluconazole (FIG. 6). This fits with previous reports in C. albicans that implicate Cdr1 in azole efflux but not Cdr4-1, despite both being transcriptionally upregulated in response to fluconazole.

FIGS. 5A, 5B and 6 illustrate that azoffluxin increases fluconazole (FLC) bioavailability by inhibiting Cdr1-mediated efflux in C. auris. FIG. 5A show C. auris strains grown to exponential phase and treated with 50 µM azoffluxin for 10 minutes when indicated, followed by addition of Nile red for 20 minutes. Cells were then imaged on the DIC and DsRed channels at equivalent exposure times. FIG. 5B: depicts a flow cytometer and histograms of the cells, showing the fluorescence on the PE channel per event for ~20,000 events. The table (Upper left) displays the fold change in median fluorescence of stained CMLD012336 treated cells relative to stained untreated cells. FIG. 6 illustrates azoffluxin increases fluconazole (FLC) bioavailability by inhibiting Cdr1-mediated efflux in C. auris. Dose response assays were conducted with a C. auris parental strain, a strain with the efflux pump gene CDR1 deleted, and a strain with the efflux pump CDR4-1 deleted. FLC was titered in a two-fold dilution on the x-axis in the absence and presence of 50 µM azoffluxin. Growth was measured at 48 hours using $OD_{600}$ and normalized to a no drug control well (see color bar).

Figure 7A:
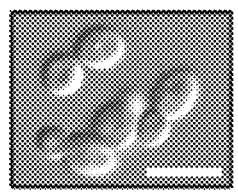
FIG. 7A shows C. auris Ci6684 strains with efflux pumps deleted that were grown to exponential phase and either treated with azoffluxin or untreated, followed by addition of Nile red.
Figure 7A:
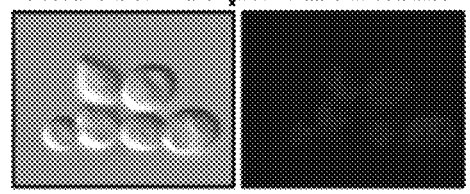
Figure 7A:
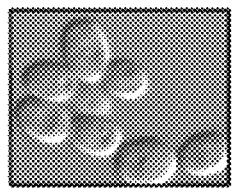
Figure 7A:
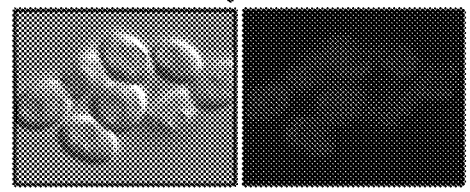
Figure 7B:
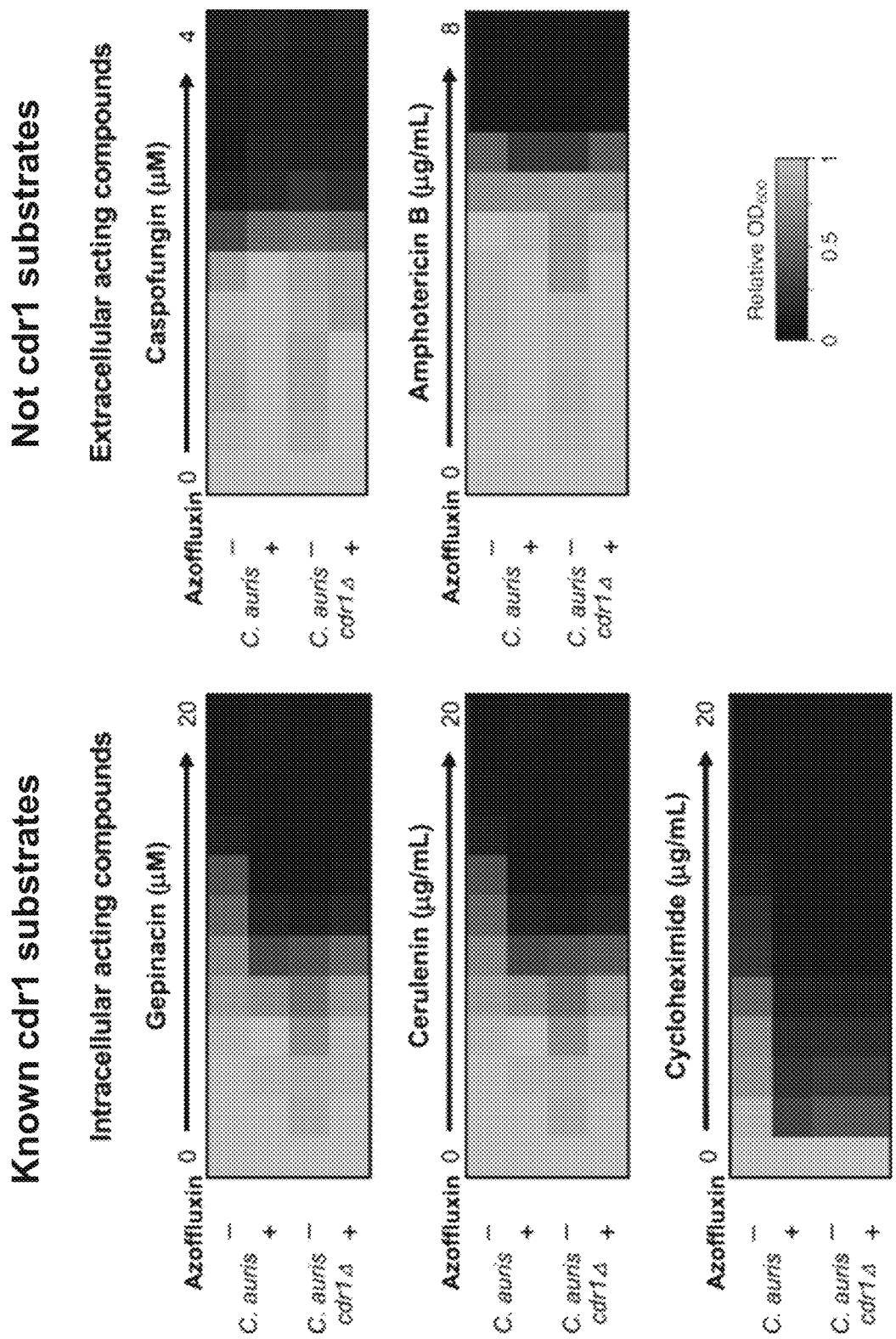
FIG. 7B depicts dose-response assays conducted with a C. auris parental strain in the absence and presence of 50 μM azoffluxin where indicated, as well as with a strain with the efflux pump gene CDR1 deleted. Indicated compounds were titered in a two-fold dilution on the x-axis. Growth was measured after 48 hours in YPD using $OD_{600}$ and normalized to a no drug control well (see color bar).

Given the extensive range of substrates that Cdr1 is reported to efflux, whether azoffluxin potentiated the effects of other intracellularly acting compounds to the same extent as deletion of CDR1 was investigated. Consistent with the herein proposed model for its mode of action, azoffluxin sensitized C. auris to the compounds gepinacin, cerulenin, and cycloheximide to the same extent as CDR1 deletion. Although mechanistically diverse, these compounds all act intracellularly and are known to be Cdr1 efflux substrates. In contrast, azoffluxin had no impact on sensitivity to the extracellularly acting compounds caspofungin and amphotericin B[11] (FIGS. 7A and 7B). Considering all these findings, it is concluded that azoffluxin enhances the antifungal activity of intracellularly acting compounds, such as fluconazole, by inhibiting drug transporters, most notably Cdr1, in C. auris.

FIGS. 7A and 7B illustrates that azoffluxin potentiates intracellular acting compounds against C. auris, to a similar degree as deletion of CDR1. FIG. 7A shows C. auris Ci6684 strains with the efflux pumps CDR1 and CDR4-1 deleted that were grown to exponential phase and treated with azoffluxin, followed by addition of Nile red. Cells were then imaged on the DIC and DsRed channels at equivalent exposure times as those in FIG. 5A. FIG. 7B depicts a dose response assays conducted with a C. auris parental strain in the absence and presence of 50 µM azoffluxin where indicated, as well as with a strain with the efflux pump gene CDR1 deleted. Indicated compounds were titered in a two-fold dilution on the x-axis. Growth was measured after 48 hours in YPD using $OD_{600}$ and normalized to a no drug control well (see color bar).

Azoffluxin Exhibits Broad Spectrum Activity Against Multiple C. auris Strains, but not Those from Clade III.

Figure 8A:
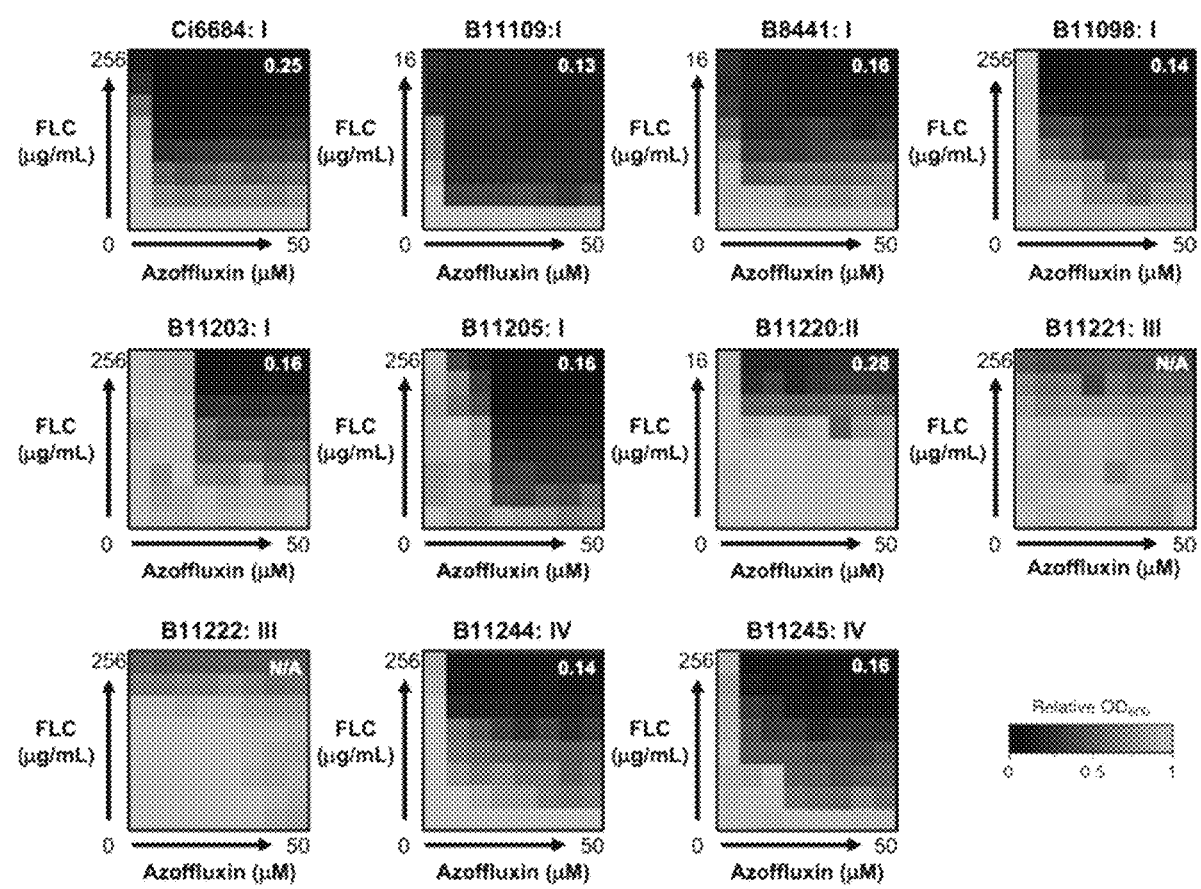
FIG. 8A depicts checkerboard assays performed with fluconazole (FLC) and azoffluxin as described in FIG. 2B with isolates from each major clade of C. auris.
Figure 8B:
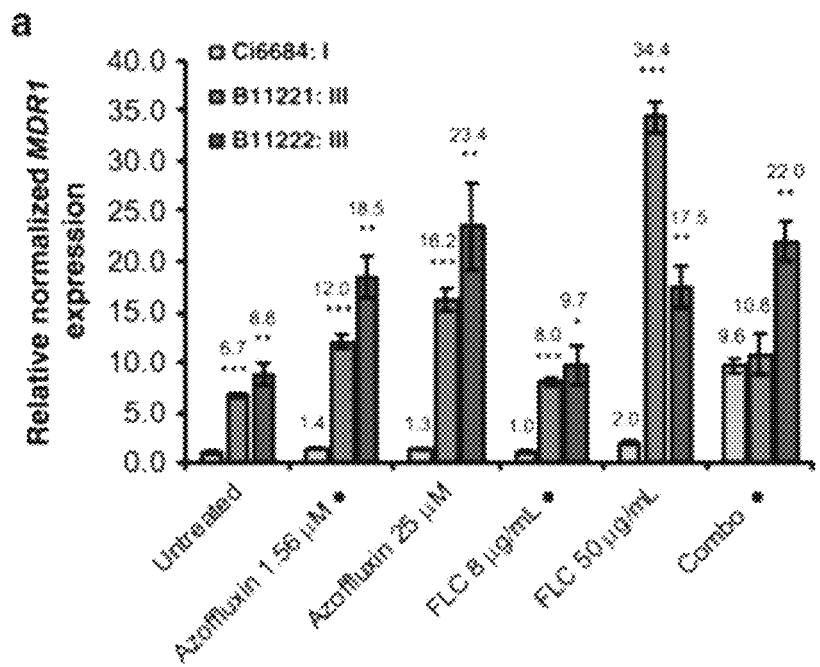
FIG. 8B depicts expression of MDR1 (B9J08_003981) measured in Ci6684 (clade I isolate) and Clade III isolates B11221 and B11222 by RT-qPCR as described in FIG. 4B.
Figure 8C:
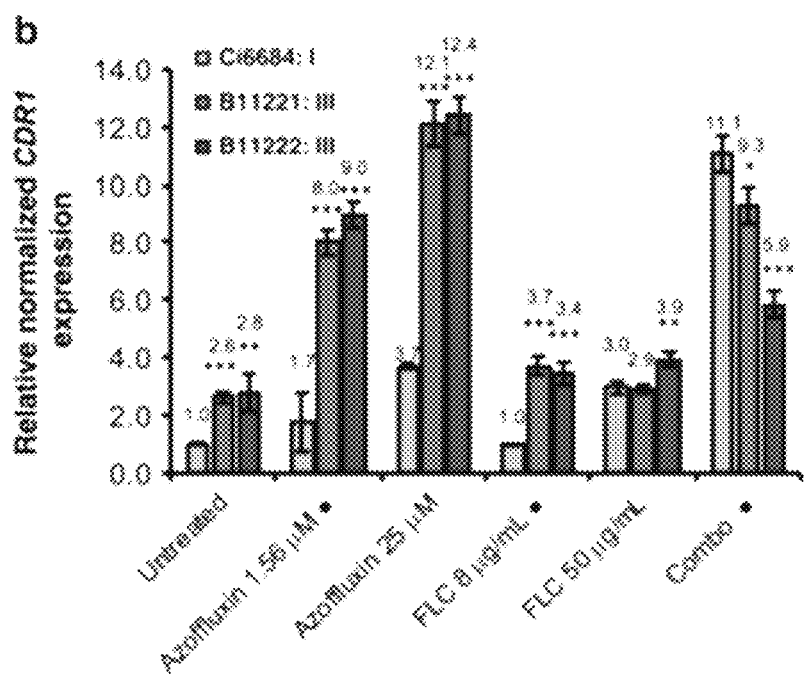
FIG. 8C depicts expression of CDR1 measured in Ci6684 (clade I isolate) and Clade III isolates B11221 and B11222 by RT-qPCR as described in FIG. 4B.

Given the extensive genetic diversity identified amongst different clades of C. auris, experimentation was conducted to investigated if azoffluxin synergized with fluconazole against representative isolates from all four major clades. Intriguingly, when synergistic activity was assessed by checkerboard assay, azoffluxin potentiated fluconazole in multiple isolates from three of the four major clades, with a Clade III isolate from South Africa being the exception (FIG. 8A). Clade III is generally distinguishable from the others by both a V125A and F126L substitution in Erg11 and the absence of drug resistant mutations in TAC1B, the transcriptional regulator of Cdr1, commonly found in Clades I and IV. By examining whole genome sequences of 304 isolates representing each of the four major clades, a unique non-synonymous substitution, N647T in the transcription factor domain of MRR1 (B9J08_004061), was identified in 49 of the 51 Clade III isolates. Mrr1 is a transcription factor that controls the expression of the major facilitator transporter Mdr1, which is involved in fluconazole efflux in C. albicans. Indeed, when expression of MDR1 (B9J08_003981) was assessed in the Clade III isolates B11221 and B11222, increased expression in nearly all conditions tested compared to the Clade I screening strain Ci6684 was detected, confirming that MDR1 is constitutively upregulated in Clade III isolates (FIGS. 8B, 8C). The lack of fluconazole potentiation by azoffluxin in Clade III isolates could be due to an efflux-independent fluconazole-resistance mechanism or to azoffluxin failing to inhibit efflux in these strains. To assess if azoffluxin was able to inhibit drug efflux activity in Clade III strains, cellular accumulation of Nile red which is a substrate for both ABC and Major Facilitator Superfamily efflux pumps was performed in the absence and presence of compound. Treatment with azoffluxin led to a 36-40-fold increase in Nile red accumulation in B11221 and B11222 (FIG. 8D), similar to the increase observed with the Clade I screening isolate Ci6684 (FIG. 5B). Furthermore, LC-MS confirmed that azoffluxin accumulated intracellularly in B11221 and B11222 (FIG. 8E), and levels of intracellular fluconazole were comparable between Clade I and Clade III strains when treated with the compound combination (FIG. 8F). These results suggest the lack of fluconazole potentiation by azoffluxin in Clade III isolates is not due to the inability of the compound to inhibit efflux pumps for which Nile red is a substrate.

To evaluate whether the Erg11$^{V125A/F126L}$ and Mrr1$^{N647}$T activating substitutions were responsible for resistance to the fluconazole-enhancing effects of azoffluxin in Clade III isolates, the activity of azoffluxin against a Clade III isolate (B12037) that does not contain the Erg11 substitutions or the Mrr1 activating substitution shared by most members of this clade was assessed. While more sensitive to fluconazole than other clade members at baseline, this strain did show a potent synergistic interaction between azoffluxin and fluconazole (FIG. 8G). Together, these results suggest that it is the Erg11 substitutions and/or Mrr1 activating mutations in B11222 and B11221 that enable fluconazole resistance which is recalcitrant to the effects of azoffluxin.

Figure 8D:
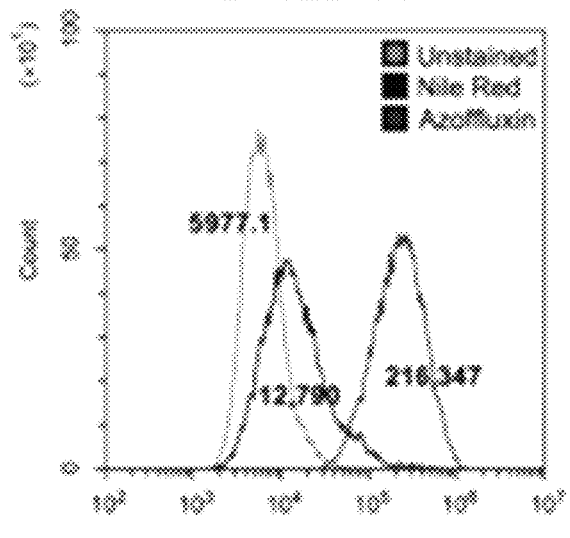
FIG. 8D depicts Nile red accumulation measured as described in FIG. 5B.
Figure 8D:
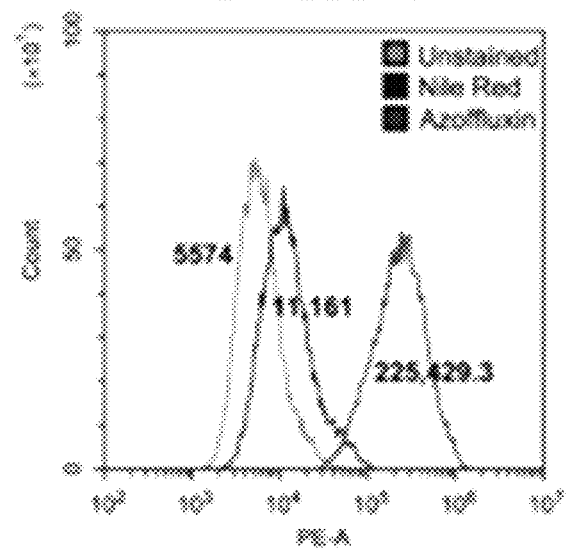
Figure 8D:
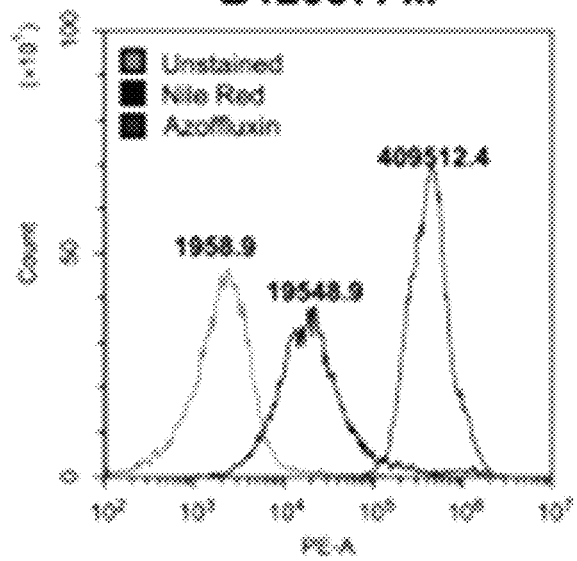
Figure 8E:
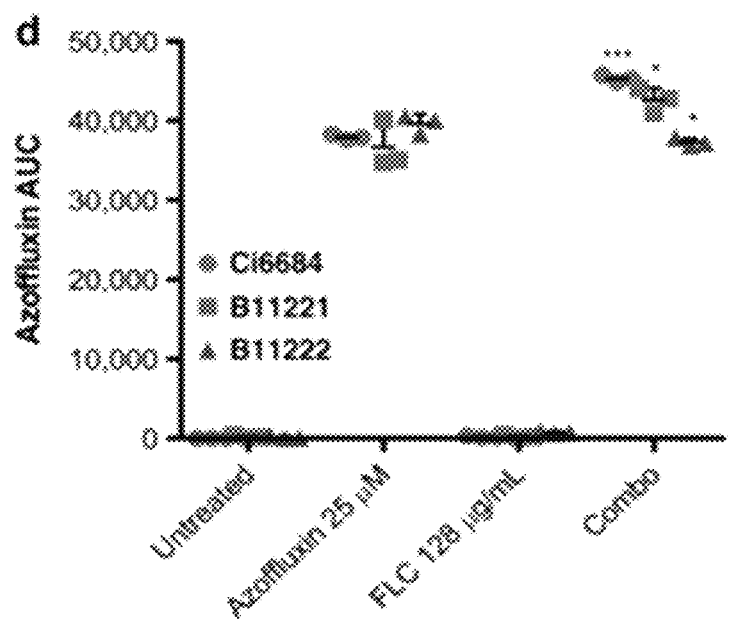
FIG. 8E depicts the intracellular Azoffluxin abundance quantified by LC-MS in the clade I isolate Ci6684 and the clade III isolates B11221 and B11222 after 1-hour treatment.
Figure 8F:
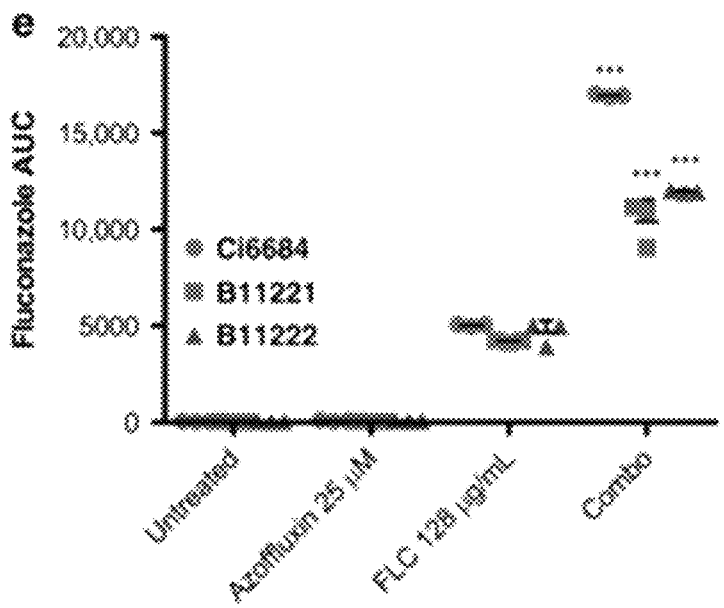
FIG. 8F depicts the intracellular FLC abundance quantified by LC-MS in the clade I isolate Ci6684 and the clade III isolates B11221 and B11222 after a 1-hour treatment.
Figure 8G:
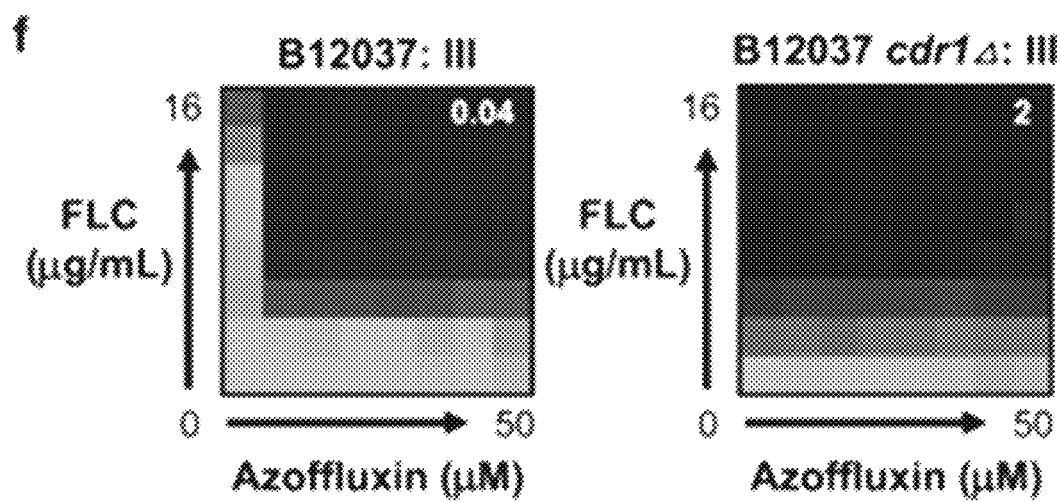
FIG. 8G shows a checkerboard assay as described in FIG. 2B with the clade III isolate B12037 lacking the V125A/F126L Erg11 substitution and the N647T activating substitution in Mrr1 (B9J08_004061).

FIGS. 8A-8G illustrates that the synergistic activity of azoffluxin displays clade specificity-azoffluxin potentiates fluconazole (FLC) against multiple *C. auris* isolates except Clade III, irrespective of intracellular permeability. FIG. 8A depicts a checkerboard assays performed with fluconazole (FLC) and azoffluxin as described in FIG. 2B with isolates from each major clade of *C. auris*. CDC identifying number is followed by the clade number to which the isolate belongs. Growth was measured at 24 hours using $OD_{600}$ and normalized to a no drug control well (see color bar). The FICI calculated for each checkerboard is shown in the top right of each plot, with values <0.5 indicating synergy and N/A indicating an FICI that could not be calculated due to a lack of growth inhibition. FIG. 8B depicts expression of MDR1 (B9J08_003981) measured in Ci6684 (clade I isolate) and Clade III isolates B11221 and B11222 by RT-qPCR as described in FIG. 4B. () indicates a p-value<0.01 and (*) indicates a p-value<0.01 comparing Ci6684 to each Clade III isolate for each condition (• indicates combo treatment concentrations). FIG. 8C depicts expression of CDR1 measured in Ci6684 (clade I isolate) and Clade III isolates B11221 and B11222 by RT-qPCR as described in FIG. 4B. () indicates a p-value<0.01 and (*) indicates a p-value<0.01 comparing Ci6684 to each Clade III isolate for each condition (• indicates combo treatment concentrations). FIG. 8D depicts Nile red accumulation measured as described in FIG. 5B. Fold change upon treatment with azoffluxin is show in the table (bottom right). FIG. 8E depicts intracellular azoffluxin accumulation in Clade I isolate Ci6684 and both Clade III isolates B11222 and B11221, measured as described in FIG. 3B. (*) indicates a p-value<0.001. FIG. 8F depicts the intracellular FLC abundance quantified by LC-MS in the clade I isolate Ci6684 and the clade III isolates B11221 and B11222 after a 1-hour treatment. Combo indicates 25 µM azoffluxin and 128 µg/mL FLC, () indicates a p-value<0.01 comparing each strain untreated to combo treatment condition. FIG. 8G shows a checkerboard assay as described in FIG. 2B with the clade III isolate B12037 lacking the V125A/F126L Erg11 substitution and the N647T activating substitution in Mrr1 (B9J08_004061). Growth was normalized to no drug control, see color bar in FIG. 8A.

Fluconazole-Resistant *C. albicans* is Sensitized to Fluconazole by Azoffluxin.

Figure 9A:
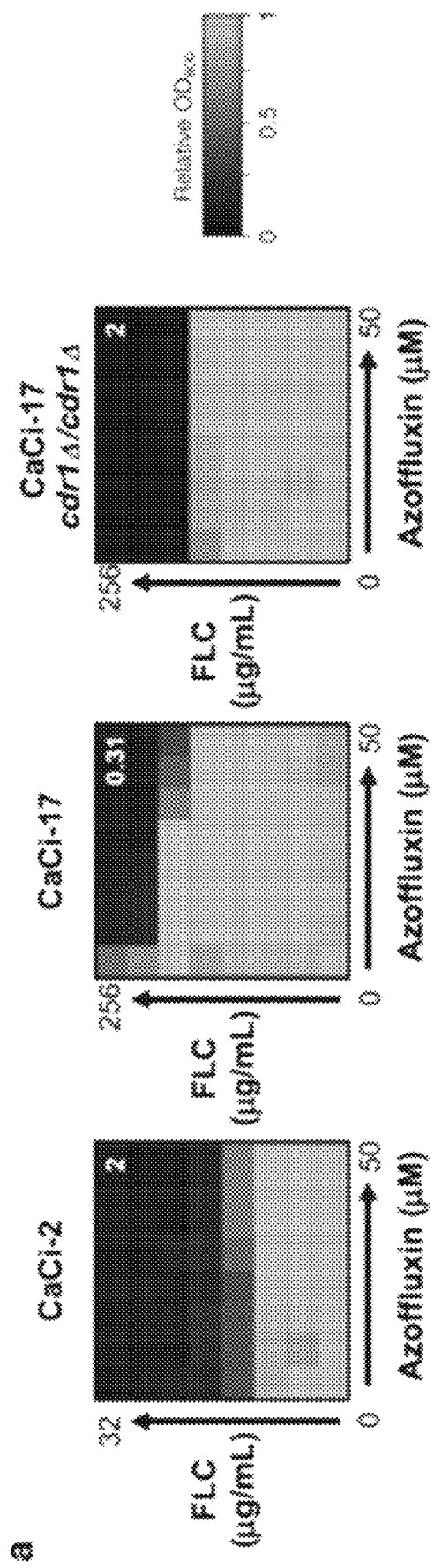
FIG. 9A depicts checkerboard assays as described in FIG. 2B and performed with fluconazole-resistant isolates of C. albicans.

A model in which azoffluxin inhibits Cdr1 to augment fluconazole activity against most *C. auris* isolates has thus far been proposed. Notably, the initial findings suggested this compound combination was ineffective against *C. albicans, C. glabrata*, or *S. cerevisiae* (FIG. 2E), indicating either species-specific differences in the manner by which azoffluxin inhibits efflux pumps, or that efflux does not play a role in the azole-sensitivity of the strains that were tested. To learn whether azoffluxin had activity against strains of *C. albicans* in which fluconazole resistance is mediated through enhanced efflux, the activity of azoffluxin-fluconazole combination treatment against isolates from a patient who had received intermittent therapy with fluconazole over the course of two years was assessed. No potentiation was observed in the early clinical isolate, CaCi-2 (FIG. 9A), which is reported to have no bonafide resistance mutations, consistent with our finding of no potentiation in an azole-sensitive laboratory strain (FIG. 2E). Interestingly, azoffluxin did potentiate fluconazole against the late clinical isolate, CaCi-17, which possesses the substitution A736V in Tac1 that leads to upregulation of multiple efflux genes in addition to mutations that lead to the overexpression of an $ERG11^{R467K}$ allele. This ability of azoffluxin to potentiate fluconazole in CaCi-17 was abolished upon deletion of CDR1 (FIG. 9A), similar to what was observed in *C. auris* (FIG. 6). To confirm that azoffluxin inhibited efflux in *C. albicans*, Nile red accumulation in CaCi-17 was assessed by flow cytometry. Compared to the parental CaCi-17 isolate, the cdr1Δ/cdr1Δ mutant showed enhanced Nile red accumulation as would be expected. Importantly, an increase in Nile red accumulation upon azoffluxin treatment in both CaCi-17 strains was observed; however, the fold change was reduced in the CDR1 null (FIG. 9C), which was the same trend seen in *C. auris* (FIG. 2e). Overall, the fold-change upon treatment was less than that observed in *C. auris* isolates, which is consistent with the reduced ability of azoffluxin to enhance fluconazole activity in *C. albicans* CaCi-17 (FIGS. 8A and 9A). Finally, to confirm that combination treatment was blocking efflux and resulting in increased fluconazole accumulation, LC-MS was used to measure intracellular compound concentrations in CaCi-17. A significant increase in both intracellular fluconazole (FIG. 9D) and azoffluxin (FIG. 9E) in the combination treatment group was detected compared to untreated cells. These data indicate that azoffluxin blocks fluconazole efflux in a resistant clinical isolate of *C. albicans*, increasing its sensitivity to fluconazole, and they establish a broader spectrum of bioactivity for azoffluxin beyond *C. auris* alone.

Figures 9B, 9C:
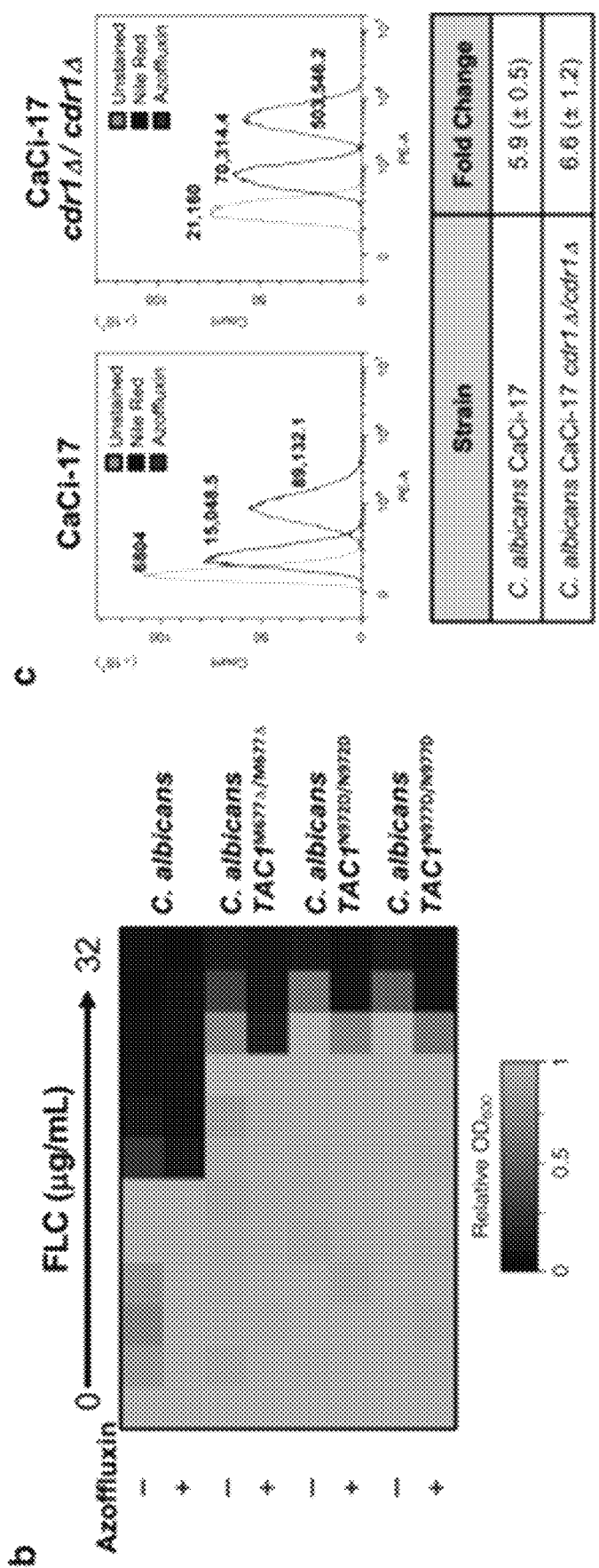
FIG. 9B depicts dose-response assays conducted in YPD medium with a C. albicans parental strain, and strains with gain-of-function mutations in TAC1 as indicated.
FIG. 9C depicts flow cytometric measurements of Nile red accumulation in C. albicans strains as described in FIG. 5B.
Figure 9E:
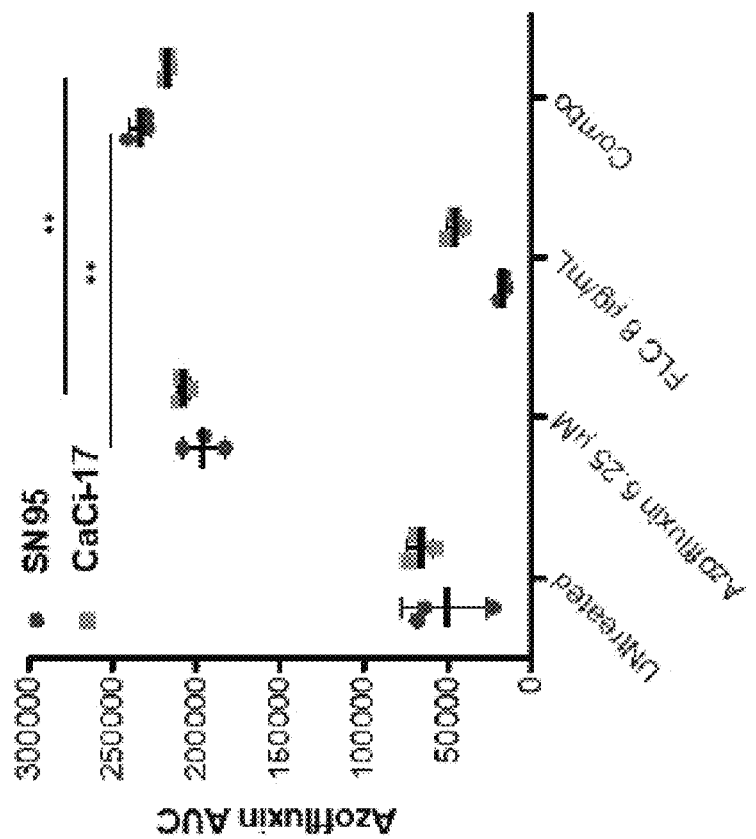
FIGS. 9D and 9E depict the intracellular concentrations of FLC and azoffluxin measured after treatment (combo treatment at 6.25 μM azoffluxin and 8 μg/mL FLC) for 1 hour by LC-MS.
Figure 9D:
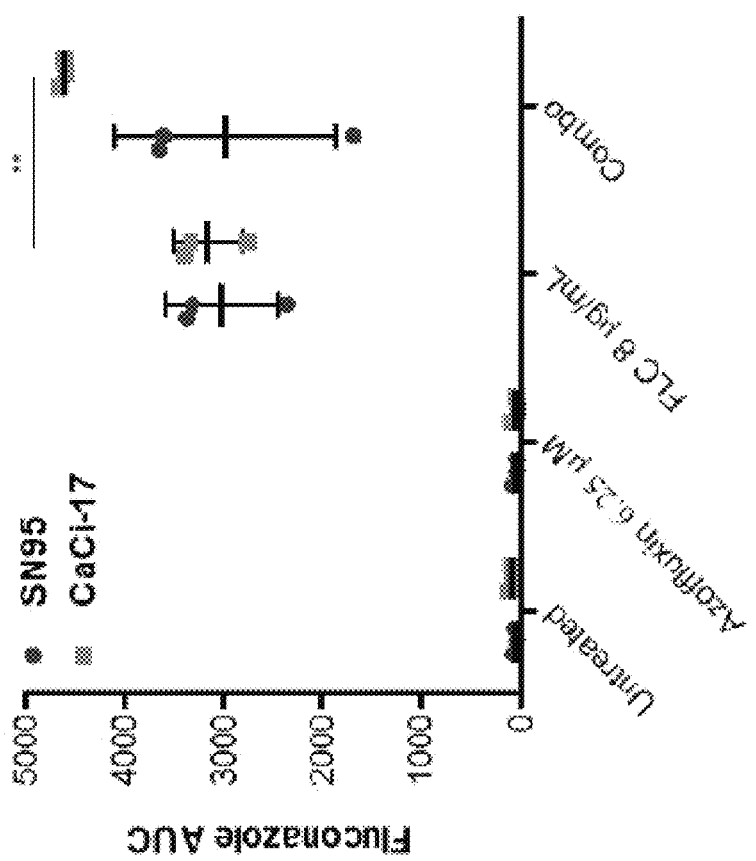

FIGS. 9A-9E show that azoffluxin enhances fluconazole (FLC) activity against azole-resistant isolates in *C. albicans*. FIG. 9A depicts checkerboard assays as described in FIG. 2B and performed with isolates of *C. albicans*. CaCi-2 and CaCi-17 represent early and late clinical isolates in which FLC resistance evolved over time. Growth was measured at 24 hours using $OD_{600}$ and normalized to a no drug control well (see color bar). FIG. 9B depicts dose response assays conducted in YPD medium with a *C. albicans* parental strain, and strains with gain of function mutations in TAC1 as indicated. FLC was tittered in a two-fold dilution on the x-axis in the absence and presence of 50 µM azoffluxin. Growth was measured at 24 hours using $OD_{600}$ and normalized to a no drug control well (see color bar). FIG. 9C depicts flow cytometry used to measure the Nile red accumulation in *C. albicans* strains as described in FIG. 5B. FIGS. 9D and 9E depict the intracellular concentrations of FLC and azoffluxin measured after treatment (combo treatment at 6.25 µM azoffluxin and 8 µg/mL FLC) for 1 hour by LC-MS. Error bars indicate standard deviation between technical triplicates. Significance was determined by an unpaired student t-test of each combination to the respective compound alone treatment, (*) indicates a p-value<0.05 and (**) indicates a p-value<0.01.

Combination Treatment Rescues Human Cells and Reduces Fungal Burden in Co-Culture.

The therapeutic potential of combining azoffluxin with fluconazole, given the dearth of effective antifungal treatments available for systemic *C. auris* infections was assessed. The ability of this combination to rescue human kidney-derived (293T) cells when co-cultured with *C. auris* was first examined. 293T cells constitutively expressing firefly luciferase as a reporter were either grown alone or in co-culture with *C. auris* under various treatment conditions. Luminescence was used as an indicator of viable human cell number present in each well. In the case of the solvent control, azoffluxin alone, or low fluconazole, *C. auris* growth was unhindered, which resulted in near complete human cell loss and an absence of luminescent signal (FIG. 10A). However, with the combination treatment (azoffluxin and low fluconazole) a dramatic rescue of the human cells was see, comparable to that achieved with a 16-fold higher concentration of fluconazole alone (FIG. 10A). Notably, in 293T cells grown in the absence of *C. auris* we saw no significant change in luciferase signal under any treatment condition, indicating that the treatments caused no detectable mammalian cytotoxicity in vitro (FIG. 10A). The same experimental design was used in a 24-well plate format followed by Periodic-acid Schiff (PAS) staining of polysaccharides to visualize effects of the various treatments on both the fungal and human elements within the co-cultures. Results supported findings obtained using the quantitative assay. In co-cultures, extensive damage to the human cell monolayer (stained pale blue) and extensive sloughing in conjunction with the presence of abundant C. auris (stained pink-purple) in wells exposed to azofluxin alone or low fluconazole alone was seen, comparable to the untreated co-culture. With combination treatment, an intact human cell monolayer, which was similar to the no fungus control, and scant fungal burden, was observed. In the high fluconazole condition, some disruption of the human cell monolayer was evident and fungal cells were readily apparent, suggesting that high fluconazole was effective at reducing fungal toxicity to the monolayer, but less effective than our combination treatment in arresting fungal proliferation (FIG. 10B). Overall, results are consistent with a non-toxic exposure to azofluxin transforming fluconazole from relatively ineffective to effective in controlling azole-resistant C. auris in a co-culture model.

FIGS. 10A-10G illustrate that combination treatment rescues mammalian cell growth and fungal burden in murine infection model-azofluxin markedly increases the antifungal activity of fluconazole (FLC) in culture and in mice. FIG. 10A depicts mammalian embryonic kidney (293T) cells expressing luciferase used to quantify mammalian cell growth in co-culture. Mammalian cells were seeded in 384-well plates in DMEM medium at $5 \times 10^5$ cells/mL overnight. After 24 hours the indicated concentration of compound (• indicates combo treatment concentrations) was added along with $2.5 \times 10^3$ cells/mL of C. auris. Co-cultures were incubated for 48 hours at 37° C. and then the luminescence was measured as an output of mammalian cell growth. Error represents standard deviation between technical quadruplicates, (*) indicates a p-value<0.001 between 293T cells alone and co-culture growth for each condition. FIG. 10B depicts Periodic-Acid Schiff (PAS) staining used to visualize cells in co-culture where light purple staining shows 293T cells and the bright pink shows C. auris. FIG. 10C depicts checkerboard assays performed as described in FIG. 2B with C. auris Clade IV isolate B11801. Relative growth was measured after 24 hours using OD600 and normalized to no-drug control wells (see color bar). The FICI calculated for each checkerboard is shown in the top right of each plot, with values<0.5 indicating synergy. FIG. 10D depicts kidney fungal burden (CFU) in mice from each treatment group (n=3) that had been infected with C. auris B11801. Input is the CFU recovered in an aliquot of the fungal suspension use to inoculate mice. All other values are the CFU recovered from kidney homogenates after four days of treatment. Fluconazole was administered at 32 mg/Kg IP twice daily and azofluxin at 10 mg/Kg SC four-times daily. Error bars; SD, n=3 mice/treatment group. The significance of differences between combination treatment and treatment with each compound alone was determined by two-tailed unpaired student t-test, (*) p-value<0.001. FIG. 10E is plot showing azofluxin is stable and retains activity in plasma. FIG. 10F is a plot tracking the concentration of azofluxin over time. A half-life of 2.6 hours was calculated. FIG. 10G is a plot showing that azofluxin (10 mg/Kg BID for 4 days) is well tolerated.

Azofluxin Also Inhibits Efflux in Other Fungal Pathogens.

FIGS. 11A and 11B illustrate Nile red Accumulation in C. albicans, C. glabrata, and C. neoformans. Despite increasing Nile red, azofluxin did not enhance the efficacy of fluconazole against C. glabrata or C. neoformans. FIG. 11A shows a bar graph of dose dependent increase in Nile red. FIG. 11B shows a list of fold change accumulation for C. albicans, C. glabrata, and C. neoformans at 10 μM and 100 μM of azofluxin.

Azofluxin Inhibits Mammalian Efflux Pumps.

Figure 12A:
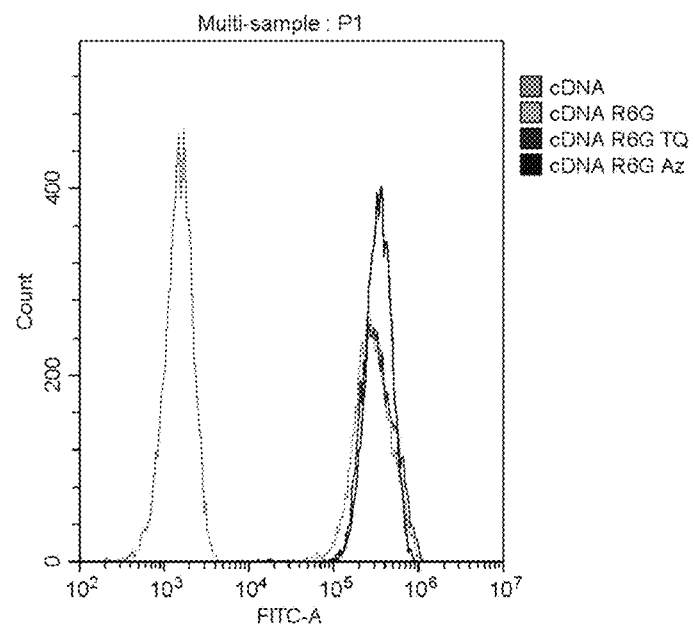
Figure 12B:
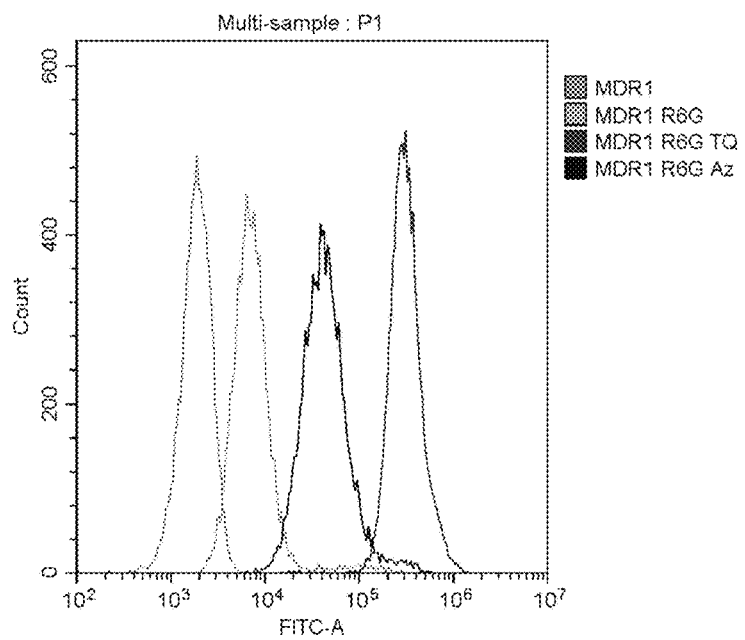
Figure 12C:
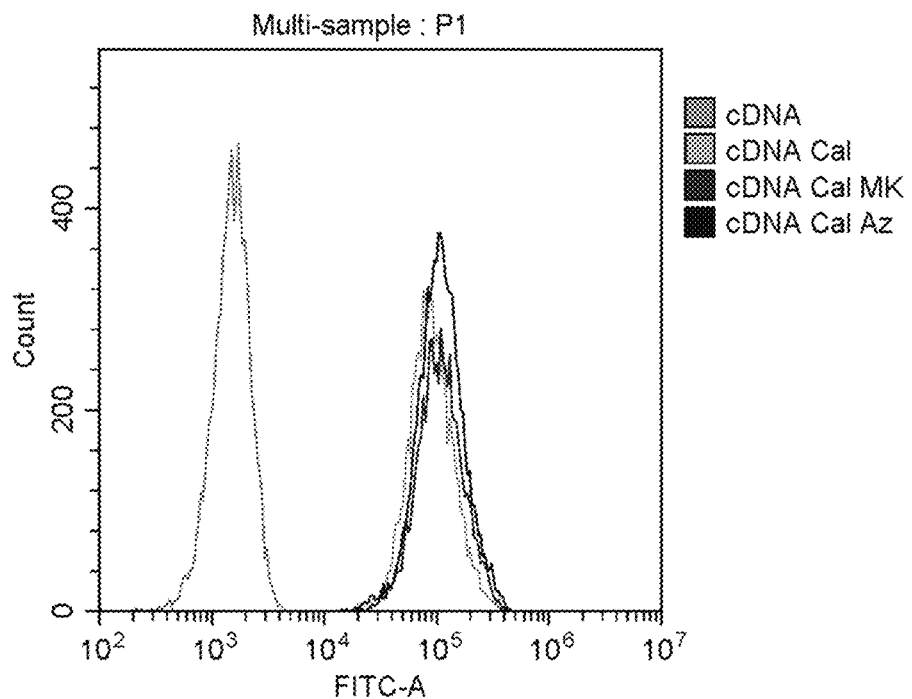
Figure 12D:
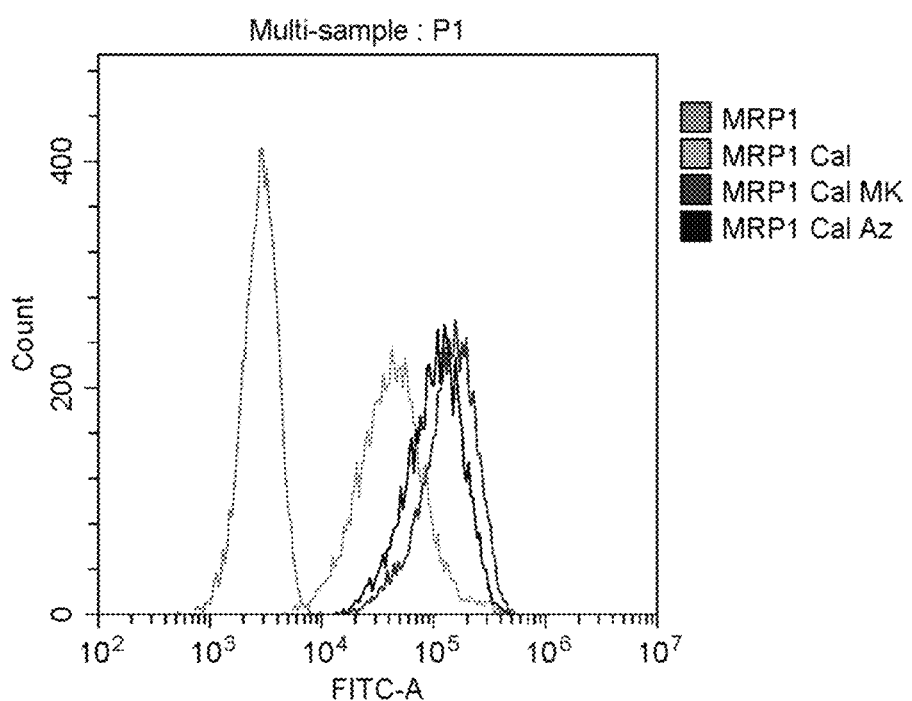

P-gp overexpressing HEK293 cell lines were used to determine if azofluxin treatment leads to a greater accumulation of fluorescent substrates (MFI) as determined by flow cytometry. The plotted results are shown in FIGS. 12A-12D. MDR1 (ABCB1) and MRP1 (ABCC1) was assessed using the fluorescent dyes rhodamine 6G (0.5 μg/mL) and Calcein AM (2.5 μg/mL), for each pump respectively, and the known inhibitor controls tariquidar (60 nM) and MK571 (30 μM) for each pump respectively. Listed data is shown by FIG. 12E (R6G) and FIG. 12F (Cal). While no effect was seen in control cDNA, azofluxin lead to a 6-fold increase in rhodamine 6G (R6G) in MDR1 overexpressing cells, and a 2.5-fold increase in calcein AM (Cal) in MRP1 overexpressing cells.

Structure Activity Relationships (SAR)

Stereochemical sensitivity. A SAR study of analogues showed stereochemical sensitivity. FIG. 13A shows structure of azofluxin (top, CMLD012336), and antifungal activity alone (middle) in combination with FLC (bottom). FIG. 13B shows structure of an azofluxin enantiomer (top, CMLD012337) and antifungal activity along (middle) and in combination with FLC (bottom).

Substations on aryl groups. FIG. 14 shows FICI values for diarylated oxindoles, where FICI values<0.5 indicates a strong synergistic interaction. The "R" groups are indicated in the top row, and the "X" group is show in the skeletal structure as the first column. The FICI color code and numbers are shown in the cells for each compound.

Other Analogs. FIG. 15 shows the structures (top) and effects (bottom checkerboard assays) of mixed analogues. In these structures, the two aryl groups are not symmetrically substituted. FIG. 16 shows compounds where the two aryl groups are the same.

Listing of compounds and resultant synergies. Table 1 is a listing of compounds and FICI values. FIGS. 17A and 17B plot efflux results for Nile Red assays for compounds in Table 1 showing strong synergy with FLC (FICI<0.5). FIG. 17A is a Biological Replicate 1 and FIG. 17B is a Biological Replicate 2.

Table 1. Fractional Inhibitory Concentration Index (FICI) for Diarylated Oxindoles Enhancement of FLC Activity in FLC-Resistant Candida auris

TABLE 1

Fractional inhibitory concentration index (FICI) for diarylated oxindoles enhancement of FLC activity in FLC-resistant *Candida auris*

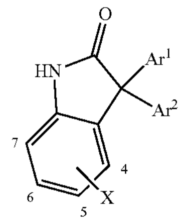

| Row | Identifier | X | $Ar^1$ | $Ar^2$ | FICI |
|---|---|---|---|---|---|
| Compounds exhibiting strong synergy with FLC (FICI <0.5) | | | | | |
| 1 | CMLD013623 | 7-F | 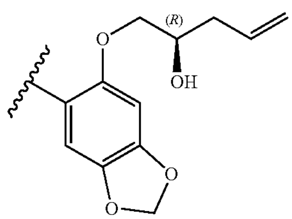  | 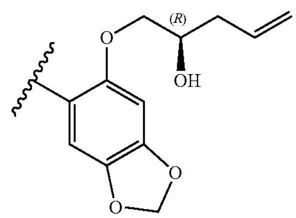  | 0.036 |
| 2 | CMLD012440 | 7-F | 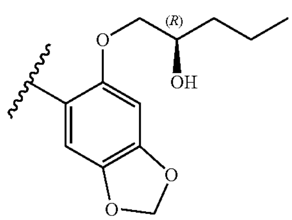  | 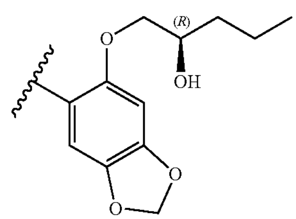  | 0.058 |
| 3 | CMLD012443 | 6-F | 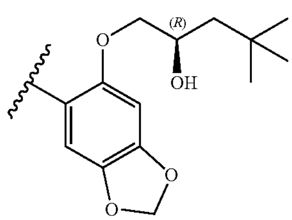  | 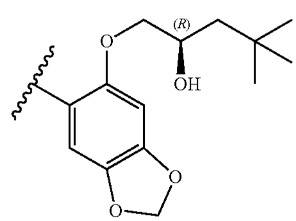  | 0.068 |
| 4 | CMLD012444 | 5-F | 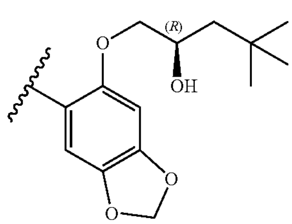  | 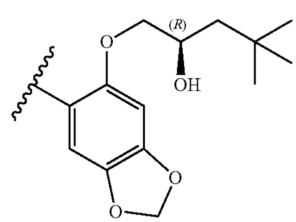  | 0.068 |
| 5 | CMLD012446 | 6-Br | 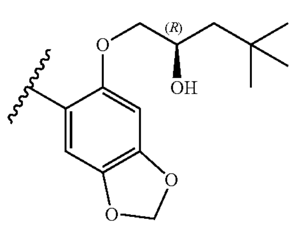  | 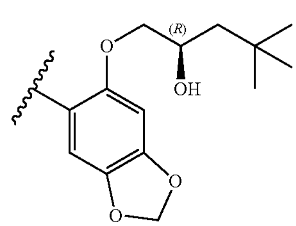  | 0.068 |

TABLE 1-continued

Fractional inhibitory concentration index (FICI) for diarylated oxindoles enhancement of FLC activity in FLC-resistant *Candida auris*

| Row | Identifier | X | Ar¹ | Ar² | FICI |
|-----|------------|---|-----|-----|------|
| 6 | CMLD013624 | 7-F | (R)-2-hydroxy-4,4-dimethylpentyloxy-benzo[1,3]dioxole | (R)-2-hydroxy-4,4-dimethylpentyloxy-benzo[1,3]dioxole | 0.068 |
| 7 | CMLD013655 | 7-F | (R)-2-hydroxypentyloxy-benzo[1,3]dioxole | OEt-benzo[1,3]dioxole | 0.113 |
| 8 | CMLD012402 | 7-F | (R)-2-hydroxypent-4-enyloxy-benzo[1,3]dioxole | (R)-2-hydroxypent-4-enyloxy-benzo[1,3]dioxole | 0.113 |
| 9 | CMLD012449 | 7-F | (R)-2-hydroxyhex-5-enyloxy-benzo[1,3]dioxole | (R)-2-hydroxyhex-5-enyloxy-benzo[1,3]dioxole | 0.113 |
| 10 | CMLD012336 "azoffluxin" | 6-F | (R)-2-hydroxy-4-methylpent-4-enyloxy-benzo[1,3]dioxole | (R)-2-hydroxy-4-methylpent-4-enyloxy-benzo[1,3]dioxole | 0.130 |
| 11 | CMLD012393 | 6-F | (R)-2-hydroxy-4-methylpentyloxy-benzo[1,3]dioxole | (R)-2-hydroxy-4-methylpentyloxy-benzo[1,3]dioxole | 0.130 |

TABLE 1-continued
Fractional inhibitory concentration index (FICI) for diarylated oxindoles enhancement of FLC activity in FLC-resistant *Candida auris*
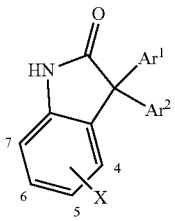
| Row | Identifier | X | Ar¹ | Ar² | FICI |
|---|---|---|---|---|---|
| 12 | CMLD012400 | 6-F | 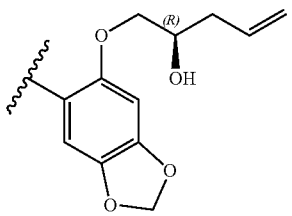 | 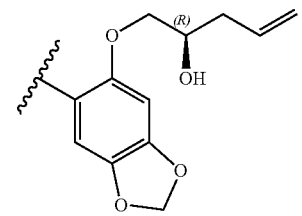 | 0.130 |
| 13 | CMLD012439 | 6-F | 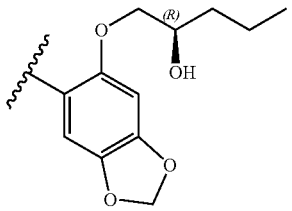 | 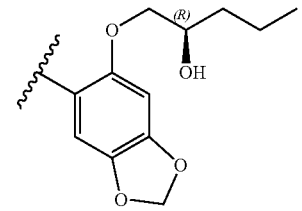 | 0.130 |
| 14 | CMLD012447 | 6-F | 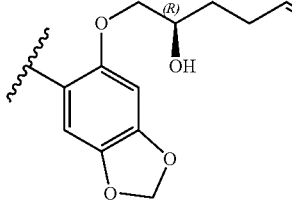 | 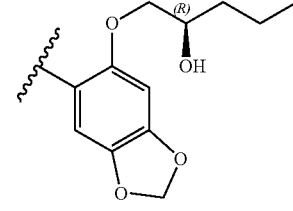 | 0.130 |
| 15 | CMLD013622 | 5-F | 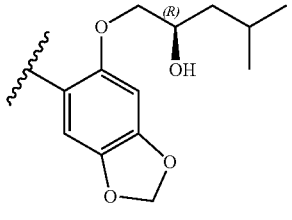 | 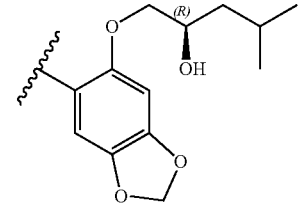 | 0.130 |
| 16 | CMLD013651 | 6-Br | 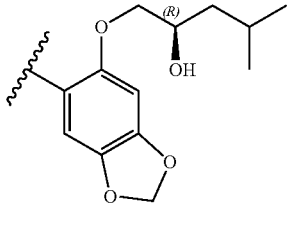 | 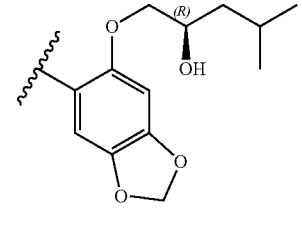 | 0.130 |

TABLE 1-continued

Fractional inhibitory concentration index (FICI) for diarylated oxindoles enhancement of FLC activity in FLC-resistant *Candida auris*

| Row | Identifier | X | Ar¹ | Ar² | FICI |
|---|---|---|---|---|---|
| 17 | RT-162S-015 | 6-F | (R)-4-methylpent-4-en-2-ol ether of benzo[d][1,3]dioxol-5-ol | 6-ethoxybenzo[d][1,3]dioxole TABLE 1-continued Fractional inhibitory concentration index (FICI) for diarylated oxindoles
enhancement of FLC activity in FLC-resistant *Candida auris*

| Row | Identifier | X | Ar¹ | Ar² | FICI |
|---|---|---|---|---|---|
| 22 | CMLD01361 9 | 5-F | (R)-1-(benzo[d][1,3]dioxol-5-yloxy)pentan-2-ol | (R)-1-(benzo[d][1,3]dioxol-5-yloxy)pentan-2-ol | 0.255 |
| 23 | CMLD01245 3 | 4-Br | (R)-1-(benzo[d][1,3]dioxol-5-yloxy)hex-5-en-2-ol | (R)-1-(benzo[d][1,3]dioxol-5-yloxy)hex-5-en-2-ol | 0.257 |
| 24 | CMLD01239 4 | 6-F | (R)-1-(benzo[d][1,3]dioxol-5-yloxy)butan-2-ol | (R)-1-(benzo[d][1,3]dioxol-5-yloxy)butan-2-ol | 0.266 |
| 25 | CMLD01245 0 | 5-F | (R)-1-(benzo[d][1,3]dioxol-5-yloxy)hex-5-en-2-ol | (R)-1-(benzo[d][1,3]dioxol-5-yloxy)hex-5-en-2-ol | 0.266 |
| 26 | CMLD01245 2 | 6-Br | (R)-1-(benzo[d][1,3]dioxol-5-yloxy)hex-5-en-2-ol | (R)-1-(benzo[d][1,3]dioxol-5-yloxy)hex-5-en-2-ol | 0.266 |
| 27 | CMLD01365 0 | 5-Br | (R)-1-(benzo[d][1,3]dioxol-5-yloxy)-4-methylpentan-2-ol | (R)-1-(benzo[d][1,3]dioxol-5-yloxy)-4-methylpentan-2-ol | 0.300 |

TABLE 1-continued

Fractional inhibitory concentration index (FICI) for diarylated oxindoles
enhancement of FLC activity in FLC-resistant *Cand TABLE 1-continued Fractional inhibitory concentration index (FICI) for diarylated oxindoles
enhancement of FLC activity in FLC-resistant *Candida auris*

| Row | Identifier | X | Ar¹ | Ar² | FICI |
|---|---|---|---|---|---|
| 33 | CMLD01240 1<br>CMLD01242 7 | 6-Br | (R)-OCH₂CH(OH)CH₂CH=CH₂ on methylenedioxyphenyl | (R)-OCH₂CH(OH)CH₂CH=CH₂ on methylenedioxyphenyl | 2 |
| 34 | CMLD01239 6<br>CMLD01242 4<br>CMLD01242 9 | 5-F | (R)-OCH₂CH(OH)CH₂CH₃ on methylenedioxyphenyl | (R)-OCH₂CH(OH)CH₂CH₃ on methylenedioxyphenyl | 2 |
| 35 | CMLD01239 8<br>CMLD01243 1 | 5-Me | (R)-OCH₂CH(OH)CH₂CH₃ on methylenedioxyphenyl | (R)-OCH₂CH(OH)CH₂CH₃ on methylenedioxyphenyl | 2 |
| 36 | CMLD01245 4 | 5-Me | (R)-OCH₂CH(OH)CH₂CH₂CH=CH₂ on methylenedioxyphenyl | (R)-OCH₂CH(OH)CH₂CH₂CH=CH₂ on methylenedioxyphenyl | 2 |
| 37 | CMLD01244 1 | 6-Br | (R)-OCH₂CH(OH)CH₂CH₂CH₃ on methylenedioxyphenyl | (R)-OCH₂CH(OH)CH₂CH₂CH₃ on methylenedioxyphenyl | 2 |
| 38 | CMLD01239 5 | 6-Br | (R)-OCH₂CH(OH)CH₂CH₃ on methylenedioxyphenyl | (R)-OCH₂CH(OH)CH₂CH₃ on methylenedioxyphenyl | 2 |

TABLE 1-continued

Fractional inhibitory concentration index (FICI) for diarylated oxindoles
enhancement of FLC activity in FLC-resistant *Candida auris*

| Row | Identifier | X | Ar¹ | Ar² | FICI |
|---|---|---|---|---|---|
| 39 | CMLD01242 | 5-Br | (R)-1-(2-hydroxypentyloxy)-benzodioxole | (R)-1-(2-hydroxypentyloxy)-benzodioxole | 2 |
| 40 | CMLD01397 | 4-Br | (R)-1-(2-hydroxybutyloxy)-benzodioxole | (R)-1-(2-hydroxybutyloxy)-benzodioxole | 2 |
| 41 | CMLD01318 | 6-Me | (R)-1-(2-hydroxypentyloxy)-benzodioxole | (R)-1-(2-hydroxypentyloxy)-benzodioxole | 2 |
| 42 | CMLD01315 | 6-F | 2-hydroxy-4-methylphenyl | 2-hydroxy-4-methylphenyl | 2 |
| 43 | CMLD01316 | 6-F | 2-hydroxy-4-chlorophenyl | 2-hydroxy-4-chlorophenyl | 2 |
| 44 | RT-162S-017-04 | 6-F | (R)-1-(2-hydroxybutyloxy)-benzodioxole | OEt-benzodioxole | 2 |

TABLE 1-continued

Fractional inhibitory concentration index (FICI) for diarylated oxindoles enhancement of FLC activity in FLC-resistant *Candida auris*

| Row | Identifier | X | Ar¹ | Ar² | FICI |
|---|---|---|---|---|---|
| 45 | RT162S-024 | 6-F | 6-(((R)-2-hydroxybutoxy)-benzo[1,3]dioxole | 6-((hex-5-yn-1-yloxy))-benzo[1,3]dioxole | 2 |
| 46 | RT162S-029 | 6-F | 6-(((R)-2-hydroxypent-4-en-1-yloxy))-benzo[1,3]dioxole | 6-((2-(3-(but-3-yn-1-yl)-3H-diazirin-3-yl)ethoxy))-benzo[1,3]dioxole | 2 |
| 47 | CMLD012338 | 6-F | 6-OH-benzo[1,3]dioxole | 6-OH-benzo[1,3]dioxole | 2 |
| 48 | CMLD012340 | 6-F | 6-OMe-benzo[1,3]dioxole | 6-OMe-benzo[1,3]dioxole | 2 |
| 49 | CMLD012341 | 6-F | 6-OEt-benzo[1,3]dioxole | 6-OEt-benzo[1,3]dioxole | 2 |

TABLE 1-continued

Fractional inhibitory concentration index (FICI) for diarylated oxindoles
enhancement of FLC activity in FLC-resistant *Candida auris*

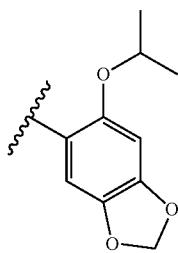 [SMILES: *c1cc2c(cc1OC(C)C)OCO2]

| Row | Identifier | X | Ar¹ | Ar² | FICI |
|---|---|---|---|---|---|
| 50 | CMLD012342 | 6-F | 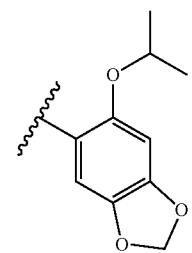 [SMILES: *c1cc2c(cc1OC(C)C)OCO2] | 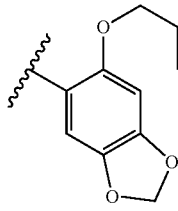 | 2 |
| 51 | CMLD013625 | 6-F | 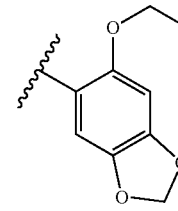 | 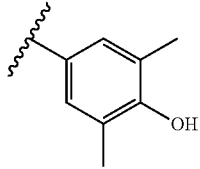 [SMILES: *c1cc(C)c(O)c(C)c1] | 2 |
| 52 | CMLD012339 | 6-F | 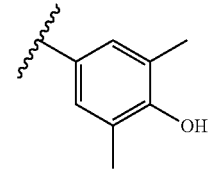 [SMILES: *c1cc(C)c(O)c(C)c1] | 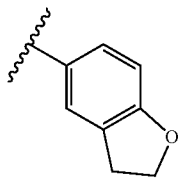 [SMILES: *c1ccc2c(c1)CCO2] | 2 |
| 53 | CMLD012343 | 6-F | 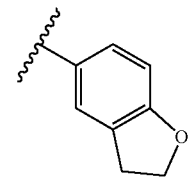 [SMILES: *c1ccc2c(c1)CCO2] | 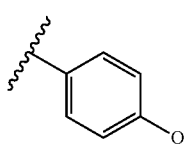 | 2 |
| 54 | Oxyphenisatin | Unsub. | 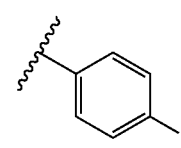 |  | 2 |

Azoffluxin and known (Table 1) analogues can be administered in combination with amphotericin B to enhance the activity of amphotericin B against *Candida auris, Candida albicans*, and *Cryptococcus neoformans*. (CD cin, moxidectin, and selamectin, in order to enhance antimicrobial activity of these agents against bacteria and parasites, and restore susceptibility of drug-resistant bacteria and parasites to drug treatment.

Additional Exemplary Compounds

FIG. 18A shows generic scaffolds of compounds encompassed by Formula (I) and FIGS. 18B and 18C shows some specific exemplary compounds of Formula (I). These compounds can be administered in combination therapies. Without wishing to be bound by a theory, these compounds can be used to:

(1) enhance the activity of azole antifungal agents (e.g., fluconazole) against fungal pathogens from the genus Candida spp., such as Candida auris, Candida albicans, and Cryptococcus neoformans;

(2) enhance the activity of amphotericin B against Candida auris, Candida albicans, and Cryptococcus neoformans (Cdr1 efflux is connected to AmB tolerance in C. albicans);

(2) to restore susceptibility multi-drug resistant cancer cells to drug treatment, where the oncology drugs are known to be substrates of MDR1 aka P-glycoprotein 1 (Pgp1), and suffer from compromised activity in multi-drug-resistant cancers (without limitation, these oncology drugs include doxorubicin, daunorubicin, actinomycin, camptothecins such as irinotecan and topotecan, epipodophyllotoxins such as etoposide and teniposide, taxane such as paclitaxel and docetaxel, tyrosine kinase inhibitors such as, rucaparib, olaparib, imatinib, masitinib, nilotinib and toceranib, and vinca alkaloids such as vinblastine, vincristine, and vinorelbine); and (3) to enhance antimicrobial activity of agents against bacteria and parasites, and restore susceptibility of drug-resistant bacteria and parasites to drug treatment administered in combination with antimicrobial drugs known to be substrates of human and microbial ABC efflux pumps (without limitation, these antimicrobial agents include erythromycin, tetracycline, doxycycline, levofloxacin, ofloxacin, sparfloxacin, dorametin, ivermectin, milbemycin, moxidectin, and selamectin).

Discussion

This study leveraged a diversity-oriented chemical library to discover CMLD012336 (azoffluxin), a novel compound that enhances the susceptibility of resistant fungal pathogens to diverse intracellularly acting antimicrobial agents. It was found that this compound inhibits the activity of multidrug efflux transporters, the best defined by this study being the ABC transporter Cdr1. One of the most frequently encountered and most problematic mechanisms of antimicrobial resistance is activation of multidrug efflux. With the escalating problem of antifungal-resistance threatening human health world-wide, the ability of azoffluxin to inhibit drug efflux in a non-toxic manner could have unusually broad, readily translatable therapeutic implications.

Azoffluxin, a 3,3-diarylated oxindole, was identified as an unexpected side product in a Lewis-acid mediated Friedel-Crafts/Prins reaction process intended to generate spirocyclic oxindoles. 3,3-Diarylated oxindoles, are a subset of the medicinally "privileged" 3,3-disubstituted oxindole class, which have a rich history of reported biological activities. For example, the diphenolic oxindole oxyphenisatin and other 3,3-diarylated oxindoles have been widely reported to exhibit antiproliferative activity against diverse cancer cell lines, in many cases the activity is ascribed to inhibition of eIF2α-mediated translation initiation. The 3,3-diarylated oxindole BHPI, a non-classical estrogen receptor α-agonist, has been recently shown to deplete intracellular ATP in estrogen receptor-positive cancer cells and inhibit ATP-dependent processes including ABC transporter-mediated drug efflux. Whether the compound might directly inhibit human ABC transporters is unknown. Other 3,3-bisaryl oxindoles have been reported with mineralocorticoid receptor antagonism, as well as antioxidant activity. Although azoffluxin falls into the general class of 3,3-disubstituted oxindoles, it is structurally distinct. Given the divergence between mammalian and fungal cells in the processes reported to be impacted by other class members as well as the lack of toxicity we observed in mammalian cells, it seems unlikely that azoffluxin is operating through the mechanisms previously described for other 3,3-disubstituted oxindoles.

Using azoffluxin as a chemical probe, C. auris strains for which efflux is a major mechanism of fluconazole resistance were identified. Specifically, strains belonging to Clades I, II, and IV were susceptible to the azoffluxin-fluconazole combination, implicating efflux as a dominant factor contributing to their high-level azole resistance. Inhibition of efflux in these strains markedly reduces fluconazole resistance, despite the fact that these C. auris strains harbor many Erg11 substitutions, most notably Erg11$^{Y132F}$ and Erg11$^{K143R}$ that have been reported to yield a >4-fold increase in azole MIC. azoffluxin reduced the azole-resistance of an efflux-dependent C. albicans strain harboring an Erg11$^{R467K}$ mutation as well, which has been reported to also result in an approximately >4-fold increase in azole resistance. The deletion of Cdr1 in either of these species abolished the potentiation effects seen by azoffluxin. These data suggest that the mechanisms by which azoffluxin inhibits it target(s), most clearly defined being Cdr1, are conserved across these species. Notably, any potentiation activity for azoffluxin in the more divergent fungal species C. glabrata and S. cerevisiae was not observed. This lack of activity may indicate that despite Cdr1 being the homolog of the efflux pump Pdr5 in these species and sharing 56% sequence identity with it, Pdr5 is not a relevant target for azoffluxin.

By exploring the fluconazole-sensitizing activity of azoffluxin against genetically diverse isolates of C. auris, it was discovered that isolates from Clade III were not susceptible to the compound combination. Clade III is unique in that it contains Erg11$^{V125A/F126L}$ substitutions, harbors a unique activating substitution in Mrr1 (N647T), which leads to upregulation of the major facilitator superfamily pump Mdr1, and unlike Clade I and IV does not possess candidate drug-resistance substitutions in Tac1b. It was found that while MDR1 is upregulated in Clade III isolates compared to Clade I, azoffluxin treatment still resulted in increased Nile red accumulation in these strains. This suggests that azoffluxin is able to inhibit the function of additional efflux pumps for which Nile red is a substrate, such as Cdr1, Cdr2, and Mdr1. Furthermore, the observation that azoffluxin was able to potently synergize with fluconazole against a Clade III isolate that did not possess the Erg11$^{V125A/F126L}$ or Mrr1$^{N647T}$ substitutions implies that one or more of these resistance-conferring mutations is responsible for the inability of azoffluxin to potentiate the activity of fluconazole against most Clade III isolates. These insights, paired with a previous report finding that Mdr1 does not play a role in fluconazole resistance in Clade I isolates, suggests that the impact of Mdr1 on azole resistance in Clade III strains may be negligible. Rather, the specific Erg11$^{V125A/F126L}$ substitutions are likely key contributors to fluconazole resistance in Clade III strains. The F126L substitution has been implicated in high-level azole resistance in C. albicans and S.

*cerevisiae*, but the precise contribution of this substitution combination is not known. If the substitution renders Erg11 completely recalcitrant to inhibition by fluconazole, then azole resistance could become independent of efflux. However, while in this work strong evidence that azoffluxin inhibits the function of Cdr1 was found, the full spectrum of this compound's targets, specifically with regards to Mdr1, remains undefined. It is also possible that additional resistance mechanisms contribute to fluconazole resistance of Clade III isolates. Together, these findings highlight the utility of a chemical probe such as azoffluxin in dissecting the functional relationships important for drug resistance in genetically complex clinical isolates.

Efflux is regulated by complex and highly interconnected genetic circuitry. Recent analyses of *S. cerevisiae* genetic interaction networks show that perturbing the network through deletion of specific ABC transporter genes can paradoxically lead to an increase in azole resistance. This response was partially mediated by compensatory upregulation of PDR5, as deletion of PDR5 restored fluconazole sensitivity. The herein reported finding that expression levels of several efflux genes such as Cdr1, Mdr1, and Cdr4-1 were upregulated in *C. auris* response to azoffluxin, highlights the connectivity of the efflux network. Remarkably, this upregulation did not translate to reduced ability to sensitize to fluconazole. The robust activity of azoffluxin despite the compensatory upregulation of efflux genes reflects the strong dependence of fluconazole resistance on Cdr1. Consistent with this observation, it was determined that the highly resistant *C. albicans* clinical isolate CaCi-17 was susceptible to the azoffluxin-fluconazole combination. In contrast, azoffluxin had no impact on azole sensitivity of the less resistant earlier clinical isolate CaCi-2, suggesting that more sensitive strains of *C. albicans* do not rely on drug efflux for fluconazole tolerance. These findings underscore the value of azoffluxin and related reagents as chemical probes to discern the relative role of efflux in antifungal drug resistance across diverse fungal pathogens.

From a therapeutic perspective, utilizing a chemical combination in which one compound targets an essential process and the other disables a major resistance mechanism provides an attractive strategy that has been explored for both antimicrobial and cancer treatment. In the case of efflux inhibitors, not only does this strategy enhance the efficacy of the other compound, but if applied early in the course of intervention, it can also reduce the rate at which resistance emerges. Despite the conceptual appeal, however, no efflux inhibitor combination therapies have proven effective in the patients to date. This failure in clinical translation has largely been due to host toxicity, off target effects, and/or the poor pharmacokinetics that have plagued current efflux inhibitors such as verapamil, cyclosporin A, and valspodar. The lack of toxicity herein observed to human cells in culture for azoffluxin at exposures demonstrating good bioactivity is encouraging. An additional, distinct challenge to the efficacy of efflux inhibitors is the emergence of target-based and other resistance mechanisms that can render efflux a less important factor contributing to the overall resistance level of a fungal pathogen. Encouragingly, azoffluxin is able to sensitize azole-resistant *Candida* strains harboring some target-based resistance mechanisms.

As the number of drug-resistant infections continues to rise, there is a pressing need to understand the relative contribution of different resistance mechanisms to the diminishing efficacy of our limited antifungal armamentarium and to design new resistance-evasive treatment strategies. To address these needs, discovery of azoffluxin provides a useful tool for further study of fungal drug-efflux biology in the lab and a promising lead for further preclinical development efforts.

Methods

Strain Construction

All strains, plasmids and oligonucleotides used in this study are listed in Tables 2-4 respectively.

TABLE 2

| Strain ID | Description | Genotype | Source |
|---|---|---|---|
| CaLC79 | *C. albicans* CaCi-2 | Clinical isolate | *Antimicrob. Agents Chemother.* 41, 1482-1487 (1997). |
| CaLC91 | *C. albicans* CaCi-17 | Clinical isolate | *Antimicrob. Agents Chemother.* 41, 1482-1487 (1997). |
| ScLC151 | *S. cerevisiae* BY4741 | MATa his3Δ1 leu2Δ0 met15Δ0 ura3Δ0 | *Nature* 418, 387-391 (2002). |
| CaLC239 | *C. albicans* SN95 | arg4Δ/arg4Δ, his1Δ/his1Δ, URA3/ura3Δ::imm434 IRO1/iro1Δ::imm434 | *Eukaryot. Cell* 4, 298-309 (2005). |
| CgLC1002 | *C. glabrata* BG2 | Clinical isolate | *Genetics* 151, 979-87 (1999). |
| CauLC3438 | *C. auris* | VPCI 673/P/12 | Gift from Anuradha Chowdhary |
| CaLC4255 | *C. albicans* SN152 tac1Δ/tac1Δ | arg4Δ/arg4Δ, leu2Δ/leu2Δ::LEU2, his1Δ/his1Δ::HIS1, URA3/ura3Δ, IRO1/iro1Δ, tac1Δ/tac1Δ | *PLoS Genet.* 5, e1000783 (2009). |
| CauLC5083 | *C. auris* Ci6684 | Clinical isolate Clade I | *BMC Genomics* 16, 686 (2015). |
| CauLC5280 | *C. auris* Ci6684 cdr1Δ | CauLC5083 + cdr1Δ::NatMX | *mBio* 10, e02529-18 (2019). |
| CauLC5288 | *C. auris* B11220 | Clinical isolate Clade II | *Clin. Infect. Dis.* 64, 134-140 (2017)., CDC & FDA Antibiotic Resistance Isolate Bank. Atlanta |
| CauLC5289 | *C. auris* B11109 | Clinical isolate Clade I | |
| CauLC5290 | *C. auris* B11221 | Clinical isolate Clade III | |
| CauLC5291 | *C. auris* B11222 | Clinical isolate Clade III | |
| CauLC5292 | *C. auris* B11244 | Clinical isolate Clade IV | |
| CauLC5293 | *C. auris* B11245 | Clinical isolate Clade IV | |
| CauLC5294 | *C. auris* B8441 | Clinical isolate Clade I | |

TABLE 2-continued

| Strain ID | Description | Genotype | Source |
|---|---|---|---|
| CauLC5295 | C. auris B11098 | Clinical isolate Clade I | (GA):CDC (2020) |
| CauLC5296 | C. auris B11203 | Clinical isolate Clade I | |
| CauLC5297 | C. auris B11205 | Clinical isolate Clade I | |
| CalC5447 | C. albicans CaCi-17 cdr1Δ/cdr1Δ | Clinical isolate cdr1Δ/cdr1Δ | This study |
| CaLC5589 | C. albicans TAC1/TAC1 | CaLC4255 (tac1::HIS1)::TAC1WT-SAT1/(tac1::LEU)::TAC1WT-HIS1 | This study |
| CaLC5591 | C. albicans $TAC1^{M677\Delta}/TAC1^{M677\Delta}$ | CaLC4255 (tac1::HIS1)::TAC1 M677Δ-SAT1/(tac1::LEU2)::TAC1 M677Δ-HIS1 | This study |
| CaLC5593 | C. albicans $TAC1^{N972D}/TAC1^{N972D}$ | CaLC4255 (tac1::HIS1)::TAC1 N972D-SAT1/(tac1::LEU2)::TAC1 N972D-HIS1 | This study |
| CaLC5595 | C. albicans $TAC1^{N977D}/TAC1^{N977D}$ | CaLC4255 (tac1::HIS1)::TAC1 N977D-SAT1/(tac1::LEU2)::TAC1 N977D- | This study |
| CauLC6410 | C. auris cdr1Δ | CauLC5083 + cdr4-1Δ::NatMX | This study |
| CauLC6554 | C. auris B12037 | Clinical isolate Clade III | Gift from Philippe Dufresne |
| CauLC6750 | C. auris B12037 cdr1Δ | CauLC6654 + cdr1Δ::NatMX | This study |
| B11801 | C. auris B11801 | Clinical isolate Clade IV | Clin. Infect. Dis. 64, 134-140 (2017)., CDC & FDA Antibiotic Resistance Isolate Bank. Atlanta (GA):CDC (2020) |
| HEK 293T | HEK 293T | Firefly luciferase expressing | J. Am. Chem. Soc. 137, 525-530 (2015). |

TABLE 3

| Plasmid ID | Description | Source |
|---|---|---|
| pLC1049 | C. auris NATMX marker | mBio 10, e02529-18 (2019). |
| pLC1081 | C. albicans CAS9 vector pV1093 | mSphere 1, 1-9 (2016). Antimicrob. Agents Chemother. 61, 1-20 (2017). |
| pLC1083 | C. albicans CDR1-SAT1 flipper | Antimicrob. Agents Chemother. 61, 1-20 (2017). |
| pLC1092 | C. albicans TAC1 vector pFA-TAC1-HIS-T3) | Antimicrob. Agents Chemother. 62, e00968-18 (2018). |
| pLC1093 | C. albicans $TAC1^{M677\Delta}$ vector pFA-TAC1 M677Δ-HIS-T3 | |
| pLC1094 | C. albicans $TAC1^{N972D}$ vector pFA-TAC1N972D-HIS-T3 | |
| pLC1095 | C. albicans $TAC1^{N977D}$ vector pFA-TAC1N977D-HIS-T3 | |

TABLE 4

| Oligo ID | Description | Sequence (5' to 3') | SEQ ID NO: |
|---|---|---|---|
| oLC274 | pJK863down-F | CTGTCAAGGAGGGTATTCTGG | 1 |
| oLC1096 | CaCDC37 + 505 + SacI-R | CCCGAGCTCCGTCGATCCTGTTTCTATGT | 2 |
| oLC1097 | CaCDC37 + 662-R | GGAGCTTTTGGTTTATCTTG | 3 |
| oLC1098 | 6xHIS-CaCTA8 + 1814 + Apa1-F | TTGCGGGCCCGCAATTAGTTGGTCATCAACC | 4 |

TABLE 4-continued

| Oligo ID | Description | Sequence (5' to 3') | SEQ ID NO: |
|---|---|---|---|
| oLC1099 | 6XHIS-CaCTA8 + 2286 + Apa1-R | TTGCGGGCCCTTAGTGGTGGTGGTGGTGGT GATGATCGCTAACTTCTTCG | 5 |
| oLC5727 | CaurisACT1 + 121F | ACCCCAAGTCCAACAGAGAG | 6 |
| oLC5728 | CaurisACT1 + 316R | TCCAGCCAAGTCAAGTCTCA | 7 |
| oLC5729 | CaurisGPD1 + 141F | ATCCTTGCTGAAAACGCTGC | 8 |
| oLC5730 | CaurisGPD1 + 318R | TCCTCGGCCACCTTTACAAT | 9 |
| oLC6020 | CaurisCDR1 − 989F | TAACGCAAAAGGACCATGGC | 10 |
| oLC6023 | CaurisCDR1 + 5493R | CGCCCTTGATAATGTCCACG | 11 |
| oLC6024 | CaurisCDR1 − 925F | CGGCCCATGATAACCCTCTA | 12 |
| oLC6025 | CaurisCDR1 + 5426R | TTTCTGTCTCTCTGAGGGCA | 13 |
| oLC6125 | CauCDR1 + 3359F | CGCTGAATGGATGTTGGAGG | 14 |
| oLC6126 | CauCDR1 + 3514R | CTTCTTTCTGGACTCCGGGT | 15 |
| oLC6169 | CaurisCDR1 + 2679R | GCAGTGATCTGACCTGGCTT | 16 |
| oLC6221 | CaurisCDR1 − 1298F | ACAGCTGGATTCGACATGGG | 17 |
| oLC6231 | CaurisCDR1 + 2175F | TTTGTGCCTTCAGGAGGACC | 18 |
| oLC6296 | pLC605 NAT F | ACTGGATGGCGGCGTTAGTA | 19 |
| oLC6304 | pLC605 NAT R | ATCAAGCTTGCCTCGTCC | 20 |
| oLC6305 | NAT_CaurisCDR1 − 35R | CTATACTGCTGTCGATTCGATACTAACGCC G CCATCCAGTACTACATGCGATATATATAT | 21 |
| oLC6306 | NAT_CaurisCDR1 + 69F | CGCTGGCCGGGTGACCCGGCGGGGACGAG G CAAGCTTGATTGAGCTCGTGTGTGTCATCA | 22 |
| oLC6307 | CaurisCDR1 − 797R | CCCACATTTCGAGAAAAGGA | 23 |
| oLC6308 | pLC605NAT_26 | TGGTCGCTATACTGCTGTCG | 24 |
| oLC6926 | SNR52/F | AAGAAAGAAAGAAAACCAGGAGTGAA | 25 |
| oLC6927 | sgRNA/R | ACAAATATTTAAACTCGGGACCTGG | 26 |
| oLC6928 | SNR52/N | GCGGCCGCAAGTGATTAGACT | 27 |
| oLC6929 | sgRNA/N | GCAGCTCAGTGATTAAGAGTAAAGATGG | 28 |
| oLC6966 | SNR52/R_CDR1 | ATACAAGTGAAAACATTCAGCAAATTAAA A ATAGTTTACGCAAGTC | 29 |
| oLC6967 | sgRNA/F_CDR1 | CTGAATGTTTTCACTTGTATGTTTTAGAGCT AGAAATAGCAAGTTAAA | 30 |
| oLC6968 | sCdr1 NQ sense | ATTCTAAGATGTCGTCGCAAGATG | 31 |
| oLC6969 | sCdr1 NQ anti | AGTTCTGGCTAAATTCTGAATGTTTTC | 32 |
| oLC7041 | oLC7041_Tac1 check sense 1 | TAAATGCAATGGGTCTTATCCATGTGG | 33 |
| oLC7042 | oLC7042_Tac1 check anti 1 | GTCAAATATTCTTCACCGTATGAACCT | 34 |
| oLC8050 | CauMDR1orf_21 F | AGAGAGAGCTTCTTCGGCAG | 35 |
| oLC8051 | CauMDR1orf_174 R | AGATCAACGGGGGTGTCTGA | 36 |
| oLC8052 | CauCDR4_942orf_2102 F | TCCAGAACTGGGCAATAGCG | 37 |
| oLC8053 | CauCDR4_942orf_2286 R | TGCATGGCTCCCTTGTTGAT | 38 |

TABLE 4-continued

| Oligo ID | Description | Sequence (5' to 3') | SEQ ID NO: |
|---|---|---|---|
| oLC8054 | CauCDR4_069orf_1447 F | TTCGACTCAAAGGTGACCCG | 39 |
| oLC8055 | CauCDR4_069orf_1596 R | AGGGAGCAGAACGCATTGAA | 40 |
| oLC8056 | CauSNQ2_644orf_2600 F | ACCTGGTAAGTTGACCGCCT | 41 |
| oLC8057 | CauSNQ2_644orf_2790 R | CGAAGGGCTTCTCTGACAGT | 42 |
| oLC8058 | CauSNQ2_421orf_2042 F | CACTGTTTGTGGCTTCACCG | 43 |
| oLC8059 | CauSNQ2_421orf_2210 R | CGCCTGAAACAGGTCTCACT | 44 |
| oLC8164 | Cau_CDR4_942orf - 943 F | GGATTTGGGATTTGGACACT | 45 |
| oLC8165 | NAT_CauCDR4_942orf - 5R | CTATACTGCTGTCGATTCGATACTAACGCCG CCATCCAGTGGTCCTGAGAAGTCGTGGAC | 46 |
| oLC8166 | NAT_CaurisCDR4_942 + 33F | CGCTGGCCGGGTGACCCGGCGGGGACGAGG CAAGCTTGATCCACGGTAAAAACGATGGAC | 47 |
| oLC8167 | Cauris_CDR4_942orf + 965 R | ACCAGGCTTGGAATTGACAG | 48 |
| oLC8168 | Cauris_CDR4_942orf - 880 F | GCTGTGAGAGTTGGCAAGG | 49 |
| oLC8169 | Cauris_CDR4_942orf + 863 R | GCCAAATTCGCCATTAAAGA | 50 |

CauLC6410: *C. auris* cdr4-1Δ::NAT

The *C. auris* strain with CDR4-1 (B9J08_000479) deleted was constructed using homologous recombination and an electroporation transformation approach, as described previously. Approximately 1 kb of sequence homology upstream of CDR4-1 was amplified using primers oLC8164/oLC8165 and ~1 kb of homology downstream of CDR4-1 was amplified with oLC8166/oLC8167. The interior primer of each set contained 40 bp homology to a nourseothricin (NAT) resistance marker from pLC1049, which was amplified with primers oLC6296/oLC6304. Using fusion PCR with nested primers oLC8168/oLC8169, the NAT cassette and CDR4-1 homology regions were combined into a single DNA fragment. This PCR product was ethanol precipitated, 3 μg of DNA was electroporated into CaLC5083, and transformants were plated on YPD plates containing 150 μg/mL NAT. Colonies were patched and genotyped for integration of the deletion construct (oLC8164/oLC6308 and oLC274/oLC8167) and for the absence of the wild-type allele (oLC8052/oLC8053).

CaLC5447: *C. albicans* CaCi-17 cdr1Δ/cdr1Δ

Both alleles of CDR1 (C3_05220W) were deleted by a transient CRISPR method. The guide construct was made of two components from pLC1081: the SNR52 promoter amplified with the universal primer oLC6929 and guide specific primer oLC6966, and the guide scaffold and terminator amplified with the guide specific primer oLC6967 and universal primer oLC6927. The fusion construct was PCR amplified with the universal nested primers oLC6928/olC6929. Repair template was digested from pLC1083 by ApaI (NEB) and SacI (NEB). Gene deletion was verified by the absence of the CDR1 specific amplicon with oLC6968/oCL6969.

Culture Conditions

All fungal strains were stored in 25% glycerol in YPD medium (YPD: 1% yeast extract, 2% peptone, and 2% D-glucose) and maintained at −80° C. Strains were grown in either YPD alone or RPMI medium (10.4 g/L RPMI-1640, 3.5% MOPS, 2% D-glucose, supplemented with an additional 5 mg/mL histidine as required, pH 7). The mammalian cell line of human embryonic kidney 293T cells was stored in glycerol and cultured in DMEM media (Sigma) with 10% fetal bovine serum (FBS; Gibco).

BU-CMD Library Screen 2,456 compounds from the Boston University Center for Molecular Discovery (BU-CMD) library were used to identify compounds that enhance fluconazole activity against *C. auris*. All compounds were dissolved in DMSO (dimethyl sulfoxide; Sigma) at 5 mM. RPMI medium alone or containing 128 μg/mL fluconazole (Sequoia Research Products) was inoculated with ~1×10$^3$ cells/mL of *C. auris* (VPCI 673/P/12) from a saturated overnight culture. Both types of media were dispensed at 100 μL per well into 96-well, flat-bottom, microtiter plates (Sarstedt) plates. 1 μL of DMSO solubilized compound from the library was added into each well to a final concentration of 50 μM. Cells were incubated for 48 hours at 30° C. and OD$_{600}$ was read (Molecular Devices SpectraMax Plus 384). After the initial screen, all secondary chemical susceptibility assays were performed on fresh sample aliquots that were first assessed for purity by UPLC-MS-ELSD analysis.

Chemical Susceptibility Assays

Compound potency was assessed alone by dose response assays or in combination with another compound by dose-response matrixes in 96-well plates, or 384-well, flat-bottom, microtiter plates (Corning) as previously described. Plates were incubated at 30° C. for the indicated time period. Growth was quantified by measuring OD$_{600}$ and corrected for medium background. All strains were assessed in biological duplicate experiments with technical duplicates. Growth was normalized to untreated controls and plotted as a heat map using Java TreeView 1.1.6r4. For dose-response matrixes fractional inhibitory concentration index at 90% growth inhibition ($FICI_{90}$) was calculated as previously described. The fluconazole Etest susceptibility assay was performed as previously described. Briefly, 200 μL of $5\times10^6$ cells/mL were plated on YPD agar (1%) plates with either with 50 μM azoffluxin or containing DMSO. Etest strips (bioMérieux) were placed on top after drying and plates were incubated for 24 hours at 30° C. and imaged.

BU-CMD hit compounds were newly supplied and dissolved in DMSO. Gepinacin (Toronto Research Chemicals), cerulenin (Cayman Chemical Company), cycloheximide (BioShop), caspofungin (generously provided by Merck), and amphotericin B (Sigma) were dissolved in DMSO and fluconazole was dissolved in sterile dd$H_2O$ or DMSO.

Chemical Synthesis

General Methods. $^1H$ NMR spectra were recorded at 400 or 500 MHz at ambient temperature unless otherwise stated. $^{13}C$ NMR spectra were recorded at 100 or 125 MHz at ambient temperature unless otherwise stated. Chemical shifts are reported in parts per million. Data for $^1H$ NMR are reported as follows: chemical shift, multiplicity (app=apparent, br=broad, s=singlet, d=doublet, t=triplet, q=quartet, sxt=sextet, m=multiplet, ovrlp=overlap), coupling constants, and integration. All $^{13}C$ NMR spectra were recorded with complete proton decoupling. Analytical thin layer chromatography was performed using 0.25 mm silica gel 60-F plates. Flash chromatography was performed using 200-400 mesh silica gel (Sorbent Technologies, Inc.) or prepack column (SI-HC, puriFlash) by Interchim. Isolated yields refer to chromatographically and spectroscopically pure compounds, unless otherwise stated. Analytical LC-MS experiments were performed using a Waters Acquity UPLC (ultra performance liquid chromatography) with a binary solvent manager, SQ mass spectrometer, Waters 2996 PDA (photodiode array) detector, and evaporative light scattering detector (ELSD).

All compounds tested in biological assays were determined to be >95% pure by UPLC-MS-ELSD analysis. For validation, the screening hit CMLD012336 (azoffluxin) was resynthesized via Lewis-acid mediated condensation of 6-fluoro-3,3-dimethoxyindolin-2-one and (R)-1-(benzo[d][1,3]dioxol-5-yloxy)-4-methylpent-4-en-2-ol.

6-Fluoro-3,3-dimethoxyindolin-2-one: To a flame-dried 100 mL round bottomed flask equipped with a reflux condenser under an atmosphere of $N_2$ was added 6-fluoroisatin (1.0 g, 6.06 mmol), trimethylorthoformate (729 uL, 6.66 mmol), and methanol (30 mL). p-Toluenesulfonic acid monohydrate (172.80 mg, 0.908 mmol) was added and the reaction was heated to reflux for 5.5 h. After cooling to ambient temperature, the reaction was diluted with diethyl ether and neutralized with a saturated solution of sodium bicarbonate. The organic layer was separated and the aqueous layer was extracted twice with diethyl ether. The combined organics were dried over sodium sulfate, filtered and concentrated under reduced pressure. The residue was taken up in diethyl ether, filtered over a pad of celite/$Na_2SO_4$, and concentrated to give a yellow solid. The crude yellow solid was purified flash column chromatography ($SiO_2$, gradient elution 1→7% methanol/dichloromethane, Interchim PuriFlash 450) to give product 6-fluoro-3,3-dimethoxyindolin-2-one (1.06 g; 82.8% yield). LCMS m/z [M-OMe]$^+$ 180. $^1H$ NMR (400 MHz, acetone-$d_6$) δ 9.57 (br s, 1H), 7.44 (dd, J=8.21, 5.47, 1H), 6.79 (m, 1H), 6.72 (dd, J=8.99, 2.34, 1H), 3.48 (s, 6H).

(R)-1-(Benzo[d][1,3]dioxol-5-yloxy)-4-methylpent-4-en-2-ol: In a flame-dried 50 mL round bottom flask under an atmosphere $N_2$ was stirred a suspension of copper iodide (65.4 mg, 0.21 mmol) in THF (2 mL) cooled to −40° C. using an acetonitrile/$CO_2$ bath. To this suspension was added isopropenylmagnesium bromide (0.5 M in THF, 6.18 mL). The reaction was stirred at −40° C. for 35 minutes. Next, a solution of 5-[[(2R)-oxiran-2-yl]methoxy]-1,3-benzodioxole (400 mg, 2.06 mmol) in tetrahydrofuran was added dropwise. The reaction was stirred at −40° C. for 150 minutes. The brown colored mixture was quenched at −40° C. by dropwise addition of saturated aqueous ammonium chloride (0.4 mL). The mixture was stirred for 5 minutes, followed by dilution with 60% ethyl acetate in hexanes. This mixture was then filtered over a pad of Celite/$SiO_2$/$Na_2SO_4$. This pad was eluted with 60% ethyl acetate in hexanes (100 mL) and ethyl acetate (60 mL) to the desired product (493 mg) as a colorless oil in quantitative yield. LCMS m/z [M-OH]$^+$ 219. $^1H$ NMR (400 MHz, CDCl$_3$) δ 6.71 (d, J=8.6 Hz, 1H), 6.53 (d, J=2.7, 1H), 6.35 (dd, J=8.4, 2.4, 1H), 5.93 (s, 2H), 4.91 (s, 1H), 4.85 (s, 1H), 4.14 (m, 1H), 3.92 (dd, J=9.3, 3.7, 1H), 3.83 (dd, J=9.3, 7.1, 1H), 2.32 (d, J=6.6, 2H), 1.81 (s, 3H).

(6-Fluoro-3,3-bis(6-(((R)-2-hydroxy-4-methylpent-4-en-1-yl)oxy)benzo[d][1,3]dioxol-5-yl)indolin-2-one (azoffluxin; CMLD012336): In a two dram vial under $N_2$ was stirred 6-fluoro-3,3-dimethoxy-indolin-2-one (70 mg, 0.33 mmol) and (R)-1-(benzo[d][1,3]dioxol-5-yloxy)-4-methylpent-4-en-2-ol (170 mg, 0.72 mmol) in dichloromethane (4.2 mL). To this reaction was added magnesium sulfate (325 mg, 2.70 mmol). The reaction was cooled to 0° C. in an ice bath, followed by addition of scandium(III) triflate (400 mg, 0.81 mmol). The reaction was allowed to slowly warm to room temperature. After stirring at room temperature overnight, the reaction was filtered through a pad of Celite eluting with dichloromethane. After concentration in vacuo, the crude residue was purified by flash column chromatography ($SiO_2$, gradient elution 15-45% acetone in hexanes, Interchim PuriFlash 450) to give product azoffluxin (84 mg, 40.9% yield). LCMS m/z [M+H]$^+$ 620. At ambient temperature, azoffluxin exhibits multiple sets of broadened $^1H$ and $^{13}C$ NMR peaks due to rotamers (restricted rotation about the biaryl system). NMR peaks coalesce upon heating to 150° C. NMR chemical shifts at both temperatures are reported.

$^1H$ NMR (DMSO-$d_6$, 400 MHz, 25° C.) δ 10.60 (br s, 1H), 7.35-7.17 (m, 1H), 6.77-6.72 (m, 2H), 6.67-6.55 (m, 2H), 6.48 (br. s, 0.5H), 6.14 (br. d, J=12.5 Hz, 1H), 5.95-5.90 (m, 2H), 5.88-5.84 (m, 2H), 4.67-4.63 (m, 2H), 4.57-4.46 (m, 2H), 3.78-3.38 (m, 5H), 3.30-3.33 (m, 1H), 1.95-1.72 (m, 4H), 1.65-1.55 (m, 6H); $^{13}C$ NMR (DMSO-$d_6$, 100 MHz, 25° C.) δ 180.0, 179.8, 163.5, 163.3, 161.0, 160.9, 153.0, 152.5, 151.9, 151.6, 147.7, 147.5, 147.23, 147.17, 143.2, 143.0, 142.95, 141.2, 141.0, 140.8, 130.8, 130.3, 127.2, 127.1, 126.8, 126.6, 121.1, 120.7, 112.6, 112.3, 109.2, 108.25, 108.2, 108.0, 107.8, 107.6, 101.7, 101.6, 97.9, 97.6, 97.2, 97.0, 96.95, 96.8, 74.0, 73.5, 73.1, 72.9, 67.5, 67.4, 67.3, 67.0, 59.3, 59.0, 42.2, 42.0, 41.8, 41.6, 23.13, 23.08, 23.05, 22.97. $^1H$ NMR (DMSO-$d_6$, 400 MHz, 150° C.) δ 9.94 (br. s, 1H), 7.21 (dd, J=7.8, 6.3 Hz, 1H), 6.69-6.58 (m, 5H), 6.41 (br. s, 2H), 5.88 (s, 4H), 4.75-4.71 (m, 2H), 4.68 (br. s, 1H), 4.65 (br. s, 1H), 3.76-3.57 (m, 6H), 2.07-1.83 (m, 4H), 1.70 (s, 3H), 1.68 (s, 3H); $^{13}C$ NMR (DMSO-$d_6$, 100 MHz, 150° C.) δ 179.5, 162.6 (d, $^1J_{C-F}$=241

Hz), 152.7, 147.6, 143.5, 143.4, 143.1, 142.0, 130.7, 127.2, 127.1, 121.8, 112.1, 112.0, 108.8, 107.8, 107.5, 101.5, 97.8, 97.6, 97.2, 74.2, 68.3, 68.1, 59.6, 42.2, 41.4, 22.90, 22.85.

Extraction and Quantification of Sterols.

To quantify the abundance of sterols in *C. auris* the targeted metabolomics profiling protocol established by Hoepfner et al. in *S. cerevisiae* was used. Briefly, cells were subcultured to an $OD_{600}$ of 0.1 in 10 mL of RPMI supplemented with the indicated compound concentration for 18 hours with agitation. After incubation all $OD_{600}$'s were normalized and cell pellets washed and resuspended in 100 µL of PBS. Cell suspension was treated with 1 mL methanol/ $CHCl_3$ (2:1 v/v) supplemented with 0.01% w/v butylated hydroxytoluene. Acid washed glass beads were added to each sample and they were vortexed for 10 minutes. Samples were pelleted by centrifugation for 5 minutes at 16,000 g. Transferring the supernatant to a new vial, 400 µL 50 mM citric acid in $H_2O$ and 600 µL $CHCl_3$ was added and vortexed for 10 min. Samples were again centrifuged for 5 minutes at 16,000 g. The organic phase was collected and dried. For LC-MS analysis, samples were resuspended in ethanol with cholesterol included as an internal standard. Samples were separated on Acquity UPLC BEH C18 column (1.7 µm, 2.1×50 mm) using the Acquity UPLC I-Class coupled to a Xevo G2-S QToF equipped with an APCI source (Waters). Chromatographic methods were adopted from Hoepfner et al. as well as the selective reaction monitoring mass transitions specific for each sterol in subsequent quantification steps. TargetLynx (Waters) was used for peak finding, smoothing, and area calculations. All samples were run in biological duplicate and technical triplicate, and a representative replicate was plotted in Prism (Version 8.4.1).

Intracellular Fluconazole and Azofluxin Detection.

*C. auris* was subcultured from overnight cultures at a starting $OD_{600}$ of 0.4 in 5 mL of YPD in the presence of the indicated compound concentration for 1 hour with agitation. Cells were then transferred to falcon tubes and pelleted at 4,000 g for 5 minutes at 4° C. Media was removed, and cells were washed with 5 mL of cold PBS 3 times with centrifugation of 2,000 g for 5 minutes in between. Cells were resuspended in 1 mL cold PBS, flash frozen in liquid nitrogen, and stored at −80° C. overnight. The following day, cells were thawed on ice, 25 µL of 6N NaOH was added to each falcon tube, and samples were vortexed for 15 seconds. 500 µL of 10 mM sodium phosphate (pH 6.0) was added to each sample followed by vortexing for 15 seconds. Compounds were extracted with 5 mL of $CH_2Cl_2$ and vortexed for 5 minutes, followed by centrifugation for 10 minutes at 4,000 g at 4° C. The organic phase was collected and dried. Before subsequent LC-MS analysis, samples were resuspended in 50 µL MeCN:$H_2O$. The resuspended cell extracts (10 µl) were separated on an Acquity UPLC BEH C18 column (1.7 µm, 2.1×50 mm) using the Acquity UPLC I-Class coupled to a Xevo G2-S QToF equipped with an electrospray ionization (ESI) source. Chromatography followed a gradient method (A: water+0.1% (v/v) formic acid, B: MeCN+0.1% (v/v) formic acid 10-9 min: 10% B to 95% B at 0.125 µL min$^{-1}$). Both fluconazole and azofluxin were detected using selected reaction monitoring mass transitions 307.110 $[M+H]^+ \rightarrow$ 220.0685 and 602.227 $[M-H_2O+H]^+ \rightarrow$ 286.0515, respectively. TargetLynx (Waters) was used for peak finding, smoothing and area calculations. All samples were run in biological duplicate and technical triplicate and a representative replicate was plotted in Prism.

Quantitative Real-Time-PCR (RT-qPCR)

To determine changes in efflux gene expression, strains were subcultured from a saturated overnight at an $OD_{600}$ 0.1 in YPD for 3 hours in the presence of compound as indicated. Cells were then pelleted at 3000 rpm at 4° C., washed with cold PBS, flash-frozen with liquid nitrogen, and stored at −80° C. Cells were lysed by bead beating 4× for 30 seconds with 1 minute on ice in between. RNA was extracted from lysed cells using the QIAGEN RNeasy kit DNase treated using the QIAGEN RNase free DNAase Set. Complementary DNA synthesis was performed using the iScript cDNA Synthesis Kit (Bio-Rad). RT-qPCR was performed using in a 384-well plate, with a 10 µL reaction volume using Fast SYBR Green Master Mix (Applied Biosystems) and the BioRad CFX-384 Real Time System with the following cycling conditions: 95° C. for 3 mins, then 95° C. for 10 secs and 60° C. for 30 secs, for 40 cycles. The melt curve was completed with the following cycle conditions: 95° C. for 10 secs and 65° C. for 10 secs with an increase of 0.5° C. per cycle up to 95° C. Reactions were performed in technical triplicate using the primer pairs: CDR1 (oLC6125/oLC6126), MDR1 (oLC8050/oLC8051), CDR4-1 (oLC8052/oLC8053), CDR4-2 (oLC8054/oLC8055), SNQ2-1 (oLC8060/oLC8057), SNQ2-2 (oLC8058/oLC8059) and normalized to the house keeping genes ACT1 (oLC5727/oLC5728) and GPD1 (oLC5729/oLC5730). Primer sequences are included in Table 4. Data was analyzed using the BioRad CFX Manager 3.1. Error bars depict standard error of the means of technical triplicates, representing the data from one of two biological replicates.

Nile Red Accumulation Assay.

Cellular efflux was determined by measuring Nile red accumulation, as previously described. Cells were subcultured from an $OD_{600}$ 0.1 in YPD for 4 hours until exponential phase was reached. For cells treated with azofluxin, 50 µM was added for 10 minutes prior to a 20 minute incubation of all stained cells with 7 µM (3.5 µM in DMSO stock) of Nile red (Sigma). Cells were then pelleted for 1 min at 14,000 rpm and resuspended in PBS. To quantify fluorescence, a CytoFlex Flow Cytometer (Beckman Coulter) was used. Cells were added to flat bottom, transparent, 96-well plate (Beckman Coulter). Each sample was run using the CytExpert Software until ~20,000 events had been recorded. Populations were gated to exclude debris and doublets, and the median PE value was taken for each sample. To visualize samples, PBS cell suspensions were imaged by differential interference contrast (DIC) microscopy and the DsRed channel on a Zeiss Axio Imager.M1 (Carl Zeiss) at the same exposure time. All experiments were performed in biological duplicate.

Co-Culture Experiments

To assess the ability of azofluxin to rescue mammalian cell growth in co-culture experiments, 20 µL of 293T cells were seeded at 5×10$^5$ cells/mL in DMEM media containing 10% FBS and incubated overnight at 37° C. in 5.5% $CO_2$. The following day 20 µL of DMEM inoculated with 2.5×10$^3$ exponential phase *C. auris* cells was added to the cells. A Tecan D300e compound dispenser was used to add DMSO-based compounds to each well at the indicated final concentrations. Co-cultures were incubated for 48 hours at 37° C. in 5.5% $CO_2$. The mammalian cell growth was measured by replacing the media with 20 µL PBS, and adding 20 µL Titer-glow (Promega) to each well, incubating for 10 minutes, and reading luminescence on a Tecan Infinite 200 Pro. All experiments were performed in technical quadruplicate and biological duplicate.

The cellular glycoproteins were stained in co-culture experiments with using a periodic-acid Schiff (PAS) staining kit (Sigma) as per manufacturer's instructions. Briefly, mammalian 293T cells were seeded at $5 \times 10^5$ for 24 hours in 6-well plates (Corning). $2.5 \times 10^3$ exponential phase C. auris cells were added to mammalian cells followed by indicated drug or solvent concentrations. Plates were incubated for 48 hours at 37° C. Cultures were fixed with 4% formaldehyde (BioShop) in medium overnight, fixative was removed, and the plate was dried. Fixed cells were then hydrated with 1 mL ddH$_2$O and this was removed from each well. 1 mL PAS solution was added can cells were incubated for 5 minutes, followed by removal and 2× washes with ddH$_2$O by pipetting. 1 ml Schiff's reagent was added, and plates were incubated for 15 minutes. The cells were then thoroughly rinsed for 5 minutes with ddH$_2$O. 1 mL hematoxylin was applied for 3 minutes and cell were rinsed again. Cells were allowed to dry and were then imaged. Experiments were performed in biological duplicate.

Additional Chemical Synthesis and Synthetic Schemes.

Non-Symmetrical 3,3'-Diarylated Oxindoles.

FIG. 19A illustrates general schemes for the preparation of starting input reagents. These are used as illustrated by FIG. 19B, which is a scheme and general procedure for two-step production of non-symmetrical 3,3'-diarylated oxindoles.

The general scheme (FIG. 19B) includes two steps.

In step 1, the starting istain dimethoxy ketal (1.0 equiv) and ARENE 1 (1.0 equiv) are combined in dichloromethane (40 mM reaction concentration) and cooled to –40° C., Boron trifluoride diethyl etherate (0.9 equiv) is added dropwise, slowly over 5 minutes. The reaction is stirred at –40° C. for 40 minutes, and quenched with slow dropwise addition of 1N HCl followed by stirring for 5 minutes at –40° C., and warming to 0° C. over the course of 10 minutes. Na$_2$SO$_4$ is added and the mixture is filtered through a pad of Celite, rinsing with dichloromethane. The crude reaction mixture is concentrated and directly purified via flash column chromatography (acetone/hexanes) to afford the monoarylated methyl ether product.

In step 2, the monoarylated methyl ether from step 1 (1.0 equiv) and ARENE 2 (2.2 equiv) are combined in dichloromethane (40 mM reaction concentration) in the presence of magnesium sulfate and cooled to 0° C. Scandium (III) triflate (1.0 equiv) is added in one portion and the reaction is allowed to slowly warm to room temperature and react overnight. The reaction mixture is then filtered through a pad of Celite, rinsing with dichloromethane. The crude reaction mixture is concentrated and directly purified via flash column chromatography (acetone/hexanes) to afford the diarylated product.

FIG. 20 is an alternate route to non-symmetrical 3,3'-diarylated oxindoles.

Symmetrical 3,3'-diarylated oxindoles.

FIG. 21 shows a scheme and general procedure for the synthesis of symmetrical 3,3'-diarylated oxindoles. The starting istain dimethoxy ketal (1.0 equiv) and the ARENE 3 (2.2 equiv) are combined in dichloromethane (40 mM reaction concentration) in the presence of 5A molecular sieves and cooled to 0° C. Scandium (III) triflate (1.0 equiv) is added in one portion and the reaction is allowed to slowly warm to room temperature and react for 18-24 hours, tracking by TLC. Upon completion, the reaction mixture is filtered through a pad of Celite, rinsing with dichloromethane. The crude reaction mixture is concentrated and directly purified via flash column chromatography (acetone/hexanes) to afford the diarylated product.

Synthesis of Azoffluxin

6-Fluoro-3,3-dimethoxyindolin-2-one (2)

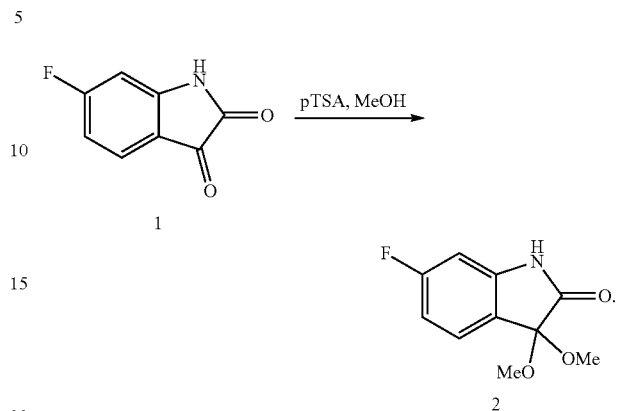

To aflame-dried 100 mL round bottomed flask equipped with a reflux condenser under an atmosphere of N$_2$ was added 6-fluoroisatin (1) (1.0 g, 6.06 mmol), trimethylorthoformate (729 uL, 6.66 mmol), and methanol (30 mL). p-Toluenesulfonic acid monohydrate (172.80 mg, 0.908 mmol) was added and the reaction was heated to reflux for 5.5 h. After cooling to ambient temperature, the reaction was diluted with diethyl ether and neutralized with a saturated solution of sodium bicarbonate. The organic layer was separated and the aqueous layer was extracted twice with diethyl ether. The combined organics were dried over sodium sulfate, filtered and concentrated under reduced pressure. The residue was taken up in diethyl ether, filtered over a pad of celite/Na$_2$SO$_4$, and concentrated to give a yellow solid. The crude yellow solid was purified flash column chromatography (SiO$_2$, gradient elution 1→7% methanol/dichloromethane, Interchim PuriFlash 450) to give product 6-fluoro-3,3-dimethoxyindolin-2-one 2 (1.06 g; 82.8% yield). LCMS m/z [M-OMe]$^+$ 180. $^1$H NMR (400 MHz, acetone-d$_6$) δ 9.57 (br s, 1H), 7.44 (dd, J=8.2, 5.5, 1H), 6.79 (m, 1H), 6.72 (dd, J=9.0, 2.3, 1H), 3.48 (s, 6H).

(R)-1-(Benzo[d][1,3]dioxol-5-yloxy)-4-methylpent-4-en-2-ol (4)

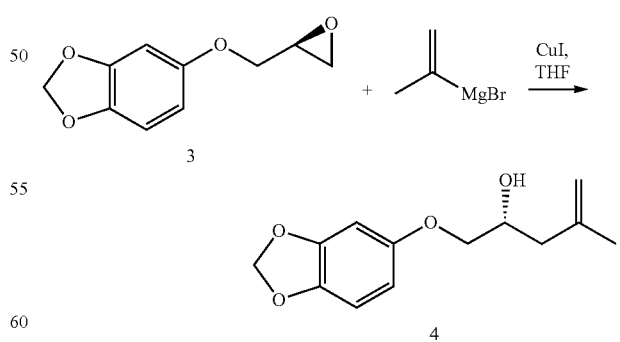

In a flame-dried 50 mL round bottom flask under an atmosphere N$_2$ was stirred a suspension of copper iodide (65.4 mg, 0.21 mmol) in THF (2 mL) cooled to –40° C. using an acetonitrile/CO$_2$ bath. To this suspension was added isopropenylmagnesium bromide (0.5 M in THF, 6.18 mL).

The reaction was stirred at −40° C. for 35 minutes. Next, a solution of 5-[[(2R)-oxiran-2-yl]methoxy]-1,3-benzodioxole 3 (400 mg, 2.06 mmol) in tetrahydrofuran was added dropwise. The reaction was stirred at −40° C. for 150 minutes. The brown colored mixture was quenched at −40° C. by dropwise addition of saturated aqueous ammonium chloride (0.4 mL). The mixture was stirred for 5 minutes, followed by dilution with 60% ethyl acetate in hexanes. This mixture was then filtered over a pad of Celite/SiO$_2$/Na$_2$SO$_4$. This pad was eluted with 60% ethyl acetate in hexanes (100 mL) and ethyl acetate (60 mL) to the desired product 4 (493 mg) as a colorless oil in quantitative yield. LCMS m/z [M-OH]$^+$ 219. $^1$H NMR (400 MHz, CDCl$_3$) δ 6.71 (d, J=8.6 Hz, 1H), 6.53 (d, J=2.7, 1H), 6.35 (dd, J=8.4, 2.4, 1H), 5.93 (s, 2H), 4.91 (s, 1H), 4.85 (s, 1H), 4.14 (m, 1H), 3.92 (dd, J=9.3, 3.7, 1H), 3.83 (dd, J=9.3, 7.1, 1H), 2.32 (d, J=6.6, 2H), 1.81 (s, 3H).

(6-Fluoro-3,3-bis(6-(((R)-2-hydroxy-4-methylpent-4-en-1-yl)oxy)benzo[d][1,3]dioxol-5-yl)indolin-2-one (azoffluxin; 5; CMLD012336)

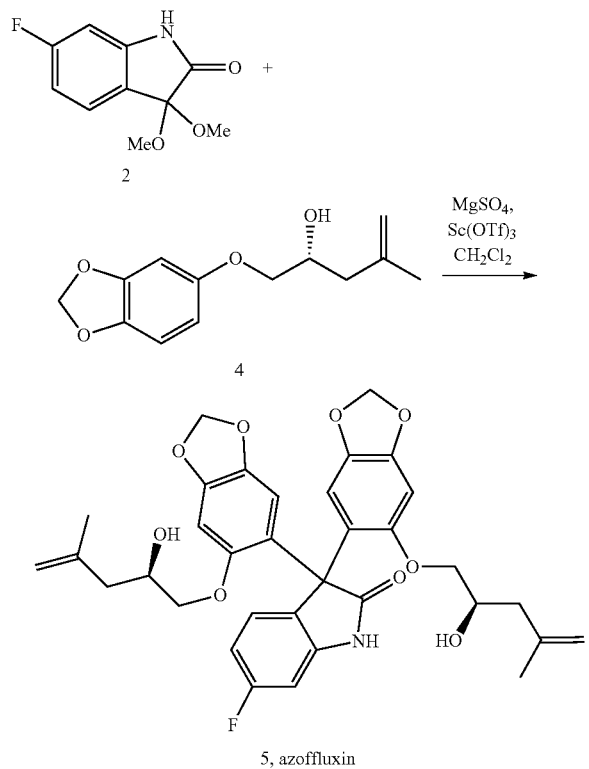

5, azoffluxin

In a two dram vial under N$_2$ was stirred 6-fluoro-3,3-dimethoxy-indolin-2-one 2 (70 mg, 0.33 mmol) and (R)-1-(benzo[d][1,3]dioxol-5-yloxy)-4-methylpent-4-en-2-ol 4 (170 mg, 0.72 mmol) in dichloromethane (4.2 mL). To this reaction was added magnesium sulfate (325 mg, 2.70 mmol). The reaction was cooled to 0° C. in an ice bath, followed by addition of scandium(III) triflate (400 mg, 0.81 mmol). The reaction was allowed to slowly warm to room temperature. After stirring at room temperature overnight, the reaction was filtered through a pad of Celite eluting with dichloromethane. After concentration in vacuo, the crude residue was purified by flash column chromatography (SiO$_2$, gradient elution 15-45% acetone in hexanes, Interchim Puri-Flash 450) to give product 5 (84 mg, 40.9% yield). LCMS m/z [M+H]+ 620. At ambient temperature, 5 exhibits multiple sets of broadened $^1$H and $^{13}$C NMR peaks due to rotamers (restricted rotation about the biaryl system). NMR peaks coalesce upon heating to 150° C. NMR chemical shifts at both temperatures are reported.

$^1$H NMR (DMSO-d$_6$, 400 MHz, 25° C.) δ 10.60 (br s, 1H), 7.35-7.17 (m, 1H), 6.77-6.72 (m, 2H), 6.67-6.55 (m, 2H), 6.48 (br. s, 0.5H), 6.14 (br. d, J=12.5 Hz, 1H), 5.95-5.90 (m, 2H), 5.88-5.84 (m, 2H), 4.67-4.63 (m, 2H), 4.57-4.46 (m, 2H), 3.78-3.38 (m, 5H), 3.30-3.33 (m, 1H), 1.95-1.72 (m, 4H), 1.65-1.55 (m, 6H); $^{13}$C NMR (DMSO-d$_6$, 100 MHz, 25° C.) δ 180.0, 179.8, 163.5, 163.3, 161.0, 160.9, 153.0, 152.5, 151.9, 151.6, 147.7, 147.5, 147.23, 147.17, 143.2, 143.0, 142.95, 141.2, 141.0, 140.8, 130.8, 130.3, 127.2, 127.1, 126.8, 126.6, 121.1, 120.7, 112.6, 112.3, 109.2, 108.25, 108.2, 108.0, 107.8, 107.6, 101.7, 101.6, 97.9, 97.6, 97.2, 97.0, 96.95, 96.8, 74.0, 73.5, 73.1, 72.9, 67.5, 67.4, 67.3, 67.0, 59.3, 59.0, 42.2, 42.0, 41.8, 41.6, 23.13, 23.08, 23.05, 22.97. $^1$H NMR (DMSO-d$_6$, 400 MHz, 150° C.) δ 9.94 (br. s, 1H), 7.21 (dd, J=7.8, 6.3 Hz, 1H), 6.69-6.58 (m, 5H), 6.41 (br. s, 2H), 5.88 (s, 4H), 4.75-4.71 (m, 2H), 4.68 (br. s, 1H), 4.65 (br. s, 1H), 3.76-3.57 (m, 6H), 2.07-1.83 (m, 4H), 1.70 (s, 3H), 1.68 (s, 3H); $^{13}$C NMR (DMSO-d$_6$, 100 MHz, 150° C.) δ 179.5, 162.6 (d, $^1J_{C-F}$=241 Hz), 152.7, 147.6, 143.5, 143.4, 143.1, 142.0, 130.7, 127.2, 127.1, 121.8, 112.1, 112.0, 108.8, 107.8, 107.5, 101.5, 97.8, 97.6, 97.2, 74.2, 68.3, 68.1, 59.6, 42.2, 41.4, 22.90, 22.85.

7-fluoro-3,3-bis(6-(((R)-2-hydroxy-4-methylpentyl)oxy)benzo[d][1,3]dioxol-5-yl)indolin-2-one (CMLD013623, Table 1, Entry 1)

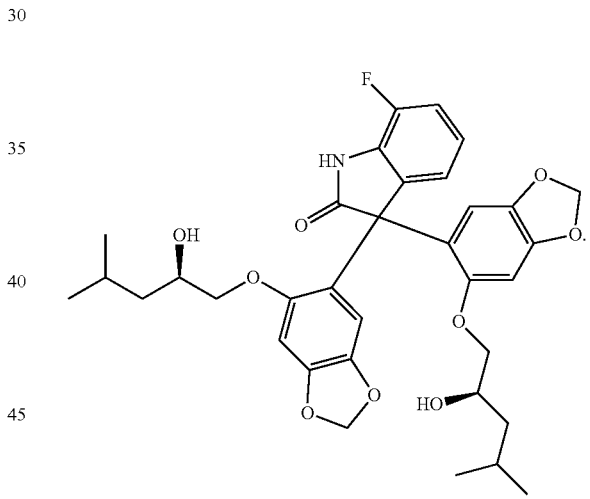

7-fluoro-3,3-dimethoxyindolin-2-one (1.0 equiv) and (R)-1-(benzo[d][1,3]dioxol-5-yloxy)-4-methylpentan-2-ol (2.2 equiv) were combined in dichloromethane (40 mM reaction concentration) in the presence of 5 Å molecular sieves and cooled to 0° C. Scandium (III) triflate (1.0 equiv) was added in one portion and allowed to slowly warm to room temperature and react for 18-24 hours, tracking by TLC. Upon completion, the reaction mixture was filtered through a pad of Celite, rinsing with dichloromethane. The crude reaction mixture was concentrated and directly purified via flash column chromatography (acetone/hexanes) to afford the product 7-fluoro-3,3-bis(6-(((R)-2-hydroxy-4-methylpentyl)oxy)benzo[d][1,3]dioxol-5-yl)indolin-2-one. $^1$H NMR (400 MHz, acetone-d$_6$) δ=7.16-7.09 (m, 1H), 7.07-7.00 (m, 1H), 6.92-6.83 (m, 1H), 6.71 (d, J=14.8 Hz, 2H), 6.59 (s, 1H), 6.21-6.14 (m, 1H), 6.00-5.89 (m, 4H), 3.95-3.51 (m, 6H), 3.45-3.32 (m, 1H), 1.86-1.58 (m, 2H), 1.37-1.18 (m, 2H), 1.16-0.99 (m, 1H), 0.96-0.75 (m, 12H). LC/MS m/z=624.4 for C$_{34}$H$_{39}$FNO$_9$ [M+H]$^+$.

7-fluoro-3,3-bis(6-(((R)-2-hydroxypentyl)oxy)benzo[d][1,3]dioxol-5-yl)indolin-2-one (CMLD012440, Table 1, Entry 2)

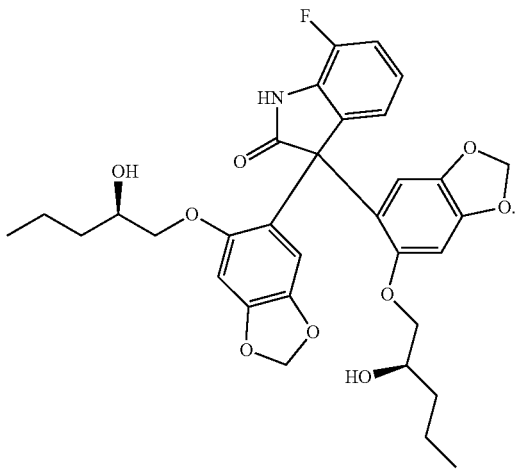 [SMILES: CCC[C@@H](O)COc1cc2c(cc1C1(c3cc4c(cc3OC[C@H](O)CCC)OCO4)C(=O)Nc3c(F)cccc31)OCO2]

7-fluoro-3,3-dimethoxyindolin-2-one (1.0 equiv) and (R)-1-(benzo[d][1,3]dioxol-5-yloxy)pentan-2-ol (2.2 equiv) were combined in dichloromethane (40 mM reaction concentration) in the presence of 5 Å molecular sieves and cooled to 0° C. Scandium (III) triflate (1.0 equiv) was added in one portion and allowed to slowly warm to room temperature and react for 18-24 hours, tracking by TLC. Upon completion, the reaction mixture was filtered through a pad of Celite, rinsing with dichloromethane. The crude reaction mixture was concentrated and directly purified via flash column chromatography (acetone/hexanes) to afford the product 7-fluoro-3,3-bis(6-(((R)-2-hydroxypentyl)oxy)benzo[d][1,3]dioxol-5-yl)indolin-2-one. $^1$H NMR (400 MHz, METHANOL-$d_4$) δ=7.05 (s, 1H), 7.02 (s, 1H), 6.98-6.94 (m, 1H), 6.84-6.72 (m, 1H), 6.66 (s, 1H), 6.63-6.62 (m, 1H), 6.51 (br s, 1H), 6.12 (br s, 1H), 5.90-5.83 (m, 4H), 3.86 (d, J=2.3 Hz, 1H), 3.80 (br d, J=3.5 Hz, 1H), 3.77-3.71 (m, 2H), 3.68-3.63 (m, 1H), 3.54-3.50 (m, 1H), 1.41 (br d, J=7.4 Hz, 1H), 1.37-1.23 (m, 5H), 1.22-1.08 (m, 1H), 0.93-0.81 (m, 7H). LC/MS m/z=596.3 for $C_{32}H_{35}FNO_9$ [M+H]$^+$.

6-fluoro-3,3-bis(6-(((R)-2-hydroxy-4,4-dimethylpentyl)oxy)benzo[d][1,3]dioxol-5-yl)indolin-2-one (CMLD012443, Table 1, Entry 3)

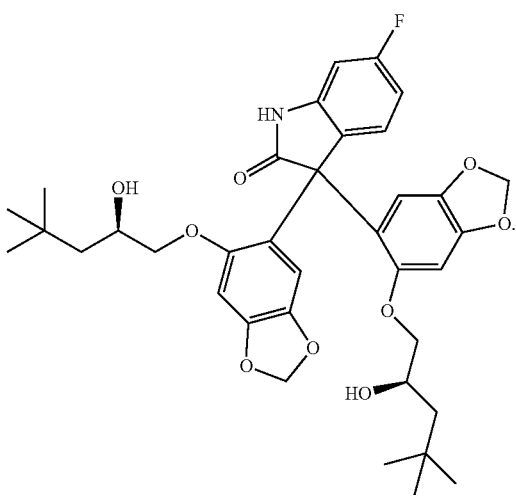 [SMILES: CC(C)(C)C[C@@H](O)COc1cc2c(cc1C1(c3cc4c(cc3OC[C@H](O)CC(C)(C)C)OCO4)C(=O)Nc3cc(F)ccc31)OCO2]

6-fluoro-3,3-dimethoxyindolin-2-one (1.0 equiv) and (R)-1-(benzo[d][1,3]dioxol-5-yloxy)-4,4-dimethylpentan-2-ol (2.2 equiv) were combined in dichloromethane (40 mM reaction concentration) in the presence of 5 Å molecular sieves and cooled to 0° C. Scandium (III) triflate (1.0 equiv) was added in one portion and allowed to slowly warm to room temperature and react for 18-24 hours, tracking by TLC. Upon completion, the reaction mixture was filtered through a pad of Celite, rinsing with dichloromethane. The crude reaction mixture was concentrated and directly purified via flash column chromatography (acetone/hexanes) to afford the product 6-fluoro-3,3-bis(6-(((R)-2-hydroxy-4,4-dimethylpentyl)oxy)benzo[d][1,3]dioxol-5-yl)indolin-2-one. $^1$H NMR (400 MHz, METHANOL-$d_4$) δ=7.03-6.80 (m, 1H), 6.75-6.61 (m, 4H), 6.57-6.39 (m, 1H), 6.23-6.04 (m, 1H), 5.93-5.81 (m, 4H), 3.93-3.64 (m, 4H), 3.68-3.48 (m, 1H), 3.47-3.33 (m, 1H), 1.34-1.13 (m, 3H), 0.98-0.79 (m, 19H). LC/MS m/z=652.4 for $C_{36}H_{43}FNO_9$ [M+H]$^+$.

5-fluoro-3,3-bis(6-(((R)-2-hydroxy-4,4-dimethylpentyl)oxy)benzo[d][1,3]dioxol-5-yl)indolin-2-one (CMLD012444, Table 1, Entry 4)

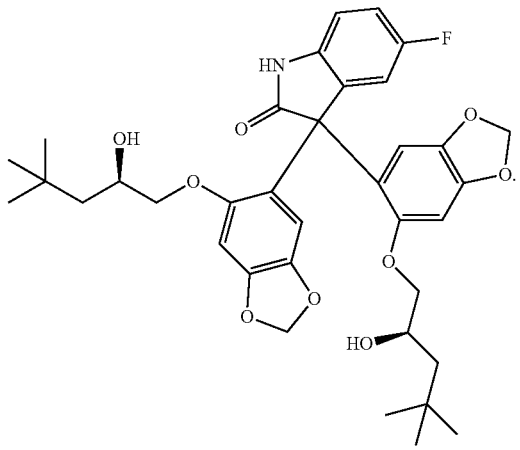 [SMILES: CC(C)(C)C[C@@H](O)COc1cc2c(cc1C1(c3cc4c(cc3OC[C@H](O)CC(C)(C)C)OCO4)C(=O)Nc3ccc(F)cc31)OCO2]

5-fluoro-3,3-dimethoxyindolin-2-one (1.0 equiv) and (R)-1-(benzo[d][1,3]dioxol-5-yloxy)-4,4-dimethylpentan-2-ol (2.2 equiv) were combined in dichloromethane (40 mM reaction concentration) in the presence of 5 Å molecular sieves and cooled to 0° C. Scandium (III) triflate (1.0 equiv) was added in one portion and allowed to slowly warm to room temperature and react for 18-24 hours, tracking by TLC. Upon completion, the reaction mixture was filtered through a pad of Celite, rinsing with dichloromethane. The crude reaction mixture was concentrated and directly purified via flash column chromatography (acetone/hexanes) to afford the product 5-fluoro-3,3-bis(6-(((R)-2-hydroxy-4,4-dimethylpentyl)oxy)benzo[d][1,3]dioxol-5-yl)indolin-2-one. $^1$H NMR (400 MHz, METHANOL-$d_4$) δ=7.11-7.02 (m, 1H), 7.00-6.91 (m, 1H), 6.84-6.70 (m, 1H), 6.68-6.58 (m, 2H), 6.51 (br s, 1H), 6.17-6.04 (m, 1H), 5.93-5.82 (m, 4H), 3.91-3.73 (m, 3H), 3.72-3.50 (m, 2H), 3.47-3.32 (m, 1H), 1.33-1.14 (m, 3H), 0.98-0.74 (m, 19H). LC/MS m/z=652.4 for $C_{36}H_{43}FNO_9$ [M+H]$^+$.

6-bromo-3,3-bis(6-(((R)-2-hydroxy-4,4-dimethylpentyl)oxy)benzo[d][1,3]dioxol-5-yl)indolin-2-one (CMLD012446, Table Entry 5)

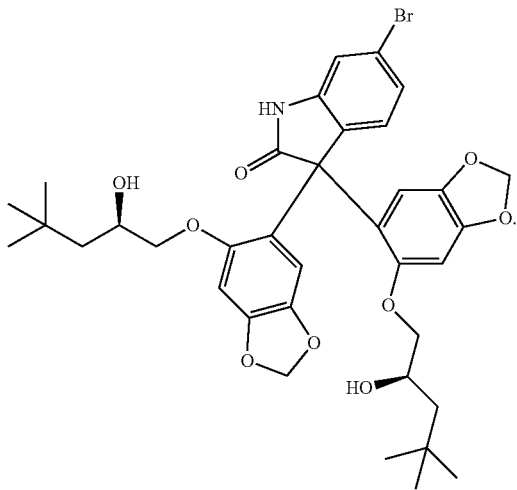 [SMILES: CC(C)(C)C[C@@H](O)COc1cc2c(cc1C1(c3cc4c(cc3OC[C@H](O)CC(C)(C)C)OCO4)C(=O)Nc3cc(Br)ccc31)OCO2]

6-bromo-3,3-dimethoxyindolin-2-one (1.0 equiv) and (R)-1-(benzo[d][1,3]dioxol-5-yloxy)-4,4-dimethylpentan-2-ol (2.2 equiv) were combined in dichloromethane (40 mM reaction concentration) in the presence of 5 Å molecular sieves and cooled to 0° C. Scandium (III) triflate (1.0 equiv) was added in one portion and allowed to slowly warm to room temperature and react for 18-24 hours, tracking by TLC. Upon completion, the reaction mixture was filtered through a pad of Celite, rinsing with dichloromethane. The crude reaction mixture was concentrated and directly purified via flash column chromatography (acetone/hexanes) to afford the product 6-bromo-3,3-bis(6-(((R)-2-hydroxy-4,4-dimethylpentyl)oxy)benzo[d][1,3]dioxol-5-yl)indolin-2-one. $^1$H NMR (400 MHz, METHANOL-$d_4$) δ=7.18-7.05 (m, 2H), 6.70-6.58 (m, 2H), 6.55-6.46 (m, 1H), 6.25-6.10 (m, 1H), 5.95-5.81 (m, 4H), 3.92-3.33 (m, 6H), 1.32-1.14 (m, 3H), 0.99-0.83 (m, 19H). LC/MS m/z=712.2 for $C_{36}H_{43}BrNO_9$ [M+H]$^+$.

7-fluoro-3,3-bis(6-(((R)-2-hydroxy-4,4-dimethylpentyl)oxy)benzo[d][1,3]dioxol-5-yl)indolin-2-one (CMLD013624, Table 1, Entry 6)

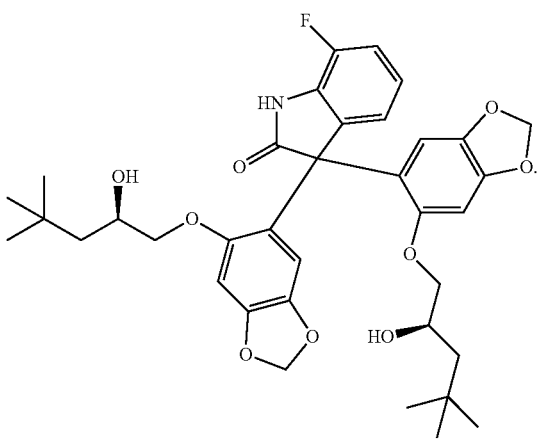 [SMILES: CC(C)(C)C[C@@H](O)COc1cc2c(cc1C1(c3cc4c(cc3OC[C@H](O)CC(C)(C)C)OCO4)C(=O)Nc3c(F)cccc31)OCO2]

7-fluoro-3,3-dimethoxyindolin-2-one (1.0 equiv) and (R)-1-(benzo[d][1,3]dioxol-5-yloxy)-4,4-dimethylpentan-2-ol (2.2 equiv) were combined in dichloromethane (40 mM reaction concentration) in the presence of 5 Å molecular sieves and cooled to 0° C. Scandium (III) triflate (1.0 equiv) was added in one portion and allowed to slowly warm to room temperature and react for 18-24 hours, tracking by TLC. Upon completion, the reaction mixture was filtered through a pad of Celite, rinsing with dichloromethane. The crude reaction mixture was concentrated and directly purified via flash column chromatography (acetone/hexanes) to afford the product 7-fluoro-3,3-bis(6-(((R)-2-hydroxy-4,4-dimethylpentyl)oxy)benzo[d][1,3]dioxol-5-yl)indolin-2-one. $^1$H NMR (400 MHz, acetone-$d_6$) δ=7.58-7.35 (m, 1H), 7.21-7.08 (m, 2H), 7.08-7.00 (m, 1H), 6.93-6.83 (m, 1H), 6.72-6.66 (m, 2H), 6.58 (s, 1H), 6.24-6.11 (m, 1H), 6.00-5.87 (m, 4H), 4.07-3.36 (m, 6H), 1.20 (s, 3H), 1.15-0.82 (m, 19H). LC/MS m/z=652.4 for $C_{36}H_{43}FNO_9$ [M+H]$^+$.

3-(6-ethoxy-2H-1,3-benzodioxol-5-yl)-7-fluoro-3-(6-(((2R)-2-hydroxypentyl)oxy)-2H-1,3-benzodioxol-5-yl)-2,3-dihydro-1H-indol-2-one (CMLD013655, Table 1, Entry 7)

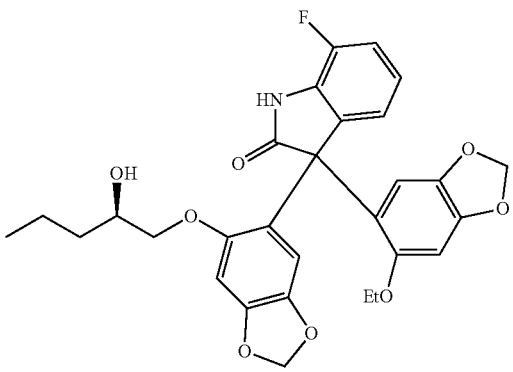 [SMILES: CCC[C@@H](O)COc1cc2c(cc1C1(c3cc4c(cc3OCC)OCO4)C(=O)Nc3c(F)cccc31)OCO2]

Step 1: 7-fluoro-3,3-dimethoxyindolin-2-one (1.0 equiv) and (R)-1-(benzo[d][1,3]dioxol-5-yloxy)pentan-2-ol (1.0 equiv) were combined in dichloromethane (40 mM reaction concentration) and cooled to −40° C. Boron trifluoride diethyl etherate (0.9 equiv) was added dropwise, slowly over 5 minutes. The reaction was stirred at −40° C. for 40 minutes, and quenched with slow dropwise addition of 1N HCl followed stirring for 5 minutes at −40° C., and warming to 0° C. over the course of 10 minutes. $Na_2SO_4$ was added and the mixture was filtered through a pad of Celite, rinsing with dichloromethane. The crude reaction mixture was concentrated and directly purified via flash column chromatography (acetone/hexanes) to afford the product 7-fluoro-3-(6-(((R)-2-hydroxypentyl)oxy)benzo[d][1,3]dioxol-5-yl)-3-methoxyindolin-2-one.

Step 2: 7-fluoro-3-(6-(((R)-2-hydroxypentyl)oxy)benzo[d][1,3]dioxol-5-yl)-3-methoxyindolin-2-one (1.0 equiv) and 5-ethoxybenzo[d][1,3]dioxole (2.2 equiv) were combined in dichloromethane (40 mM reaction concentration) in the presence of magnesium sulfate and cooled to 0° C. Scandium (III) triflate (1.0 equiv) was added in one portion and allowed to slowly warm to room temperature and react overnight. The reaction mixture was then filtered through a pad of Celite, rinsing with dichloromethane. The crude reaction mixture was concentrated and directly purified via flash column chromatography (acetone/hexanes) to afford the product 3-(6-ethoxy-2H-1,3-benzodioxol-5-yl)-7-fluoro-3-(6-(((2R)-2-hydroxypentyl)oxy)-2H-1,3-benzodioxol-5-yl)-2,3-dihydro-1H-indol-2-one. $^1$H NMR (400 MHz, acetone-d$_6$) δ=7.19-7.06 (m, 1H), 7.04-6.94 (m, 1H), 6.75-6.67 (m, 2H), 6.65-6.62 (m, 1H), 6.61-6.51 (m, 1H), 6.18-6.11 (m, 1H), 5.93 (s, 6H), 3.98-3.89 (m, 1H), 3.88-3.77 (m, 4H), 3.55-3.44 (m, 1H), 1.29 (br s, 3H), 1.20-1.09 (m, 5H), 0.92-0.77 (m, 7H). LC/MS m/z=538.5 for C$_{29}$H$_{29}$FNO$_8$ [M+H]$^+$.

7-fluoro-3,3-bis(6-(((R)-2-hydroxypent-4-en-1-yl)oxy)benzo[d][1,3]dioxol-5-yl)indolin-2-one
(CMLD012402, Table 1, Entry 8)

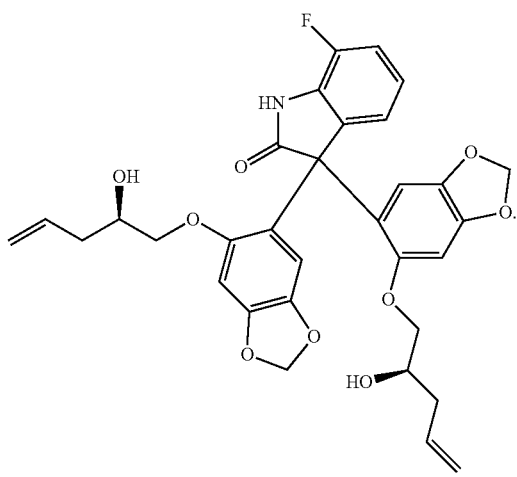 [SMILES: C=CC[C@@H](O)COc1cc2c(cc1C1(c3cc4c(cc3OC[C@H](O)CC=C)OCO4)C(=O)Nc3c(F)cccc31)OCO2]

7-fluoro-3,3-dimethoxyindolin-2-one (1.0 equiv) and (R)-1-(benzo[d][1,3]dioxol-5-yloxy)pent-4-en-2-ol (2.2 equiv) were combined in dichloromethane (40 mM reaction concentration) in the presence of 5 Å molecular sieves and cooled to 0° C. Scandium (III) triflate (1.0 equiv) was added in one portion and allowed to slowly warm to room temperature and react for 18-24 hours, tracking by TLC. Upon completion, the reaction mixture was filtered through a pad of Celite, rinsing with dichloromethane. The crude reaction mixture was concentrated and directly purified via flash column chromatography (acetone/hexanes) to afford the product 7-fluoro-3,3-bis(6-(((R)-2-hydroxypent-4-en-1-yl)oxy)benzo[d][1,3]dioxol-5-yl)indolin-2-one. $^1$H NMR (400 MHz, METHANOL-d$_4$) δ=7.11-6.99 (m, 1H), 6.99-6.90 (m, 1H), 6.85-6.67 (m, 1H), 6.65-6.58 (m, 2H), 6.55-6.49 (m, 1H), 6.18-6.06 (m, 1H), 5.91-5.82 (m, 4H), 5.80-5.59 (m, 1H), 5.10-4.91 (m, 4H), 3.77 (br s, 3H), 3.66 (s, 2H), 3.43-3.31 (m, 1H), 2.30-1.90 (m, 3H), 1.81-1.52 (m, 1H). LC/MS m/z=592.3 for C$_{32}$H$_{31}$FNO$_9$ [M+H]$^+$.

7-fluoro-3,3-bis(6-(((R)-2-hydroxyhex-5-en-1-yl)oxy)benzo[d][1,3]dioxol-5-yl)indolin-2-one
(CMLD012449, Table 1, Entry 9)

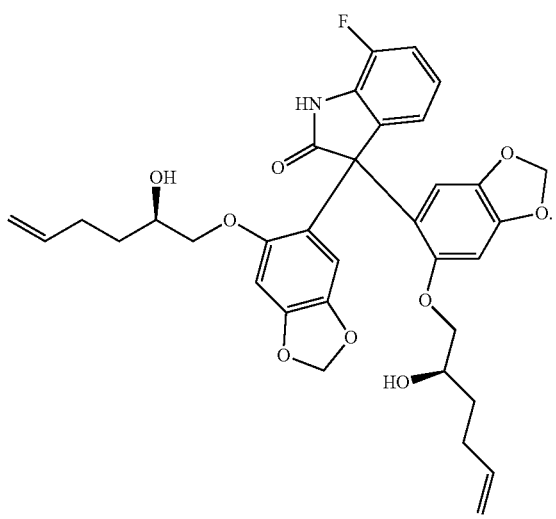 [SMILES: C=CCC[C@@H](O)COc1cc2c(cc1C1(c3cc4c(cc3OC[C@H](O)CCC=C)OCO4)C(=O)Nc3c(F)cccc31)OCO2]

7-fluoro-3,3-dimethoxyindolin-2-one (1.0 equiv) and (R)-1-(benzo[d][1,3]dioxol-5-yloxy)hex-5-en-2-ol (2.2 equiv) were combined in dichloromethane (40 mM reaction concentration) in the presence of 5 Å molecular sieves and cooled to 0° C. Scandium (III) triflate (1.0 equiv) was added in one portion and allowed to slowly warm to room temperature and react for 18-24 hours, tracking by TLC. Upon completion, the reaction mixture was filtered through a pad of Celite, rinsing with dichloromethane. The crude reaction mixture was concentrated and directly purified via flash column chromatography (acetone/hexanes) to afford the product 7-fluoro-3,3-bis(6-(((R)-2-hydroxyhex-5-en-1-yl)oxy)benzo[d][1,3]dioxol-5-yl)indolin-2-one. $^1$H NMR (400 MHz, METHANOL-d$_4$) δ=7.09-6.88 (m, 2H), 6.79-6.58 (m, 3H), 6.57-6.45 (m, 1H), 6.39-6.20 (m, 1H), 6.17-6.01 (m, 1H), 5.85 (br d, J=7.4 Hz, 4H), 5.80-5.66 (m, 1H), 5.08-4.89 (m, 2H), 4.18 (br s, 1H), 4.05-3.95 (m, 1H), 3.93-3.82 (m, 1H), 3.82-3.73 (m, 2H), 3.72-3.62 (m, 1H), 3.59-3.49 (m, 1H), 2.27-2.04 (m, 1H), 1.93-1.82 (m, 1H), 1.57-1.30 (m, 2H), 1.20-1.12 (m, 2H), 1.13-0.91 (m, 2H). LC/MS m/z=620.3 for C$_{34}$H$_{35}$FNO$_9$ [M+H]$^+$.

6-fluoro-3,3-bis(6-(((R)-2-hydroxy-4-methylpentyl)oxy)benzo[d][1,3]dioxol-5-yl)indolin-2-one (CMLD012393, Table 1, Entry 11)

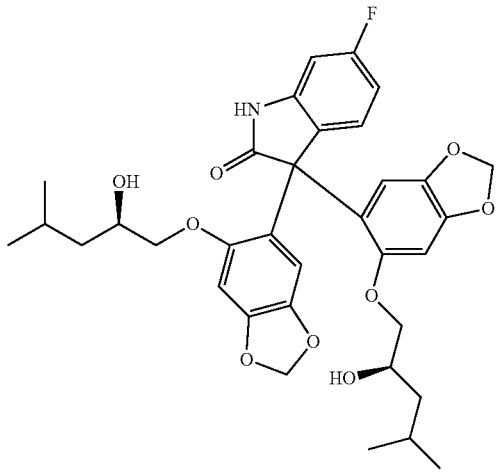 [SMILES: CC(C)C[C@@H](O)COc1cc2c(cc1C1(c3cc4c(cc3OC[C@H](O)CC(C)C)OCO4)C(=O)Nc3cc(F)ccc31)OCO2]

6-fluoro-3,3-dimethoxyindolin-2-one (1.0 equiv) and (R)-1-(benzo[d][1,3]dioxol-5-yloxy)-4-methylpentan-2-ol (2.2 equiv) were combined in dichloromethane (40 mM reaction concentration) in the presence of 5 Å molecular sieves and cooled to 0° C. Scandium (III) triflate (1.0 equiv) was added in one portion and allowed to slowly warm to room temperature and react for 18-24 hours, tracking by TLC. Upon completion, the reaction mixture was filtered through a pad of Celite, rinsing with dichloromethane. The crude reaction mixture was concentrated and directly purified via flash column chromatography (acetone/hexanes) to afford the product 6-fluoro-3,3-bis(6-(((R)-2-hydroxy-4-methylpentyl)oxy)benzo[d][1,3]dioxol-5-yl)indolin-2-one. $^1$H NMR (400 MHz, METHANOL-$d_4$) δ=6.77-6.58 (m, 4H), 6.55-6.47 (m, 1H), 6.23-6.10 (m, 1H), 5.95-5.78 (m, 4H), 3.94-3.33 (m, 6H), 1.84-1.52 (m, 2H), 1.44-1.00 (m, 3H), 0.97-0.72 (m, 13H). LC/MS m/z=624.2 for $C_{34}H_{39}FNO_9$ [M+H]$^+$.

6-fluoro-3,3-bis(6-(((R)-2-hydroxypent-4-en-1-yl)oxy)benzo[d][1,3]dioxol-5-yl)indolin-2-one (CMLD012400, Table 1, Entry 12)

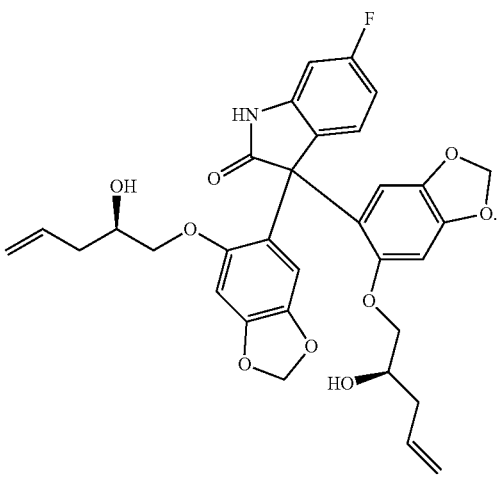 [SMILES: C=CC[C@@H](O)COc1cc2c(cc1C1(c3cc4c(cc3OC[C@H](O)CC=C)OCO4)C(=O)Nc3cc(F)ccc31)OCO2]

6-fluoro-3,3-dimethoxyindolin-2-one (1.0 equiv) and (R)-1-(benzo[d][1,3]dioxol-5-yloxy)pent-4-en-2-ol (2.2 equiv) were combined in dichloromethane (40 mM reaction concentration) in the presence of 5 Å molecular sieves and cooled to 0° C. Scandium (III) triflate (1.0 equiv) was added in one portion and allowed to slowly warm to room temperature and react for 18-24 hours, tracking by TLC. Upon completion, the reaction mixture was filtered through a pad of Celite, rinsing with dichloromethane. The crude reaction mixture was concentrated and directly purified via flash column chromatography (acetone/hexanes) to afford the product 6-fluoro-3,3-bis(6-(((R)-2-hydroxypent-4-en-1-yl)oxy)benzo[d][1,3]dioxol-5-yl)indolin-2-one. $^1$H NMR (400 MHz, METHANOL-$d_4$) δ=7.05-6.87 (m, 1H), 6.76-6.58 (m, 5H), 6.52 (s, 1H), 6.50 (s, 1H), 6.16 (br d, J=9.4 Hz, 1H), 5.93-5.85 (m, 4H), 5.81 (br s, 1H), 5.11-4.93 (m, 4H), 3.98-3.85 (m, 1H), 3.85-3.72 (m, 3H), 3.61-3.60 (m, 1H), 3.70-3.60 (m, 1H), 3.60-3.51 (m, 1H), 3.43-3.33 (m, 1H), 2.33-1.96 (m, 3H), 1.80-1.57 (m, 1H). LC/MS m/z=592.3 for $C_{32}H_{31}FNO_9$ [M+H]$^+$.

6-fluoro-3,3-bis(6-(((R)-2-hydroxypentyl)oxy)benzo[d][1,3]dioxol-5-yl)indolin-2-one (CMLD012439, Table 1, Entry 13)

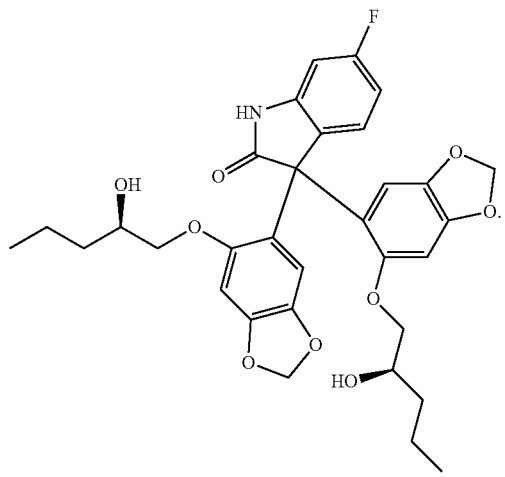 [SMILES: CCC[C@@H](O)COc1cc2c(cc1C1(c3cc4c(cc3OC[C@H](O)CCC)OCO4)C(=O)Nc3cc(F)ccc31)OCO2]

6-fluoro-3,3-dimethoxyindolin-2-one (1.0 equiv) and (R)-1-(benzo[d][1,3]dioxol-5-yloxy)pentan-2-ol (2.2 equiv) were combined in dichloromethane (40 mM reaction concentration) in the presence of 5 Å molecular sieves and cooled to 0° C. Scandium (III) triflate (1.0 equiv) was added in one portion and allowed to slowly warm to room temperature and react for 18-24 hours, tracking by TLC. Upon completion, the reaction mixture was filtered through a pad of Celite, rinsing with dichloromethane. The crude reaction mixture was concentrated and directly purified via flash column chromatography (acetone/hexanes) to afford the product 6-fluoro-3,3-bis(6-(((R)-2-hydroxypentyl)oxy)benzo[d][1,3]dioxol-5-yl)indolin-2-one. $^1$H NMR (400 MHz, METHANOL-$d_4$) δ=7.01-6.87 (m, 1H), 6.77-6.59 (m, 4H), 6.50 (s, 1H), 6.22-6.11 (m, 1H), 5.86 (br d, J=8.6 Hz, 4H), 3.89-3.78 (m, 1H), 3.77-3.63 (m, 3H), 3.59-3.45 (m, 1H), 1.53-1.40 (m, 1H), 1.38-1.11 (m, 6H), 0.97-0.80 (m, 7H). LC/MS m/z=596.3 for $C_{32}H_{35}FNO_9$ [M+H]$^+$.

6-fluoro-3,3-bis(6-(((R)-2-hydroxyhex-5-en-1-yl)oxy)benzo[d][1,3]dioxol-5-yl)indolin-2-one (CMLD012447, Table 1, Entry 14)

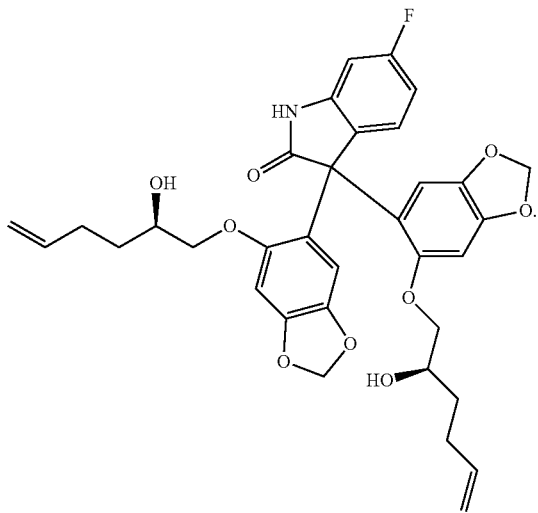 [SMILES: C=CCC[C@@H](O)COc1cc2c(cc1C1(c3cc4c(cc3OC[C@H](O)CCC=C)OCO4)C(=O)Nc3cc(F)ccc31)OCO2]

6-fluoro-3,3-dimethoxyindolin-2-one (1.0 equiv) and (R)-1-(benzo[d][1,3]dioxol-5-yloxy)hex-5-en-2-ol (2.2 equiv) were combined in dichloromethane (40 mM reaction concentration) in the presence of 5 Å molecular sieves and cooled to 0° C. Scandium (III) triflate (1.0 equiv) was added in one portion and allowed to slowly warm to room temperature and react for 18-24 hours, tracking by TLC. Upon completion, the reaction mixture was filtered through a pad of Celite, rinsing with dichloromethane. The crude reaction mixture was concentrated and directly purified via flash column chromatography (acetone/hexanes) to afford the product 6-fluoro-3,3-bis(6-(((R)-2-hydroxyhex-5-en-1-yl)oxy)benzo[d][1,3]dioxol-5-yl)indolin-2-one. $^1$H NMR (400 MHz, METHANOL-$d_4$) δ=7.07-6.85 (m, 1H), 6.77-6.57 (m, 4H), 6.54-6.42 (m, 1H), 6.21-6.06 (m, 1H), 5.94-5.84 (m, 4H), 5.81-5.62 (m, 1H), 5.10-4.91 (m, 3H), 3.95-3.44 (m, 5H), 2.28-1.83 (m, 4H), 1.56-0.94 (m, 5H). LC/MS m/z=620.3 for $C_{34}H_{35}FNO_9$ [M+H]$^+$.

5-fluoro-3,3-bis(6-(((R)-2-hydroxy-4-methylpentyl)oxy)benzo[d][1,3]dioxol-5-yl)indolin-2-one (CMLD013622, Table 1, Entry 15)

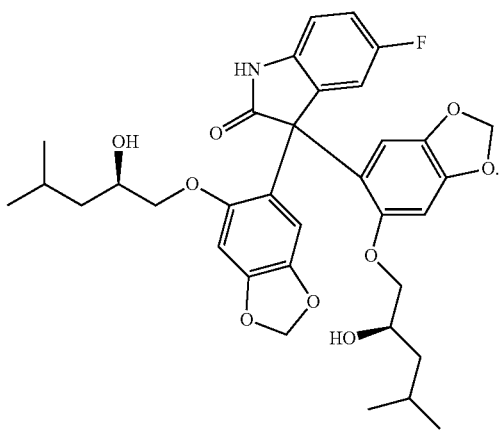 [SMILES: CC(C)C[C@@H](O)COc1cc2c(cc1C1(c3cc4c(cc3OC[C@H](O)CC(C)C)OCO4)C(=O)Nc3ccc(F)cc31)OCO2]

5-fluoro-3,3-dimethoxyindolin-2-one (1.0 equiv) and (R)-1-(benzo[d][1,3]dioxol-5-yloxy)-4-methylpentan-2-ol (2.2 equiv) were combined in dichloromethane (40 mM reaction concentration) in the presence of 5 Å molecular sieves and cooled to 0° C. Scandium (III) triflate (1.0 equiv) was added in one portion and allowed to slowly warm to room temperature and react for 18-24 hours, tracking by TLC. Upon completion, the reaction mixture was filtered through a pad of Celite, rinsing with dichloromethane. The crude reaction mixture was concentrated and directly purified via flash column chromatography (acetone/hexanes) to afford the product 5-fluoro-3,3-bis(6-(((R)-2-hydroxy-4-methylpentyl)oxy)benzo[d][1,3]dioxol-5-yl)indolin-2-one. $^1$H NMR (400 MHz, acetone-$d_6$) δ=9.79-9.43 (m, 1H), 7.10-7.00 (m, 2H), 6.98-6.87 (m, 1H), 6.75-6.71 (m, 1H), 6.71-6.66 (m, 1H), 6.63-6.54 (m, 1H), 6.30-6.20 (m, 1H), 5.95 (br d, J=10.2 Hz, 4H), 3.97-3.84 (m, 1H), 3.82-3.66 (m, 3H), 3.54 (s, 1H), 3.43-3.29 (m, 1H), 1.86-1.58 (m, 2H), 1.37-1.18 (m, 2H), 1.14-0.98 (m, 1H), 0.93-0.77 (m, 13H). LC/MS m/z=624.4 for $C_{34}H_{39}FNO_9$ [M+H]$^+$.

6-bromo-3,3-bis(6-(((2R)-2-hydroxy-4-methylpentyl)oxy)-2H-1,3-benzodioxol-5-yl)-2,3-dihydro-1H-indol-2-one (CMLD013651, Table 1, Entry 16)

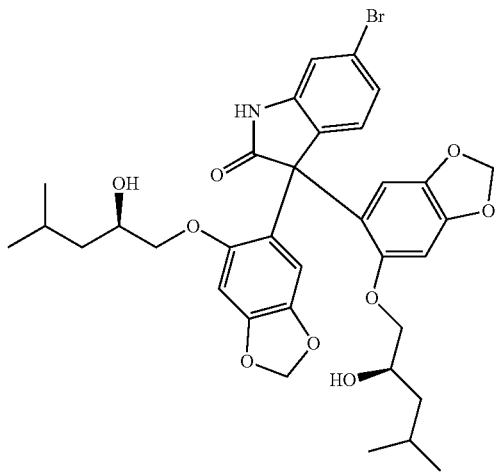 [SMILES: CC(C)C[C@@H](O)COc1cc2c(cc1C1(c3cc4c(cc3OC[C@H](O)CC(C)C)OCO4)C(=O)Nc3cc(Br)ccc31)OCO2]

6-bromo-3,3-dimethoxyindolin-2-one (1.0 equiv) and (R)-1-(benzo[d][1,3]dioxol-5-yloxy)-4-methylpentan-2-ol (2.2 equiv) were combined in dichloromethane (40 mM reaction concentration) in the presence of 5 Å molecular sieves and cooled to 0° C. Scandium (III) triflate (1.0 equiv) was added in one portion and allowed to slowly warm to room temperature and react for 18-24 hours, tracking by TLC. Upon completion, the reaction mixture was filtered through a pad of Celite, rinsing with dichloromethane. The crude reaction mixture was concentrated and directly purified via flash column chromatography (acetone/hexanes) to afford the product 6-bromo-3,3-bis(6-(((2R)-2-hydroxy-4-methylpentyl)oxy)-2H-1,3-benzodioxol-5-yl)-2,3-dihydro-1H-indol-2-one. $^1$H NMR (400 MHz, CHLOROFORM-d) δ=9.03-8.47 (m, 1H), 7.21-7.04 (m, 2H), 6.83-6.38 (m, 3H), 6.32-6.09 (m, 1H), 6.06-5.68 (m, 4H), 4.14-3.19 (m, 5H), 1.87-1.45 (m, 1H), 1.25 (s, 3H), 1.01-0.50 (m, 12H). LC/MS m/z=686.5 for $C_{34}H_{39}BrNO_9$ [M+H]$^+$.

3-(6-ethoxybenzo[d][1,3]dioxol-5-yl)-6-fluoro-3-(6-(((R)-2-hydroxy-4-methylpent-4-en-1-yl)oxy)benzo[d][1,3]dioxol-5-yl)indolin-2-one (RT-162S-015, Table 1, Entry 17)

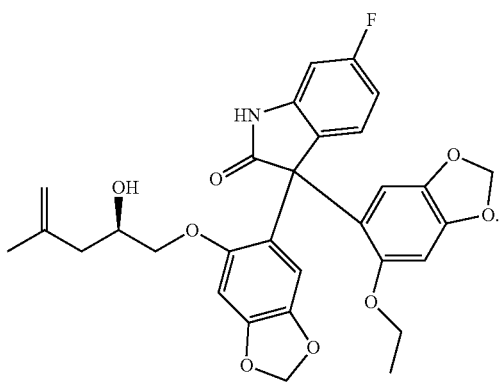 [SMILES: C=C(C)C[C@@H](O)COc1cc2c(cc1C1(c3cc4c(cc3OCC)OCO4)C(=O)Nc3cc(F)ccc31)OCO2]

Step 1: 6-fluoro-3,3-dimethoxyindolin-2-one (1.0 equiv) and (R)-1-(benzo[d][1,3]dioxol-5-yloxy)-4-methylpent-4-en-2-ol (1.0 equiv) were combined in dichloromethane (40 mM reaction concentration) and cooled to −40° C. Boron trifluoride diethyl etherate (0.9 equiv) was added dropwise, slowly over 5 minutes. The reaction was stirred at −40° C. for 40 minutes, and quenched with slow dropwise addition of 1N HCl followed stirring for 5 minutes at −40° C., and warming to 0° C. over the course of 10 minutes. Na$_2$SO$_4$ was added and the mixture was filtered through a pad of Celite, rinsing with dichloromethane. The crude reaction mixture was concentrated and directly purified via flash column chromatography (acetone/hexanes) to afford the product 6-fluoro-3-(6-(((R)-2-hydroxy-4-methylpent-4-en-1-yl)oxy)benzo[d][1,3]dioxol-5-yl)-3-methoxyindolin-2-one.

Step 2: 6-fluoro-3-(6-(((R)-2-hydroxy-4-methylpent-4-en-1-yl)oxy)benzo[d][1,3]dioxol-5-yl)-3-methoxyindolin-2-one (1.0 equiv) and 5-ethoxybenzo[d][1,3]dioxole (2.2 equiv) were combined in dichloromethane (40 mM reaction concentration) in the presence of magnesium sulfate and cooled to 0° C. Scandium (III) triflate (1.0 equiv) was added in one portion and allowed to slowly warm to room temperature and react overnight. The reaction mixture was then filtered through a pad of Celite, rinsing with dichloromethane. The crude reaction mixture was concentrated and directly purified via flash column chromatography (acetone/hexanes) to afford the product 3-(6-ethoxybenzo[d][1,3]dioxol-5-yl)-6-fluoro-3-(6-(((R)-2-hydroxy-4-methylpent-4-en-1-yl)oxy)benzo[d][1,3]dioxol-5-yl)indolin-2-one. $^1$H NMR (400 MHz, acetone-d$_6$) δ=6.97-6.51 (m, 5H), 6.27-6.13 (m, 1H), 5.94 (br d, J=18.8 Hz, 4H), 4.94-4.48 (m, 2H), 4.03-3.38 (m, 5H), 1.81-1.58 (m, 4H), 1.35-0.97 (m, 3H). LC/MS m/z=550.4 for C$_{30}$H$_{29}$FNO$_8$ [M+H]$^+$.

7-fluoro-3,3-bis(6-(((R)-2-hydroxy-4-methylpent-4-en-1-yl)oxy)benzo[d][1,3]dioxol-5-yl)indolin-2-one (CMLD012436, Table 1, Entry 18)

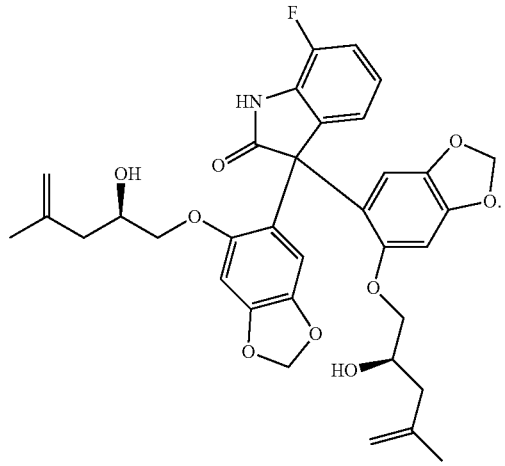 [SMILES: C=C(C)C[C@@H](O)COc1cc2c(cc1C1(c3cc4c(cc3OC[C@H](O)CC(=C)C)OCO4)C(=O)Nc3c(F)cccc31)OCO2]

7-fluoro-3,3-dimethoxyindolin-2-one (1.0 equiv) and (R)-1-(benzo[d][1,3]dioxol-5-yloxy)-4-methylpent-4-en-2-ol (2.2 equiv) were combined in dichloromethane (40 mM reaction concentration) in the presence of 5 Å molecular sieves and cooled to 0° C. Scandium (III) triflate (1.0 equiv) was added in one portion and allowed to slowly warm to room temperature and react for 18-24 hours, tracking by TLC. Upon completion, the reaction mixture was filtered through a pad of Celite, rinsing with dichloromethane. The crude reaction mixture was concentrated and directly purified via flash column chromatography (acetone/hexanes) to afford the product 7-fluoro-3,3-bis(6-(((R)-2-hydroxy-4-methylpent-4-en-1-yl)oxy)benzo[d][1,3]dioxol-5-yl)indolin-2-one. $^1$H NMR (400 MHz, METHANOL-d$_4$) δ=6.66 (s, 4H), 6.59-6.45 (m, 1H), 6.22-6.06 (m, 1H), 5.92-5.83 (m, 4H), 4.80-4.57 (m, 4H), 3.97-3.63 (m, 5H), 3.61-3.42 (m, 1H), 2.15-2.01 (m, 2H), 1.75-1.66 (m, 7H). LC/MS m/z=620.3 for C$_{34}$H$_{35}$FNO$_9$ [M+H]$^+$.

5-bromo-3,3-bis(6-(((2R)-2-hydroxy-4,4-dimethylpentyl)oxy)-2H-1,3-benzodioxol-5-yl)-2,3-dihydro-1H-indol-2-one (CMLD013652, Table 1, Entry 19)

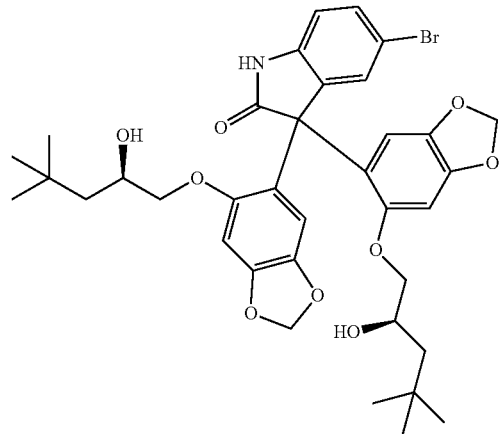 [SMILES: CC(C)(C)C[C@@H](O)COc1cc2c(cc1C1(c3cc4c(cc3OC[C@H](O)CC(C)(C)C)OCO4)C(=O)Nc3ccc(Br)cc31)OCO2]

5-bromo-3,3-dimethoxyindolin-2-one (1.0 equiv) and (R)-1-(benzo[d][1,3]dioxol-5-yloxy)-4,4-dimethylpentan-2-ol (2.2 equiv) were combined in dichloromethane (40 mM reaction concentration) in the presence of 5 Å molecular sieves and cooled to 0° C. Scandium (III) triflate (1.0 equiv) was added in one portion and allowed to slowly warm to room temperature and react for 18-24 hours, tracking by TLC. Upon completion, the reaction mixture was filtered through a pad of Celite, rinsing with dichloromethane. The crude reaction mixture was concentrated and directly purified via flash column chromatography (acetone/hexanes) to afford the product 5-bromo-3,3-bis(6-(((2R)-2-hydroxy-4,4-dimethylpentyl)oxy)-2H-1,3-benzodioxol-5-yl)-2,3-dihydro-1H-indol-2-one. $^1$H NMR (400 MHz, CHLOROFORM-d) δ=7.46-7.29 (m, 1H), 7.06-6.97 (m, 1H), 6.95-6.80 (m, 1H), 6.66-6.53 (m, 1H), 6.51-6.40 (m, 2H), 6.08-5.70 (m, 4H), 3.99-3.48 (m, 5H), 1.37-1.15 (m, 3H), 1.05-0.60 (m, 22H). LC/MS m/z=712.6 for $C_{36}H_{43}BrNO_9$ [M+H]$^+$.

7-fluoro-3,3-bis(7-(((2R)-2-hydroxy-4-methylpentyl)oxy)-2,3-dihydro-1,4-benzodioxin-6-yl)-2,3-dihydro-1H-indol-2-one (CMLD013654, Table 1, Entry 20)

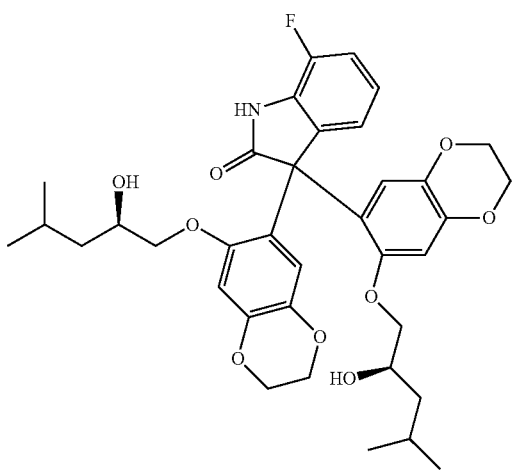 [SMILES: CC(C)C[C@@H](O)COc1cc2c(cc1C1(c3cc4c(cc3OC[C@H](O)CC(C)C)OCCO4)C(=O)Nc3c(F)cccc31)OCCO2]

7-fluoro-3,3-dimethoxyindolin-2-one (1.0 equiv) and (R)-1-((2,3-dihydrobenzo[b][1,4]dioxin-6-yl)oxy)-4-methylpentan-2-ol (2.2 equiv) were combined in dichloromethane (40 mM reaction concentration) in the presence of 5 Å molecular sieves and cooled to 0° C. Scandium (III) triflate (1.0 equiv) was added in one portion and allowed to slowly warm to room temperature and react for 18-24 hours, tracking by TLC. Upon completion, the reaction mixture was filtered through a pad of Celite, rinsing with dichloromethane. The crude reaction mixture was concentrated and directly purified via flash column chromatography (acetone/hexanes) to afford the product 7-fluoro-3,3-bis(7-(((2R)-2-hydroxy-4-methylpentyl)oxy)-2,3-dihydro-1,4-benzodioxin-6-yl)-2,3-dihydro-1H-indol-2-one. $^1$H NMR (400 MHz, acetone-d$_6$) δ=9.88-9.87 (m, 1H), 10.17-9.65 (m, 1H), 7.17-7.08 (m, 1H), 7.05-6.98 (m, 1H), 6.93-6.84 (m, 1H), 6.48 (br d, J=15.2 Hz, 3H), 6.26-6.19 (m, 1H), 4.32-4.11 (m, 9H), 3.93-3.75 (m, 3H), 3.74-3.54 (m, 3H), 3.52-3.44 (m, 1H), 3.41-3.30 (m, 1H), 1.85-1.72 (m, 1H), 1.86-1.60 (m, 2H), 1.70-1.59 (m, 1H), 1.35-1.19 (m, 2H), 1.16-0.96 (m, 2H), 1.35-0.95 (m, 3H), 0.91-0.77 (m, 13H). LC/MS m/z=652.7 for $C_{36}H_{43}FNO_9$ [M+H]$^+$.

6-fluoro-3,3-bis(7-(((2R)-2-hydroxy-4-methylpentyl)oxy)-2,3-dihydro-1,4-benzodioxin-6-yl)-2,3-dihydro-1H-indol-2-one (CMLD013648, Table 1, Entry 21)

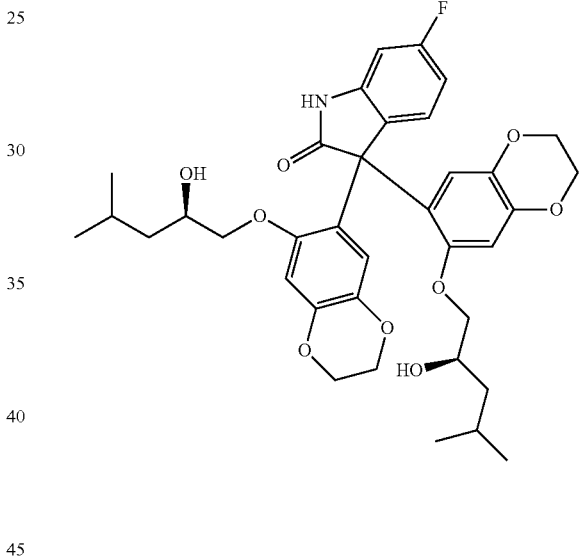

6-fluoro-3,3-dimethoxyindolin-2-one (1.0 equiv) and (R)-1-((2,3-dihydrobenzo[b][1,4]dioxin-6-yl)oxy)-4-methylpentan-2-ol (2.2 equiv) were combined in dichloromethane (40 mM reaction concentration) in the presence of 5 Å molecular sieves and cooled to 0° C. Scandium (III) triflate (1.0 equiv) was added in one portion and allowed to slowly warm to room temperature and react for 18-24 hours, tracking by TLC. Upon completion, the reaction mixture was filtered through a pad of Celite, rinsing with dichloromethane. The crude reaction mixture was concentrated and directly purified via flash column chromatography (acetone/hexanes) to afford the product 6-fluoro-3,3-bis(7-(((2R)-2-hydroxy-4-methylpentyl)oxy)-2,3-dihydro-1,4-benzodioxin-6-yl)-2,3-dihydro-1H-indol-2-one. $^1$H NMR (400 MHz, acetone-d$_6$) δ=9.88-9.42 (m, 1H), 7.09-6.96 (m, 1H), 6.85-6.68 (m, 2H), 6.61-6.40 (m, 3H), 6.25 (s, 1H), 4.27-4.12 (m, 8H), 3.90-3.76 (m, 2H), 3.74-3.63 (m, 2H), 3.61-3.46 (m, 1H), 3.43-3.30 (m, 1H), 1.84-1.60 (m, 2H), 1.34-1.19 (m, 2H), 1.17-0.99 (m, 1H), 0.95-0.76 (m, 13H). LC/MS m/z=652.6 for $C_{36}H_{43}FNO_9$ [M+H]$^+$.

5-fluoro-3,3-bis(6-(((R)-2-hydroxypentyl)oxy)benzo[d][1,3]dioxol-5-yl)indolin-2-one (CMLD013619, Table 1, Entry 22)

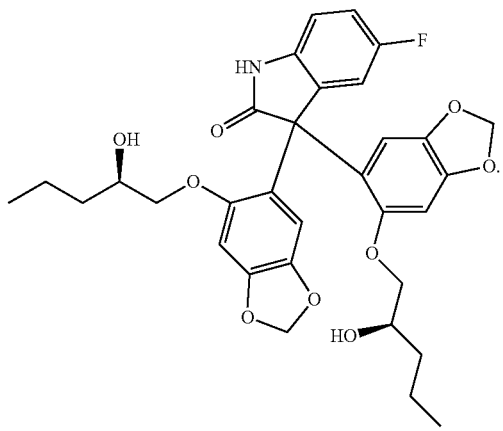 [SMILES: CCC[C@@H](O)COc1cc2c(cc1C1(c3cc4c(cc3OC[C@H](O)CCC)OCO4)C(=O)Nc3ccc(F)cc31)OCO2]

5-fluoro-3,3-dimethoxyindolin-2-one (1.0 equiv) and (R)-1-(benzo[d][1,3]dioxol-5-yloxy)pentan-2-ol (2.2 equiv) were combined in dichloromethane (40 mM reaction concentration) in the presence of 5 Å molecular sieves and cooled to 0° C. Scandium (III) triflate (1.0 equiv) was added in one portion and allowed to slowly warm to room temperature and react for 18-24 hours, tracking by TLC. Upon completion, the reaction mixture was filtered through a pad of Celite, rinsing with dichloromethane. The crude reaction mixture was concentrated and directly purified via flash column chromatography (acetone/hexanes) to afford the product 5-fluoro-3,3-bis(6-(((R)-2-hydroxypentyl)oxy)benzo[d][1,3]dioxol-5-yl)indolin-2-one. $^1$H NMR (400 MHz, acetone-d$_6$) δ=9.86-9.22 (m, 1H), 7.13-6.99 (m, 2H), 6.97-6.87 (m, 1H), 6.78-6.63 (m, 2H), 6.62-6.52 (m, 1H), 6.26-6.18 (m, 1H), 6.03-5.82 (m, 4H), 3.95-3.86 (m, 1H), 3.86-3.79 (m, 1H), 3.79-3.67 (m, 3H), 3.60-3.49 (m, 1H), 3.45-3.37 (m, 1H), 3.36-3.25 (m, 1H), 3.47-3.25 (m, 1H), 1.54-1.37 (m, 2H), 1.34-1.21 (m, 5H), 1.21-1.06 (m, 1H), 0.97-0.76 (m, 7H). LC/MS m/z=596.3 for C$_{32}$H$_{35}$FNO$_9$ [M+H]$^+$.

4-bromo-3,3-bis(6-(((R)-2-hydroxyhex-5-en-1-yl)oxy)benzo[d][1,3]dioxol-5-yl)indolin-2-one (CMLD012453, Table 1, Entry 23)

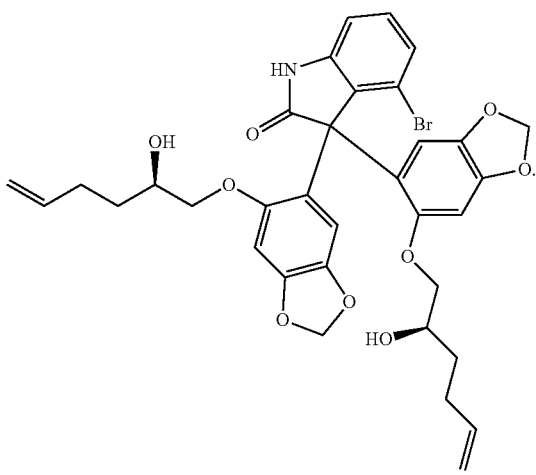 [SMILES: C=CCC[C@@H](O)COc1cc2c(cc1C1(c3cc4c(cc3OC[C@H](O)CCC=C)OCO4)C(=O)Nc3cccc(Br)c31)OCO2]

4-bromo-3,3-dimethoxyindolin-2-one (1.0 equiv) and (R)-1-(benzo[d][1,3]dioxol-5-yloxy)hex-5-en-2-ol (2.2 equiv) were combined in dichloromethane (40 mM reaction concentration) in the presence of 5 Å molecular sieves and cooled to 0° C. Scandium (III) triflate (1.0 equiv) was added in one portion and allowed to slowly warm to room temperature and react for 18-24 hours, tracking by TLC. Upon completion, the reaction mixture was filtered through a pad of Celite, rinsing with dichloromethane. The crude reaction mixture was concentrated and directly purified via flash column chromatography (acetone/hexanes) to afford the product 4-bromo-3,3-bis(6-(((R)-2-hydroxyhex-5-en-1-yl)oxy)benzo[d][1,3]dioxol-5-yl)indolin-2-one. $^1$H NMR (400 MHz, METHANOL-d$_4$) δ=7.21-7.09 (m, 3H), 6.90 (br d, J=1.2 Hz, 1H), 6.73-6.68 (m, 2H), 6.59 (d, J=5.1 Hz, 1H), 6.18-6.09 (m, 1H), 5.91 (s, 1H), 5.89-5.84 (m, 4H), 5.83-5.67 (m, 2H), 5.05-4.92 (m, 4H), 4.13-4.03 (m, 1H), 4.01-3.90 (m, 1H), 3.86 (br s, 1H), 3.82-3.75 (m, 1H), 3.69 (br s, 1H), 3.58 (br s, 2H), 3.51-3.35 (m, 1H), 2.21-2.10 (m, 1H), 2.10-1.95 (m, 3H), 1.95-1.84 (m, 1H), 1.49-1.25 (m, 5H), 1.16 (s, 2H), 1.03-0.80 (m, 2H). LC/MS m/z=680.2 for C$_{34}$H$_{35}$BrNO$_9$ [M+H]$^+$.

6-fluoro-3,3-bis(6-((R)-2-hydroxybutoxy)benzo[d][1,3]dioxol-5-yl)indolin-2-one (CMLD012394, Table 1, Entry 24)

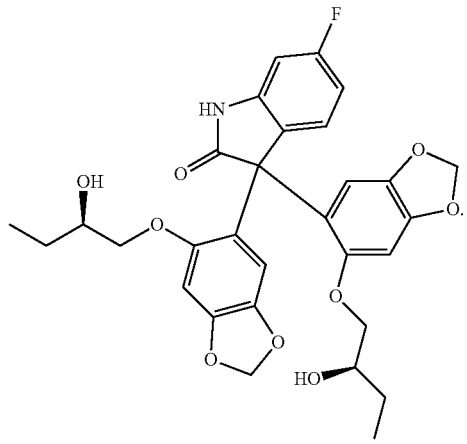 [SMILES: CC[C@@H](O)COc1cc2c(cc1C1(c3cc4c(cc3OC[C@H](O)CC)OCO4)C(=O)Nc3cc(F)ccc31)OCO2]

6-fluoro-3,3-dimethoxyindolin-2-one (1.0 equiv) and (R)-1-(benzo[d][1,3]dioxol-5-yloxy)butan-2-ol (2.2 equiv) were combined in dichloromethane (40 mM reaction concentration) in the presence of 5 Å molecular sieves and cooled to 0° C. Scandium (III) triflate (1.0 equiv) was added in one portion and allowed to slowly warm to room temperature and react for 18-24 hours, tracking by TLC. Upon completion, the reaction mixture was filtered through a pad of Celite, rinsing with dichloromethane. The crude reaction mixture was concentrated and directly purified via flash column chromatography (acetone/hexanes) to afford the product 6-fluoro-3,3-bis(6-((R)-2-hydroxybutoxy)benzo[d][1,3]dioxol-5-yl)indolin-2-one. $^1$H NMR (400 MHz, METHANOL-d$_4$) δ=7.00-6.91 (m, 1H), 6.64 (br dd, J=1.8, 12.7 Hz, 4H), 6.55-6.46 (m, 1H), 6.20-6.12 (m, 1H), 5.93-5.82 (m, 4H), 3.91-3.77 (m, 1H), 3.78 (br s, 1H), 3.73 (br s, 3H), 3.44-3.18 (m, 3H), 1.23 (s, 4H), 1.03-0.82 (m, 6H), 0.74 (s, 2H). LC/MS m/z=568.2 for C$_{30}$H$_{31}$FNO$_9$ [M+H]$^+$.

5-fluoro-3,3-bis(6-(((R)-2-hydroxyhex-5-en-1-yl)oxy)benzo[d][1,3]dioxol-5-yl)indolin-2-one (CMLD012450, Table 1, Entry 25)

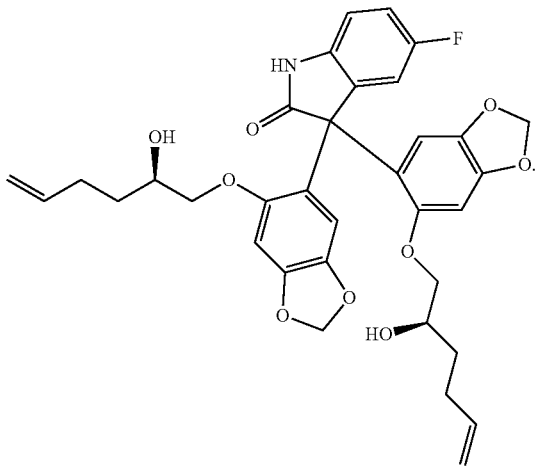 [SMILES: C=CCC[C@@H](O)COc1cc2c(cc1C1(c3cc4c(cc3OC[C@H](O)CCC=C)OCO4)C(=O)Nc3ccc(F)cc31)OCO2]

5-fluoro-3,3-dimethoxyindolin-2-one (1.0 equiv) and (R)-1-(benzo[d][1,3]dioxol-5-yloxy)hex-5-en-2-ol (2.2 equiv) were combined in dichloromethane (40 mM reaction concentration) in the presence of 5 Å molecular sieves and cooled to 0° C. Scandium (III) triflate (1.0 equiv) was added in one portion and allowed to slowly warm to room temperature and react for 18-24 hours, tracking by TLC. Upon completion, the reaction mixture was filtered through a pad of Celite, rinsing with dichloromethane. The crude reaction mixture was concentrated and directly purified via flash column chromatography (acetone/hexanes) to afford the product 5-fluoro-3,3-bis(6-(((R)-2-hydroxyhex-5-en-1-yl)oxy)benzo[d][1,3]dioxol-5-yl)indolin-2-one. $^1$H NMR (400 MHz, METHANOL-$d_4$) δ=7.04-6.92 (m, 1H), 6.88 (td, J=5.1, 8.5 Hz, 1H), 6.83-6.72 (m, 1H), 6.67 (s, 2H), 6.56-6.44 (m, 1H), 6.22-6.09 (m, 1H), 5.88 (br d, J=3.1 Hz, 4H), 5.85 (s, 1H), 5.07-4.91 (m, 3H), 3.92-3.78 (m, 1H), 3.76-3.65 (m, 2H), 3.61-3.51 (m, 1H), 3.50-3.42 (m, 1H), 2.01 (s, 4H), 1.49-1.32 (m, 2H), 1.19-1.08 (m, 1H), 1.05-0.85 (m, 1H). LC/MS m/z=620.3 for $C_{34}H_{35}FNO_9$ [M+H]$^+$.

6-bromo-3,3-bis(6-(((R)-2-hydroxyhex-5-en-1-yl)oxy)benzo[d][1,3]dioxol-5-yl)indolin-2-one (CMLD012452, Table 1, Entry 26)

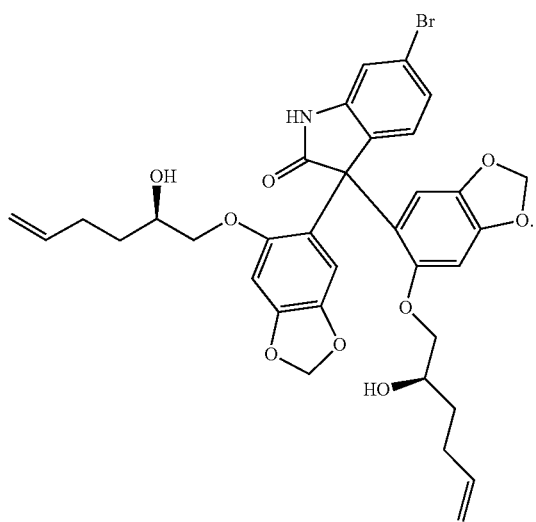 [SMILES: C=CCC[C@@H](O)COc1cc2c(cc1C1(c3cc4c(cc3OC[C@H](O)CCC=C)OCO4)C(=O)Nc3cc(Br)ccc31)OCO2]

6-bromo-3,3-dimethoxyindolin-2-one (1.0 equiv) and (R)-1-(benzo[d][1,3]dioxol-5-yloxy)hex-5-en-2-ol (2.2 equiv) were combined in dichloromethane (40 mM reaction concentration) in the presence of 5 Å molecular sieves and cooled to 0° C. Scandium (III) triflate (1.0 equiv) was added in one portion and allowed to slowly warm to room temperature and react for 18-24 hours, tracking by TLC. Upon completion, the reaction mixture was filtered through a pad of Celite, rinsing with dichloromethane. The crude reaction mixture was concentrated and directly purified via flash column chromatography (acetone/hexanes) to afford the product 6-bromo-3,3-bis(6-(((R)-2-hydroxyhex-5-en-1-yl)oxy)benzo[d][1,3]dioxol-5-yl)indolin-2-one. $^1$H NMR (400 MHz, METHANOL-$d_4$) δ=7.16-6.97 (m, 2H), 6.94-6.79 (m, 1H), 6.63 (s, 2H), 6.54 (s, 1H), 5.92-5.81 (m, 4H), 5.81-5.65 (m, 1H), 4.88 (s, 4H), 4.22-4.14 (m, 1H), 4.03-3.92 (m, 1H), 3.90-3.81 (m, 1H), 3.72 (br s, 2H), 3.65-3.47 (m, 1H), 2.20-2.05 (m, 1H), 1.97-1.83 (m, 1H), 1.71 (br s, 1H), 1.53-1.30 (m, 2H), 1.20-1.07 (m, 2H), 1.06-0.96 (m, 1H). LC/MS m/z=680.2 for $C_{34}H_{35}BrNO_9$ [M+H]$^+$.

5-bromo-3,3-bis(6-(((2R)-2-hydroxy-4-methylpentyl)oxy)-2H-1,3-benzodioxol-5-yl)-2,3-dihydro-1H-indol-2-one (CMLD013650, Table 1, Entry 27)

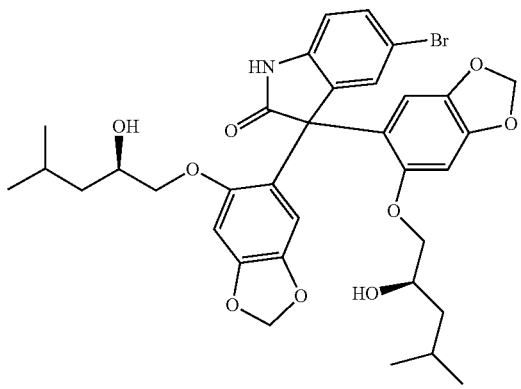 [SMILES: CC(C)C[C@@H](O)COc1cc2c(cc1C1(c3cc4c(cc3OC[C@H](O)CC(C)C)OCO4)C(=O)Nc3ccc(Br)cc31)OCO2]

5-bromo-3,3-dimethoxyindolin-2-one (1.0 equiv) and (R)-1-(benzo[d][1,3]dioxol-5-yloxy)-4-methylpentan-2-ol (2.2 equiv) were combined in dichloromethane (40 mM reaction concentration) in the presence of 5 Å molecular sieves and cooled to 0° C. Scandium (III) triflate (1.0 equiv) was added in one portion and allowed to slowly warm to room temperature and react for 18-24 hours, tracking by TLC. Upon completion, the reaction mixture was filtered through a pad of Celite, rinsing with dichloromethane. The crude reaction mixture was concentrated and directly purified via flash column chromatography (acetone/hexanes) to afford the product 5-bromo-3,3-bis(6-(((2R)-2-hydroxy-4-methylpentyl)oxy)-2H-1,3-benzodioxol-5-yl)-2,3-dihydro-1H-indol-2-one. $^1$H NMR (400 MHz, CHLOROFORM-d) δ=9.05-8.62 (m, 1H), 7.38-7.28 (m, 1H), 6.99 (br s, 1H), 6.66-6.55 (m, 1H), 6.52-6.41 (m, 1H), 6.29-6.14 (m, 1H), 5.98-5.85 (m, 3H), 4.08-3.33 (m, 5H), 1.81-1.53 (m, 1H), 1.43-1.01 (m, 4H), 0.97-0.60 (m, 12H) LC/MS m/z=686.5 for $C_{34}H_{39}BrNO_9$ [M+H]$^+$.

7-fluoro-3,3-bis(6-((R)-2-hydroxybutoxy)benzo[d][1,3]dioxol-5-yl)indolin-2-one CMLD12399, Table 1, Entry 28)

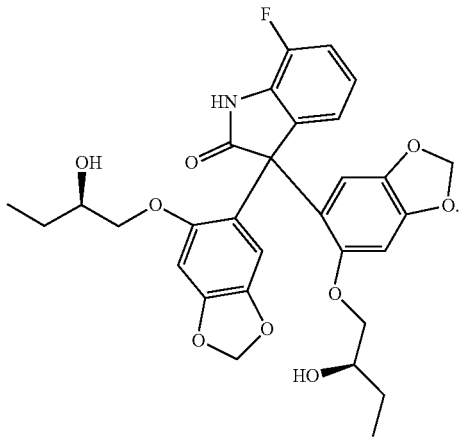 [SMILES: CC[C@@H](O)COc1cc2c(cc1C1(c3cc4c(cc3OC[C@H](O)CC)OCO4)C(=O)Nc3c(F)cccc31)OCO2]

7-fluoro-3,3-dimethoxyindolin-2-one (1.0 equiv) and (R)-1-(benzo[d][1,3]dioxol-5-yloxy)butan-2-ol (2.2 equiv) were combined in dichloromethane (40 mM reaction concentration) in the presence of 5 Å molecular sieves and cooled to 0'° C. Scandium (III) triflate (1.0 equiv) was added in one portion and allowed to slowly warm to room temperature and react for 18-24 hours, tracking by TLC. Upon completion, the reaction mixture was filtered through a pad of Celite, rinsing with dichloromethane. The crude reaction mixture was concentrated and directly purified via flash column chromatography (acetone/hexanes) to afford the product 7-fluoro-3,3-bis(6-((R)-2-hydroxybutoxy)benzo[d][1,3]dioxol-5-yl)indolin-2-one. $^1$H NMR (400 MHz, METHANOL-d$_4$) δ=7.08-7.01 (m, 1H), 6.96 (br d, J=5.1 Hz, 1H), 6.82-6.72 (m, 1H), 6.66 (s, 1H), 6.63 (d, J=2.3 Hz, 1H), 6.51 (br d, J=3.5 Hz, 1H), 5.92-5.85 (m, 4H), 3.93-3.71 (m, 3H), 3.69-3.60 (m, 1H), 3.53 (s, 1H), 3.41 (br s, 1H), 3.34-3.28 (m, 2H), 3.27-3.16 (m, 1H), 1.53-1.27 (m, 3H), 1.01-0.83 (m, 6H), 0.79-0.70 (m, 1H), 0.74 (br t, J=7.2 Hz, 1H). LC/MS m/z=568.2 for C$_{30}$H$_{31}$FNO$_9$ [M+H]$^+$.

6-fluoro-3-(6-(((R)-2-hydroxyoct-7-yn-1-yl)oxy)benzo[d][1,3]dioxol-5-yl)-3-(6-(((R)-2-hydroxypent-4-en-1-yl)oxy)benzo[d][1,3]dioxol-5-yl)indolin-2-one (RT162S-027, Table 1, Entry 29)

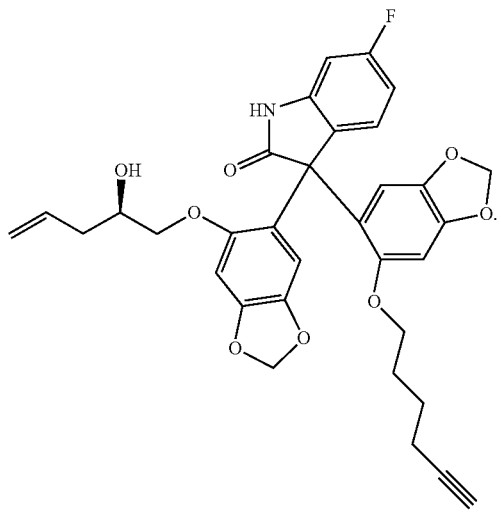 [SMILES: C#CCCCCOc1cc2c(cc1C1(c3cc4c(cc3OC[C@H](O)CC=C)OCO4)C(=O)Nc3cc(F)ccc31)OCO2]

Step 1: 6-fluoro-3,3-dimethoxyindolin-2-one (1.0 equiv) and (R)-1-(benzo[d][1,3]dioxol-5-yloxy)-pent-4-en-2-ol (1.0 equiv) were combined in dichloromethane (40 mM reaction concentration) and cooled to −40° C. Boron trifluoride diethyl etherate (0.9 equiv) was added dropwise, slowly over 5 minutes. The reaction was stirred at −40° C. for 40 minutes, and quenched with slow dropwise addition of 1N HCl followed stirring for 5 minutes at −40° C., and warming to 0° C. over the course of 10 minutes. Na$_2$SO$_4$ was added and the mixture was filtered through a pad of Celite, rinsing with dichloromethane. The crude reaction mixture was concentrated and directly purified via flash column chromatography (acetone/hexanes) to afford the product 6-fluoro-3-(6-(((R)-2-hydroxy-pent-4-en-1-yl)oxy)benzo[d][1,3]dioxol-5-yl)-3-methoxyindolin-2-one.

Step 2: 6-fluoro-3-(6-(((R)-2-hydroxy-pent-4-en-1-yl)oxy)benzo[d][1,3]dioxol-5-yl)-3-methoxyindolin-2-one (1.0 equiv) and 5-(hex-5-yn-1-yloxy)benzo[d][1,3]dioxole (2.2 equiv) were combined in dichloromethane (40 mM reaction concentration) in the presence of magnesium sulfate and cooled to 0° C. Scandium (III) triflate (1.0 equiv) was added in one portion and allowed to slowly warm to room temperature and react overnight. The reaction mixture was then filtered through a pad of Celite, rinsing with dichloromethane. The crude reaction mixture was concentrated and directly purified via flash column chromatography (acetone/hexanes) to afford the product 6-fluoro-3-(6-(((R)-2-hydroxyoct-7-yn-1-yl)oxy)benzo[d][1,3]dioxol-5-yl)-3-(6-(((R)-2-hydroxypent-4-en-1-yl)oxy)benzo[d][1,3]dioxol-5-yl)indolin-2-one. $^1$H NMR (400 MHz, DMSO-d$_6$) δ=6.83-6.77 (m, 1H), 6.77-6.74 (m, 1H), 6.74-6.65 (m, 2H), 6.64-6.51 (m, 2H), 6.50-6.41 (m, 1H), 6.29-6.21 (m, 1H), 6.16-6.03 (m, 1H), 5.98-5.87 (m, 4H), 5.04-4.87 (m, 2H), 4.85-4.75 (m, 1H), 4.73-4.67 (m, 1H), 3.88-3.74 (m, 1H), 3.72-3.59 (m, 2H), 3.59-3.50 (m, 1H), 3.49-3.42 (m, 1H), 3.40-3.36 (m, 1H), 3.20-3.08 (m, 1H), 2.76-2.67 (m, 1H), 2.15-2.04 (m, 1H), 2.01-1.96 (m, 1H), 1.95-1.88 (m, 1H), 1.87-1.76 (m, 1H), 1.63-1.47 (m, 2H), 1.33-1.18 (m, 2H). LC/MS m/z=588.4 for C$_{35}$H$_{35}$FNO$_9$ [M+H]$^+$.

REFERENCES

1. World Bank. Drug-resistant infections: A threat to our economic future. Washington, D.C.: World Bank. License: Creative Commons Attribution CC BY 3.0 IGO. (2017).
2. Council of Canadian Academies. When Antibiotics Fail. Ottawa (ON): The Expert Panel on the Potential Socio-Economic Impacts of Antimicrobial Resistance in Canada, Council of Canadian Academies. (2019).
3. Eyre, D. W. et al. A *Candida auris* autbreak and its control in an intensive care setting. N. Engl. J. Med. 379, 1322-1331 (2018).
4. Lockhart, S. R. et al. Simultaneous emergence of multi-drug-resistant *Candida auris* on 3 continents confirmed by whole-genome sequencing and epidemiological analyses. Clin. Infect. Dis. 64, 134-140 (2017).
5. Centers for Disease Control and Prevention. Antibiotic resistance threats in the United States. Centers Dis. Control Prev. 114 (2019). doi:CS239559-B
6. Satoh, K. et al. *Candida auris* sp. nov., a novel ascomycetous yeast isolated from the external ear canal of an inpatient in a Japanese hospital. Microbiol. Immunol. 53, 41-44 (2009).
7. Rhodes, J. & Fisher, M. C. Global epidemiology of emerging *Candida auris*. Curr. Opin. Microbiol. 52, 84-89 (2019).

8. Chow, N. et al. Tracing the evolutionary history and global expansion of *Candida auris* using population genomic analyses. MBio In Press, (2020).
9. Schelenz, S. et al. First hospital outbreak of the globally emerging *Candida auris* in a European hospital. 5, 35 (2016).
10. Ruiz-Gaitin, A. et al. An outbreak due to *Candida auris* with prolonged colonisation and candidaemia in a tertiary care European hospital. Mycoses 61, 498-505 (2018).
11. Robbins, N., Caplan, T. & Cowen, L. E. Molecular Evolution of Antifungal Drug Resistance. Annu. Rev. Microbiol. 71, 753-775 (2017).
12. Revie, N. M., Iyer, K. R., Robbins, N. & Cowen, L. E. Antifungal drug resistance: evolution, mechanisms and impact. Curr. Opin. Microbiol. 45, 70-76 (2018).
13. Martel, C. M. et al. Identification and characterization of four azole-resistant erg3 mutants of *Candida albicans*. Antimicrob. Agents Chemother. 54, 4527-4533 (2010).
14. Hoepfner, D. et al. An integrated approach for identification and target validation of antifungal compounds active against Erg11p. Antimicrob. Agents Chemother. 56, 4233-40 (2012).
15. Flowers, S. A., Colón, B., Whaley, S. G., Schuler, M. A. & David Rogers, P. Contribution of clinically derived mutations in ERG11 to azole resistance in *Candida albicans*. Antimicrob. Agents Chemother. 59, 450-460 (2015).
16. Perea, S. et al. Prevalence of molecular mechanisms of resistance to azole antifungal agents in *Candida albicans* strains displaying high-level fluconazole resistance isolated from human immunodeficiency virus-infected patients. Antimicrob. Agents Chemother. 45, 2676-2684 (2001).
17. Healey, K. R. et al. Limited ERG11 mutations identified in isolates of *Candida auris* directly contribute to reduced azole susceptibility. Antimicrob. Agents Chemother. 62, (2018).
18. Wasi, M. et al. ABC transporter genes show upregulated expression in drug-resistant clinical isolates of *Candida auris*: A genome-wide characterization of atp-binding cassette (abc) transporter genes. Front. Microbiol. 10, (2019).
19. Muñoz, J. F. et al. Genomic insights into multidrug-resistance, mating and virulence in *Candida auris* and related emerging species. Nat. Commun. 9, 5346 (2018).
20. Kean, R. et al. Transcriptome assembly and profiling of *Candida auris* reveals novel insights into biofilm-mediated resistance. mSphere 3, 1-14 (2018).
21. Rybak, J. M. et al. Abrogation of triazole resistance upon deletion of CDR1 in a clinical isolate of *Candida auris*. Antimicrob. Agents Chemother. 63, 1-7 (2019).
22. Chowdhary, A. et al. A multicentre study of antifungal susceptibility patterns among 350 *Candida auris* isolates (2009-17) in India: role of the ERG11 and FKS1 genes in azole and echinocandin resistance. J. Antimicrob. Chemother. 73, 891-899 (2018).
23. Nishikawa, J. L. et al. Inhibiting fungal multidrug resistance by disrupting an activator-Mediator interaction. *Nature* 530, 485-489 (2016).
24. Brown, L. E. et al. Discovery of new antimalarial chemotypes through chemical methodology and library development. Proc. Natl. Acad. Sci. U.S.A. 108, 6775-80 (2011).
25. Roemer, T. et al. Confronting the challenges of natural product-based antifungal discovery. Chem. Biol. 18, 148-164 (2011).
26. Perfect, J. R. The antifungal pipeline: A reality check. Nature Reviews Drug Discovery 16, 603-16 (2017).
27. Iyer, K. R. et al. Translation inhibition by rocaglates activates a species-specific cell death program in the emerging fungal pathogen *Candida auris*. MBio 11, 1-17 (2020).
28. Odds, F. C. Synergy, antagonism, and what the chequerboard puts between them. J. Antimicrob. Chemother. 52, 1 (2003).
29. Spitzer, M., Robbins, N. & Wright, G. D. Combinatorial strategies for combating invasive fungal infections. Virulence 1-17 (2016). doi:10.1080/21505594.2016.1196300
30. Iskar, M. et al. Drug-induced regulation of target expression. PLoS Comput. Biol. 6, (2010).
31. Henry, K. W., Nickels, J. T. & Edlind, T. D. Upregulation of ERG genes in *Candida* species by azoles and other sterol biosynthesis inhibitors. Antimicrob. Agents Chemother. 44, 2693-2700 (2000).
32. Ivnitski-Steele, I. et al. Identification of Nile red as a fluorescent substrate of the *Candida albicans* ATP-binding cassette transporters Cdr1p and Cdr2p and the major facilitator superfamily transporter Mdr1p. Anal. Biochem. 394, 87-91 (2009).
33. Kim, S. H. et al. Genetic analysis of *Candida auris* implicates Hsp90 in morphogenesis and azole tolerance and Cdr1 in azole resistance. MBio 10, e02529-18 (2019).
34. Prasad, R., Banerjee, A., Khandelwa, N. K. & Dhamgaye, S. The ABCs of *Candida albicans* multidrug transporter Cdr1. Eukaryot. Cell 14, 1154-1164 (2015).
35. Prasad, R., Sharma, M. & Rawal, M. K. Functionally relevant residues of Cdr1p: A multidrug ABC transporter of human pathogenic *Candida albicans*. J. Amino Acids 2011, 1-12 (2011).
36. Copping, V. M. S. et al. Exposure of *Candida albicans* to antifungal agents affects expression of SAP2 and SAP9 secreted proteinase genes. J. Antimicrob. Chemother. 55, 645-654 (2005).
37. Mann, P. A. et al. Chemical genomics-based antifungal drug discovery: targeting glycosylphosphatidylinositol (GPI) precursor biosynthesis. ACS Infect. Dis. 1, 59-72 (2015).
38. Holmes, A. R. et al. Targeting efflux pumps to overcome antifungal drug resistance. Futur. Med. Chem 8, 1485-1501 (2016).
39. J M, R. et al. Mutations in TAC1B: a novel genetic determinant of clinical fluconazole resistance in *C. auris*. bioRxiv 1-38 (2020).
40. White, T. C. Increased mRNA levels of ERG16, CDR, and MDR1 correlate with increases in azole resistance in *Candida albicans* isolates from a patient infected with human immunodeficiency virus. Antimicrob. Agents Chemother. 41, (1997).
41. Morschhäuser, J. et al. The transcription factor Mrr1p controls expression of the MDR1 efflux pump and mediates multidrug resistance in *Candida albicans*. PLoS Pathog. 3, e164 (2007).
42. Hill, J. A., O'Meara, T. R. & Cowen, L. E. Fitness trade-offs associated with the evolution of resistance to antifungal drug combinations. Cell Rep. 10, 809-819 (2015).
43. Morschhäuser, J. The genetic basis of fluconazole resistance development in *Candida albicans*. Biochimica et Biophysica Acta—Molecular Basis of Disease 1587, 240-248 (2002).
44. Sharma, A., Gupta, V. & Pathania, R. Efflux pump inhibitors for bacterial pathogens: From bench to bedside. Indian J. Med. Res. 149, 129 (2019).
45. Shriram, V., Khare, T., Bhagwat, R., Shukla, R. & Kumar, V. Inhibiting bacterial drug efflux pumps via phyto-therapeutics to combat threatening antimicrobial resistance. Front. Microbiol. 9, 2990 (2018).
46. Castaldi, M. P., Troast, D. M. & Porco Jr., J. Stereoselective Synthesis of Spirocyclic Oxindoles via Prins Cyclizations M. Org. Lett. 11, 3362-3365. (2009).
47. Morrison, B. L. et al. Oxyphenisatin acetate (NSC 59687) triggers a cell starvation response leading to autophagy, mitochondrial dysfunction, and autocrine TNFα-mediated apoptosis. Cancer Med. 2, 687-700 (2013).
48. Denoyelle, S. et al. Synthesis and SAR study of novel 3,3-diphenyl-1,3-dihydroindol-2-one derivatives as potent eIF2 GTP Met-tRNAiMet ternary complex inhibitors. Eur. J. Med. Chem. 69, 537-553 (2013).
49. Zheng, X. et al. Targeting multidrug-resistant ovarian cancer through estrogen receptor a dependent ATP depletion caused by hyperactivation of the unfolded protein response. Oncotarget 9, 14741-14753 (2018).
50. Neel, D. A. et al. 3,3-Bisaryloxindoles as mineralocorticoid receptor antagonists. Bioorganic Med. Chem. Lett. 15, 2553-2557 (2005).
51. Andreani, A. et al. New isatin derivatives with antioxidant activity. Eur. J. Med. Chem. 45, 1374-1378 (2010).
52. Prasad, R., De Wergifosse, P., Goffeau, A. & Balzi, E. Molecular cloning and characterization of a novel gene of *Candida albicans*, CDR1, conferring multiple resistance to drugs and antifungals. Curr. Genet. 27, 320-329 (1995).
53. Celaj, A. et al. Highly Combinatorial Genetic Interaction Analysis Reveals a Multi-Drug Transporter Influence Network. Cell Syst. 10, 25-38.e10 (2020).
54. Tsao, S., Rahkhoodaee, F. & Raymond, M. Relative contributions of the *Candida albicans* ABC transporters Cdr1p and Cdr2p to clinical azole resistance. Antimicrob. Agents Chemother. 53, 1344-52 (2009).
55. Shekhar-Guturja, T. et al. Dual action antifungal small molecule modulates multidrug efflux and TOR signaling. Nat. Chem. Biol. 12, 867-875 (2016).
56. Robey, R. W. et al. Revisiting the role of ABC transporters in multidrug-resistant cancer. *Nat. Rev. Cancer* 18, 452-464 (2018).
57. Wright, G. D. Antibiotic adjuvants: rescuing antibiotics from resistance. Trends Microbiol. 24, 862-871 (2016).
58. Min, K., Ichikawa, Y., Woolford, C. A. & Mitchell, A. P. *Candida albicans* Gene Deletion with a Transient CRISPR-Cas9 System. mSphere 1, 1-9 (2016).
59. Liu, Z. & Myers, L. C. Mediator tail module is required for Tac1-activated CDR1 expression and azole resistance in *Candida albicans*. Antimicrob. Agents Chemother. 61, 1-20 (2017).
60. Xie, J., Singh-Babak, S. & Cowen, L. Minimum inhibitory concentration (MIC) assay for antifungal drugs. Bio-Protocol 2, (2012).

All patents and other publications identified are expressly incorporated herein by reference for the purpose of describing and disclosing, for example, the methodologies described in such publications that might be used in connection with the present disclosure. These publications are provided solely for their disclosure prior to the filing date of the present application. Nothing in this regard should be construed as an admission that the inventors are not entitled to antedate such disclosure by virtue of prior disclosure or for any other reason. All statements as to the date or representation as to the contents of these documents are based on the information available to the applicants and do not constitute any admission as to the correctness of the dates or contents of these documents.

What is claimed is:

1. A compound of Formula (I):

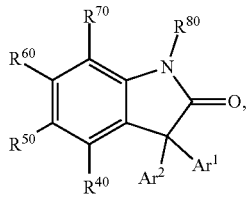

Formula (I)

or enantiomers, prodrugs, and pharmaceutically acceptable salts thereof,
wherein:
each of $R^{40}$, $R^{50}$, $R^{60}$, $R^{70}$, and $R^{80}$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, provided that at least one of $R^{40}$, $R^{50}$, $R^{60}$, $R^{70}$, and $R^{80}$ is not H; and $Ar^1$ and $Ar^2$ are each independently aryl or heteroaryl; and provided that (i) at least one of $Ar^1$ and $Ar^2$ is of the structure (Ar'):

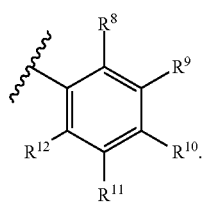

(Ar')

wherein:
each $R^8$ independently is halogen, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl;

each of $R^9$, $R^{10}$, $R^{11}$ and $R^{12}$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted; or at least a vicinal pair formed from selecting two of $R^9$, $R^{10}$, $R^{11}$, or $R^{12}$ and the carbons to which they are attached form an optionally substituted 5- or 6-member cycloalkyl or an optionally substituted 5- or 6-member heterocyclyl, and the remaining $R^9$, $R^{10}$, $R^{11}$ or $R^{12}$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted;

or (ii) $Ar^1$ and $Ar^2$ are independently of the structure (Ar'):

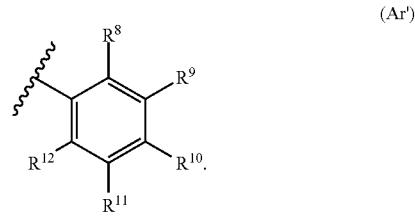

(Ar')

wherein:
each $R^8$ independently is halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl;

each of $R^9$, $R^{10}$, $R^{11}$ and $R^{12}$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted; or at least a vicinal pair formed from selecting two of $R^9$, $R^{10}$, $R^{11}$ or $R^{12}$ and the carbons to which they are attached form an optionally substituted 5- or 6-member cycloalkyl or an optionally substituted 5- or 6-member heterocyclyl, and the remaining $R^9$, $R^{10}$, $R^{11}$ or $R^{12}$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and each of which can be optionally substituted; and wherein any alkoxy, alkylamino, dialkylamino, acylamino, alkylthio, carbonyl, carboxyl, alkoxycarbonyl, acyl, acyloxy, alkyl, haloalkyl, heteroalkyl, alkenyl, alkynyl, sulfinyl, sulfonyl, thiocarbonyl, carbamoyl, cycloalkyl, heterocyclyl, aryl and heteroaryl can be optionally substituted with 1, 2, 3 or 4 substituents independently selected from the group consisting of halogen, hydroxy, carboxyl, oxo, nitro, haloalkyl, alkyl, alkenyl, alkynyl, alkaryl, aryl, heteroaryl, cycloalkyl, heterocyclyl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano and ureido, and where any heterocyclyl is a nonaromatic 3-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected independently from O, N, and S.

2. The compound of claim 1, wherein at least one of $R^{40}$, $R^{50}$, $R^{60}$, and $R^{70}$ is halogen, hydroxyl, amino, alkylamino, dialkylamino, thiol, alkylthio, carboxyl, nitro, acyl, acyloxy, alkyl, haloalkyl, heteroalkyl, or alkoxy; and the remaining of $R^{40}$, $R^{50}$, $R^{60}$ and $R^{70}$ are H, and wherein any alkylamino, dialkylamino, alkylthio, carboxyl, acyl, acyloxy, alkyl, haloalkyl, heteroalkyl, or alkoxy can be optionally substituted with 1, 2, 3 or 4 substituents independently selected from the group consisting of halogen, hydroxy, carboxyl, oxo, nitro, haloalkyl, alkyl, alkenyl, alkynyl, alkaryl, aryl, heteroaryl, cycloalkyl, heterocyclyl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano and ureido, and where any heterocyclyl is a nonaromatic 3-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected independently from O, N, and S.

3. The compound of claim 2, wherein one of $R^{40}$, $R^{50}$, $R^{60}$, and $R^{70}$ is halogen or $C_1$-$C_6$ alkyl and the remaining of $R^{40}$, $R^{50}$, $R^{60}$ and $R^{70}$ are H.

4. The compound of claim 1, wherein $R^{80}$ is hydrogen, $C_1$-$C_6$ alkyl, $C_2$-$C_{8a}$ alkenyl, or $C_2$-$C_{8a}$ alkynyl, and wherein any $C_1$-$C_6$ alkyl, $C_2$-$C_6$ alkenyl and $C_2$-$C_8$ alkynyl can be optionally substituted with 1, 2, 3 or 4 substituents independently selected from the group consisting of halogen, hydroxy, carboxyl, oxo, nitro, haloalkyl, alkyl, alkenyl, alkynyl, alkaryl, aryl, heteroaryl, cycloalky, heterocyclyl, aralkyl, alkoxy, aryloxy, amino, acylamino, alkylcarbanoyl, arylcarbanoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano and ureido, and where any heterocyclyl is a nonaromatic 3-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected independently from O, N, and S.

5. The compound of claim 1, wherein $Ar^1$ and $Ar^2$ are each independently of the structure Ar'.

6. The compound of claim 5, wherein $Ar^1$ and $Ar^2$ are the same.

7. The compound of claim 5, wherein $Ar^1$ and $Ar^2$ are different.

8. The compound of claim 1, wherein at least one of $Ar^1$ and $Ar^2$ is of the structure (Ar').

9. The compound of claim 1, wherein each of $R^9$, $R^{10}$, $R^{11}$, and $R^{12}$ independently are hydrogen, halogen, or $C_1$-$C_6$ alkoxy.

10. The compound of claim 1, wherein $R^8$ is an alkoxy optionally substituted with 1, 2 or 3 substituents independently selected from the group consisting of halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and where any heterocyclyl is a nonaromatic 3-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected independently from O, N, and S.

11. The compound of claim 10 wherein $R^8$ is methoxy, ethoxy, —O-n-propyl, —O-isopropyl, —O-sec-butyl, —O-tert-butyl, —O-n-butyl, O-isobutyl, —O-neopentyl, —O-isopropenyl, —O-n-propenyl, or —O-n-butenyl; or $R^8$ is

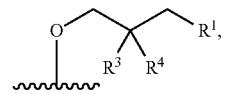

wherein each of $R^1$, $R^3$ and $R^4$ independently are hydrogen, halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and where any alkylamino, dialkylamino, acylamino, alkylthio, carbonyl, carboxyl, alkoxycarbonyl, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl and heteroaryl can be optionally substituted with 1, 2 or 3 substituents independently selected from the group consisting of halogen, hydroxyl, amino, alkylamino, dialkylamino, acylamino, thiol, alkylthio, cyano, carbonyl, carboxyl, alkoxycarbonyl, nitro, acyl, acyloxy, alkyl, haloalkyl, heteroalkyl, alkoxy, alkenyl, alkynyl, sulfinyl, sulfonyl, thiocarbonyl, carbamoyl, cycloalkyl, heterocyclyl, aryl or heteroaryl, and where any heterocyclyl is a nonaromatic 3-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected independently from O, N, and S.

12. The compound of claim 11, wherein $R^1$ is methyl, ethyl, n-propyl, isopropyl, sec-butyl, tert-butyl, n-butyl, isobutyl, neopentyl (—$CH_2C(CH_3)_3$), vinyl (—$CH=CH_2$), isopropenyl (—$C(=CH_2)CH_3$), 1-propenyl, 2-propenyl (—$CH_2C=CH_2$), propargyl (—$CH_2C≡CH$), or n-butenyl.

13. The compound of claim 11, wherein $R^3$ is hydrogen or halogen.

14. The compound of claim 11, wherein $R^4$ is hydrogen, amino or $C_1$-$C_6$ alkoxy halogen.

15. The compound of claim 11, wherein $R^8$ is

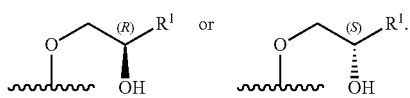

16. The compound of claim 11, wherein each $R^8$ is independently

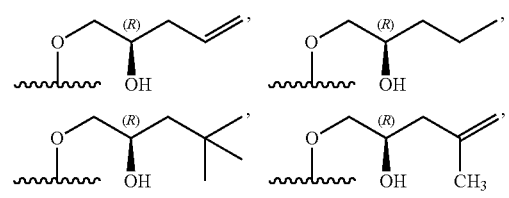

-continued

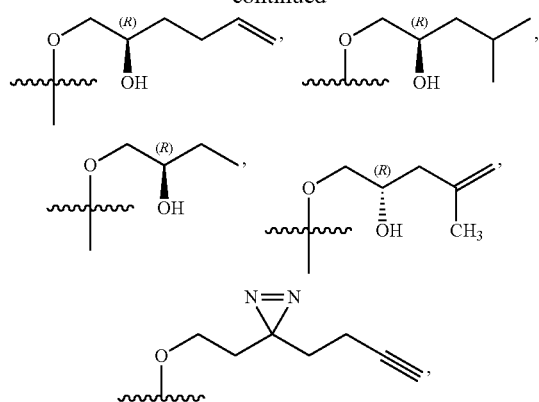

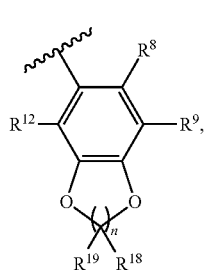

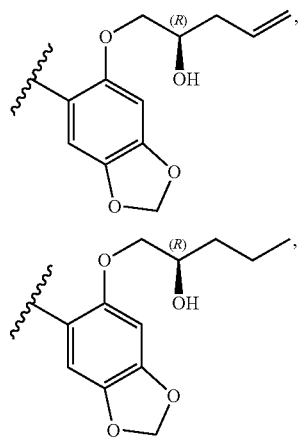

methoxy, ethoxy, —O-n-propyl, —O-isopropyl, —O-sec-butyl, —O-tert-butyl, —O-n-butyl, O-isobutyl, —O-neopentyl, —O-isopropenyl, —O-n-propenyl, or —O-n-butenyl.

17. The compound of claim 11, wherein at least one of $Ar^1$ and $Ar^2$ is of the structure (Ar"):

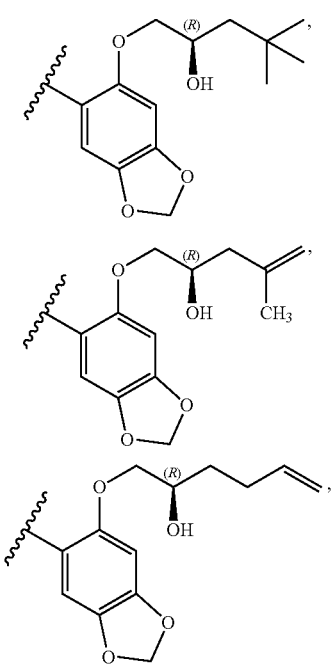

(Ar")

wherein:

n is 1 or 2; and each of $R^{18}$ and $R^{19}$ independently are hydrogen or halogen.

18. The compound of claim 11, wherein at least one of $Ar^1$ and $Ar^2$ is selected from the group consisting of:

-continued

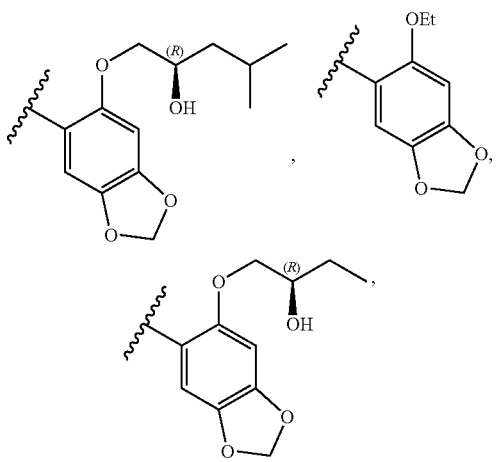

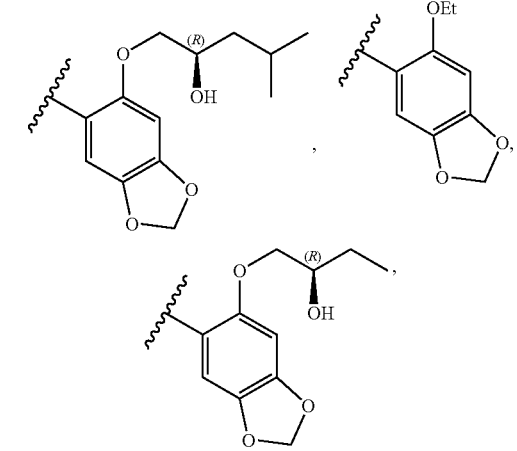

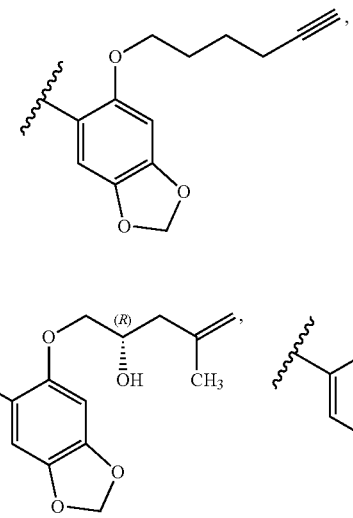

-continued
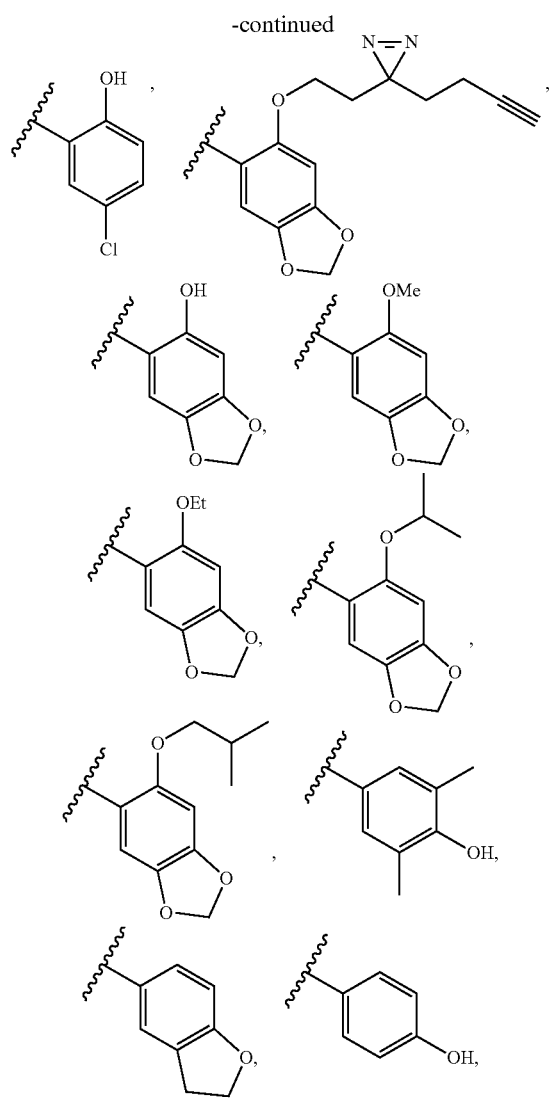
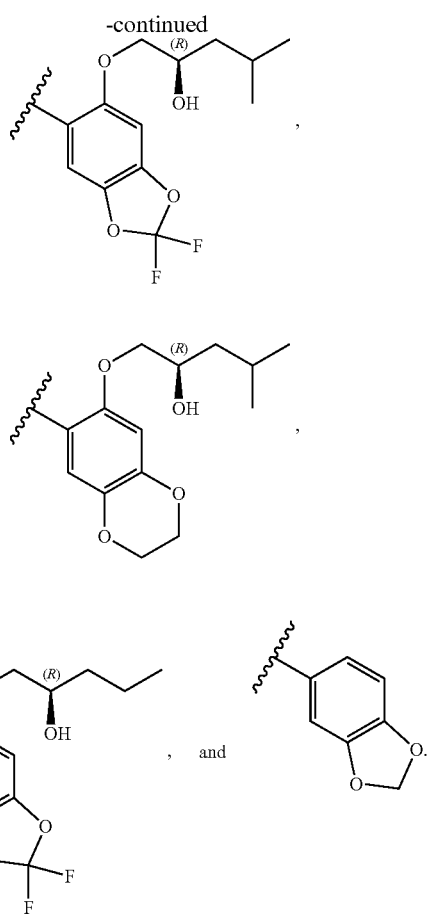
19. A pharmaceutical composition comprising a compound of claim 1 and a pharmaceutically acceptable carrier.
20. A method of inhibiting an efflux pump in a cell, the method comprising administering to the cell a compound of claim 1.
* * * * *

SEQUENCE LISTING

```
<160> NUMBER OF SEQ ID NOS: 50

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ctgtcaagga gggtattctg g                                                    21

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
cccgagctcc gtcgatcctg tttctatgt                                            29

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 3
ggagcttttg gtttatcttg					20

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ttgcgggccc gcaattagtt ggtcatcaac c					31

<210> SEQ ID NO 5
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ttgcgggccc ttagtggtgg tggtggtggt gatgatcgct aacttcttcg					50

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
accccaagtc caacagagag					20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tccagccaag tcaagtctca					20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
atccttgctg aaaacgctgc					20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

```
tcctcggcca cctttacaat                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
taacgcaaaa ggaccatggc                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cgcccttgat aatgtccacg                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
cggcccatga taaccctcta                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tttctgtctc tctgagggca                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cgctgaatgg atgttggagg                                              20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
```
cttctttctg gactccgggt                                                20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gcagtgatct gacctggctt                                                20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
acagctggat tcgacatggg                                                20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
tttgtgcctt caggaggacc                                                20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
actggatggc ggcgttagta                                                20

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
atcaagcttg cctcgtcc                                                  18

<210> SEQ ID NO 21
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
ctatactgct gtcgattcga tactaacgcc gccatccagt actacatgcg atatatatat    60

<210> SEQ ID NO 22
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cgctggccgg gtgacccggc ggggacgagg caagcttgat tgagctcgtg tgtgtcatca    60

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
cccacatttc gagaaaagga                                                 20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tggtcgctat actgctgtcg                                                 20

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
aagaaagaaa gaaaaccagg agtgaa                                          26

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
acaaatattt aaactcggga cctgg                                           25

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gcggccgcaa gtgattagac t                                               21

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
gcagctcagt gattaagagt aaagatgg                                        28

<210> SEQ ID NO 29
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
atacaagtga aaacattcag caaattaaaa atagtttacg caagtc                    46

<210> SEQ ID NO 30
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ctgaatgttt tcacttgtat gttttagagc tagaaatagc aagttaaa                  48

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
attctaagat gtcgtcgcaa gatg                                            24

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
agttctggct aaattctgaa tgttttc                                         27

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
taaatgcaat gggtcttatc catgtgg                                         27

-continued

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
gtcaaatatt cttcaccgta tgaacct                                          27

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
agagagagct tcttcggcag                                                  20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
agatcaacgg gggtgtctga                                                  20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tccagaactg ggcaatagcg                                                  20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tgcatggctc ccttgttgat                                                  20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ttcgactcaa aggtgacccg                                                  20

<210> SEQ ID NO 40

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
agggagcaga acgcattgaa                                                  20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
acctggtaag ttgaccgcct                                                  20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
cgaagggctt ctctgacagt                                                  20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cactgtttgt ggcttcaccg                                                  20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cgcctgaaac aggtctcact                                                  20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 45
ggatttggga tttggacact                                                    20

<210> SEQ ID NO 46
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
ctatactgct gtcgattcga tactaacgcc gccatccagt ggtcctgaga agtcgtggac         60

<210> SEQ ID NO 47
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
cgctggccgg gtgacccggc ggggacgagg caagcttgat ccacggtaaa aacgatggac         60

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
accaggcttg gaattgacag                                                    20

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
gctgtgagag ttggcaagg                                                     19

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
gccaaattcg ccattaaaga                                                    20